US009067937B2

(12) United States Patent
Matsuo et al.

(10) Patent No.: US 9,067,937 B2
(45) Date of Patent: Jun. 30, 2015

(54) 1,5-NAPHTHYRIDINE DERIVATIVES AND MELK INHIBITORS CONTAINING THE SAME

(71) Applicant: OncoTherapy Science, Inc., Kanagawa (JP)

(72) Inventors: Yo Matsuo, Kanagawa (JP); Shoji Hisada, Kanagawa (JP); Yusuke Nakamura, Tokyo (JP); Feryan Ahmed, New York, NY (US); Joel R. Walker, New York, NY (US); Raymond Huntley, New York, NY (US)

(73) Assignee: OncoTherapy Science, Inc., Kanagawa (JP)

( * ) Notice: Subject to any disclaimer, the term of this patent is extended or adjusted under 35 U.S.C. 154(b) by 0 days.

(21) Appl. No.: 14/371,375

(22) PCT Filed: Dec. 21, 2012

(86) PCT No.: PCT/US2012/071434
§ 371 (c)(1),
(2) Date: Jul. 9, 2014

(87) PCT Pub. No.: WO2013/109388
PCT Pub. Date: Jul. 25, 2013

(65) Prior Publication Data

US 2015/0005302 A1 Jan. 1, 2015

Related U.S. Application Data

(60) Provisional application No. 61/588,496, filed on Jan. 19, 2012.

(51) Int. Cl.
*C07D 471/04* (2006.01)
*A61K 31/4375* (2006.01)

(52) U.S. Cl.
CPC .................................... *C07D 471/04* (2013.01)

(58) Field of Classification Search
CPC .......................... C07D 471/04; A61K 31/4375
USPC .......................................... 546/123; 514/300
See application file for complete search history.

(56) References Cited

U.S. PATENT DOCUMENTS

| | | | | |
|---|---|---|---|---|
| 4,996,213 | A | 2/1991 | Mendes et al. | |
| 5,240,916 | A | 8/1993 | Caley et al. | |
| 8,791,131 | B2 * | 7/2014 | Cheng et al. | 514/274 |
| 2007/0032485 | A1 | 2/2007 | Kubota et al. | |
| 2010/0179143 | A1 | 7/2010 | Adams et al. | |
| 2011/0150831 | A1 | 6/2011 | Schuster et al. | |

FOREIGN PATENT DOCUMENTS

| | | | |
|---|---|---|---|
| WO | 2004/031413 | A3 | 4/2004 |
| WO | 2006/016525 | A3 | 2/2006 |
| WO | 2006/085684 | A3 | 8/2006 |
| WO | 2007/013665 | A3 | 2/2007 |
| WO | 2008/023841 | A1 | 2/2008 |

OTHER PUBLICATIONS

International Search Report and Written Opinion dated Mar. 5, 2013 of International Patent Application No. PCT/US2012/071434, 15 pages.
Blot et al., “Cell Cycle Regulation of pEg3, a New Xenopus Protein Kinase of the KIN1/PAR-1/MARK Family”, *Dev. Biol.*, vol. 241, No. 2, pp. 327-338 (2002).
Heyer et al., “Expression of Melk, a New Protein Kinase, During Early Mouse Development”, *Dev Dyn*, vol. 215, No. 4, pp. 344-351 (1999).
Lin et al., “Involvement of maternal embryonic leucine zipper kinase (MELK) in mammary carcinogenesis through interaction with Bcl-G, a pro-apoptotic member of the Bcl-2 family”, Breast Cancer Res, vol. 9, No. 1, R17 (2007), 13 pages.
Nakano et al., “Maternal embryonic leucine zipper kinase (MELK) regulates multipotent neural progenitor proliferation”, *J Cell Biol.*, vol. 170, No. 3, pp. 413-427 (2005).
Seong et al., Phosphorylation of a novel zing-finger-like protein, ZPR9, by murine protein serine/threonine kinase 38 (MPK38), *Biochem J.*, vol. 361, pp. 597-604 (2002).
Vulsteke et al., “Inhibition of Splicesome Assembly by the Cell Cycle-regulated Protein Kinase MELK and Involvement of Splicing Factor NIPP1”, *J Biol Chem*, vol. 279, No. 10, pp. 8642-8647 (2004).

* cited by examiner

*Primary Examiner* — Niloofar Rahmani
(74) *Attorney, Agent, or Firm* — Kilpatrick Townsend & Stockton LLP

(57) ABSTRACT

The present invention directs a compound represented by formula (I).

15 Claims, 6 Drawing Sheets

1,5-NAPHTHYRIDINE DERIVATIVES AND MELK INHIBITORS CONTAINING THE SAME

CROSS-REFERENCES TO RELATED APPLICATIONS

This application is a National Stage of International Application No. PCT/US2012/071434, filed Dec. 21, 2012, and which claims the benefit of U.S. Provisional Application No. 61,588,496, filed Jan. 19, 2012, the disclosure of which is here by incorporated by reference in its entirety for all purposes.

TECHNICAL FIELD

The present invention relates to a 1,5-naphthyridine derivative having an inhibitory activity against MELK, a method for the preparation thereof, and a pharmaceutical composition containing the compound as an active ingredient.

BACKGROUND ART

MELK, maternal embryonic leucine zipper kinase, was previously identified as a new member of the snfl/AMPK serine-threonine kinase family that is involved in mammalian embryonic development (Heyer B S et al., Dev Dyn. 1999 August 215(4):344-51). The gene was shown to play an important role in stem cell renewal (Nakano I et al., J Cell Biol. 2005 Aug. 1, 170(3):413-27), cell-cycle progression (Blot J et al., Dev Biol. 2002 Jan. 15, 241(2):327-38; Seong H A et al., Biochem J. 2002 Feb. 1, 361(Pt 3):597-604) and pre-mRNA splicing (Vulsteke V et al., J Biol Chem. 2004 Mar. 5, 279(10):8642-7. Epub 2003 Dec. 29). In addition, through gene expression profile analysis using a genome-wide cDNA microarray containing 23,040 genes, MELK was recently shown to be up-regulated in breast cancer (Lin M L et al., Breast Cancer Res. 2007; 9 (1):R17, WO2006/016525, WO2008/023841). In fact, MELK is up-regulated in several cancer cells, for example lung, bladder, lymphoma and cervical cancer cells (See WO2004/031413, WO2007/013665, and WO2006/085684, the disclosures of which are incorporated by reference herein). Northern blot analysis on multiple human tissues and cancer cell lines demonstrated that MELK was over-expressed at a significantly high level in a great majority of breast cancers and cell lines, but was not expressed in normal vital organs (heart, liver, lung and kidney) (WO2006/016525). Furthermore, suppression of MELK expression by siRNA was shown to significantly inhibit growth of human breast cancer cells. Accordingly, MELK is considered to be a suitable target for cancer therapy in the treatment of a wide array of cancer types.

SUMMARY OF INVENTION

The present inventors have endeavored to develop an effective inhibitor of MELK and have found that a compound can selectively inhibit the activity of MELK.

The present invention relates to the following (1) to (24).

(1) A compound represented by formula (I) or a pharmaceutically acceptable salt thereof:

(I)

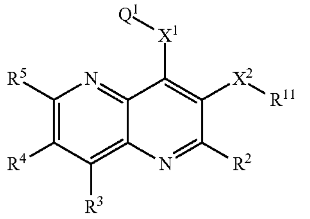

wherein, $X^1$ is selected from the group consisting of a direct bond, —$NR^{12}$—, —O—, and —S—;

$R^{12}$ is selected from the group consisting of a hydrogen atom, $C_1$-$C_6$ alkyl and $C_3$-$C_{10}$ cycloalkyl;

$Q^1$ is selected from the group consisting of $C_3$-$C_{10}$ cycloalkyl, $C_6$-$C_{10}$ aryl, 5- to 10-membered heteroaryl, 3- to 10-membered non-aromatic heterocyclyl, ($C_3$-$C_{10}$ cycloalkyl)-$C_1$-$C_6$ alkyl, ($C_6$-$C_{10}$ aryl)-$C_1$-$C_6$ alkyl, (5- to 10-membered heteroaryl)-$C_1$-$C_6$ alkyl, and (3- to 10-membered non-aromatic heterocyclyl)-$C_1$-$C_6$ alkyl; wherein $Q^1$ is optionally substituted with one or more substituents independently selected from $A^1$;

$X^2$ is selected from the group consisting of —CO—, —S—, —SO—, and —$SO_2$—;

$R^{11}$ is selected from the group consisting of $C_1$-$C_6$ alkyl, $C_3$-$C_{10}$ cycloalkyl, $C_6$-$C_{10}$ aryl, 5- to 10-membered heteroaryl, and 3- to 10-membered non-aromatic heterocyclyl; wherein $R^{11}$ is optionally substituted with one or more substituents independently selected from $A^2$;

$R^5$ is selected from the group consisting of a halogen atom, $C_3$-$C_{10}$ cycloalkyl, $C_6$-$C_{10}$ aryl, 5- to 10-membered heteroaryl, and 3- to 10-membered non-aromatic heterocyclyl; wherein the cycloalkyl, aryl, heteroaryl, and heterocyclyl are optionally substituted with one or more substituents independently selected from $A^3$;

$R^2$, $R^3$, and $R^4$ are independently selected from the group consisting of a hydrogen atom, a halogen atom, and $C_1$-$C_6$ alkyl;

$A^1$ and $A^3$ are independently selected from the group consisting of a halogen atom, cyano, —$COOR^{13}$, —$CONR^{14}R^{15}$, formyl, ($C_1$-$C_6$ alkyl)carbonyl, $C_1$-$C_6$ alkyl, $C_2$-$C_6$ alkenyl, $C_2$-$C_6$ alkynyl, nitro, —$NR^{16}R^{17}$, —$OR^{18}$, —$S(O)_nR^{19}$, $C_3$-$C_{10}$ cycloalkyl, $C_6$-$C_{10}$ aryl, 5- to 10-membered heteroaryl, and 3- to 10-membered non-aromatic heterocyclyl; wherein the alkylcarbonyl, alkyl, alkenyl, alkynyl, cycloalkyl, aryl, heteroaryl, and heterocyclyl are optionally substituted with one or more substituents independently selected from $A^4$;

$A^2$ is independently selected from the group consisting of a halogen atom, cyano, $C_3$-$C_{10}$ cycloalkyl, carboxy, formyloxy, ($C_1$-$C_6$ alkyl)carbonyloxy, hydroxy, $C_1$-$C_6$ alkoxy, amino, $C_1$-$C_6$ alkylamino, and di($C_1$-$C_6$ alkyl)amino;

$R^{13}$, $R^{14}$, and $R^{15}$ are independently selected from the group consisting of a hydrogen atom, $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 5- to 10-membered heteroaryl, and 3- to 10-membered non-aromatic heterocyclyl; wherein the alkyl, alkenyl, alkynyl, cycloalkyl, aryl, heteroaryl, and heterocyclyl are optionally substituted with one or more substituents independently selected from $A^4$; or $R^{14}$ and $R^{15}$ together with the nitrogen atom to which they are attached form 3- to 10-membered nitrogen-containing heterocyclyl, which is optionally substituted with one or more substituents independently selected from $A^4$;

$R^{16}$ and $R^{18}$ are independently selected from the group consisting of a hydrogen atom, $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 5- to 10-membered heteroaryl, 3- to 10-membered non-aromatic heterocyclyl, and —$COR^{20}$; wherein the alkyl, alkenyl, alkynyl, cycloalkyl, aryl, heteroaryl, and heterocyclyl are optionally substituted with one or more substituents independently selected from $A^4$; $R^{17}$ is selected from the group consisting of a hydrogen atom, and $C_1$-$C_6$ alkyl that is optionally substituted with one or more substituents independently selected from $A^4$; or $R^{16}$ and $R^{17}$ together with the nitrogen atom to which they are attached form 3- to 10-membered nitrogen-containing heterocyclyl, which is optionally substituted with one or more substituents independently selected from $A^4$;

$R^{19}$ is selected from the group consisting of $C_1$-$C_6$ alkyl, $C_3$-$C_{10}$ cycloalkyl, $C_6$-$C_{10}$ aryl, and 5- to 10-membered heteroaryl; wherein the alkyl, cycloalkyl, aryl, and heteroaryl are optionally substituted with one or more substituents independently selected from $A^4$;

$R^{20}$ is selected from the group consisting of a hydrogen atom, —$NR^{14}R^{15}$, $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 5- to 10-membered heteroaryl, and 3- to 10-membered non-aromatic heterocyclyl; wherein the alkyl, alkenyl, alkynyl, cycloalkyl, aryl, heteroaryl, and heterocyclyl are optionally substituted with one or more substituents independently selected from $A^4$;

n is an integer independently selected from 0 to 2;

$A^4$ is independently selected from consisting of a halogen atom, cyano, —$COOR^{21}$, —$CONR^{22}R^{23}$, formyl, ($C_1$-$C_6$ alkyl)carbonyl, $C_1$-$C_6$ alkyl, $C_2$-$C_6$ alkenyl, $C_2$-$C_6$ alkynyl, nitro, —$NR^{24}R^{25}$, —$OR^{26}$, —$S(O)_nR^{27}$, $C_3$-$C_{10}$ cycloalkyl, $C_6$-$C_{10}$ aryl, 5- to 10-membered heteroaryl, and 3- to 10-membered non-aromatic heterocyclyl; wherein the alkylcarbonyl, alkyl, alkenyl, alkynyl, cycloalkyl, aryl, heteroaryl, and heterocyclyl are optionally substituted with one or more substituents independently selected from $A^5$;

$R^{21}$, $R^{22}$, and $R^{23}$ are independently selected from the group consisting of a hydrogen atom, $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 5- to 10-membered heteroaryl, and 3- to 10-membered non-aromatic heterocyclyl; wherein the alkyl, alkenyl, alkynyl, cycloalkyl, aryl, heteroaryl, and heterocyclyl are optionally substituted with one or more substituents independently selected from $A^5$; or $R^{22}$ and $R^{23}$ together with the nitrogen atom to which they are attached form 3- to 10-membered nitrogen-containing heterocyclyl, which is optionally substituted with one or more substituents independently selected from $A^5$;

$R^{24}$ and $R^{26}$ are independently selected from the group consisting of a hydrogen atom, $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 5- to 10-membered heteroaryl, 3- to 10-membered non-aromatic heterocyclyl, and —$COR^{28}$; wherein the alkyl, alkenyl, alkynyl cycloalkyl, aryl, heteroaryl, and heterocyclyl are optionally substituted with one or more substituents independently selected from $A^5$; $R^{25}$ is selected from the group consisting of a hydrogen atom, and $C_1$-$C_6$ alkyl that is optionally substituted with one or more substituents independently selected from $A^5$; or $R^{24}$ and $R^{25}$ together with the nitrogen atom to which they are attached form 3- to 10-membered nitrogen-containing heterocyclyl, which is optionally substituted with one or more substituents independently selected from $A^5$;

$R^{27}$ is selected from the group consisting of $C_1$-$C_6$ alkyl, $C_3$-$C_{10}$ cycloalkyl, $C_6$-$C_{10}$ aryl, and 5- to 10-membered heteroaryl; wherein the alkyl, cycloalkyl, aryl, and heteroaryl are optionally substituted with one or more substituents independently selected from $A^5$;

$R^{28}$ is independently selected from the group consisting of a hydrogen atom, —$NR^{22}R^{23}$, $C_1$-$C_6$ alkyl, $C_2$-$C_6$ alkenyl, $C_2$-$C_6$ alkynyl $C_3$-$C_{10}$ cycloalkyl, $C_6$-$C_{10}$ aryl, 5- to 10-membered heteroaryl, and 3- to 10-membered non-aromatic heterocyclyl; wherein the alkyl, alkenyl, alkynyl, cycloalkyl, aryl, heteroaryl, and heterocyclyl are optionally substituted with one or more substituents independently selected from $A^5$;

$A^5$ is independently selected from consisting of a halogen atom, cyano, —$COOR^{31}$, —$CONR^{32}R^{33}$, formyl, ($C_1$-$C_6$ alkyl)carbonyl, $C_1$-$C_6$ alkyl, $C_2$-$C_6$ alkenyl, $C_2$-$C_6$ alkynyl, nitro, —$NR^{34}R^{35}$, —$OR^{36}$, —$S(O)_nR^{37}$, $C_3$-$C_{10}$ cycloalkyl, $C_6$-$C_{10}$ aryl, 5- to 10-membered heteroaryl, and 3- to 10-membered non-aromatic heterocyclyl; wherein the alkylcarbonyl, alkyl, alkenyl, alkynyl, cycloalkyl, aryl, heteroaryl, and heterocyclyl are optionally substituted with one or more substituents independently selected from $A^6$;

$R^{31}$, $R^{32}$, and $R^{33}$ are independently selected from the group consisting of a hydrogen atom, $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 5- to 10-membered heteroaryl, and 3- to 10-membered non-aromatic heterocyclyl; wherein the alkyl, alkenyl, alkynyl, cycloalkyl, aryl, heteroaryl, and heterocyclyl are optionally substituted with one or more substituents independently selected from $A^6$; or $R^{32}$ and $R^{33}$ together with the nitrogen atom to which they are attached form 3- to 10-membered nitrogen-containing heterocyclyl, which is optionally substituted with one or more substituents independently selected from $A^6$;

$R^{34}$ and $R^{36}$ are independently selected from the group consisting of a hydrogen atom, $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 5- to 10-membered heteroaryl, 3- to 10-membered non-aromatic heterocyclyl, and —$COR^{38}$; wherein the alkyl, alkenyl, alkynyl, cycloalkyl, aryl, heteroaryl, and heterocyclyl are optionally substituted with one or more substituents independently selected from $A^6$; $R^{35}$ is selected from the group consisting of a hydrogen atom, and $C_1$-$C_6$ alkyl that is optionally substituted with one or more substituents independently selected from $A^6$; or $R^{34}$ and $R^{35}$ together with the nitrogen atom to which they are attached form 3- to 10-membered nitrogen-containing heterocyclyl, which is optionally substituted with one or more substituents independently selected from $A^6$;

$R^{37}$ is selected from the group consisting of $C_1$-$C_6$ alkyl, $C_3$-$C_{10}$ cycloalkyl, $C_6$-$C_{10}$ aryl, and 5- to 10-membered heteroaryl; wherein the alkyl, cycloalkyl, aryl, and heteroaryl are optionally substituted with one or more substituents independently selected from $A^6$;

$R^{38}$ is independently selected from the group consisting of a hydrogen atom, —$NR^{32}R^{33}$, $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 5- to 10-membered heteroaryl, and 3- to 10-membered non-aromatic heterocyclyl; wherein the alkyl, alkenyl, alkynyl, cycloalkyl, aryl, heteroaryl, and heterocyclyl are optionally substituted with one or more substituents independently selected from $A^6$;

$A^6$ is independently selected from consisting of a halogen atom, cyano, carboxy, —$COOR^{41}$, —$CONR^{42}R^{43}$, formyl, ($C_1$-$C_6$ alkyl)carbonyl, $C_1$-$C_6$ alkyl, $C_2$-$C_6$ alkenyl, $C_2$-$C_6$ alkynyl, nitro, —$NR^{44}R^{45}$, —$OR^{46}$, $S(O)_nR^{47}$, $C_3$-$C_{10}$ cycloalkyl, $C_6$-$C_{10}$ aryl, 5- to 10-membered heteroaryl, and 3- to 10-membered non-aromatic heterocyclyl; wherein the alkylcarbonyl, alkyl, alkenyl, alkynyl, cycloalkyl, aryl, heteroaryl, and heterocyclyl are optionally substituted with one or more substituents independently selected from the group consisting of a halogen atom, hydroxy, $C_1$-$C_6$ alkoxy, amino, $C_1$-$C_6$ alkylamino, and di($C_1$-$C_6$ alkyl)amino;

$R^{41}$, $R^{42}$, and $R^{43}$ are independently selected from the group consisting of a hydrogen atom, $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 5- to 10-membered heteroaryl, and 3- to 10-membered non-aromatic heterocyclyl; wherein the alkyl, alkenyl, alkynyl, cycloalkyl, aryl, heteroaryl, and heterocyclyl are optionally substituted with one or more substituents independently selected from the group consisting of a halogen atom, hydroxy, $C_1$-$C_6$ alkoxy, amino, $C_1$-$C_6$ alkylamino, and di($C_1$-$C_6$ alkyl)amino;

$R^{44}$ and $R^{46}$ are independently selected from the group consisting of a hydrogen atom, $C_1$-$C_6$ alkyl, $C_3$-$C_{10}$ cycloalkyl, $C_6$-$C_{10}$ aryl, 5- to 10-membered heteroaryl, 3- to 10-membered non-aromatic heterocyclyl, and —$COR^{48}$;

$R^{45}$ is selected from the group consisting of a hydrogen atom, and $C_1$-$C_6$ alkyl; $R^{47}$ is selected from the group consisting of $C_1$-$C_6$ alkyl, $C_3$-$C_{10}$ cycloalkyl, $C_6$-$C_{10}$ aryl, and 5- to 10-membered heteroaryl; and $R^{48}$ is independently selected from the group consisting of $C_1$-$C_6$ alkyl, $C_3$-$C_{10}$ cycloalkyl, $C_6$-$C_{10}$ aryl, 5- to 10-membered heteroaryl, and 3- to 10-membered non-aromatic heterocyclyl.

(2) The compound or a pharmaceutically acceptable salt thereof according to above-mentioned (1), wherein $Q^1$ is selected from the group consisting of $C_5$-$C_7$ cycloalkyl, phenyl, pyridyl, pyrazolyl, pyrimidinyl, and piperidyl; wherein $Q^1$ is optionally substituted with one or more substituents independently selected from $A^1$.

(3) The compound or a pharmaceutically acceptable salt thereof according to above-mentioned (1) or (2), wherein $X^2$ is selected from the group consisting of —CO— and —$SO_2$—; and $R^{11}$ is selected from the group consisting of $C_1$-$C_6$ alkyl and $C_3$-$C_7$ cycloalkyl, which are optionally substituted with one or more substituents independently selected from the group consisting of hydroxy and a halogen atom.

(4) The compound or a pharmaceutically acceptable salt thereof according to any one of above-mentioned (1) to (3), wherein $R^5$ is phenyl substituted with one to three substituents independently selected from the group consisting of hydroxy, a halogen atom, $C_1$-$C_6$ alkyl, and $C_1$-$C_6$ alkoxy, wherein the alkyl and alkoxy are optionally substituted with one or more halogen atoms.

(5) The compound or a pharmaceutically acceptable salt thereof according to any one of above-mentioned (1) to (4), wherein $R^2$ is a hydrogen atom.

(6) The compound or a pharmaceutically acceptable salt thereof according to any one of above-mentioned (1) to (5), wherein $R^3$ is a hydrogen atom.

(7) The compound or a pharmaceutically acceptable salt thereof according to any one of above-mentioned (1) to (6), wherein $R^4$ is a hydrogen atom.

(8) The compound or a pharmaceutically acceptable salt thereof according to any one of above-mentioned (1) to (7), wherein $X^1$ is —NH—.

(9) The compound or a pharmaceutically acceptable salt thereof according to any one of above-mentioned (1) to (8), wherein the optional substituent of $Q^1$ is selected from the group consisting of hydroxy, amino, $C_1$-$C_6$ alkoxy, $C_1$-$C_6$ alkylamino, di($C_1$-$C_6$ alkyl)amino, amino-$C_1$-$C_6$ alkyl, ($C_1$-$C_6$ alkylamino)-$C_1$-$C_6$ alkyl, di($C_1$-$C_6$ alkyl)amino-$C_1$-$C_6$ alkyl, amino-$C_1$-$C_6$ alkoxy, ($C_1$-$C_6$ alkylamino)-$C_1$-$C_6$ alkoxy, di($C_1$-$C_6$ alkyl)amino-$C_1$-$C_6$ alkoxy, hydroxy-$C_1$-$C_6$ alkyl, ($C_1$-$C_6$ alkoxy)-$C_1$-$C_6$ alkyl, carboxy-$C_1$-$C_6$ alkyl, [($C_1$-$C_6$ alkoxy)carbonyl]-$C_1$-$C_6$ alkyl, carbamoyl-$C_1$-$C_6$ alkyl, [N—($C_1$-$C_6$ alkyl)carbamoyl]-$C_1$-$C_6$ alkyl, [N,N-di ($C_1$-$C_6$ alkyl)carbamoyl]-$C_1$-$C_6$ alkyl, ($C_1$-$C_6$ alkyl)carbonylamino, N—($C_1$-$C_6$ alkyl)carbonyl-N—($C_1$-$C_6$ alkyl)amino, pyrrolidinyl, piperidyl, and piperazinyl;

wherein the alkyl moiety of the group defined as the optional substituent of $Q^1$ is optionally substituted with a substituent selected from the group consisting of amino, $C_1$-$C_6$ alkylamino, di($C_1$-$C_6$ alkyl)amino, hydroxy, $C_1$-$C_6$ alkoxy, pyrrolidinyl, piperidyl, and piperazinyl; and wherein the pyrrolidinyl, piperidyl, and piperazinyl defined as the optional substituent of $Q^1$ are optionally substituted with a substituent selected from the group consisting of $C_1$-$C_6$ alkyl, amino, $C_1$-$C_6$ alkylamino, di($C_1$-$C_6$ alkyl) amino, hydroxy, $C_1$-$C_6$ alkoxy, pyrrolidinyl, piperidyl, and piperazinyl.

(10) The compound or a pharmaceutically acceptable salt thereof according to above-mentioned (9), wherein the optional substituent of $Q^1$ is selected from the group consisting of hydroxy, amino, di($C_1$-$C_6$ alkyl)amino, $C_1$-$C_6$ alkyl, di($C_1$-$C_6$ alkyl)amino-$C_1$-$C_6$ alkyl, di($C_1$-$C_6$ alkyl)amino-$C_1$-$C_6$ alkoxy, di($C_1$-$C_6$ alkyl)amino, [(amino-$C_1$-$C_6$ alkyl)carbonyl]amino, N—($C_1$-$C_6$ alkyl)piperidyl, di($C_1$-$C_6$ alkyl) amino-pyrrolidin-1-yl, amino-pyrrolidin-1-yl, (pyrrolidin-1-yl)-$C_1$-$C_6$ alkyl, ($C_1$-$C_6$ alkyl)amino-piperidin-1-yl, amino-piperidin-1-yl, hydroxy-$C_1$-$C_6$ alkyl, [di($C_1$-$C_6$ alkyl)amino-$C_1$-$C_6$ alkyl]amino, [4-($C_1$-$C_6$ alkyl)-piperazin-1-yl]-$C_1$-$C_6$ alkyl, (piperazin-1-yl)-$C_1$-$C_6$ alkyl, pyrrolidinylcarbonylamino, (hydroxy-pyrrolidin-1-yl)-$C_1$-$C_6$ alkyl, morpholinyl-$C_1$-$C_6$ alkyl, [N-(hydroxy-$C_1$-$C_6$ alkyl)-N—($C_1$-$C_6$ alkyl) amino]-$C_1$-$C_6$ alkyl, and $(CD_3)_2N$—$C_1$-$C_6$ alkyl.

(11) The compound or a pharmaceutically acceptable salt thereof according to above-mentioned (1), which is selected from the group consisting of the following compounds:

1-(6-chloro-4-(4-((dimethylamino)methyl)cyclohexylamino)-1,5-naphthyridin-3-yl)ethanone;

1-(6-(3,5-dichloro-4-hydroxyphenyl)-4-((4-(dimethylamino)cyclohexyl)amino)-1,5-naphthyridin-3-yl)ethanone;

1-(6-(3-chloro-5-fluoro-4-hydroxyphenyl)-4-((4-(dimethylamino)cyclohexyl)amino)-1,5-naphthyridin-3-yl)ethanone;

cyclopropyl(6-(3,5-dichloro-4-hydroxyphenyl)-4-(4-((dimethylamino)methyl)-cyclohexylamino)-1,5-naphthyridin-3-yl)methanone;

(6-(3-chloro-5-fluoro-4-hydroxyphenyl)-4-(4-((dimethylamino)methyl)-cyclohexylamino)-1,5-naphthyridin-3-yl)(cyclopropyl)methanone;

1-(6-(3,5-dichloro-4-hydroxyphenyl)-4-((4-((dimethylamino)methyl)cyclohexyl)-amino)-1,5-naphthyridin-3-yl)ethanone;

1-(6-(3-chloro-5-fluoro-4-hydroxyphenyl)-4-((4-((dimethylamino)methyl)cyclohexyl)-amino)-1,5-naphthyridin-3-yl)ethanone;

1-(6-(3-chloro-4-hydroxy-5-methoxyphenyl)-4-((4-((dimethylamino)methyl)-cyclohexyl)amino)-1,5-naphthyridin-3-yl)ethanone;

1-(6-(3,5-dichloro-4-hydroxyphenyl)-4-((4-(2-(dimethylamino)ethyl)cyclohexyl)-amino)-1,5-naphthyridin-3-yl)ethanone;

1-(6-(3-chloro-5-fluoro-4-hydroxyphenyl)-4-(4-(2-(dimethylamino)ethyl)-cyclohexylamino)-1,5-naphthyridin-3-yl)ethanone;

1-(4-(4-((dimethylamino)methyl)cyclohexylamino)-6-(4-hydroxy-3-(trifluoromethoxy)-phenyl)-1,5-naphthyridin-3-yl)ethanone;

2,6-dichloro-4-(8-((4-((dimethylamino)methyl)cyclohexyl)amino)-7-(methylsulfonyl)-1,5-naphthyridin-2-yl)phenol;

2-chloro-4-(8-((4-((dimethylamino)methyl)cyclohexyl) amino)-7-(methylsulfonyl)-1,5-naphthyridin-2-yl)-6-fluorophenol;

2-chloro-4-(8-((4-((dimethylamino)methyl)cyclohexyl) amino)-7-(methylsulfonyl)-1,5-naphthyridin-2-yl)-6-methoxyphenol;

2,6-dichloro-4-(8-((4-(dimethylamino)cyclohexyl) amino)-7-(methylsulfonyl)-1,5-naphthyridin-2-yl)phenol;

2,6-dichloro-4-(8-((4-((dimethylamino)methyl)phenyl) amino)-7-(methylsulfonyl)-1,5-naphthyridin-2-yl)phenol;

2-chloro-4-(8-((4-((dimethylamino)methyl)phenyl) amino)-7-(methylsulfonyl)-1,5-naphthyridin-2-yl)-6-fluorophenol;

2-chloro-4-(8-((4-((dimethylamino)methyl)phenyl) amino)-7-(methylsulfonyl)-1,5-naphthyridin-2-yl)-6-methoxyphenol;

1-(6-(3,5-dichloro-4-hydroxyphenyl)-4-((3-(2-(pyrrolidin-1-yl)ethyl)phenyl)amino)-1,5-naphthyridin-3-yl)ethanone;

1-(6-(3-chloro-5-fluoro-4-hydroxyphenyl)-4-(3-(2-(pyrrolidin-1-yl)ethyl)phenylamino)-1,5-naphthyridin-3-yl) ethanone;

1-(6-(3,5-dichloro-4-hydroxyphenyl)-4-((6-(2-(dimethylamino)ethoxy)pyridin-3-yl)-amino)-1,5-naphthyridin-3-yl) ethanone;

1-(6-(3-chloro-5-fluoro-4-hydroxyphenyl)-4-((6-(2-(dimethylamino)ethoxy)pyridin-3-yl)amino)-1,5-naphthyridin-3-yl)ethanone;

1-(6-(3-chloro-4-hydroxy-5-methoxyphenyl)-4-((6-(2-(dimethylamino)ethoxy)pyridin-3-yl)amino)-1,5-naphthyridin-3-yl)ethanone;

2,6-dichloro-4-(8-((6-(2-(dimethylamino)ethoxy)pyridin-3-yl)amino)-7-(methylsulfonyl)-1,5-naphthyridin-2-yl)phenol;

2-chloro-4-(8-((6-(2-(dimethylamino)ethoxy)pyridin-3-yl)amino)-7-(methylsulfonyl)-1,5-naphthyridin-2-yl)-6-fluorophenol;

2-chloro-4-(8-((6-(2-(dimethylamino)ethoxy)pyridin-3-yl)amino)-7-(methylsulfonyl)-1,5-naphthyridin-2-yl)-6-methoxyphenol;

1-(6-(3,5-dichloro-4-hydroxyphenyl)-4-((1-methylpiperidin-4-yl)methylamino)-1,5-naphthyridin-3-yl)ethanone;

1-(6-(3,5-dichloro-4-hydroxyphenyl)-4-((4-((dimethylamino-d6)methyl)cyclohexyl)-amino)-1,5-naphthyridin-3-yl)ethanone;

1-(6-(3,5-dichloro-4-hydroxyphenyl)-4-((4-(2-(dimethylamino)ethyl)phenyl)amino)-1,5-naphthyridin-3-yl)ethanone;

1-(6-(3-chloro-5-fluoro-4-hydroxyphenyl)-4-((4-(2-(dimethylamino)ethyl)phenyl)-amino)-1,5-naphthyridin-3-yl) ethanone;

1-(6-(3-chloro-4-hydroxy-5-methoxyphenyl)-4-((4-(2-(dimethylamino)ethyl)phenyl)-amino)-1,5-naphthyridin-3-yl)ethanone;

2-chloro-4-(8-((4-(dimethylamino)cyclohexyl)amino)-7-(methylsulfonyl)-1,5-naphthyridin-2-yl)-6-fluorophenol;

1-(6-(3,5-dichloro-4-hydroxyphenyl)-4-((1-(1-methylpiperidin-4-yl)-1H-pyrazol-4-yl)-amino)-1,5-naphthyridin-3-yl)ethanone;

1-(6-(3,5-dichloro-4-hydroxyphenyl)-4-(4-((4-methylpiperazin-1-yl)methyl)-phenylamino)-1,5-naphthyridin-3-yl) ethanone;

1-(6-(3-chloro-5-fluoro-4-hydroxyphenyl)-4-(4-((4-methylpiperazin-1-yl)methyl)-phenylamino)-1,5-naphthyridin-3-yl)ethanone;

1-(6-(3,5-dichloro-4-hydroxyphenyl)-4-(4-(2-(pyrrolidin-1-yl)ethyl)piperidin-1-yl)-1,5-naphthyridin-3-yl)ethanone;

1-(6-(3-chloro-5-fluoro-4-hydroxyphenyl)-4-(4-(2-(pyrrolidin-1-yl)ethyl)piperidin-1-yl)-1,5-naphthyridin-3-yl) ethanone;

1-(6-(3,5-dichloro-4-hydroxyphenyl)-4-(6-(2-(dimethylamino)ethylamino)pyridin-3-ylamino)-1,5-naphthyridin-3-yl)ethanone;

1-(6-(3-chloro-5-fluoro-4-hydroxyphenyl)-4-(6-(2-(dimethylamino)ethylamino)-pyridin-3-ylamino)-1,5-naphthyridin-3-yl)ethanone;

(S)-(4-(6-(3-aminopiperidin-1-yl)pyridin-3-ylamino)-6-(3,5-dichloro-4-hydroxyphenyl)-1,5-naphthyridin-3-yl)(cyclopropyl)methanone;

1-(4-((2-(3-aminopyrrolidin-1-yl)pyrimidin-5-yl)amino)-6-(3,5-dichloro-4-hydroxyphenyl)-1,5-naphthyridin-3-yl) ethanone;

1-(4-(4-((dimethylamino)methyl)cyclohexylamino)-6-(1H-pyrazol-4-yl)-1,5-naphthyridin-3-yl)ethanone;

1-(6-(3,5-dichloro-4-hydroxyphenyl)-4-(4-(hydroxymethyl)cyclohexylamino)-1,5-naphthyridin-3-yl)ethanone;

1-[6-(3,5-dichloro-4-hydroxyphenyl)-4-{4-[(dimethylamino)methyl]-cyclohexylamino}-1,5-naphthyridin-3-yl]-2-hydroxyethanone;

1-(6-(3,5-dichloro-4-hydroxyphenyl)-4-(1-methylpiperidin-4-ylamino)-1,5-naphthyridin-3-yl)ethanone;

1-(6-(3-chloro-5-fluoro-4-hydroxyphenyl)-4-(1-methylpiperidin-4-ylamino)-1,5-naphthyridin-3-yl)ethanone;

1-{6-[3,5-dichloro-4-hydroxyphenyl]-4-[4-(morpholinomethyl)cyclohexylamino]-1,5-naphthyridin-3-yl}ethanone;

1-(6-(3,5-dichloro-4-hydroxyphenyl)-4-(4-(((2-hydroxyethyl)(methyl)amino)methyl)-cyclohexylamino)-1,5-naphthyridin-3-yl)ethanone;

1-(6-(3-chloro-5-fluoro-4-hydroxyphenyl)-4-(4-(((2-hydroxyethyl)(methyl)amino)-methyl)cyclohexylamino)-1,5-naphthyridin-3-yl)ethanone;

1-(6-(3,5-difluoro-4-hydroxyphenyl)-4-(4-((dimethylamino)methyl)cyclohexylamino)-1,5-naphthyridin-3-yl) ethanone;

1-(6-(3,5-dichloro-4-hydroxyphenyl)-4-((6-(3-(dimethylamino)pyrrolidin-1-yl)pyridin-3-yl)amino)-1,5-naphthyridin-3-yl)ethanone;

1-(6-(3-chloro-5-fluoro-4-hydroxyphenyl)-4-((6-(3-(dimethylamino)pyrrolidin-1-yl)-pyridin-3-yl)amino)-1,5-naphthyridin-3-yl)ethanone;

1-(6-(3,5-dichloro-4-hydroxyphenyl)-4-(6-(3-(methylamino)pyrrolidin-1-yl)pyridin-3-ylamino)-1,5-naphthyridin-3-yl)ethanone;

1-(6-(3-chloro-5-fluoro-4-hydroxyphenyl)-4-(6-(3-(methylamino)pyrrolidin-1-yl)-pyridin-3-ylamino)-1,5-naphthyridin-3-yl)ethanone;

1-(6-(1H-benzo[d]imidazol-5-yl)-4-(4-((dimethylamino) methyl)cyclohexylamino)-1,5-naphthyridin-3-yl)ethanone;

1-(4-((4-((dimethylamino)methyl)cyclohexylamino)-6-(pyridin-4-yl)-1,5-naphthyridin-3-yl)ethanone;

5-(7-acetyl-8-(4-((dimethylamino)methyl)cyclohexylamino)-1,5-naphthyridin-2-yl)-pyrimidine-2-carbonitrile;

1-(6-(3,5-dimethyl-1H-pyrazol-4-yl)-4-(4-((dimethylamino)methyl)cyclohexylamino)-1,5-naphthyridin-3-yl) ethanone;

1-(4-(4-((dimethylamino)methyl)cyclohexylamino)-6-(4-hydroxy-3,5-dimethyl-phenyl)-1,5-naphthyridin-3-yl)ethanone;

1-(6-(3,5-dichloro-4-hydroxyphenyl)-4-(4-(pyrrolidin-1-ylmethyl)phenylamino)-1,5-naphthyridin-3-yl)ethanone;

1-(6-(3,5-dichloro-4-hydroxyphenyl)-4-(4-(pyrrolidin-1-ylmethyl)cyclohexylamino)-1,5-naphthyridin-3-yl)ethanone;

1-(6-(3-chloro-5-fluoro-4-hydroxyphenyl)-4-(4-(pyrrolidin-1-ylmethyl)cyclohexyl-amino)-1,5-naphthyridin-3-yl)ethanone;

1-(6-(3,5-dichloro-4-hydroxyphenyl)-4-(4-((4-methylpiperazin-1-yl)methyl)cyclo-hexylamino)-1,5-naphthyridin-3-yl)ethanone;

1-(4-(6-(3-aminopiperidin-1-yl)pyridin-3-ylamino)-6-(3,5-dichloro-4-hydroxyphenyl)-1,5-naphthyridin-3-yl)ethanone;

1-(4-(6-(3-aminopiperidin-1-yl)pyridin-3-ylamino)-6-(3-chloro-5-fluoro-4-hydroxy-phenyl)-1,5-naphthyridin-3-yl)ethanone;

1-(4-(4-aminocyclohexylamino)-6-(3,5-dichloro-4-hydroxyphenyl)-1,5-naphthyridin-3-yl)ethanone;

1-[4-(4-aminocyclohexylamino)-6-(3-chloro-5-fluoro-4-hydroxyphenyl)-1,5-naphthyridin-3-yl]ethanone;

1-(6-(3-chloro-5-fluoro-4-hydroxyphenyl)-4-(4-((4-methylpiperazin-1-yl)methyl)-cyclohexylamino)-1,5-naphthyridin-3-yl)ethanone;

N-(4-(3-acetyl-6-(3-chloro-5-fluoro-4-hydroxyphenyl)-1,5-naphthyridin-4-ylamino)-cyclohexyl)-2-amino-3-methylbutanamide;

1-(6-(3,5-dichloro-4-hydroxyphenyl)-4-(4-(piperazin-1-ylmethyl)cyclohexylamino)-1,5-naphthyridin-3-yl)ethanone;

(S)-1-(4-(6-(3-aminopiperidin-1-yl)pyridin-3-ylamino)-6-(3,5-dichloro-4-hydroxy-phenyl)-1,5-naphthyridin-3-yl)ethanone;

(S)-1-(4-(6-(3-aminopiperidin-1-yl)pyridin-3-ylamino)-6-(3-chloro-5-fluoro-4-hydroxy-phenyl)-1,5-naphthyridin-3-yl)ethanone;

N-(4-((3-acetyl-6-(3,5-dichloro-4-hydroxyphenyl)-1,5-naphthyridin-4-yl)amino)cyclo-hexyl)-2-aminopropanamide;

N-(4-(3-acetyl-6-(3-chloro-5-fluoro-4-hydroxyphenyl)-1,5-naphthyridin-4-ylamino)-cyclohexyl)-2-aminopropanamide;

(S)—N-((1R,4S)-4-(3-acetyl-6-(3,5-dichloro-4-hydroxyphenyl)-1,5-naphthyridin-4-yl-amino)cyclohexyl)pyrrolidine-2-carboxamide;

(S)—N-((1R,4S)-4-(3-acetyl-6-(3-chloro-5-fluoro-4-hydroxyphenyl)-1,5-naphthyridin-4-ylamino)cyclohexyl)pyrrolidine-2-carboxamide;

1-(6-(3-hydroxypyrrolidin-1-yl)-4-(4-((3-hydroxypyrrolidin-1-yl)methyl)cyclohexyl-amino)-1,5-naphthyridin-3-yl)ethanone;

1-(6-(pyrrolidin-1-yl)-4-(4-(pyrrolidin-1-ylmethyl)cyclohexylamino)-1,5-naphthyridin-3-yl)ethanone;

N-(4-(3-acetyl-6-(3,5-dichloro-4-hydroxy phenyl)-1,5-naphthyridin-4-ylamino)-cyclohexyl)-2-amino-3-methylbutanamide;

[6-(3-chloro-5-fluoro-4-hydroxyphenyl)-4-[4-(dimethylamino)cyclohexylamino]-1,5-naphthyridin-3-yl](cyclopropyl)methanone;

cyclopropyl[6-(3,5-dichloro-4-hydroxyphenyl)-4-[4-(dimethylamino)cyclohexyl-amino]-1,5-naphthyridin-3-yl]methanone;

1-(4-{4-[(dimethylamino)methyl]cyclohexylamino}-6-(1H-pyrrolo[2,3-b]pyridin-5-yl)-1,5-naphthyridin-3-yl)ethanone;

(S)-{4-[6-(3-aminopiperidin-1-yl)pyridin-3-ylamino]-6-(3-chloro-5-fluoro-4-hydroxyphenyl)-1,5-naphthyridin-3-yl}(cyclopropyl)methanone;

1-(4-{4-[(dimethylamino)methyl]cyclohexyl amino}-6-(4-methoxyphenyl)-1,5-naphthyridin-3-yl)ethanone;

1-[6-(3,5-dichloro-4-methoxyphenyl)-4-{4-[(dimethylamino)methyl]cyclohexyl-amino}-1,5-naphthyridin-3-yl]ethanone;

1-(4-{4-[(dimethylamino)methyl]cyclohexylamino}-6-(6-hydroxypyridin-3-yl)-1,5-naphthyridin-3-yl)ethanone;

5-(7-acetyl-8-{4-[(dimethylamino)methyl]cyclohexylamino}-1,5-naphthyridin-2-yl)picolinonitrile;

1-(4-{4-[(dimethylamino)methyl]cyclohexylamino}-6-(4-hydroxyphenyl)-1,5-naphthyridin-3-yl)ethanone;

1-[6-(3,5-dichloro-4-hydroxyphenyl)-4-{[4-(dimethylamino)cyclohexyl]methylamino}-1,5-naphthyridin-3-yl)ethanone;

1-[6-(3-chloro-5-fluoro-4-hydroxyphenyl)-4-{[4-(dimethylamino)cyclohexyl]-methylamino}-1,5-naphthyridin-3-yl]ethanone;

1-[6-(3-chloro-5-fluoro-4-hydroxyphenyl)-4-(4-hydroxy-cyclohexylamino)-1,5-naphthyridin-3-yl]ethanone;

1-[6-(3,5-dichloro-4-hydroxyphenyl)-4-(4-hydroxycyclohexylamino)-1,5-naphthyridin-3-yl]ethanone;

1-[6-(3-chloro-5-fluoro-4-hydroxyphenyl)-4-{cis-4-[(dimethylamino)methyl]cyclo-hexylamino}-1,5-naphthyridin-3-yl]ethanone;

1-[6-(3,5-dichloro-4-hydroxyphenyl)-4-{cis-4-[(dimethylamino)methyl]cyclohexyl-amino}-1,5-naphthyridin-3-yl]ethanone;

(R)-1-{4-[6-(3-aminopiperidin-1-yl)pyridin-3-ylamino]-6-(3,5-dichloro-4-hydroxy-phenyl)-1,5-naphthyridin-3-yl}ethanone;

(R)-1-{4-[6-(3-aminopiperidin-1-yl)pyridin-3-ylamino]-6-(3-chloro-5-fluoro-4-hydroxyphenyl)-1,5-naphthyridin-3-yl}ethanone;

(R)-(4-{[6-(3-aminopiperidin-1-yl)pyridin-3-yl]amino}-6-(3,5-dichloro-4-hydroxyphenyl)-1,5-naphthyridin-3-yl)(cyclopropyl)methanone;

(R)-(4-{[6-(3-aminopiperidin-1-yl)pyridin-3-yl]amino}-6-(3-chloro-5-fluoro-4-hydroxyphenyl)-1,5-naphthyridin-3-yl)(cyclopropyl) methanone;

1-[6-(3,5-dichloro-4-hydroxyphenyl)-4-{[trans-4-(dimethylamino)cyclohexyl]amino}-1,5-naphthyridin-3-yl)-2-hydroxyethanone dihydrochloride;

1-[6-(3-chloro-5-fluoro-4-hydroxyphenyl)-4-({trans-4-[(dimethylamino)methyl]cyclohexyl}amino)-1,5-naphthyridin-3-yl)]-2-hydroxyethanone dihydrochloride;

1-[6-(3-chloro-5-fluoro-4-hydroxyphenyl)-4-({trans-4-[(dimethylamino)methyl]cyclohexyl}amino)-1,5-naphthyridin-3-yl)]propan-1-one dihydrochloride;

1-[6-(3,5-dichloro-4-hydroxyphenyl)-4-({trans-4-[(dimethylamino)methyl]cyclohexyl}amino)-1,5-naphthyridin-3-yl)]propan-1-one dihydrochloride;

(S)-1-(4-{[6-(3-aminopiperidin-1-yl)pyridin-3-yl]amino}-6-(3,5-dichloro-4-hydroxyphenyl)-1,5-naphthyridin-3-yl)propan-1-one trihydrochloride;

(S)-1-(4 {[6-(3-aminopiperidin-1-yl)pyridin-3-yl]amino}-6-(3-chloro-5-fluoro-4-hydroxyphenyl)-1,5-naphthyridin-3-yl)propan-1-one trihydrochloride;

1-[6-(3,5-dichloro-4-hydroxyphenyl)-4-({4-[((R)-3-fluoropyrrolidin-1yl)methyl]cyclohexyl}amino)-1,5-naphthyridin-3-yl]ethanone dihydrochloride;

(S)-(4-((6-(3-aminopiperidin-1-yl)pyridin-3-yl)amino)-6-(3-chloro-5-fluoro-4-hydroxyphenyl)-1,5-naphthyridin-3-yl)(cyclobutyl)methanone dihydrochloride;

(6-(3,5-dichloro-4-hydroxyphenyl)-4-((4-[(dimethylamino)methyl{cyclohexyl)amino)-1,5-naphthyridin-3-yl)(cyclobutyl)methanone dihydrochloride;

(6-(3-chloro-5-fluoro-4-hydroxyphenyl)-4-((4-((dimethylamino)methyl)cyclohexyl)amino)-1,5-naphthyridin-3-yl)(cyclobutyl)methanone dihydrochloride;

(S)-(4-{[6-(3-aminopiperidin-1-yl)pyridin-3-yl]amino}-6-(3-chloro-5-fluoro-4-hydroxyphenyl)-1,5-naphthyridin-3-yl)(cyclobutyl)methanone;

(R)-1-(4-((6-(3-aminopiperidin-1-yl)pyridin-3-yl) amino)-6-(3,5-dichloro-4-hydroxyphenyl)-1,5-naphthyridin-3-yl)propan-1-one trihydrochloride;

(R)-1-(4-{[6-(3-aminopiperidin-1-yl)pyridin-3-yl] amino}-6-(3,5-dichloro-4-hydroxyphenyl)-1,5-naphthyridin-3-yl)-2-methylpropan-1-one trihydrochloride;

1-[6-(3,5-dichloro-5-4-hydroxyphenyl)-4-({trans-4-[(dimethylamino)methyl]cyclohexyl}amino)-1,5-naphthyridin-3-yl]-2-methylpropan-1-one dihydrochloride;

1-[6-chloro-4-({trans-4-[(dimethylamino)methyl] cyclohexyl}amino)-1,5-naphthyridin-3-yl]-2-methylpropan-1-one dihydrochloride;

and pharmaceutically acceptable salts thereof

(12) The compound or a pharmaceutically acceptable salt thereof according to above-mentioned (1), which is selected from the group consisting of the following compounds:

1-(6-(3,5-dichloro-4-hydroxyphenyl)-4-(trans-(4-(dimethylamino)cyclohexyl)amino)-1,5-naphthyridin-3-yl)ethanone;

cyclopropyl(6-(3,5-dichloro-4-hydroxyphenyl)-4-(trans-4-((dimethylamino)methyl)-cyclohexylamino)-1,5-naphthyridin-3-yl) methanone;

(6-(3-chloro-5-fluoro-4-hydroxyphenyl)-4-(trans-4-((dimethylamino)methyl)-cyclohexylamino)-1,5-naphthyridin-3-yl)(cyclopropyl) methanone;

1-(6-(3,5-dichloro-4-hydroxyphenyl)-4-((trans-4-((dimethylamino)methyl)cyclohexyl)-amino)-1,5-naphthyridin-3-yl) ethanone;

1-(6-(3-chloro-5-fluoro-4-hydroxyphenyl)-4-((trans-4-((dimethylamino)methyl)-cyclohexyl)amino)-1,5-naphthyridin-3-yl) ethanone;

1-(6-(3,5-dichloro-4-hydroxyphenyl)-4-((trans-4-(2-(dimethylamino)ethyl)cyclohexyl)-amino)-1,5-naphthyridin-3-yl) ethanone;

(S)-(4-(6-(3-aminopiperidin-1-yl)pyridin-3-ylamino)-6-(3,5-dichloro-4-hydroxyphenyl)-1,5-naphthyridin-3-yl)(cyclopropyl)methanone;

1-[6-(3,5-dichloro-4-hydroxyphenyl)-4-{trans-4-[(dimethylamino)methyl]cyclo-hexylamino}-1,5-naphthyridin-3-yl]-2-hydroxyethanone;

1-(4-(6-(3-aminopiperidin-1-yl)pyridin-3-ylamino)-6-(3,5-dichloro-4-hydroxyphenyl)-1,5-naphthyridin-3-yl)ethanone;

1-(4-(6-(3-aminopiperidin-1-yl)pyridin-3-ylamino)-6-(3-chloro-5-fluoro-4-hydroxy-phenyl)-1,5-naphthyridin-3-yl) ethanone;

(S)-1-(4-(6-(3-aminopiperidin-1-yl)pyridin-3-ylamino)-6-(3,5-dichloro-4-hydroxy-phenyl)-1,5-naphthyridin-3-yl) ethanone;

(S)-1-(4-(6-(3-aminopiperidin-1-yl)pyridin-3-ylamino)-6-(3-chloro-5-fluoro-4-hydroxy-phenyl)-1,5-naphthyridin-3-yl)ethanone;

(S)-{4-[6-(3-aminopiperidin-1-yl)pyridin-3-ylamino]-6-(3-chloro-5-fluoro-4-hydroxy-phenyl)-1,5-naphthyridin-3-yl}(cyclopropyl) methanone;

(R)-1-{4-[6-(3-aminopiperidin-1-yl)pyridin-3-ylamino]-6-(3,5-dichloro-4-hydroxy-phenyl)-1,5-naphthyridin-3-yl}ethanone;

(R)-1-{4-[6-(3-aminopiperidin-1-yl)pyridin-3-ylamino]-6-(3-chloro-5-fluoro-4-hydroxyphenyl)-1,5-naphthyridin-3-yl}ethanone;

and pharmaceutically acceptable salts thereof.

(13) A pharmaceutical composition comprising as an active ingredient a compound or a pharmaceutically acceptable salt thereof according to any one of above-mentioned (1) to (12).

(14) An MELK inhibitor comprising as an active ingredient a compound or a pharmaceutically acceptable salt thereof according to any one of above-mentioned (1) to (12).

(15) An MELK-expression modulating agent comprising as an active ingredient a compound or a pharmaceutically acceptable salt thereof according to any one of above-mentioned (1) to (12).

(16) An antitumor agent comprising as an active ingredient a compound or a pharmaceutically acceptable salt thereof according to any one of above-mentioned (1) to (12).

(17) A therapeutic and/or preventive agent for a disease that involves overexpression of MELK, comprising as an active ingredient a compound or a pharmaceutically acceptable salt thereof according to any one of above-mentioned (1) to (12).

(18) The therapeutic and/or preventive agent according to above-mentioned (17), wherein the disease is cancer.

(19) The therapeutic and/or preventive agent according to above-mentioned (18), wherein the cancer is selected from the group consisting of breast cancer, lung cancer, bladder cancer, lymphoma, and uterine cancer.

(20) A method for treating and/or preventing a disease that involves overexpression of MELK, which comprises administering an effective amount of a compound or a pharmaceutically acceptable salt thereof according to any one of above-mentioned (1) to (12) to a subject in need thereof

(21) A compound or a pharmaceutically acceptable salt thereof according to any one of above-mentioned (1) to (12) for use in a treatment and/or prevention of a disease that involves overexpression of MELK.

(22) Use of a compound or a pharmaceutically acceptable salt thereof according to any one of above-mentioned (1) to (12) in the manufacture of a therapeutic and/or preventive agent for a disease that involves overexpression of MELK.

(23) A process for preparing a compound of formula (I):

(I)

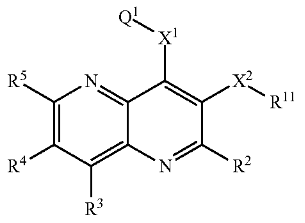

or a pharmaceutically acceptable salt thereof according to any one of above-mentioned (1) to (12), wherein $R^5$ is phenyl optionally substituted with one or more substituents independently selected from selected from $A^3$; and $Q^1$, $X^1$, $X^2$, $R^{11}$, $R^2$, $R^3$, $R^4$, and $A^3$ are the groups as defined in any one of above-mentioned (1) to (10); which comprises:

reacting a compound represented by formula (II):

(II)

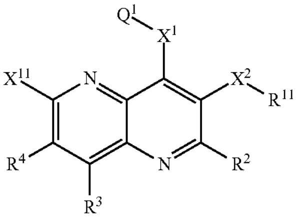

wherein $Q^1$, $X^1$, $X^2$, $R^{11}$, $R^2$, $R^3$ and $R^4$ are the groups as defined above, with the proviso that the groups may have one or more protecting groups, and $X^{11}$ is a halogen atom such as a chlorine atom; with a compound represented by formula (III):

(III)

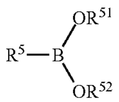

wherein $R^5$ is as defined above with the proviso that the group of $R^5$ may have one or more protecting groups, and $R^{51}$ and $R^{52}$ are independently selected from the group consisting of $C_1$-$C_6$ alkyl, or $R^{51}$ and $R^{52}$ together with the boron atom to which they are attached form 5- to 7-membered cyclic boronic acid ester optionally substituted with one or more substituents independently selected from the group consisting of $C_1$-$C_6$ alkyl.

(24) A compound represented by formula (II) or a pharmaceutically acceptable salt thereof:

(II)

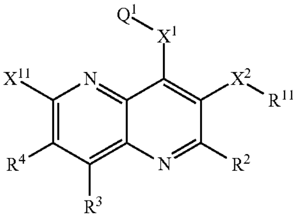

wherein $Q^1$, $X^1$, $X^2$, $R^{11}$, $R^2$, $R^3$ and $R^4$ are the groups as defined in one of above-mentioned (1) to (10) with the proviso that the groups may have one or more protecting groups, and $X^{11}$ is a halogen atom.

According to one aspect of the invention, there is provided a compound represented by formula (I) or a pharmaceutically acceptable salt thereof:

(I)

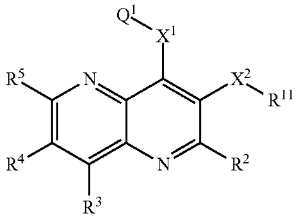

wherein, $X^1$ is —NH—;

$Q^1$ is selected from the group consisting of $C_5$-$C_7$ cycloalkyl, phenyl, pyridyl, pyrazolyl, pyrimidinyl, and piperidyl; wherein $Q^1$ is optionally substituted with one or more substituents independently selected from $A^1$;

$X^2$ is selected from the group consisting of —CO— and —$SO_2$—;

$R^{11}$ is selected from the group consisting of $C_1$-$C_6$ alkyl and $C_3$-$C_7$ cycloalkyl, which are optionally substituted with one or more substituents independently selected from the group consisting of hydroxy and a halogen atom;

$R^5$ is phenyl substituted with one to three substituents independently selected from the group consisting of hydroxy, a halogen atom, $C_1$-$C_6$ alkyl, and $C_1$-$C_6$ alkoxy wherein the alkyl and alkoxy are optionally substituted with one or more halogen atoms;

$R^2$, $R^3$, and $R^4$ are hydrogen atoms;

$A^1$ is independently selected from the group consisting of hydroxy, amino, $C_1$-$C_6$ alkoxy, $C_1$-$C_6$ alkylamino, di($C_1$-$C_6$ alkyl)amino, amino-$C_1$-$C_6$ alkyl, ($C_1$-$C_6$ alkylamino)-$C_1$-$C_6$ alkyl, di($C_1$-$C_6$ alkyl)amino-$C_1$-$C_6$ alkyl, amino-$C_1$-$C_6$ alkoxy, ($C_1$-$C_6$ alkylamino)-$C_1$-$C_6$ alkoxy, di($C_1$-$C_6$ alkyl)amino-$C_1$-$C_6$ alkoxy, hydroxy-$C_1$-$C_6$ alkyl, ($C_1$-$C_6$ alkoxy)-$C_1$-$C_6$ alkyl, carboxy-$C_1$-$C_6$ alkyl, [($C_1$-$C_6$ alkoxy)carbonyl]-$C_1$-$C_6$ alkyl, carbamoyl-$C_1$-$C_6$ alkyl, [N—($C_1$-$C_6$ alkyl)carbamoyl]-$C_1$-$C_6$ alkyl, [N,N-di($C_1$-$C_6$ alkyl)carbamoyl]-$C_1$-$C_6$ alkyl, ($C_1$-$C_6$ alkyl)carbonylamino, N—($C_1$-$C_6$ alkyl)carbonyl-N—($C_1$-$C_6$ alkyl)amino, pyrrolidinyl, piperidyl, and piperazinyl;

wherein the pyrrolidinyl, piperidyl, and piperazinyl defined as $A^1$ are optionally substituted with a substituent selected from the group consisting of $C_1$-$C_6$ alkyl, amino, $C_1$-$C_6$ alkylamino, di($C_1$-$C_6$ alkyl)amino, hydroxy, $C_1$-$C_6$ alkoxy, pyrrolidinyl, piperidyl, and piperazinyl; and wherein the alkyl moiety of the group defined as $A^1$ is optionally substituted with a substituent selected from the group consisting of amino, $C_1$-$C_6$ alkylamino, di($C_1$-$C_6$ alkyl)amino, hydroxy, $C_1$-$C_6$ alkoxy, pyrrolidinyl, piperidyl, and piperazinyl.

According to another aspect of the invention, there is provided a compound represented by formula (I):

(I)

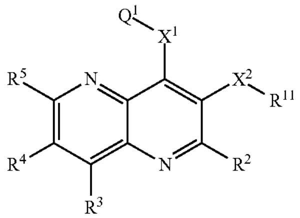

or a pharmaceutically acceptable salt thereof, wherein, $X^1$ is —NH—; and $Q^1$ is selected from the group consisting of $C_5$-$C_7$ cycloalkyl such as cyclohexyl and pyridyl; wherein $Q^1$ is optionally substituted with one or more substituents independently selected from $A^1$;

$A^1$ is independently selected from the group consisting of hydroxy, amino, $C_1$-$C_6$ alkoxy, $C_1$-$C_6$ alkylamino, di($C_1$-$C_6$ alkyl)amino, amino-$C_1$-$C_6$ alkyl, ($C_1$-$C_6$ alkylamino)-$C_1$-$C_6$ alkyl, di($C_1$-$C_6$ alkyl)amino-$C_1$-$C_6$ alkyl, amino-$C_1$-$C_6$ alkoxy, ($C_1$-$C_6$ alkylamino)-$C_1$-$C_6$ alkoxy, di($C_1$-$C_6$ alkyl)amino-$C_1$-$C_6$ alkoxy, hydroxy-$C_1$-$C_6$ alkyl, ($C_1$-$C_6$ alkoxy)-$C_1$-$C_6$ alkyl, carboxy-$C_1$-$C_6$ alkyl, [($C_1$-$C_6$ alkoxy)carbonyl]-$C_1$-$C_6$ alkyl, carbamoyl-$C_1$-$C_6$ alkyl, [N—($C_1$-$C_6$ alkyl)carbamoyl]-$C_1$-$C_6$ alkyl, [N,N-di($C_1$-$C_6$ alkyl)carbamoyl]-$C_1$-$C_6$ alkyl, ($C_1$-$C_6$ alkyl)carbonylamino, N—($C_1$-$C_6$ alkyl)carbonyl-N—($C_1$-$C_6$ alkyl)amino, pyrrolidinyl, piperidyl, and piperazinyl;

wherein the pyrrolidinyl, piperidyl, and piperazinyl defined as $A^1$ are optionally substituted with a substituent selected from the group consisting of $C_1$-$C_6$ alkyl, amino, $C_1$-$C_6$ alkylamino, di($C_1$-$C_6$ alkyl)amino, hydroxy, $C_1$-$C_6$ alkoxy, pyrrolidinyl, piperidyl, and piperazinyl; and wherein the alkyl moiety of the group defined as $A^1$ is optionally substituted with a substituent selected from the group consisting of amino, $C_1$-$C_6$ alkylamino, di($C_1$-$C_6$ alkyl)amino, hydroxy, $C_1$-$C_6$ alkoxy, pyrrolidinyl, piperidyl, and piperazinyl;

$X^2$ is selected from the group consisting of —CO—; and $R^{11}$ is selected from the group consisting of $C_1$-$C_6$ alkyl and $C_3$-$C_7$ cycloalkyl, which are optionally substituted with one substituent selected from the group consisting of hydroxy and a halogen atom;

$R^2$, $R^3$, and $R^4$ are hydrogen atoms; and $R^5$ is phenyl substituted with one hydroxy and two halogen atoms.

In one aspect of the definitions of formula (I) indicated hereinbefore, the optional substituent of $Q^1$ is selected from the group consisting of hydroxy, amino, di($C_1$-$C_6$ alkyl) amino, $C_1$-$C_6$ alkyl, di($C_1$-$C_6$ alkyl)amino-$C_1$-$C_6$ alkyl, di($C_1$-$C_6$ alkyl)amino-$C_1$-$C_6$ alkoxy, di($C_1$-$C_6$ alkyl)amino, [(amino-$C_1$-$C_6$ alkyl)carbonyl]amino, N—($C_1$-$C_6$ alkyl)piperidyl, di($C_1$-$C_6$ alkyl)amino-pyrrolidin-1-yl, amino-pyrrolidin-1-yl, (pyrrolidin-1-yl)-$C_1$-$C_6$ alkyl, ($C_1$-$C_6$ alkyl)amino-piperidin-1-yl, amino-piperidin-1-yl, hydroxy-$C_1$-$C_6$ alkyl, [di($C_1$-$C_6$ alkyl)amino-$C_1$-$C_6$ alkyl]amino, [4-($C_1$-$C_6$ alkyl)-piperazin-1-yl]-$C_1$-$C_6$ alkyl, (piperazin-1-yl)-$C_1$-$C_6$ alkyl, pyrrolidinylcarbonyl-amino, (hydroxy-pyrrolidin-1-yl)-$C_1$-$C_6$ alkyl, morpholinyl-$C_1$-$C_6$ alkyl, [N-(hydroxy-$C_1$-$C_6$ alkyl)-N—($C_1$-$C_6$ alkyl)amino]-$C_1$-$C_6$ alkyl, and $(CD_3)_2N$—$C_1$-$C_6$ alkyl.

In another aspect, $X^1$ is —NH—; and $Q^1$ is selected from the group consisting of $C_5$-$C_7$ cycloalkyl such as cyclohexyl and pyridyl; wherein $Q^1$ is optionally substituted with one or more substituents independently selected from $A^1$;

$A^1$ is independently selected from the group consisting of hydroxy, amino, $C_1$-$C_6$ alkoxy, $C_1$-$C_6$ alkylamino, di($C_1$-$C_6$ alkyl)amino, amino-$C_1$-$C_6$ alkyl, ($C_1$-$C_6$ alkylamino)-$C_1$-$C_6$ alkyl, di($C_1$-$C_6$ alkyl)amino-$C_1$-$C_6$ alkyl, amino-$C_1$-$C_6$ alkoxy, ($C_1$-$C_6$ alkylamino)-$C_1$-$C_6$ alkoxy, di($C_1$-$C_6$ alkyl) amino-$C_1$-$C_6$ alkoxy, hydroxy-$C_1$-$C_6$ alkyl, ($C_1$-$C_6$ alkoxy)-$C_1$-$C_6$ alkyl, carboxy-$C_1$-$C_6$ alkyl, [($C_1$-$C_6$ alkoxy)carbonyl]-$C_1$-$C_6$ alkyl, carbamoyl-$C_1$-$C_6$ alkyl, [N—($C_1$-$C_6$ alkyl) carbamoyl]-$C_1$-$C_6$ alkyl, [N,N-di($C_1$-$C_6$ alkyl)carbamoyl]-$C_1$-$C_6$ alkyl, ($C_1$-$C_6$ alkyl)carbonylamino, N—($C_1$-$C_6$ alkyl) carbonyl-N—($C_1$-$C_6$ alkyl)amino, pyrrolidinyl, piperidyl, and piperazinyl;

wherein the pyrrolidinyl, piperidyl, and piperazinyl defined as $A^1$ are optionally substituted with a substituent selected from the group consisting of $C_1$-$C_6$ alkyl, amino, $C_1$-$C_6$ alkylamino, di($C_1$-$C_6$ alkyl)amino, hydroxy, $C_1$-$C_6$ alkoxy, pyrrolidinyl, piperidyl, and piperazinyl; and wherein the alkyl moiety of the group defined as $A^1$ is optionally substituted with a substituent selected from the group consisting of amino, $C_1$-$C_6$ alkylamino, di($C_1$-$C_6$ alkyl)amino, hydroxy, $C_1$-$C_6$ alkoxy, pyrrolidinyl, piperidyl, and piperazinyl.

In another aspect, $X^1$ is —NH—; $Q^1$ is selected from the group consisting of cyclohaxyl and pyridyl represented by the following formulae:

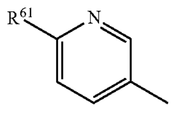

and

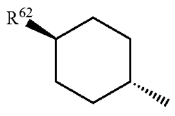

wherein $R^{61}$ is amino-piperidin-1-yl, ($C_1$-$C_6$ alkyl)amino-piperidin-1-yl and di($C_1$-$C_6$ alkyl)amino-$C_1$-$C_6$ alkyl; and $R^{62}$ is selected from the group consisting of di($C_1$-$C_6$ alkyl) amino, and di($C_1$-$C_6$ alkyl)amino-$C_1$-$C_6$ alkyl. In one embodiment, $R^{61}$ is 3-amino-piperidin-1-yl and $R^{62}$ is dimethylamino, or dimethylamino-methyl.

In one aspect, $X^1$ is a direct bond; and $Q^1$ is selected from the group consisting of 5-membered nitrogen-containing aromatic heterocyclyl such as pyrrolyl, pyrazolyl, and imidazolyl, and 3- to 10-membered nitrogen-containing non-aromatic heterocyclyl such as pyrrolidinyl, piperidyl, piperazinyl, and morpholinyl in which the nitrogen atom of the heteroaryl or heterocyclyl attaches to the naphthylidine ring; wherein $Q^1$ is optionally substituted with one or more substituents independently selected from $A^1$.

In still another aspect, $X^1$ is a direct bond; and $Q^1$ is selected from the group consisting of 5-membered nitrogen-containing aromatic heterocyclyl such as pyrrolyl, pyrazolyl, imidazolyl, and 3- to 10-membered nitrogen-containing non-aromatic heterocyclyl such as pyrrolidinyl, piperidyl, piperazinyl, and morpholinyl in which the nitrogen atom of the heteroaryl or heterocyclyl attaches to the naphthylidine ring; wherein $Q^1$ is optionally substituted with one or more substituents independently selected from $A^1$;

$A^1$ is independently selected from the group consisting of hydroxy, amino, $C_1$-$C_6$ alkoxy, $C_1$-$C_6$ alkylamino, di($C_1$-$C_6$ alkyl)amino, amino-$C_1$-$C_6$ alkyl, ($C_1$-$C_6$ alkylamino)-$C_1$-$C_6$ alkyl, di($C_1$-$C_6$ alkyl)amino-$C_1$-$C_6$ alkyl, amino-$C_1$-$C_6$ alkoxy, ($C_1$-$C_6$ alkylamino)-$C_1$-$C_6$ alkoxy, di($C_1$-$C_6$ alkyl) amino-$C_1$-$C_6$ alkoxy, hydroxy-$C_1$-$C_6$ alkyl, ($C_1$-$C_6$ alkoxy)-$C_1$-$C_6$ alkyl, carboxy-$C_1$-$C_6$ alkyl, [($C_1$-$C_6$ alkoxy)carbonyl]-$C_1$-$C_6$ alkyl, carbamoyl-$C_1$-$C_6$ alkyl, [N—($C_1$-$C_6$ alkyl) carbamoyl]-$C_1$-$C_6$ alkyl, [N,N-di($C_1$-$C_6$ alkyl)carbamoyl]-$C_1$-$C_6$ alkyl, ($C_1$-$C_6$ alkyl)carbonylamino, N—($C_1$-$C_6$ alkyl) carbonyl-N—($C_1$-$C_6$ alkyl)amino, pyrrolidinyl, piperidyl, and piperazinyl;

wherein the pyrrolidinyl, piperidyl, and piperazinyl defined as $A^1$ are optionally substituted with a substituent selected from the group consisting of $C_1$-$C_6$ alkyl, amino, $C_1$-$C_6$ alkylamino, di($C_1$-$C_6$ alkyl)amino, hydroxy, $C_1$-$C_6$ alkoxy, pyrrolidinyl, piperidyl, and piperazinyl; and wherein the alkyl moiety of the group defined as $A^1$ is optionally substituted with a substituent selected from the group consisting of amino, $C_1$-$C_6$ alkylamino, di($C_1$-$C_6$ alkyl)amino, hydroxy, $C_1$-$C_6$ alkoxy, pyrrolidinyl, piperidyl, and piperazinyl.

In one aspect, $X^2$ is selected from the group consisting of —CO—; and $R^{11}$ is selected from the group consisting of $C_1$-$C_6$ alkyl and $C_3$-$C_7$ cycloalkyl, which are optionally substituted with one substituent selected from the group consisting of hydroxy and a halogen atom.

In another aspect, $X^2$ is —CO—; and $R^{11}$ is selected from the group consisting of methyl, hydroxymethyl and cyclopropyl.

In one aspect, $R^5$ is phenyl substituted with one hydroxy and two halogen atoms. In another aspect, $R^5$ is selected from the group consisting of 3,5-dichloro-4-hydroxyphenyl, 3,5-difluoro-4-hydroxyphenyl, and 3-chloro-5-fluoro-4-hydroxyphenyl.

According to one aspect of the invention, there is provided a the compound or a pharmaceutically acceptable salt thereof, which is selected from the group consisting of the following compounds:

1-(6-chloro-4-{trans-4-[(dimethylamino)methyl]cyclohexylamino}-1,5-naphthyridin-3-yl)ethanone;

1-{6-(3,5-dichloro-4-hydroxyphenyl)-4-[trans-4-(dimethylamino)cyclohexylamino]-1,5-naphthyridin-3-yl}ethanone;

1-{6-(3-chloro-5-fluoro-4-hydroxyphenyl)-4-[trans-4-(dimethylamino)cyclohexyl-amino]-1,5-naphthyridin-3-yl}ethanone;

cyclopropyl(6-(3,5-dichloro-4-hydroxyphenyl)-4-{trans-4-[(dimethylamino)methyl]-cyclohexylamino}-1,5-naphthyridin-3-yl)methanone;

(6-(3-chloro-5-fluoro-4-hydroxyphenyl)-4-{trans-4-[(dimethylamino)methyl]cyclo-hexylamino]-1,5-naphthyridin-3-yl}(cyclopropyl)methanone;

1-{6-(3,5-dichloro-4-hydroxyphenyl)-4-({trans-4-[(dimethylamino)methyl]cyclo-hexyl}amino)-1,5-naphthyridin-3-yl}ethanone;

1-{6-(3-chloro-5-fluoro-4-hydroxyphenyl)-4-({trans-4-[(dimethylamino)methyl]cyclo-hexyl}amino)-1,5-naphthyridin-3-yl}ethanone;

1-(6-(3-chloro-4-hydroxy-5-methoxyphenyl)-4-{trans-4-[(dimethylamino)methyl]-cyclohexylamino}-1,5-naphthyridin-3-yl)ethanone;

1-[6-(3,5-dichloro-4-hydroxyphenyl)-4-({trans-4-[2-(dimethylamino)ethyl]cyclohexyl}-amino)-1,5-naphthyridin-3-yl]ethanone;

1-(6-(3-chloro-5-fluoro-4-hydroxyphenyl)-4-{trans-4-[2-(dimethylamino)ethyl]-cyclohexylamino}-1,5-naphthyridin-3-yl)ethanone;

1-(4-{trans-4-[(dimethylamino)methyl]cyclohexylamino}-6-[4-hydroxy-3-(trifluoro-methoxy)phenyl]-1,5-naphthyridin-3-yl)ethanone;

2,6-dichloro-4-(8-{trans-4-[(dimethylamino)methyl]cyclohexylamino}-7-(methylsulfonyl)-1,5-naphthyridin-2-yl) phenol;

6-(3-chloro-5-fluoro-4-hydroxyphenyl)-4-({trans-4-[(dimethylamino)methyl]cyclo-hexyl}amino)-3-methylsulfonyl-1,5-naphthyridine;

6-(3-chloro-4-hydroxy-5-methoxyphenyl)-4-{trans-4-[(dimethylamino)methyl]cyclo-hexylamino}-3-methylsulfonyl-1,5-naphthyridine;

2,6-dichloro-4-{8-[trans-4-(dimethylamino)cyclohexylamino]-7-(methylsulfonyl)-1,5-naphthyridin-2-yl}phenol;

2,6-dichloro-4-(8-(4-((dimethylamino)methyl)phenylamino)-7-(methylsulfonyl)-1,5-naphthyridin-2-yl)phenol;

2-chloro-4-(8-(4-((dimethylamino)methyl)phenylamino)-7-(methylsulfonyl)-1,5-naphthyridin-2-yl)-6-fluorophenol;

2-chloro-4-(8-(4-((dimethylamino)methyl)phenylamino)-7-(methylsulfonyl)-1,5-naphthyridin-2-yl)-6-methoxyphenol;

1-(6-(3,5-dichloro-4-hydroxyphenyl)-4-(3-(2-(pyrrolidin-1-yl)ethyl)phenylamino)-1,5-naphthyridin-3-yl)ethanone;

1-(6-(3-chloro-5-fluoro-4-hydroxyphenyl)-4-(3-(2-(pyrrolidin-1-yl)ethyl)phenylamino)-1,5-naphthyridin-3-yl) ethanone;

1-(6-(3,5-dichloro-4-hydroxyphenyl)-4-(6-(2-(dimethylamino)-ethoxy)pyridin-3-yl-amino)-1,5-naphthyridin-3-yl) ethanone;

1-(6-(3-chloro-5-fluoro-4-hydroxyphenyl)-4-(6-(2-(dimethylamino)ethoxy)pyridin-3-ylamino)-1,5-naphthyridin-3-yl)ethanone;

1-(6-(3-chloro-4-hydroxy-5-methoxyphenyl)-4-(6-(2-(dimethylamino)ethoxy)pyridin-3-ylamino)-1,5-naphthyridin-3-yl)ethanone;

2,6-dichloro-4-(8-(6-(2-(dimethylamino)ethoxy)pyridin-3-ylamino)-7-(methylsulfonyl)-1,5-naphthyridin-2-yl)phenol;

2-chloro-4-(8-(6-(2-(dimethylamino)ethoxy)pyridin-3-ylamino)-7-(methylsulfonyl)-1,5-naphthyridin-2-yl)-6-fluorophenol;

2-chloro-4-(8-(6-(2-(dimethylamino)ethoxy)pyridin-3-ylamino)-7-(methylsulfonyl)-1,5-naphthyridin-2-yl)-6-methoxyphenol;

1-(6-(3,5-dichloro-4-hydroxyphenyl)-4-((1-methylpiperidin-4-yl)methylamino)-1,5-naphthyridin-3-yl)ethanone;

1-(6-(3,5-dichloro-4-hydroxyphenyl)-4-(trans-4-((dimethylamino-$d_6$)-methyl)cyclo-hexylamino)-1,5-naphthyridin-3-yl)ethanone;

1-(6-(3,5-dichloro-4-hydroxyphenyl)-4-(4-(2-(dimethylamino)-ethyl)phenylamino)-1,5-naphthyridin-3-yl)ethanone;

1-(6-(3-chloro-5-fluoro-4-hydroxyphenyl)-4-(4-(2-(dimethylamino)ethyl)phenylamino)-1,5-naphthyridin-3-yl)ethanone;

1-(6-(3-chloro-4-hydroxy-5-methoxyphenyl)-4-(4-(2-(dimethylamino)ethyl)phenyl-amino)-1,5-naphthyridin-3-yl)ethanone;

2-chloro-4-(8-(trans-4-(dimethylamino)cyclohexylamino)-7-(methylsulfonyl)-1,5-naphthyridin-2-yl)-6-fluorophenol;

1-(6-(3,5-dichloro-4-hydroxyphenyl)-4-(1-(1-methylpiperidin-4-yl)-1H-pyrazol-4-yl-amino)-1,5-naphthyridin-3-yl) ethanone;

1-(6-(3,5-dichloro-4-hydroxyphenyl)-4-(4-((4-methylpiperazin-1-yl)methyl)phenyl-amino)-1,5-naphthyridin-3-yl) ethanone;

1-(6-(3-chloro-5-fluoro-4-hydroxyphenyl)-4-(4-((4-methylpiperazin-1-yl)methyl)-phenylamino)-1,5-naphthyridin-3-yl)ethanone;

1-(6-(3,5-dichloro-4-hydroxyphenyl)-4-(4-(2-(pyrrolidin-1-yl)ethyl)piperidin-1-yl)-1,5-naphthyridin-3-yl)ethanone;

1-(6-(3-chloro-5-fluoro-4-hydroxyphenyl)-4-(4-(2-(pyrrolidin-1-yl)ethyl)piperidin-1-yl)-1,5-naphthyridin-3-yl) ethanone;

1-(6-(3,5-dichloro-4-hydroxyphenyl)-4-(6-(2-(dimethylamino)ethylamino)pyridin-3-ylamino)-1,5-naphthyridin-3-yl)ethanone;

1-(6-(3-chloro-5-fluoro-4-hydroxyphenyl)-4-(6-(2-(dimethylamino)ethylamino)-pyridin-3-ylamino)-1,5-naphthyridin-3-yl)ethanone;

(S)-(4-(6-(3-aminopiperidin-1-yl)pyridin-3-ylamino)-6-(3,5-dichloro-4-hydroxy-phenyl)-1,5-naphthyridin-3-yl) (cyclopropyl)methanone;

1-(4-(2-(3-aminopyrrolidin-1-yl)pyrimidin-5-ylamino)-6-(3,5-dichloro-4-hydroxy-phenyl)-1,5-naphthyridin-3-yl) ethanone;

1-(4-{trans-4-[(dimethylamino)methyl]cyclohexylamino}-6-(1H-pyrazol-4-yl)-1,5-naphthyridin-3-yl)ethanone;

1-(6-(3,5-dichloro-4-hydroxyphenyl)-4-{[trans-4-(hydroxymethyl)cyclohexyl]amino}-1,5-naphthyridin-3-yl) ethanone;

1-[6-(3,5-dichloro-4-hydroxyphenyl)-4-{trans-4-[(dimethylamino)methyl]cyclohexyl-amino}-1,5-naphthyridin-3-yl]-2-hydroxyethanone;

1-{6-(3,5-dichloro-4-hydroxyphenyl)-4-[(1-methylpiperidin-4-yl)amino]-1,5-naphthyridin-3-yl}ethanone;

1-{6-(3-chloro-5-fluoro-4-hydroxyphenyl)-4-[(1-methylpiperidin-4-yl)amino]-1,5-naphthyridin-3-yl}ethanone;

1-(6-(3,5-dichloro-4-hydroxyphenyl)-4-{[trans-4-(morpholinomethyl)cyclohexyl]-amino}-1,5-naphthyridin-3-yl)ethanone;

1-[6-(3,5-dichloro-4-hydroxyphenyl)-4-(trans-4-{[(2-hydroxyethyl)(methyl)amino]-methyl}cyclohexylamino)-1,5-naphthyridin-3-yl]-ethanone;

1-[6-(3-chloro-5-fluoro-4-hydroxyphenyl)-4-(trans-4-{[(2-hydroxyethyl)(methyl)-amino]methyl}cyclohexylamino)-1,5-naphthyridin-3-yl]-ethanone;

1-(6-(3,5-difluoro-4-hydroxyphenyl)-4-{trans-4-[(dimethylamino)methyl]cyclohexyl-amino}-1,5-naphthyridin-3-yl)ethanone;

1-(6-(3,5-dichloro-4-hydroxyphenyl)-4-{6-[3-(dimethylamino)pyrrolidin-1-yl]pyridin-3-ylamino}-1,5-naphthyridin-3-yl)ethanone;

1-(6-(3-chloro-5-fluoro-4-hydroxyphenyl)-4-{6-[3-(dimethylamino)pyrrolidin-1-yl]-pyridin-3-ylamino}-1,5-naphthyridin-3-yl)ethanone;

1-(6-(3,5-dichloro-4-hydroxyphenyl)-4-{6-[3-(methylamino)pyrrolidin-1-y]pyridin-3-ylamino}-1,5-naphthyridin-3-yl)ethanone;

1-(6-(3-chloro-5-fluoro-4-hydroxyphenyl)-4-{6-[3-(methylamino)-pyrrolidin-1-yl]-pyridin-3-ylamino}-1,5-naphthyridin-3-yl)ethanone;

1-(6-(1H-benzo[d]imidazol-5-yl)-4-{trans-4-[(dimethylamino)methyl]cyclohexyl-amino}-1,5-naphthyridin-3-yl)ethanone;

1-{4-[4-(trans-4-dimethylamino)methylcyclohexylamino]-6-(pyridin-4-yl)-1,5-naphthyridin-3-yl}ethanone;

5-(7-acetyl-8-{trans-4-[(dimethylamino)methyl]cyclohexylamino}-1,5-naphthyridin-2-yl)pyrimidine-2-carbonitrile;

1-(6-(3,5-dimethyl-1H-pyrazol-4-yl)-4-{trans-4-[(dimethylamino)-methyl]-cyclohexylamino}-1,5-naphthyridin-3-yl)ethanone;

1-(4-{trans-4-[(dimethylamino)methyl]cyclohexylamino}-6-(4-hydroxy-3,5-dimethyl-phenyl)-1,5-naphthyridin-3-yl)ethanone;

1-(6-(3,5-dichloro-4-hydroxyphenyl)-4-{6-[3-(dimethylamino)pyrrolidin-1-yl]pyridin-3-ylamino}-1,5-naphthyridin-3-yl)ethanone;

1-{6-(3,5-dichloro-4-hydroxyphenyl)-4-[trans-4-(pyrrolidin-1-ylmethyl)-cyclohexyl-amino]-1,5-naphthyridin-3-yl}ethanone;

1-(6-(3-chloro-5-fluoro-4-hydroxyphenyl)-4-{[trans-4-(pyrrolidin-1-ylmethyl)cyclo-hexyl]amino}-1,5-naphthyridin-3-yl)ethanone;

1-(6-(3,5-dichloro-4-hydroxyphenyl)-4-{trans-4-[(4-methylpiperazin-1-yl)-methyl]-cyclohexylamino}-1,5-naphthyridin-3-yl)ethanone;

1-(4-{[6-(3-aminopiperidin-1-yl)pyridin-3-yl]amino}-6-(3,5-dichloro-4-hydroxy-phenyl)-1,5-naphthyridin-3-yl)ethanone;

1-(4-{[6-(3-aminopiperidin-1-yl)pyridin-3-yl]amino}-6-(3-chloro-5-fluoro-4-hydroxy-phenyl)-1,5-naphthyridin-3-yl)ethanone;

1-{4-[trans-(4-aminocyclohexyl)amino]-6-(3,5-dichloro-4-hydroxyphenyl)-1,5-naphthyridin-3-yl}ethanone;

1-{4-[trans-(4-aminocyclohexyl)amino]-6-(3-chloro-5-fluoro-4-hydroxyphenyl)-1,5-naphthyridin-3-yl}ethanone;

1-(6-(3-chloro-5-fluoro-4-hydroxyphenyl)-4-{trans-4-[(4-methylpiperazin-1-yl)-methyl]cyclohexylamino}-1,5-naphthyridin-3-yl)ethanone;

N-(trans-4-{[3-acetyl-6-(3-chloro-5-fluoro-4-hydroxyphenyl)-1,5-naphthyridin-4-yl]-amino}cyclohexyl)-2-amino-3-methylbutanamide;

1-{6-(3,5-dichloro-4-hydroxyphenyl)-4-[trans-4-(piperazin-1-ylmethyl)-cyclohexyl-amino]-1,5-naphthyridin-3-yl}ethanone;

(S)-1-(4-{[6-(3-aminopiperidin-1-yl)pyridin-3-yl]amino}-6-(3,5-dichloro-4-hydroxy-phenyl)-1,5-naphthyridin-3-yl)ethanone;

(S)-1-(4-{[6-(3-aminopiperidin-1-yl)pyridin-3-yl]amino}-6-(3-chloro-5-fluoro-4-hydroxyphenyl)-1,5-naphthyridin-3-yl)ethanone;

N-{trans-4-[3-acetyl-6-(3,5-dichloro-4-hydroxyphenyl)-1,5-naphthyridin-4-ylamino]-cyclohexyl}-2-aminopropanamide;

N-{4-[3-acetyl-6-(3-chloro-5-fluoro-4-hydroxyphenyl)-1,5-naphthyridin-trans-4-yl-amino]cyclohexyl}-2-amino-propanamide;

(S)—N-{4-[3-acetyl-6-(3,5-dichloro-4-hydroxyphenyl)-1,5-naphthyridin-trans-4-ylamino]cyclohexyl}pyrrolidine-2-carboxamide;

(S)—N-{4-[3-acetyl-6-(3-chloro-5-fluoro-4-hydroxyphenyl)-1,5-naphthyridin-trans-4-ylamino]cyclohexyl}pyrrolidine-2-carboxamide;

1-(6-(3-hydroxypyrrolidin-1-yl)-4-{trans-4-[(3-hydroxy-pyrrolidin-1-yl)methyl]cyclo-hexylamino}-1,5-naphthyridin-3-yl)ethanone;

1-{6-(pyrrolidin-1-yl)-4-[trans-4-(pyrrolidin-1-ylmethyl)-cyclohexylamino]-1,5-naphthyridin-3-yl}ethanone;

N-{trans-4-[3-acetyl-6-(3,5-dichloro-4-hydroxyphenyl)-1,5-naphthyridin-4-ylamino]-cyclohexyl}-2-amino-3-methylbutanamide;

cyclopropyl {6-(3,5-dichloro-4-hydroxyphenyl)-4-[trans-4-(dimethylamino)cyclohexyl-amino]-1,5-naphthyridin-3-yl}methanone;

1-[6-(3-chloro-5-fluoro-4-methoxyphenyl)-4-{trans-4-[(dimethylamino)methyl]-cyclohexylamino}-1,5-naphthyridin-3-yl]ethanone;

1-(4-{trans-4-[(dimethylamino)methyl]cyclohexylamino}-6-(1H-pyrrolo[2,3-b]-pyridin-5-yl)-1,5-naphthyridin-3-yl)ethanone;

(S)-{4-[6-(3-aminopiperidin-1-yl)pyridin-3-ylamino]-6-(3-chloro-5-fluoro-4-hydroxy-phenyl)-1,5-naphthyridin-3-yl}(cyclopropyl)methanone;

1-(4-{trans-4-[(dimethylamino)methyl]cyclohexylamino}-6-(4-methoxyphenyl)-1,5-naphthyridin-3-yl)ethanone;

1-[6-(3,5-dichloro-4-methoxyphenyl)-4-{trans-4-[(dimethylamino)methyl]cyclohexyl-amino}-1,5-naphthyridin-3-yl]ethanone;

1-(4-{trans-4-[(dimethylamino)methyl]cyclohexylamino}-6-(6-hydroxypyridin-3-yl)-1,5-naphthyridin-3-yl)ethanone;

5-(7-acetyl-8-{trans-4-[(dimethylamino)methyl]cyclohexylamino}-1,5-naphthyridin-2-yl)picolinonitrile;

1-(4-{trans-4-[(dimethylamino)methyl]cyclohexylamino}-6-(4-hydroxyphenyl)-1,5-naphthyridin-3-yl)ethanone dihydrochloride;

1-[6-(3,5-dichloro-4-hydroxyphenyl)-4-{[trans-4-(dimethylamino)cyclohexyl]methyl-amino}-1,5-naphthyridin-3-yl]ethanone;

1-[6-(3-chloro-5-fluoro-4-hydroxyphenyl)-4-{[trans-4-(dimethylamino)cyclohexyl]-methylamino}-1,5-naphthyridin-3-yl]ethanone;

1-[6-(3,5-dichloro-4-hydroxyphenyl)-4-(trans-4-hydroxycyclohexylamino)-1,5-naphthyridin-3-yl]ethanone;

1-[6-(3-chloro-5-fluoro-4-hydroxyphenyl)-4-(trans-4-hydroxycyclohexylamino)-1,5-naphthyridin-3-yl]ethanone;

1-{6-(3-chloro-5-fluoro-4-hydroxyphenyl)-4-({cis-4-[(dimethylamino)methyl]-cyclohexyl}amino)-1,5-naphthyridin-3-yl}ethanone;

1-{6-(3,5-dichloro-4-hydroxyphenyl)-4-({cis-4-[(dimethylamino)methyl]-cyclohexyl}amino)-1,5-naphthyridin-3-yl}ethanone;

(R)-1-{4-[6-(3-aminopiperidin-1-yl)pyridin-3-ylamino]-6-(3,5-dichloro-4-hydroxy-phenyl)-1,5-naphthyridin-3-yl}ethanone;

(R)-1-{4-[6-(3-aminopiperidin-1-yl)pyridin-3-ylamino]-6-(3-chloro-5-fluoro-4-hydroxyphenyl)-1,5-naphthyridin-3-yl}ethanone;

and pharmaceutically acceptable salts thereof.

According to another aspect of the invention, there is provided a compound represented by formula (I) or a pharmaceutically acceptable salt thereof, which is selected from the group consisting of the following compounds:

1-(6-(3,5-dichloro-4-hydroxyphenyl)-4-(4-(dimethylamino)cyclohexyl)amino)-1,5-naphthyridin-3-yl)ethanone;

cyclopropyl(6-(3,5-dichloro-4-hydroxyphenyl)-4-(4-((dimethylamino)methyl)-cyclohexylamino)-1,5-naphthyridin-3-yl) methanone;

(6-(3-chloro-5-fluoro-4-hydroxyphenyl)-4-(4-((dimethylamino)methyl)cyclohexyl-amino)-1,5-naphthyridin-3-yl) (cyclopropyl) methanone;

1-(6-(3,5-dichloro-4-hydroxyphenyl)-4-((4-((dimethylamino)methyl)cyclohexyl)-amino)-1,5-naphthyridin-3-yl) ethanone;

1-(6-(3-chloro-5-fluoro-4-hydroxyphenyl)-4-((4-((dimethylamino)methyl)cyclohexyl)-amino)-1,5-naphthyridin-3-yl) ethanone;

1-(6-(3,5-dichloro-4-hydroxyphenyl)-4-((4-(2-(dimethylamino)ethyl)cyclohexyl)-amino)-1,5-naphthyridin-3-yl) ethanone;

(4-(6-(3-aminopiperidin-1-yl)pyridin-3-ylamino)-6-(3,5-dichloro-4-hydroxyphenyl)-1,5-naphthyridin-3-yl)(cyclopropyl)methanone;

1-[6-(3,5-dichloro-4-hydroxyphenyl)-4-{trans-4-[(dimethylamino)methyl]cyclo-hexylamino}-1,5-naphthyridin-3-yl]-2-hydroxyethanone;

1-(4-(6-(3-aminopiperidin-1-yl)pyridin-3-ylamino)-6-(3,5-dichloro-4-hydroxyphenyl)-1,5-naphthyridin-3-yl)ethanone;

1-(4-(6-(3-aminopiperidin-1-yl)pyridin-3-ylamino)-6-(3-chloro-5-fluoro-4-hydroxy-phenyl)-1,5-naphthyridin-3-yl) ethanone;

1-(4-(6-(3-aminopiperidin-1-yl)pyridin-3-ylamino)-6-(3,5-dichloro-4-hydroxy-phenyl)-1,5-naphthyridin-3-yl)ethanone;

{4-[6-(3-aminopiperidin-1-yl)pyridin-3-ylamino]-6-(3-chloro-5-fluoro-4-hydroxy-phenyl)-1,5-naphthyridin-3-yl} (cyclopropyl) methanone;

1-{4-[6-(3-aminopiperidin-1-yl)pyridin-3-ylamino]-6-(3,5-dichloro-4-hydroxy-phenyl)-1,5-naphthyridin-3-yl}ethanone;

1-{4-[6-(3-aminopiperidin-1-yl)pyridin-3-ylamino]-6-(3-chloro-5-fluoro-4-hydroxyphenyl)-1,5-naphthyridin-3-yl}ethanone;

and pharmaceutically acceptable salts thereof

According to one aspect of the invention, there is provided a process for preparing a compound of formula (I):

(I)

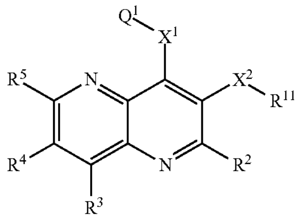

or a pharmaceutically acceptable salt thereof according to any one of above-mentioned (1) to (12), wherein $X^1$ is —NH—; and $X^2$, $R^{11}$, $R^2$, $R^3$, and $R^4$ are the groups as defined in any one of above-mentioned (1) to (10) or in the other descriptions hereinbefore, which comprises:

reacting a compound represented by formula (IV):

(IV)

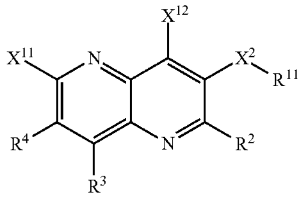

wherein $X^2$, $R^{11}$, $R^2$, $R^3$, and $R^4$ are the groups as defined hereinbefore, with the proviso that the groups may have one or more protecting groups; and $X^{11}$ and $X^{12}$ are independently selected from a halogen atom such as a chlorine atom; with a compound represented by formula (V):

$Q^1$-$NH_2$ (V)

wherein $Q^1$ is the group as defined above, with the proviso that the groups may have one or more protecting groups; to obtain a compound represented by formula (II):

(II)

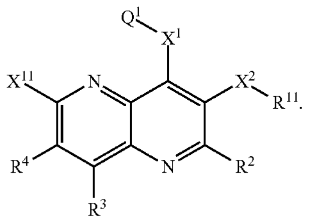

According to another aspect of the invention, there is provided a process for preparing a compound of formula (I):

(I)

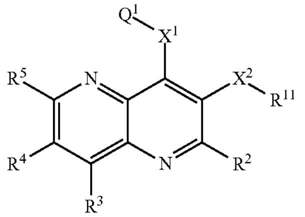

or a pharmaceutically acceptable salt thereof according to any one of above-mentioned (1) to (11), wherein $X^1$ is —NH—; $R^5$ is phenyl optionally substituted with one or more substituents independently selected from $A^3$; and $Q^1$, $X^1$, $X^2$, $R^{11}$, $R^2$, $R^3$, and $R^4$ are the groups as defined in one of above-mentioned (1) to (10) or in the other descriptions hereinbefore; which comprises:

reacting a compound represented by formula (IV):

(IV)

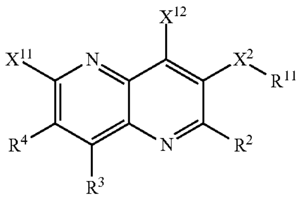

wherein $X^2$, $R^{11}$, $R^2$, $R^3$, and $R^4$ are the groups as defined hereinbefore, with the proviso that the groups may have one or more protecting groups, and $X^{11}$ and $X^{12}$ are independently selected from a halogen atom such as a chlorine atom; with a compound represented by formula (V):

$Q^1$-$NH_2$ (V)

wherein $Q^1$ is the group as defined hereinbefore, with the proviso that the groups may have one or more protecting groups; to obtain a compound represented by formula (II):

(II)

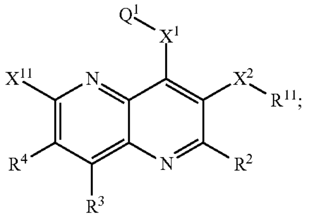

and reacting a compound represented by formula (II):

(II)

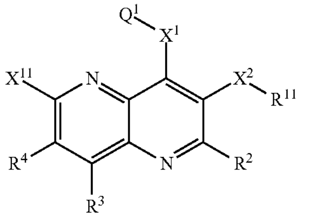

wherein $Q^1$, $X^1$, $X^2$, $R^{11}$, $R^2$, $R^3$ and $R^4$ are the groups as defined above, with the proviso that the groups may have one or more protecting groups, and $X^{11}$ is a halogen atom; with a compound represented by formula (III):

(III)

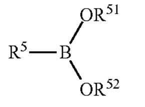

wherein $R^5$ is as defined above with the proviso that the group of $R^5$ may have one or more protecting groups; and $R^{51}$ and $R^{52}$ are independently selected from the group consisting of $C_1$-$C_6$ alkyl, or $R^{51}$ and $R^{52}$ together with the boron atom to which they are attached forms 5- to 7-membered cyclic boronic acid ester optionally substituted with one or more substituents independently selected from the group consisting of $C_1$-$C_6$ alkyl.

In one aspect, the protecting group to protect —NH— and/or —$NH_2$ is selected from the group consisting of $C_1$-$C_6$ alkylcarbonyl (e.g. acetyl), $C_1$-$C_6$ alkoxycarbonyl (e.g. methokycarbonyl, ethoxycarbonyl, and tert-butoxycarbonyl), phenyl($C_1$-$C_6$ alkoxy)carbonyl (e.g. benzyloxycarbonyl), ($C_1$-$C_6$ alkoxyl)$C_1$-$C_6$ alkyl (e.g. methoxymethyl), phenyl($C_1$-$C_6$ alkoxy)methyl (e.g. benzyloxymethyl), and (phenyl)$C_1$-$C_6$ alkyl (e.g. benzyl), and the protecting group to protect hydroxy is selected from the group consisting of $C_1$-$C_6$ alkylcarbonyl (e.g. acetyl), $C_1$-$C_6$ alkoxycarbonyl (e.g. methokycarbonyl, ethoxycarbonyl, and tert-butoxycarbonyl), phenyl ($C_1$-$C_6$ alkoxy)carbonyl (e.g. benzyloxycarbonyl), ($C_1$-$C_6$ alkoxyl)$C_1$-$C_6$ alkyl (e.g. methoxymethyl), phenyl($C_1$-$C_6$ alkoxy)methyl (e.g. benzyloxymethyl), (phenyl)$C_1$-$C_6$ alkyl (e.g. benzyl), tri($C_1$-$C_6$ alkyl)silyl (e.g. trimethylsilyl, and tert-butyl-dimethylsilyl), di($C_1$-$C_6$ alkyl)phenylsilyl, ($C_1$-$C_6$ alkyl)diphenylsilyl, and triphenylsilyl. Further, the carboxy group may be protected with $C_1$-$C_6$ alkyl (e.g. methyl and ethyl), (phenyl)$C_1$-$C_6$ alkyl (e.g. benzyl), ($C_1$-$C_6$ alkoxyl)$C_1$-$C_6$ alkyl (e.g. methoxymethyl) or phenyl($C_1$-$C_6$ alkoxy)$C_1$-$C_6$ alkyl (e.g. benzyloxymethyl) to form the corresponding ester.

According to one aspect of the invention, there is provided a compound represented by formula (II) or a pharmaceutically acceptable salt thereof:

(II)

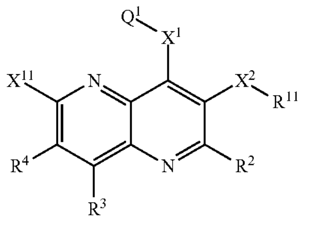

wherein $Q^1$, $X^1$, $X^2$, $R^{11}$, $R^2$, $R^3$, and $R^4$ are the groups as defined in one of above-mentioned (1) to (10) with the proviso that —NH— and/or —$NH_2$ containing in the groups may have one or more protecting groups selected from the group consisting of $C_1$-$C_6$ alkylcarbonyl (e.g. acetyl), $C_1$-$C_6$ alkoxycarbonyl (e.g. methokycarbonyl, ethoxycarbonyl, and tert-butoxycarbonyl), phenyl($C_1$-$C_6$ alkoxy)carbonyl (e.g. benzyloxycarbonyl), ($C_1$-$C_6$ alkoxyl)$C_1$-$C_6$ alkyl (e.g. methoxymethyl), phenyl($C_1$-$C_6$ alkoxy)methyl (e.g. benzyloxymethyl), and benzyl; and $X^{11}$ is a halogen atom.

DESCRIPTION OF EMBODIMENTS

Figure 1:
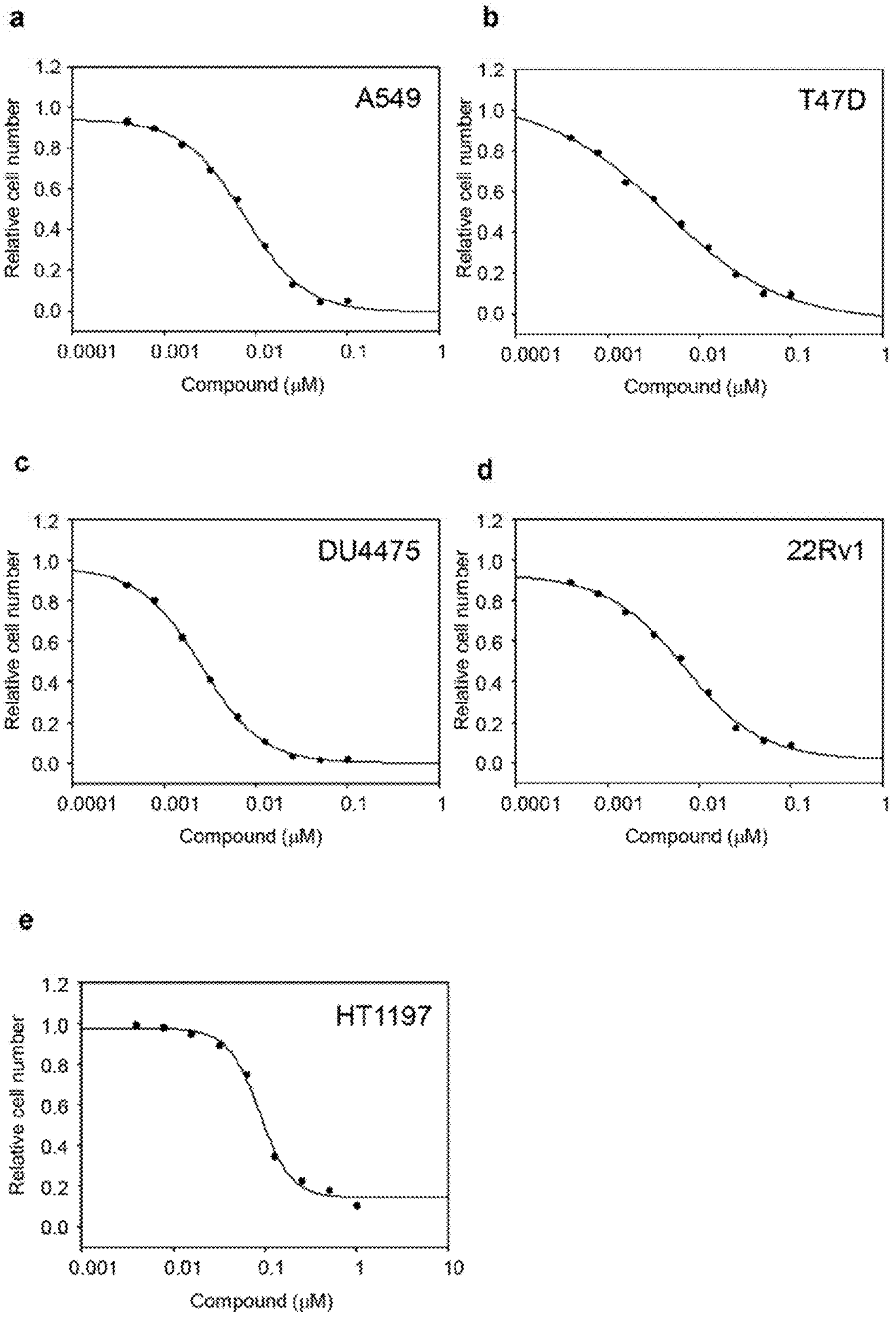
FIG. 1 is composed of a series of graphs, (a)-(e), depicting In vitro anti-proliferative activity of Compound Example 6. The graphs indicate growth inhibition curves of Compound Example 6 for various types of human cancel cell line; (a) A549 (lung cancer), (b) T47D (breast cancer), (c) DU4475 (breast cancer), and (d) 22Rv1 (prostate cancer) cells, in which MELK is highly expressed, as well as (e) HT1197 (bladder cancer) cell line, in which MELK expression is hardly detectable.

An object of the present invention to provide a compound having inhibitory activity against MELK, which is useful for treating proliferative diseases such as cancer, and a pharmaceutical composition comprising the compound. Another object of the present invention is to provide a method for treating and/or preventing a proliferative disease. A further object is to provide a process for preparing the compound.

Hereinafter, a compound represented by formula (I) will be referred to as compound (I). The same applies to the compounds represented by the other formula numbers. It must be noted that as used herein and in the appended claims, the singular forms "a", "an", and "the" include plural reference unless the context clearly dictates otherwise. Thus, for example, reference to a "group" is a reference to one or more groups, unless otherwise noted.

In the definitions of each of the groups of formulas indicated above, the "$C_1$-$C_6$ alkyl", and the $C_1$-$C_6$ alkyl portion of "$C_1$-$C_6$ alkoxy", "$C_1$-$C_6$ alkylamino", "di($C_1$-$C_6$ alkyl)amino", ($C_1$-$C_6$ alkyl)carbonyl and the like mean a straight-chain or branched-chain alkyl group having one to six carbon atoms. Specifically, examples of the "$C_1$-$C_6$ alkyl" and the "$C_1$-$C_6$ alkyl portion" include methyl, ethyl, propyl, isopropyl, butyl, isobutyl, sec-butyl, tert-butyl, pentyl, 1-methylbutyl, 1-ethylpropyl, 2-methylbutyl, isopentyl, tert-pentyl, 1,2-dimethylpropyl, neopentyl, hexyl, 1-methylpentyl, 1-ethylbutyl, 2-methylpentyl, 3-methylpentyl, 4-methylpentyl, isohexyl, 1,1-dimethylbutyl, 1,2-dimethylbutyl, 1,3-dimethylbutyl, 1-isopropylpropyl, 1-ethyl-1-methylpropyl, 2,3-dimethylbutyl, 3,3-dimethylbutyl, 2,2-dimethylbutyl, 2-ethylbutyl, and 3-ethylbutyl, but are not limited thereto.

The "$C_2$-$C_6$ alkenyl", and the $C_2$-$C_6$ alkenyl portion of "$C_2$-$C_6$ alkenyloxy" and the like mean a straight-chain or branched-chain alkenyl group having two to six carbon atoms and one to three double bonds. Specifically, examples of the "$C_1$-$C_6$ alkenyl" and the "$C_1$-$C_6$ alkenyl portion" include ethenyl (vinyl), 1-propen-1-yl, 2-propen-1-yl(allyl), propen-2-yl, 1-buten-1-yl, 2-buten-1-yl, and 1,3-but-dien-1-yl, but are not limited thereto.

The "$C_2$-$C_6$ alkynyl", and the $C_2$-$C_6$ alkynyl portion of "$C_2$-$C_6$ alkynyloxy" and the like mean a straight-chain or branched-chain alkynyl group having two to six carbon atoms and one to three triple bonds. Specifically, examples of the "$C_1$-$C_6$ alkynyl" and the "$C_1$-$C_6$ alkynyl portion" include ethynyl, 1-propyn-1-yl, 2-propyn-1-yl(propargyl), propyn-2-yl, 1-butyn-1-yl, 2-butyn-1-yl, and 1,3-but-diyn-1-yl, but are not limited thereto.

In this specification, the $C_1$-$C_6$ alkyl portion in each group has the same definition as the aforementioned "$C_1$-$C_6$ alkyl portion" unless otherwise noted. In a case that a group contains plural $C_1$-$C_6$ alkyl portions, the $C_1$-$C_6$ alkyl portions may be same or different.

Specific examples of "$C_1$-$C_6$ alkoxy" include methoxy, ethoxy, propoxy, isopropoxy, isobutyloxy, tert-butyloxy, butoxy, pentyloxy, and hexyloxy, but are not limited thereto.

The "$C_1$-$C_6$ alkoxycarbonyl" refers to a monovalent group represented by —C(═O)O—($C_1$-$C_6$ alkyl). Specific examples of "$C_1$-$C_6$ alkoxycarbonyl" include methoxycarbonyl, ethoxycarbonyl, propoxycarbonyl, isopropoxycarbonyl, isobutyloxycarbonyl, tert-butoxycarbonyl, butoxycarbonyl, pentyloxycarbonyl, and hexyloxycarbonyl, but are not limited thereto.

The "($C_1$-$C_6$ alkyl)carbonyl" refers to a monovalent group represented by —C(═O)—($C_1$-$C_6$ alkyl). Specific examples of "$C_1$-$C_6$ alkylcarbonyl" include methylcarbonyl (i.e. acetyl), ethylcarbonyl, propylcarbonyl, isopropylcarbonyl, isobutylcarbonyl, tert-butylcarbonyl, butylcarbonyl, pentylcarbonyl, and hexylcarbonyl, but are not limited thereto.

Specific examples of "$C_1$-$C_6$ alkylamino" include methylamino, ethylamino, propylamino, isopropylamino, butylamino, isobutylamino, sec-butylamino, and tert-butylamino, pentylamino, but are not limited thereto.

The alkyl portions of "di($C_1$-$C_6$ alkyl)amino" may be same or different. Specific examples of "di($C_1$-$C_6$ alkyl)amino" include dimethylamino, diethylamino, dipropylamino, diisopropylamino, dibutylamino, diisobutylamino, di(sec-butyl)amino, di(tert-butyl)amino, dipentylamino, ethyl(methyl)amino, propyl(methyl)amino, isopropyl(methyl)amino, butyl(methyl)amino, isobutyl(methyl)amino, sec-butyl(methyl)amino, tert-butyl(methyl)amino, and pentyl(methyl)amino, but are not limited thereto.

The formula: $—S(O)_nR^{19}$ represents $—SR^{19}$ (n=0), $—SOR^{19}$ (n=1), and $—SO_2R^{19}$ (n=2), and the examples include "$C_1$-$C_6$ alkylthio" such as methylthio, ethylthio, and isopropylthio, "$C_1$-$C_6$ alkylsulfonyl" such as methylsulfonyl, ethylsulfonyl, and isopropylsulfonyl, and "$C_1$-$C_6$ alkylsulfinyl" such as methylsulfinyl, ethylsulfinyl, and isopropylsulfinyl, but are not limited thereto. This will apply to definitions of the formulae $—S(O)_nR^{27}$, and $—S(O)_nR^{37}$.

Specific examples of "a halogen atom" include a fluorine, a chlorine, a bromine, and an iodine atoms.

The term "$C_3$-$C_{10}$ cycloalkyl" refers to a saturated monocyclic hydrocarbon group having three to ten carbon atoms, and a bridged cyclic hydrocarbon group having four to ten carbon atoms which is formed when two or more saturated monocyclic hydrocarbons share two or more carbon atoms. The term "$C_3$-$C_{10}$ cycloalkyl" also encompasses a cycloalkyl group condensed with an aromatic or non-aromatic carbocyclic ring to form a bicyclic group. Specifically, examples of "$C_3$-$C_{10}$ cycloalkyl" include saturated monocyclic hydrocarbon groups such as cyclopropyl, cyclobutyl, cyclopentyl, cyclohexyl, cycloheptyl, and cyclooctyl, and bridged cyclic hydrocarbon groups such as adamantyl, but are not limited thereto.

The term "$C_6$-$C_{10}$ aryl" refers to an aromatic carbocyclic group having six to ten carbon atoms, and encompasses an aromatic carbocyclic group condensed with an aromatic or non-aromatic carbocyclic ring to form a bicyclic group. Specific examples include phenyl, 1-naphthyl, 2-naphthyl, and 2,3-dihydro-1H-indenyl, but are not limited thereto.

The term "5- to 10-membered heteroaryl" refers to an aromatic heterocyclic group having one or more heteroatoms, preferably one to three heteroatoms, selected from the group consisting of a nitrogen atom, an oxygen atom, and a sulfur atom. The term "5- to 10-membered heteroaryl" encompasses an aromatic heterocyclic group condensed with an aromatic or non-aromatic carbocyclic ring or an aromatic or non-aromatic heterocyclic ring to form a bicyclic group, and also encompasses an aromatic carbocyclic group condensed with an aromatic or non-aromatic heterocyclic ring to form a bicyclic group. Specific examples include furyl, thienyl, pyrrolyl, imidazolyl, pyrazolyl, oxazolyl, isoxazolyl, oxadiazolyl, thiazolyl, isothiazolyl, thiadiazolyl, triazolyl, tetrazolyl, pyridyl, pyridazinyl, pyrimidinyl, pyrazinyl, triazinyl, benzofuranyl, benzothiophenyl, benzoxazolyl, benzothiazolyl, isoindolyl, indolyl, 1H-indazolyl, benzimidazolyl, benzotriazolyl, oxazolopyrimidinyl, thiazolopyrimidinyl, pyrrolopyridinyl, pyrrolopyrimidinyl, imidazopyridinyl, purinyl, quinolinyl, isoquinolinyl, cinnolinyl, phthalazinyl, quinazolinyl, quinoxalinyl, naphthyridinyl, pyridopyrimidinyl, [1,2,4]triazolo[1,5-a]pyridyl, and pyrrolo[2,3-b]pyridyl, but are not limited thereto. Particularly, thienyl, pyrrolyl, imidazolyl, isoxazolyl, pyridyl, pyrimidinyl, pyrazolyl, 1H-indazolyl, benzimidazolyl, [1,2,4]triazolo[1,5-a]pyridyl, or pyrrolo[2,3-b]pyridyl is preferred.

The term "3- to 10-membered non-aromatic heterocyclyl" refers to a non-aromatic heterocyclic group having one or more heteroatoms, preferably one to three heteroatoms, selected from the group consisting of a nitrogen atom, an oxygen atom, and a sulfur atom. The term "3- to 10-membered non-aromatic heterocyclyl" encompasses a non-aromatic heterocyclic group condensed with an aromatic or non-aromatic carbocyclic ring or an aromatic or non-aromatic heterocyclic ring to form a bicyclic group, and also encompasses a non-aromatic carbocyclic group condensed with an aromatic or non-aromatic heterocyclic ring to form a bicyclic group. Specific examples include aziridinyl, azetidinyl, pyrrolidinyl, piperidyl (including piperidino), azepanyl, 1,2,5,6-tetrahydropyridyl, 1,2,3,6-tetrahydropyridyl, imidazolidinyl, pyrazolidinyl, piperazinyl, homopiperazinyl, pyrazolinyl, oxiranyl, tetrahydrofuranyl, tetrahydro-2H-pyranyl, 5,6-dihydro-2H-pyranyl, oxazolidinyl, morpholinyl (including morpholino), tetrahydrothiophenyl, tetrahydro-2H-thiopyranyl, thioxazolidinyl, thiomorpholinyl, 2H-oxazolyl, 2H-thioxazolyl, dihydroindolyl, dihydroisoindolyl, dihydrobenzofuranyl, benzoimidazolidinyl, 2,3-dihydrobenzimidazolyl, 2,3-dihydrobenzoxazolyl, dihydrobenzothioxazolyl, benzodioxolinyl, tetrahydroquinolyl, tetrahydroisoquinolyl, dihydro-2H-chromanyl, dihydro-1H-chromanyl, dihydro-2H-thiochromanyl, dihydro-1H-thiochromanyl, tetrahydroquinoxalinyl, tetrahydroquinazolinyl, dihydrobenzodioxanyl, oxetanyl, 1,2-dihydropyridyl, 1-azabicyclo[2.2.2]octan-3-yl, 2,5-azabicyclo[2.2.1]heptyl, 8-azabicyclo[3.2.1]octyl, piperidin-4-spiro-3'-pyrrolidin-1-yl, and isoindolyl, but are not limited thereto. In particular, azetidinyl, pyrrolidinyl, piperidino, piperidyl, piperazinyl, morpholino, morpholinyl, 1,2-dihydropyridyl, 1,2,5,6-tetrahydropyridyl, 1-azabicyclo[2.2.2]octan-3-yl, 2,5-azabicyclo[2.2.1]heptyl, 8-azabicyclo[3.2.1]octyl, 2,3-dihydrobenzimidazolyl, or piperidin-4-spiro-3'-pyrrolidin-1-yl is preferred.

The term "3- to 10-membered nitrogen-containing heterocyclyl" refers to an aromatic or non-aromatic heterocyclic group having one nitrogen atom and one or more additional heteroatoms, preferably one to three heteroatoms, selected from the group consisting of a nitrogen atom, an oxygen atom, and a sulfur atom. The term "3- to 10-membered nitrogen-containing heterocyclyl" encompasses a heterocyclic group condensed with an aromatic or non-aromatic carbocyclic ring or an aromatic or non-aromatic heterocyclic ring to form a bicyclic group. Specific examples include aziridinyl, azetidinyl, pyrrolyl, pyrrolidinyl, piperidyl (including piperidino), azepanyl, imidazolyl, pyrazolyl, triazolyl, tetrazolyl, piperazinyl, and morpholinyl.

Specific examples of "($C_3$-$C_{10}$ cycloalkyl)-$C_1$-$C_6$ alkyl" include ($C_3$-$C_{10}$ cycloalkyl)-$C_1$-$C_2$ alkyl, namely ($C_3$-$C_{10}$ cycloalkyl)-methyl such as cyclopropylmethyl, cyclobutylmethyl, cyclopentylmethyl, cyclohexylmethyl, cycloheptylmethyl and cyclooctylmethyl; 1-($C_3$-$C_{10}$ cycloalkyl)-ethyl such as 1-cyclopropylethyl, 1-cyclobutylethyl, 1-cyclopentylethyl, 1-cyclohexylethyl, 1-cycloheptylethyl and 1-cyclooctylethyl; and 2-($C_3$-$C_{10}$ cycloalkyl)-ethyl such as 2-cyclopropylethyl, 2-cyclobutylethyl, 2-cyclopentylethyl, 2-cyclohexylethyl, 2-cycloheptylethyl and 2-cyclooctylethyl. Specific examples of "($C_6$-$C_{10}$ aryl)-$C_1$-$C_6$ alkyl" include ($C_6$-$C_{10}$ aryl)-$C_1$-$C_2$ alkyl, namely ($C_6$-$C_{10}$ aryl)-methyl, such as benzyl, 2-phenylethyl and 1-phenylethyl. Specific examples of (5- to 10-membered heteroaryl)-$C_1$-$C_6$ alkyl include (5- to 10-membered heteroaryl)-$C_1$-$C_2$ alkyl, namely (5- to 10-membered heteroaryl)-methyl such as pyridylmethyl, namely pyridin-2-ylmethyl, pyridin-3-ylmethyl, and pyridin-4-ylmethyl. Specific examples of "(3- to 10-membered non-aromatic heterocyclyl)-$C_1$-$C_6$ alkyl" include namely (3- to 10-membered non-aromatic heterocyclyl)-$C_1$-$C_2$ alkyl, (3- to 10-membered non-aromatic heterocyclyl)-methyl such as piperidylmethyl, namely piperidin-1-ylmethyl (i.e. piperidinomethyl), piperidin-2-ylmethyl, piperidin-3-ylmethyl, and piperidin-4-ylmethyl; piperazinylmethyl, namely piperazin-1-ylmethyl, and piperazin-2-ylmethyl; and morpholinylmethyl, namely morpholin-2-ylmethyl, morpholin-3-ylmethyl, and morpholin-4-ylmethyl (i.e. morpholinomethyl).

Specific examples of amino-$C_1$-$C_6$ alkyl include aminomethyl, 1-aminoethyl, 2-aminoethyl, 1-aminopropyl, 2-aminopropyl, 3-aminopropyl. Specific examples of ($C_1$-$C_6$ alkylamino)-$C_1$-$C_6$ alkyl include (methylamino)-$C_1$-$C_6$ alkyl such as (methylamino)methyl, 1-(methylamino)ethyl, 2-(methylamino)ethyl, 1-(methylamino)propyl, 2-(methylamino)propyl, 3-(methylamino)propyl, and ($C_1$-$C_6$ alkylamino)-methyl such as (methylamino)methyl, (ethylamino)methyl, (propylamino)methyl, (isopropylamino)methyl, (butylamino)methyl, (isobutylamino)methyl, (sec-butylamino)methyl, (tert-butylamino)methyl, and (pentylamino)methyl, but are not limited thereto. Specific examples of di($C_1$-$C_6$ alkyl)amino-$C_1$-$C_6$ alkyl include (dimethylamino)-$C_1$-$C_6$ alkyl such as (dimethylamino)methyl, 1-(dimethylamino)ethyl, 2-(dimethylamino)ethyl, 1-(dimethylamino)propyl, 2-(dimethylamino)propyl, 3-(dimethylamino)propyl, and di($C_1$-$C_6$ alkyl)amino-methyl such as (dimethylamino)methyl, (diethylamino)methyl, (dipropylamino)methyl, (diisopropylamino)methyl, (dibutylamino)methyl, (diisobutylamino)methyl, [di(sec-butyl)amino]-methyl, [(tert-butyl)amino]methyl, (dipentylamino)methyl, [ethyl(methyl)amino]methyl, [propyl(methyl)amino]methyl, [isopropyl(methyl)amino]methyl, [butyl(methyl)amino]methyl, [isobutyl(methyl)amino]methyl, [sec-butyl(methyl)amino]methyl, [tert-butyl(methyl)amino]methyl, and [pentyl(methyl)amino]methyl, but are not limited thereto.

Specific examples of amino-$C_1$-$C_6$ alkoxy include aminomethoxy, 1-aminoethoxy, 2-aminoethoxy, 1-aminopropoxy, 2-aminopropoxy, 3-aminopropoxy. Specific examples of ($C_1$-$C_6$ alkylamino)-$C_1$-$C_6$ alkoxy include (methylamino)-$C_1$-$C_6$ alkoxy such as (methylamino)methoxy, 1-(methylamino)ethoxy, 2-(methylamino)ethoxy, 1-(methylamino)propoxy, 2-(methylamino)propoxy, 3-(methylamino)propoxy, and ($C_1$-$C_6$ alkylamino)-methoxy such as (methylamino)methoxy, (ethylamino)methoxy, (propylamino)methoxy, (isopropylamino)methoxy, (butylamino)methoxy, (isobutylamino)methoxy, (sec-butylamino)methoxy, (tert-butylamino)methoxy, and (pentylamino)methoxy, but are not limited thereto. Specific examples of di($C_1$-$C_6$ alkyl)amino-$C_1$-$C_6$ alkoxy include (dimethylamino)-$C_1$-$C_6$ alkoxy such as (dimethylamino)methoxy, 1-(dimethylamino)ethoxy, 2-(dimethylamino)ethoxy, 1-(dimethylamino)propoxy, 2-(dimethylamino)propoxy, 3-(dimethylamino)propoxy, and di($C_1$-$C_6$ alkyl)amino-methoxy such as (dimethylamino)methoxy, (diethylamino)methoxy, (dipropylamino)methoxy, (diisopropylamino)methoxy, (dibutylamino)methoxy, (diisobutylamino)methoxy, [di(sec-butyl)amino]-methoxy, [di(tert-butyl)amino]methoxy, (dipentylamino)methoxy, [ethyl(methyl)amino]methoxy, [propyl(methyl)amino]methoxy, [isopropyl(methyl)amino]methoxy, [butyl(methyl)amino]methoxy, [isobutyl(methyl)amino]methoxy, [sec-butyl(methyl)amino]methoxy, [tert-butyl(methyl)amino]methoxy, and [pentyl(methyl)amino]methoxy, but are not limited thereto.

Specific examples of hydroxy-$C_1$-$C_6$ alkyl include hydroxymethyl, 1-hydroxyethyl, 2-hydroxyethyl, 1-hydroxypropyl, 2-hydroxypropyl, 3-hydroxypropyl. Specific examples of ($C_1$-$C_6$ alkoxy)-$C_1$-$C_6$ alkyl include methoxy-$C_1$-$C_6$ alkyl such as methoxymethyl, 1-(methoxy)ethyl, 2-(methoxy)ethyl, 1-(methoxy)propyl, 2-(methoxy)propyl, 3-(methoxy)propyl, and ($C_1$-$C_6$ alkoxy)-methyl such as (methoxy)methyl, (ethoxy)methyl, (propoxy)methyl, (isopropoxy)methyl, (butoxy)methyl, (isobutoxy)methyl, (sec-butoxy)methyl, (tert-butoxy)methyl, and (pentoxy)methyl; but are not limited thereto.

Specific examples of carboxy-$C_1$-$C_6$ alkyl include carboxymethyl, 1-carboxyethyl, 2-carboxyethyl, 1-carboxypropyl, 2-carboxypropyl, and 3-carboxypropyl, but are not limited thereto. Specific examples of [($C_1$-$C_6$ alkoxy)carbonyl]-$C_1$-$C_6$ alkyl include methoxycarbonyl-$C_1$-$C_6$ alkyl such as methoxycarbonyl-methyl, 1-(methoxycarbonyl)ethyl, 2-(methoxycarbonyl)ethyl, 1-(methoxycarbonyl)propyl, 2-(methoxycarbonyl)propyl, and 3-(methoxycarbonyl)propyl; and [($C_1$-$C_6$ alkoxy)carbonyl]-methyl such as (methoxycarbonyl)methyl, 1-(methoxycarbonyl)ethyl, 2-(methoxycarbonyl)ethyl, 1-(methoxycarbonyl)propyl, 2-(methoxycarbonyl)propyl, and 3-(methoxycarbonyl)propyl; but are not limited thereto.

Specific examples of carbamoyl-$C_1$-$C_6$ alkyl include carbamoylmethyl, 1-carbamoylethyl, 2-carbamoylethyl, 1-carbamoylpropyl, 2-carbamoylpropyl, and 3-carbamoylpropyl, but are not limited thereto. Specific examples of [N—($C_1$-$C_6$ alkyl)carbamoyl]-$C_1$-$C_6$ alkyl include N-methylcarbamoyl-$C_1$-$C_6$ alkyl such as N-methylcarbamoyl-methyl, 1-(N-methylcarbamoyl)ethyl, 2-(N-methylcarbamoyl)ethyl, 1-(methylcarbamoyl)propyl, 2-(N-methylcarbamoyl)propyl, and 3-(N-methylcarbamoyl)propyl; and [N—($C_1$-$C_6$ alkxyl)carbamoyl]-methyl such as (N-methylcarbamoyl)methyl, (N-ethylcarbamoyl)methyl, (N-propylcarbamoyl)methyl, (N-isopropylcarbamoyl)methyl, (N-butylcarbamoyl)methyl, [N-(tert-butyl)carbamoyl]methyl and [N-(sec-butyl)carbamoyl]methyl; but are not limited thereto. Specific examples of [N,N-di($C_1$-$C_6$ alkyl)carbamoyl]-$C_1$-$C_6$ alkyl include (N,N-dimethylcarbamoyl)-$C_1$-$C_6$ alkyl such as (N,N-dimethylcarbamoyl)methyl, 1-(N,N-dimethylcarbamoyl)ethyl, 2-(N,N-dimethylcarbamoyl)ethyl, 1-(N,N-dimethyl carbamoyl)propyl, 2-(N,N-dimethylcarbamoyl)propyl, and 3-(N,N-dimethylcarbamoyl)propyl; and [N,N-di($C_1$-$C_6$ alkyl)carbamoyl]-methyl such as (N,N-dimethyl carbamoyl)methyl, (N,N-diethylcarbamoyl)methyl, (N,N-dipropylcarbamoyl)methyl, (N,N-diisopropylcarbamoyl)methyl, (N,N-dibutylcarbamoyl)methyl, (N,N-diisobutylcarbamoyl)methyl, [N,N-di(sec-butyl)carbamoyl]methyl, [N,N-di(tert-butyl)carbamoyl]methyl, (N,N-dipentylcarbamoyl)methyl, [N-ethyl-N-(methyl)carbamoyl]methyl, [N-propyl-N-(methyl)carbamoyl]methyl, [N-isopropyl-N-(methyl)carbamoyl]methyl, [N-butyl-N-(methyl)carbamoyl]methyl, [N-isobutyl-N-(methyl)carbamoyl]methyl, [N-sec-butyl-N-(methyl)carbamoyl]methyl, [N-tert-butyl-N-(methyl)carbamoyl]methyl, and [N-pentyl-N-(methyl)carbamoyl]methyl; but are not limited thereto.

Specific examples of ($C_1$-$C_6$ alkyl)carbonylamino include methylcarbonylamino, ethylcarbonylamino, propylcarbonylamino, isopropylcarbonylamino, butylcarbonylamino, isobutylcarbonylamino, sec-butylcarbonylamino, tert-butylcarbonylamino, and pentylcarbonylamino, but are not limited thereto. Specific examples of N—($C_1$-$C_6$ alkyl)carbonyl-N—($C_1$-$C_6$ alkyl)amino include N-acetyl-N—($C_1$-$C_6$ alkyl)amino such as N-acetyl-N-methylamino, N-acetyl-N-ethylamino, N-acetyl-N-propylamino, N-acetyl-N-isopropylamino, N-acetyl-N-butylamino, N-acetyl-N-isobutylamino, N-acetyl-N-sec-butylamino, N-acetyl-N-tert-butylamino, and N-acetyl-N-pentylamino; and N—($C_1$-$C_6$ alkyl)carbonyl-N-(methyl)amino such as N-acetyl-N-(methyl)amino, N-ethylcarbonyl-N-(methyl)amino, N-propylcarbonyl-N-(methyl)amino, N-isopropylcarbonyl-N-(methyl)amino, N-isobutylcarbonyl-N-(methyl)amino, N-tert-butylcarbonyl-N-(methyl)amino, N-butylcarbonyl-N-(methyl)amino, N-pentylcarbonyl-N-(methyl)amino, and N-hexylcarbonyl-N-(methyl)amino, but are not limited thereto.

Specific examples of 5- to 7-membered cyclic boronic acid ester are indicated by the following formulae:

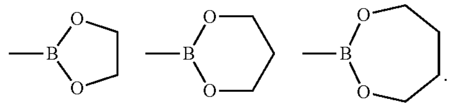

Pharmaceutically acceptable salts of compound (I) mean, for example, pharmaceutically acceptable acid-added salts, amino acid-added salts, or such. Specific examples of the pharmaceutically acceptable acid-added salts of compound (I) include inorganic acid salts such as hydrochloride, sulfate, and phosphate, organic acid salts such as acetate, maleate, fumarate, citrate, and such, and examples of pharmaceutically acceptable amino acid-added salts include addition salts such as of lysine, glycine, phenylalanine, asparagine acid, or glutamic acid. Particularly, Pharmaceutically acceptable salts of compound (I) include hydrochloride salt, dihydrochloride salt, and trihydrochloride salt.

Examples of diseases involving overexpression of MELK, which may be treated and/or prevented by pharmaceutical compositions comprising as an active ingredient a compound or a pharmaceutically acceptable salt thereof of the present invention, include cancer, breast cancer, bladder cancer, cervical cancer, cholangiocellular carcinoma, chronic myeloid leukemia (CML), colorectal cancer, endometriosis, esophagus cancer, gastric cancer, liver cancer, non-small cell lung cancer (NSCLC), lymphoma, osteosarcoma, ovarian cancer, pancreatic cancer, prostate cancer, renal carcinoma and small cell lung cancer (SCC), but are not limited thereto. Examples of the cancer which may be treated and/or prevented include breast cancer, bladder cancer, cervical cancer, cholangiocellular carcinoma, CML, colorectal cancer, endometriosis, esophagus cancer, gastric cancer, liver cancer, NSCLC, lymphoma, osteosarcoma, ovarian cancer, pancreatic cancer, prostate cancer, renal carcinoma and SCC, but are not limited thereto.

Compound (I) includes compounds which may have stereoisomers such as regioisomers, geometrical isomers, optical isomers, and tautomers, and all possible isomers including them and mixtures thereof are included in the present invention.

Compound (I) also includes compounds having one or more minor stable isotopes or radio isotopes such as $^{2}H$, $^{3}H$, $^{13}C$, $^{14}C$, $^{15}N$, $^{18}O$ and the like, which can be prepared in line with conventional procedures for preparing a compound with one or more isotopes indicated above.

Furthermore, compound (I) and pharmaceutically acceptable salts thereof may exist in a form of solvate with water (hydrate) or various other solvents, and these solvates are also included in the present invention.

Specific examples of Compound (I) of the present invention are shown in Table 1. However, compounds of the present invention are not limited thereto.

TABLE 1

| Example No. | Structure | Name | ESI MS (m/z) |
|---|---|---|---|
| 1 | 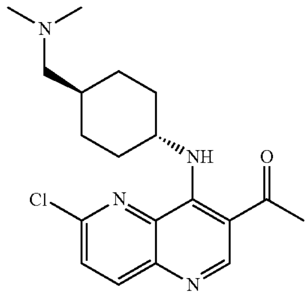 [SMILES: CC(=O)c1cnc2ccc(Cl)nc2c1N[C@H]1CC[C@H](CN(C)C)CC1] | 1-(6-Chloro-4-{trans-4-[(dimethylamino)-methyl]cyclohexylamino}-1,5-naphthyridin-3-yl)-ethanone | 361.1 |
| 2 | 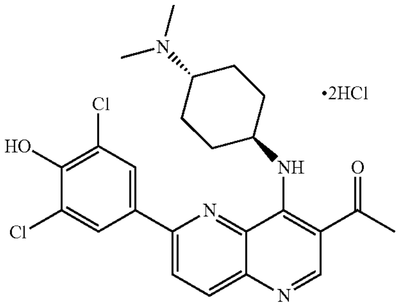 [SMILES: CC(=O)c1cnc2ccc(-c3cc(Cl)c(O)c(Cl)c3)nc2c1N[C@H]1CC[C@H](N(C)C)CC1] | 1-{6-(3,5-Dichloro-4-hydroxyphenyl)-4-[trans-4-(dimethylamino)cyclohexyl-amino]-1,5-naphthyridin-3-yl}ethanone dihydrochloride | 473.1 |
| 3 | 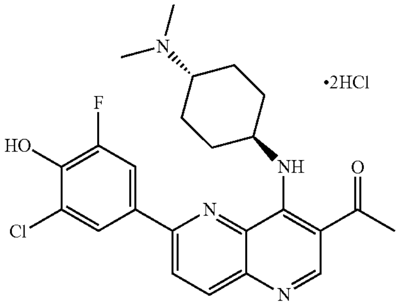 [SMILES: CC(=O)c1cnc2ccc(-c3cc(F)c(O)c(Cl)c3)nc2c1N[C@H]1CC[C@H](N(C)C)CC1] | 1-{6-(3-Chloro-5-fluoro-4-hydroxyphenyl)-4-[trans-4-(dimethylamino)cyclohexyl amino]-1,5-naphthyridin-3-yl}ethanone dihydrochloride | 457.1 |

TABLE 1-continued

| Example No. | Structure | Name | ESI MS (m/z) |
|---|---|---|---|
| 4 | 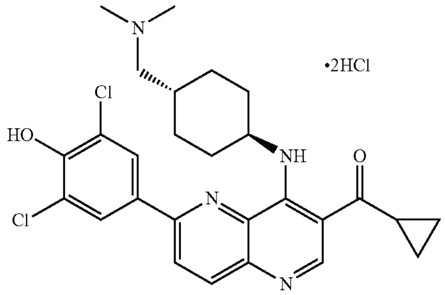 | Cyclopropyl(6-(3,5-dichloro-4-hydroxyphenyl)-4-{trans-4-[(dimethylamino)methyl]-cyclohexylamino}-1,5-naphthyridin-3-yl)methanone dihydrochloride | 513.1 |
| 5 | 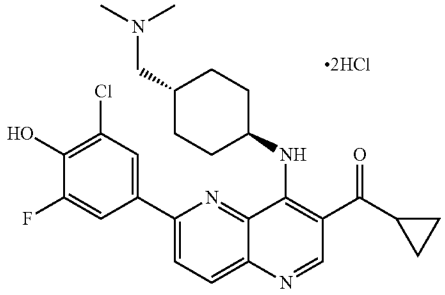 [SMILES: CN(C)C[C@H]1CC[C@H](Nc2c(C(=O)C3CC3)cnc3ccc(-c4cc(F)c(O)c(Cl)c4)nc23)CC1] | (6-(3-Chloro-5-fluoro-4-hydroxyphenyl)-4-{trans-4-[(dimethylamino)methyl)-cyclohexyl-amino]-1,5-naphthyridin-3-yl}(cyclopropyl)methanone dihydrochloride | 497.1 |
| 6 | 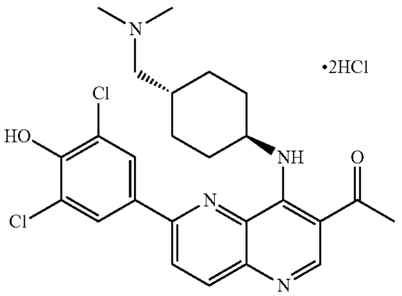 [SMILES: CC(=O)c1cnc2ccc(-c3cc(Cl)c(O)c(Cl)c3)nc2c1N[C@H]1CC[C@H](CN(C)C)CC1] | 1-{6-(3,5-Dichloro-4-hydroxyphenyl)-4-({trans-4-[(dimethylamino)methyl]-cyclohexyl}amino)-1,5-naphthyridin-3-yl}ethanone dihydrochloride | 487.1 |
| 7 | 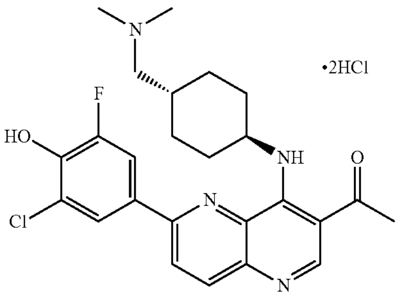 [SMILES: CC(=O)c1cnc2ccc(-c3cc(F)c(O)c(Cl)c3)nc2c1N[C@H]1CC[C@H](CN(C)C)CC1] | 1-{6-(3-Chloro-5-fluoro-4-hydroxyphenyl)-4-({trans-4-[(dimethylamino)methyl]cyclohexyl}-amino)-1,5-naphthyridin-3-yl}ethanone dihydrochloride | 471.2 |
| 8 | 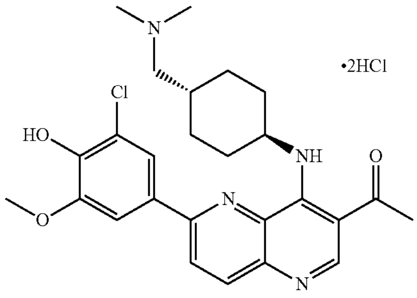 [SMILES: COc1cc(-c2ccc3ncc(C(C)=O)c(N[C@H]4CC[C@H](CN(C)C)CC4)c3n2)cc(Cl)c1O] | 1-(6-(3-Chloro-4-hydroxy-5-methoxyphenyl)-4-{trans-4-[(dimethylamino)methyl]cyclohexyl-amino}-1,5-naphthyridin-3-yl)ethanone dihydrochloride | 483.2 |

TABLE 1-continued

| Example No. | Structure | Name | ESI MS (m/z) |
| --- | --- | --- | --- |
| 9 | 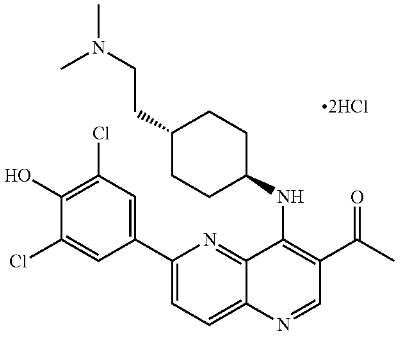 [SMILES: CC(=O)c1cnc2ccc(-c3cc(Cl)c(O)c(Cl)c3)nc2c1N[C@H]1CC[C@H](CCN(C)C)CC1] •2HCl | 1-[6-(3,5-Dichloro-4-hydroxyphenyl)-4-({trans-4-[2-(dimethylamino)ethyl]-cyclohexyl}amino)-1,5-naphthyridin-3-yl]ethanone dihydrochloride | 501.1 |
| 10 | 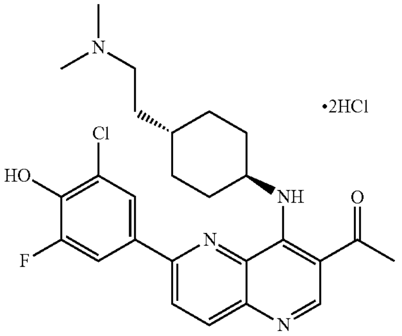 [SMILES: CC(=O)c1cnc2ccc(-c3cc(F)c(O)c(Cl)c3)nc2c1N[C@H]1CC[C@H](CCN(C)C)CC1] •2HCl | 1-(6-(3-Chloro-5-fluoro-4-hydroxy-phenyl)-4-{trans-4-[2-(dimethylamino)-ethyl]cyclohexylamino}-1,5-naphthyridin-3-yl)ethanone dihydrochloride | 485.1 |
| 11 | 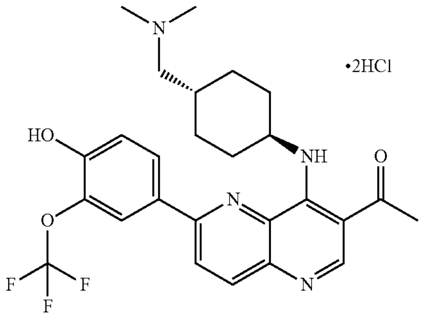 [SMILES: CC(=O)c1cnc2ccc(-c3ccc(O)c(OC(F)(F)F)c3)nc2c1N[C@H]1CC[C@H](CN(C)C)CC1] •2HCl | 1-(4-{trans-4-[(Dimethylamino)methyl]-cyclohexylamino}-6-[4-hydroxy-3-(trifluoromethoxy)-phenyl]-1,5-naphthyridin-3-yl)ethanone dihydrochloride | 503.1 |
| 12 | 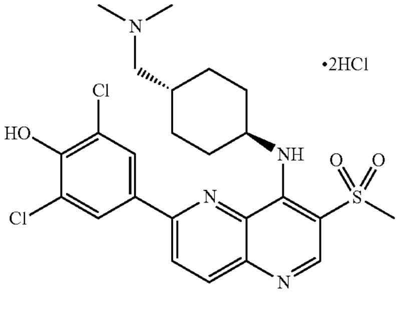 [SMILES: CN(C)C[C@H]1CC[C@H](Nc2c(S(C)(=O)=O)cnc3ccc(-c4cc(Cl)c(O)c(Cl)c4)nc23)CC1] •2HCl | 2,6-Dichloro-4-(8-{trans-4-[(dimethylamino)methyl]-cyclohexylamino}-7-(methylsulfonyl)-1,5-naphthyridin-2-yl)phenol dihydrochloride | 523.1 |

TABLE 1-continued

| Example No. | Structure | Name | ESI MS (m/z) |
|---|---|---|---|
| 13 | 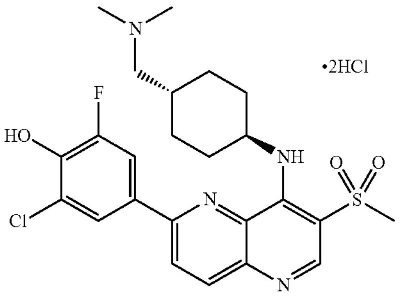 •2HCl | 6-(3-Chloro-5-fluoro-4-hydroxyphenyl)-4-({trans-4-[(dimethylamino)-methyl]cyclohexyl}-amino)-3-methylsulfonyl-1,5-naphthyridine dihydrochloride | 507.1 |
| 14 | 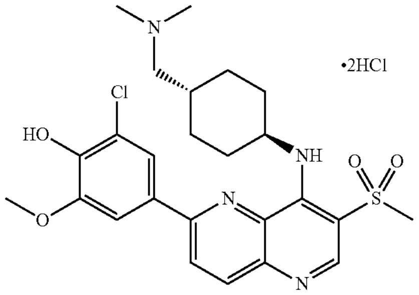 •2HCl | 6-(3-Chloro-4-hydroxy-5-methoxy-phenyl)-4-{trans-4-[(dimethylamino)-methyl]cyclohexylamino}-3-methyl-sulfonyl-1,5-naphthyridine dihydrochloride | 519.1 |
| 15 | 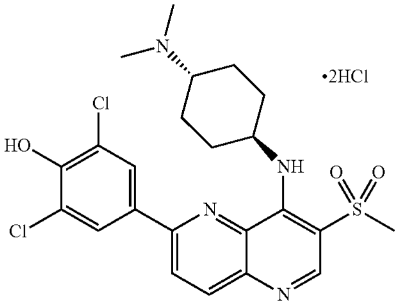 [SMILES: CN(C)[C@H]1CC[C@H](Nc2c(S(C)(=O)=O)cnc3ccc(-c4cc(Cl)c(O)c(Cl)c4)nc23)CC1] •2HCl | 2,6-Dichloro-4-{8-[trans-4-(dimethylamino)cyclohexylamino]-7-(methylsulfonyl)-1,5-naphthyridin-2-yl}phenol dihydrochloride | 509.1 |
| 16 | 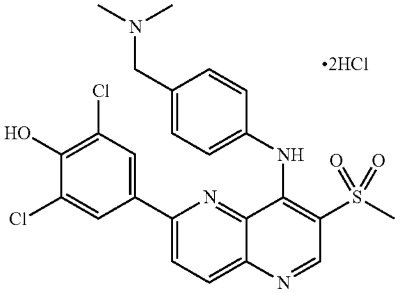 [SMILES: CN(C)Cc1ccc(Nc2c(S(C)(=O)=O)cnc3ccc(-c4cc(Cl)c(O)c(Cl)c4)nc23)cc1] •2HCl | 2,6-Dichloro-4-(8-{4-[(dimethylamino)-methyl]phenylamino}-7-(methyl-sulfonyl)-1,5-naphthyridin-2-yl)phenol dihydrochloride | 517.1 |
| 17 | 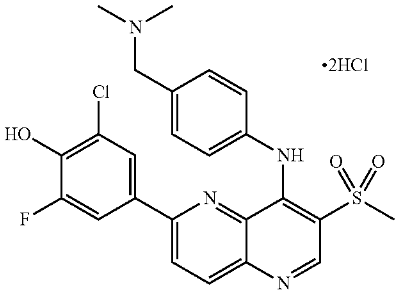 [SMILES: CN(C)Cc1ccc(Nc2c(S(C)(=O)=O)cnc3ccc(-c4cc(F)c(O)c(Cl)c4)nc23)cc1] •2HCl | 2-Chloro-4-(8-(4-((dimethylamino)-methyl)phenylamino)-7-(methylsulfonyl)-1,5-naphthyridin-2-yl)-6-fluorophenol dihydrochloride | 501.0 |

TABLE 1-continued

| Example No. | Structure | Name | ESI MS (m/z) |
|---|---|---|---|
| 18 | 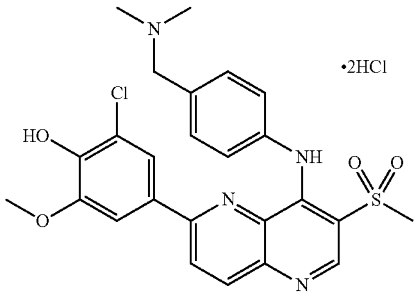 | 2-Chloro-4-(8-(4-((dimethylamino)-methyl)phenylamino)-7-(methylsulfonyl)-1,5-naphthyridin-2-yl)-6-methoxyphenol dihydrochloride | 513.1 |
| 19 | 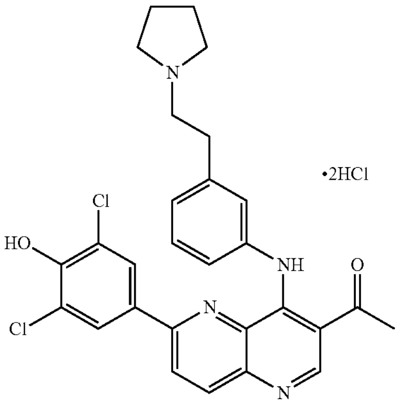 [SMILES: CC(=O)c1cnc2ccc(-c3cc(Cl)c(O)c(Cl)c3)nc2c1Nc1cccc(CCN2CCCC2)c1] | 1-(6-(3,5-Dichloro-4-hydroxyphenyl)-4-(3-(2-(pyrrolidin-1-yl)ethyl)phenyl-amino)-1,5-naphthyridin-3-yl)ethanone dihydrochloride | 521.1 |
| 20 | 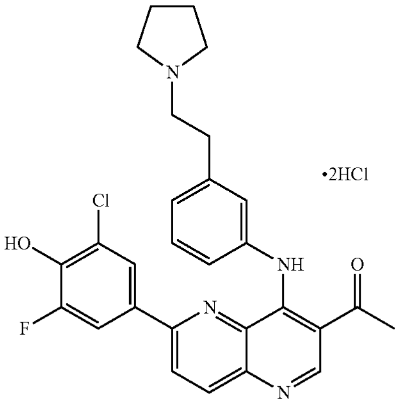 [SMILES: CC(=O)c1cnc2ccc(-c3cc(F)c(O)c(Cl)c3)nc2c1Nc1cccc(CCN2CCCC2)c1] | 1-(6-(3-Chloro-5-fluoro-4-hydroxy-phenyl)-4-(3-(2-(pyrrolidin-1-yl)-ethyl)phenylamino)-1,5-naphthyridin-3-yl)ethanone dihydrochloride | 505.2 |
| 21 | 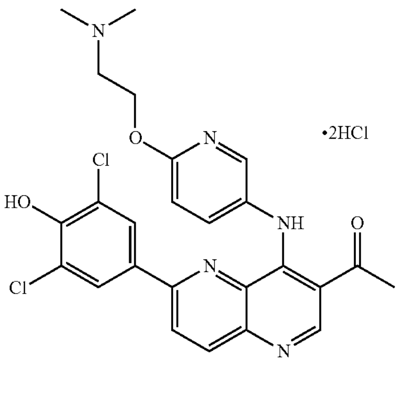 [SMILES: CC(=O)c1cnc2ccc(-c3cc(Cl)c(O)c(Cl)c3)nc2c1Nc1ccc(OCCN(C)C)nc1] | 1-(6-(3,5-Dichloro-4-hydroxyphenyl)-4-(6-(2-(dimethylamino)ethoxy)pyridin-3-ylamino)-1,5-naphthyridin-3-yl) ethanone dihydrochloride | 512.1 |

TABLE 1-continued

| Example No. | Structure | Name | ESI MS (m/z) |
|---|---|---|---|
| 22 | 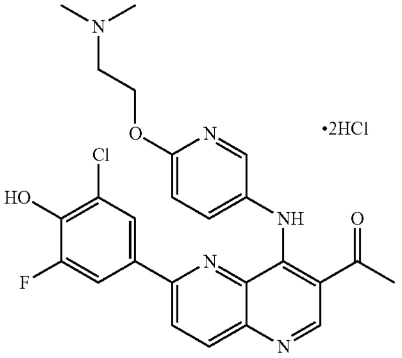 | 1-(6-(3-Chloro-5-fluoro-4-hydroxy-phenyl)-4-(6-(2-(dimethylamino)ethoxy)-pyridin-3-ylamino)-1,5-naphthyridin-3-yl) ethanone dihydrochloride | 496.1 |
| 23 | 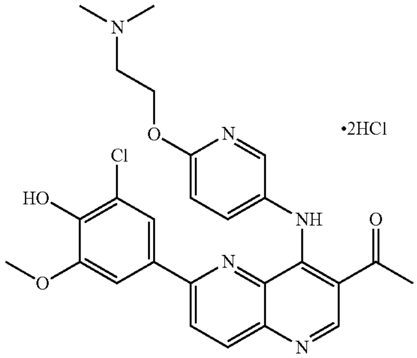 [SMILES: COc1cc(-c2ccc3ncc(C(C)=O)c(Nc4ccc(OCCN(C)C)nc4)c3n2)cc(Cl)c1O] | 1-(6-(3-Chloro-4-hydroxy-5-methoxy-phenyl)-4-(6-(2-(dimethylamino)ethoxy)-pyridin-3-ylamino)-1,5-naphthyridin-3-yl)ethanone dihydrochloride | 508.1 |
| 24 | 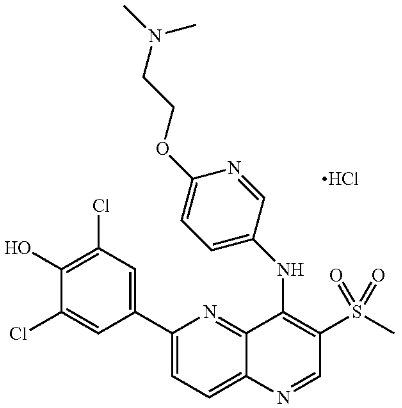 [SMILES: CN(C)CCOc1ccc(Nc2c(S(C)(=O)=O)cnc3ccc(-c4cc(Cl)c(O)c(Cl)c4)nc23)cn1 ; Cl] | 2,6-Dichloro-4-(8-(6-(2-(dimethyl-amino)ethoxy)pyridin-3-ylamino)-7-(methylsulfonyl)-1,5-naphthyridin-2-yl)-phenol hydrochloride | 548.0 |
| 25 | 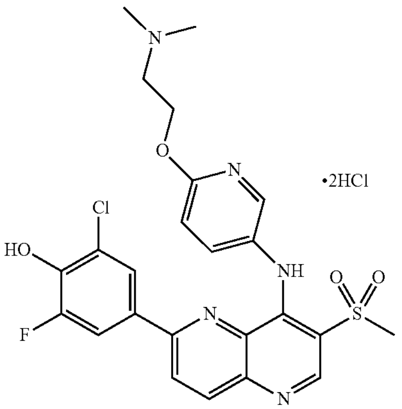 [SMILES: CN(C)CCOc1ccc(Nc2c(S(C)(=O)=O)cnc3ccc(-c4cc(F)c(O)c(Cl)c4)nc23)cn1] | 2-Chloro-4-(8-(6-(2-(dimethylamino)-ethoxy)pyridin-3-ylamino)-7-(methylsulfonyl)-1,5-naphthyridin-2-yl)-6-fluorophenol dihydrochloride | 532.1 |

TABLE 1-continued

| Example No. | Structure | Name | ESI MS (m/z) |
|---|---|---|---|
| 26 | 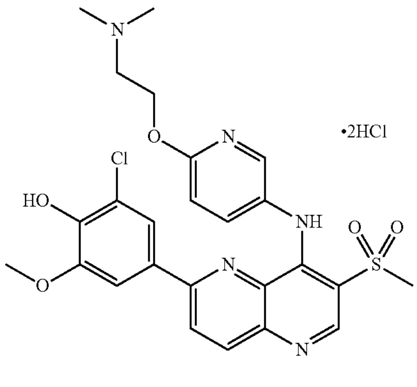 | 2-Chloro-4-(8-(6-(2-(dimethylamino)-ethoxy)pyridin-3-ylamino)-7-(methylsulfonyl)-1,5-naphthyridin-2-yl)-6-methoxyphenol dihydrochloride | 544.2 |
| 27 | 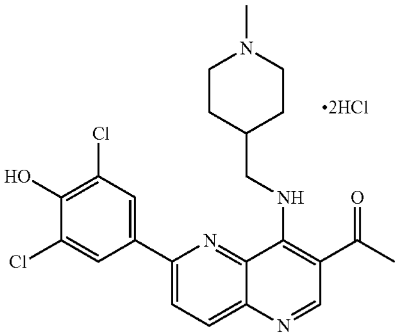 [SMILES: CC(=O)c1cnc2ccc(-c3cc(Cl)c(O)c(Cl)c3)nc2c1NCC1CCN(C)CC1] | 1-(6-(3,5-Dichloro-4-hydroxyphenyl)-4-((1-methylpiperidin-4-yl)methylamino)-1,5-naphthyridin-3-yl)ethanone dihydrochloride | 459.2 |
| 28 | 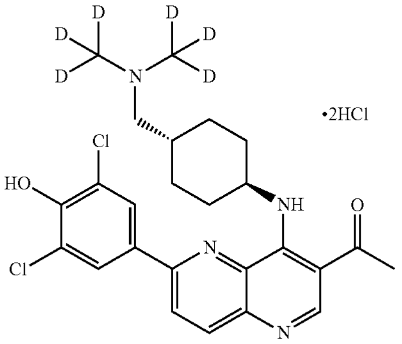 [SMILES: [2H]C([2H])([2H])N(C[C@H]1CC[C@H](Nc2c(C(C)=O)cnc3ccc(-c4cc(Cl)c(O)c(Cl)c4)nc23)CC1)C([2H])([2H])[2H]] | 1-(6-(3,5-Dichloro-4-hydroxyphenyl)-4-(trans-4-((dimethylamino-$d_6$)methyl)-cyclohexylamino)-1,5-naphthyridin-3-yl)ethanone dihydrochloride | 493.2 |
| 29 | 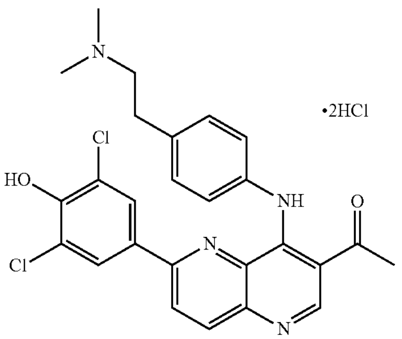 [SMILES: CC(=O)c1cnc2ccc(-c3cc(Cl)c(O)c(Cl)c3)nc2c1Nc1ccc(CCN(C)C)cc1] | 1-(6-(3,5-Dichloro-4-hydroxyphenyl)-4-(4-(2-(dimethylamino)ethyl)phenyl-amino)-1,5-naphthyridin-3-yl)ethanone dihydrochloride | 495.1 |

TABLE 1-continued

| Example No. | Structure | Name | ESI MS (m/z) |
|---|---|---|---|
| 30 | 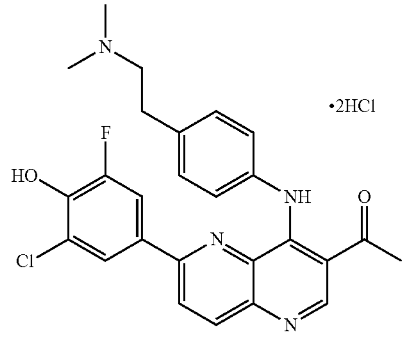 [SMILES: CC(=O)c1cnc2ccc(-c3cc(F)c(O)c(Cl)c3)nc2c1Nc1ccc(CCN(C)C)cc1] | 1-(6-(3-chloro-5-fluoro-4-hydroxy-phenyl)-4-(4-(2-(dimethylamino)-ethyl)phenylamino)-1,5-naphthyridin-3-yl)ethanone dihydrochloride | 479.1 |
| 31 | 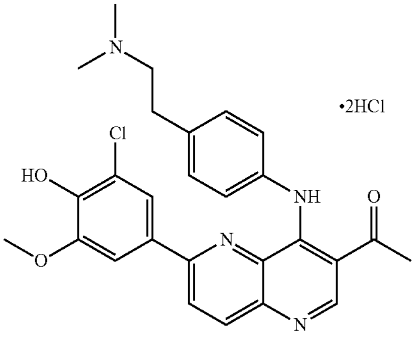 [SMILES: COc1cc(-c2ccc3ncc(C(C)=O)c(Nc4ccc(CCN(C)C)cc4)c3n2)cc(Cl)c1O] | 1-(6-(3-Chloro-4-hydroxy-5-methoxyphenyl)-4-(4-(2-(dimethyl-amino)ethyl)phenylamino)-1,5-naphthyridin-3-yl) ethanone dihydrochloride | 491.1 |
| 32 | 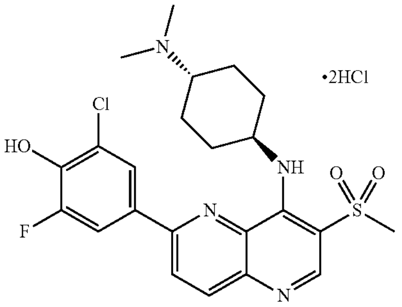 [SMILES: CN(C)[C@H]1CC[C@H](Nc2c(S(C)(=O)=O)cnc3ccc(-c4cc(F)c(O)c(Cl)c4)nc23)CC1] | 2-Chloro-4-(8-(trans-4-(dimethylamino)-cyclohexylamino)-7-(methylsulfonyl)-1,5-naphthyridin-2-yl)-6-fluorophenol dihydrochloride | 493.0 |
| 33 | 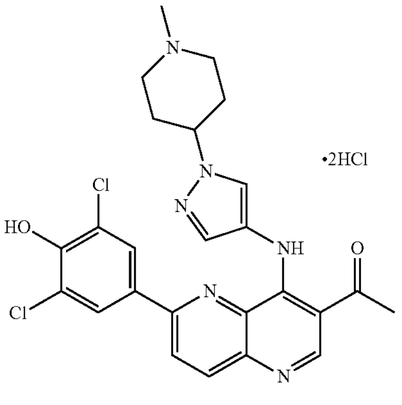 [SMILES: CC(=O)c1cnc2ccc(-c3cc(Cl)c(O)c(Cl)c3)nc2c1Nc1cnn(C2CCN(C)CC2)c1] | 1-(6-(3,5-Dichloro-4-hydroxyphenyl)-4-(1-(1-methylpiperidin-4-yl)-1H-pyrazol-4-ylamino)-1,5-naphthyridin-3-yl) ethanone dihydrochloride | 511.1 |

TABLE 1-continued

| Example No. | Structure | Name | ESI MS (m/z) |
|---|---|---|---|
| 34 | 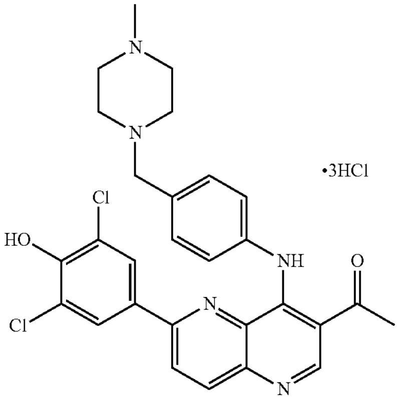 [SMILES: CC(=O)c1cnc2ccc(-c3cc(Cl)c(O)c(Cl)c3)nc2c1Nc1ccc(CN2CCN(C)CC2)cc1] •3HCl | 1-(6-(3,5-Dichloro-4-hydroxyphenyl)-4-(4-((4-methylpiperazin-1-yl)methyl)-phenylamino)-1,5-naphthyridin-3-yl) ethanone trihydrochloride | 536.1 |
| 35 | 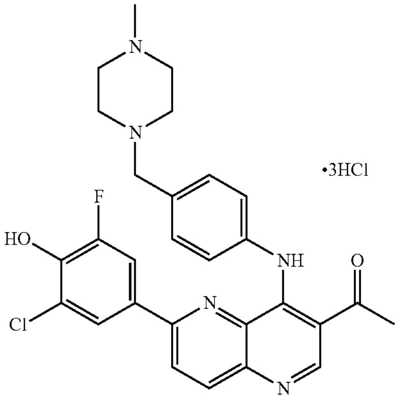 [SMILES: CC(=O)c1cnc2ccc(-c3cc(F)c(O)c(Cl)c3)nc2c1Nc1ccc(CN2CCN(C)CC2)cc1] •3HCl | 1-(6-(3-Chloro-5-fluoro-4-hydroxy-phenyl)-4-(4-((4-methylpiperazin-1-yl)-methyl)phenylamino)-1,5-naphthyridin-3-yl) ethanone trihydrochloride | 520.1 |
| 36 | 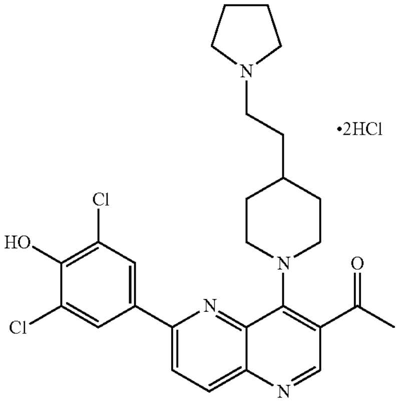 [SMILES: CC(=O)c1cnc2ccc(-c3cc(Cl)c(O)c(Cl)c3)nc2c1N1CCC(CCN2CCCC2)CC1] •2HCl | 1-(6-(3,5-Dichloro-4-hydroxyphenyl)-4-(4-(2-(pyrrolidin-1-yl)ethyl)piperidin-1-yl)-1,5-naphthyridin-3-yl)ethanone dihydrochloride | 513.2 |

TABLE 1-continued

| Example No. | Structure | Name | ESI MS (m/z) |
|---|---|---|---|
| 37 | 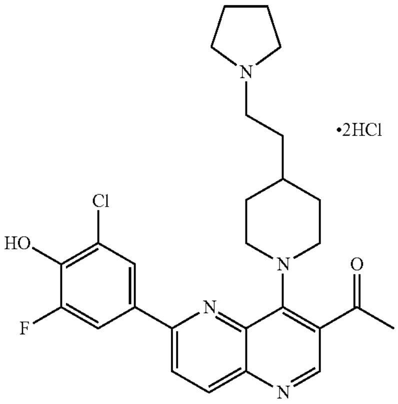 [SMILES: CC(=O)c1cnc2ccc(-c3cc(F)c(O)c(Cl)c3)nc2c1N1CCC(CCN2CCCC2)CC1] •2HCl | 1-(6-(3-Chloro-5-fluoro-4-hydroxy-phenyl)-4-(4-(2-(pyrrolidin-1-yl)ethyl)-piperidin-1-yl)-1,5-naphthyridin-3-yl)-ethanone dihydrochloride | 497.1 |
| 38 | 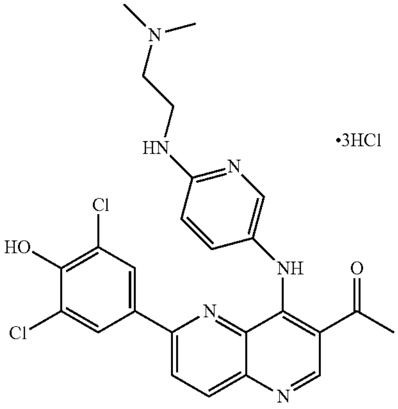 [SMILES: CC(=O)c1cnc2ccc(-c3cc(Cl)c(O)c(Cl)c3)nc2c1Nc1ccc(NCCN(C)C)nc1] •3HCl | 1-(6-(3,5-Dichloro-4-hydroxyphenyl)-4-(6-(2-(dimethylamino)ethylamino)-pyridin-3-ylamino)-1,5-naphthyridin-3-yl) ethanone trihydrochloride | 511.1 |
| 39 | 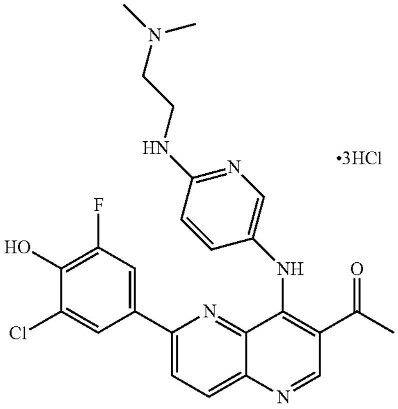 [SMILES: CC(=O)c1cnc2ccc(-c3cc(F)c(O)c(Cl)c3)nc2c1Nc1ccc(NCCN(C)C)nc1] •3HCl | 1-(6-(3-Chloro-5-fluoro-4-hydroxy-phenyl)-4-(6-(2-(dimethylamino)ethyl-amino)pyridin-3-ylamino)-1,5-naphthyridin-3-yl) ethanone trihydrochloride | 495.1 |
| 40 | 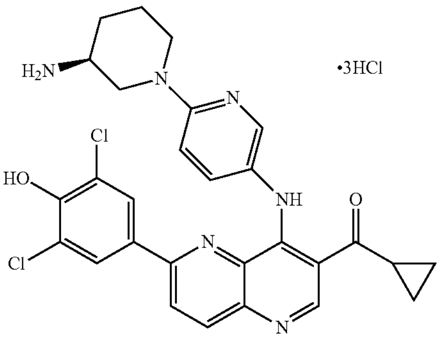 [SMILES: N[C@H]1CCCN(c2ccc(Nc3c(C(=O)C4CC4)cnc4ccc(-c5cc(Cl)c(O)c(Cl)c5)nc34)cn2)C1] •3HCl | (S)-(4-(6-(3-Aminopiperidin-1-yl)-pyridin-3-ylamino)-6-(3,5-dichloro-4-hydroxyphenyl)-1,5-naphthyridin-3-yl)(cyclopropyl) methanone trihydrochloride | 549.1 |

TABLE 1-continued

| Example No. | Structure | Name | ESI MS (m/z) |
|---|---|---|---|
| 41 | 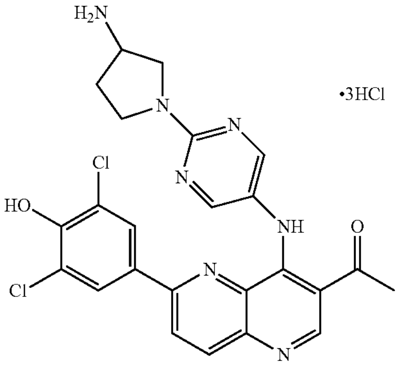 [SMILES: CC(=O)c1cnc2ccc(-c3cc(Cl)c(O)c(Cl)c3)nc2c1Nc1cnc(N2CCC(N)C2)nc1] •3HCl | 1-(4-(2-(3-Aminopyrrolidin-1-yl)-pyrimidin-5-ylamino)-6-(3,5-dichloro-4-hydroxyphenyl)-1,5-naphthyridin-3-yl)ethanone trihydrochloride | 510.1 |
| 42 | 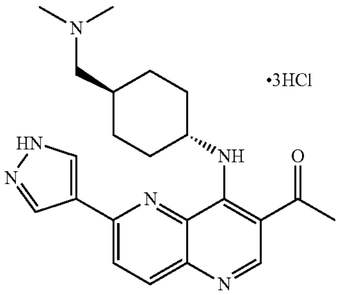 [SMILES: CC(=O)c1cnc2ccc(-c3cn[nH]c3)nc2c1N[C@H]1CC[C@H](CN(C)C)CC1] •3HCl | 1-(4-{trans-4-[(Dimethylamino)methyl]-cyclohexylamino}-6-(1H-pyrazol-4-yl)-1,5-naphthyridin-3-yl)ethanone trihydrochloride | 393.2 |
| 43 | 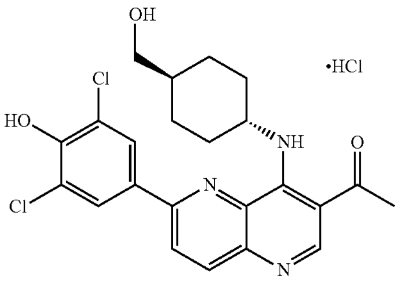 [SMILES: CC(=O)c1cnc2ccc(-c3cc(Cl)c(O)c(Cl)c3)nc2c1N[C@H]1CC[C@H](CO)CC1 ; Cl] •HCl | 1-(6-{3,5-Dichloro-4-hydroxyphenyl)-4-[trans-4-(hydroxymethyl)cyclohexyl]-amino}-1,5-naphthyridin-3-yl) ethanone hydrochloride | 460.1 |
| 44 | 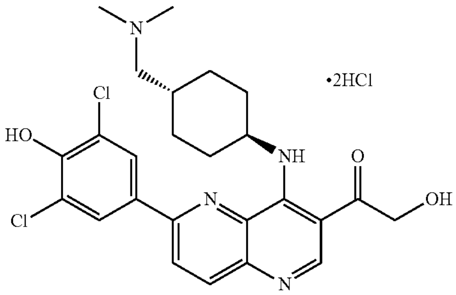 [SMILES: CN(C)C[C@H]1CC[C@H](Nc2c(C(=O)CO)cnc3ccc(-c4cc(Cl)c(O)c(Cl)c4)nc23)CC1] •2HCl | 1-[6-(3,5-Dichloro-4-hydroxyphenyl)-4-{trans-4-[(dimethylamino)methyl]-cyclohexylamino}-1,5-naphthyridin-3-yl]-2-hydroxyethanone dihydrochloride | 503.1 |
| 45 | 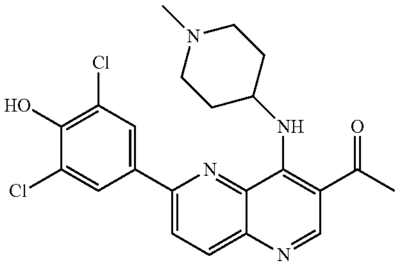 [SMILES: CC(=O)c1cnc2ccc(-c3cc(Cl)c(O)c(Cl)c3)nc2c1NC1CCN(C)CC1] | 1-{6-(3,5-Dichloro-4-hydroxyphenyl)-4-[(1-methylpiperidin-4-yl)amino]-1,5-naphthyridin-3-yl}ethanone | 445.1 |

TABLE 1-continued

| Example No. | Structure | Name | ESI MS (m/z) |
| --- | --- | --- | --- |
| 46 | 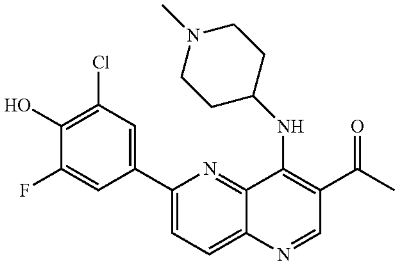 | 1-{6-(3-Chloro-5-fluoro-4-hydroxy-phenyl)-4-[(1-methylpiperidin-4-yl)-amino]-1,5-naphthyridin-3-yl}ethanone | 429.0 |
| 47 | 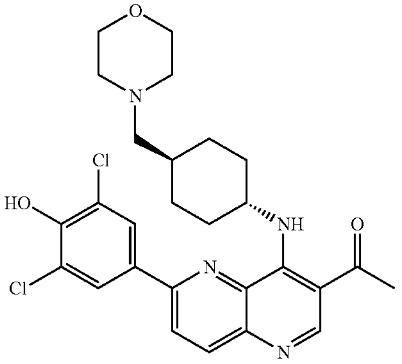 [SMILES: CC(=O)c1cnc2ccc(-c3cc(Cl)c(O)c(Cl)c3)nc2c1N[C@H]1CC[C@H](CN2CCOCC2)CC1] | 1-(6-(3,5-Dichloro-4-hydroxyphenyl)-4-{[trans-4-(morpholinomethyl)-cyclohexyl]-amino}-1,5-naphthyridin-3-yl)ethanone | 529.1 |
| 48 | 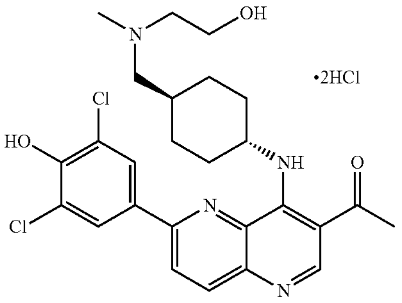 •2HCl | 1-[6-(3,5-Dichloro-4-hydroxyphenyl)-4-(trans-4-{[(2-hydroxyethyl)-(methyl)amino]methyl}-cyclohexylamino)-1,5-naphthyridin-3-yl]ethanone dihydrochloride | 517.1 |
| 49 | 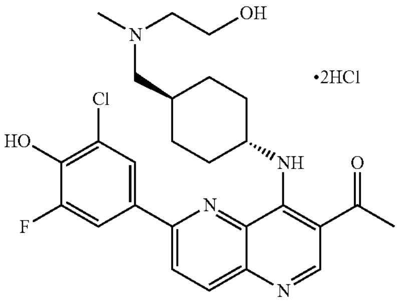 [SMILES: CC(=O)c1cnc2ccc(-c3cc(F)c(O)c(Cl)c3)nc2c1N[C@H]1CC[C@H](CN(C)CCO)CC1] •2HCl | 1-[6-(3-Chloro-5-fluoro-4-hydroxy-phenyl)-4-(trans-4-{[(2-hydroxyethyl)-(methyl)amino]methyl}cyclohexyl-amino)-1,5-naphthyridin-3-yl]ethanone dihydrochloride | 500.1 |
| 50 | 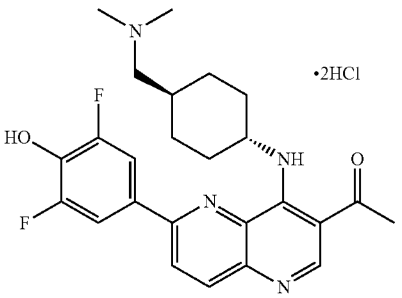 [SMILES: CC(=O)c1cnc2ccc(-c3cc(F)c(O)c(F)c3)nc2c1N[C@H]1CC[C@H](CN(C)C)CC1] •2HCl | 1-(6-(3,5-Difluoro-4-hydroxyphenyl)-4-{trans-4-[(dimethylamino)methyl]-cyclohexylamino}-1,5-naphthyridin-3-yl)ethanone dihydrochloride | 455.1 |

TABLE 1-continued

| Example No. | Structure | Name | ESI MS (m/z) |
|---|---|---|---|
| 51 | 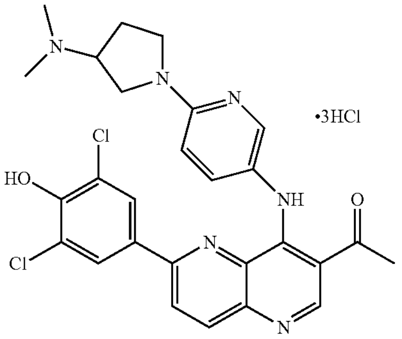 [SMILES: CC(=O)c1cnc2ccc(-c3cc(Cl)c(O)c(Cl)c3)nc2c1Nc1ccc(N2CCC(N(C)C)C2)nc1] | 1-(6-(3,5-Dichloro-4-hydroxyphenyl)-4-{6-[3-(dimethylamino)pyrrolidin-1-yl]-pyridin-3-ylamino}-1,5-naphthyridin-3-yl) ethanone trihydrochloride | 537.3 |
| 52 | 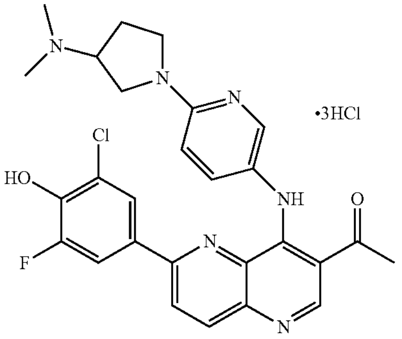 [SMILES: CC(=O)c1cnc2ccc(-c3cc(F)c(O)c(Cl)c3)nc2c1Nc1ccc(N2CCC(N(C)C)C2)nc1] | 1-(6-(3-Chloro-5-fluoro-4-hydroxy-phenyl)-4-{6-[3-(dimethylamino)-pyrrolidin-1-yl]pyridin-3-ylamino}-1,5-naphthyridin-3-yl)ethanone trihydrochloride | 521.3 |
| 53 | 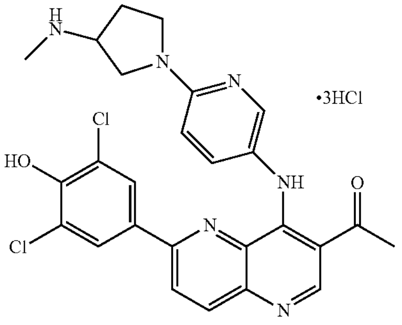 [SMILES: CNC1CCN(c2ccc(Nc3c(C(C)=O)cnc4ccc(-c5cc(Cl)c(O)c(Cl)c5)nc34)cn2)C1] | 1-(6-(3,5-Dichloro-4-hydroxyphenyl)-4-{6-[3-(methylamino)pyrrolidin-1-y]-pyridin-3-ylamino}-1,5-naphthyridin-3-yl) ethanone trihydrochloride | 523.1 |
| 54 | 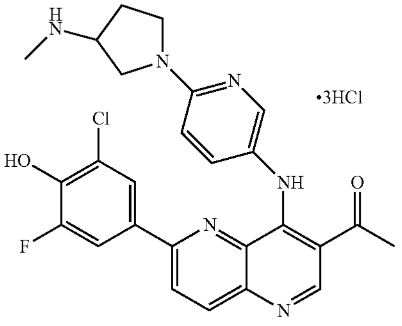 [SMILES: CNC1CCN(c2ccc(Nc3c(C(C)=O)cnc4ccc(-c5cc(F)c(O)c(Cl)c5)nc34)cn2)C1] | 1-(6-(3-Chloro-5-fluoro-4-hydroxy-phenyl)-4-{6-[3-(methylamino)-pyrrolidin-1-yl]pyridin-3-ylamino}-1,5-naphthyridin-3-yl) ethanone trihydrochloride | 507.0 |

TABLE 1-continued

| Example No. | Structure | Name | ESI MS (m/z) |
|---|---|---|---|
| 55 | 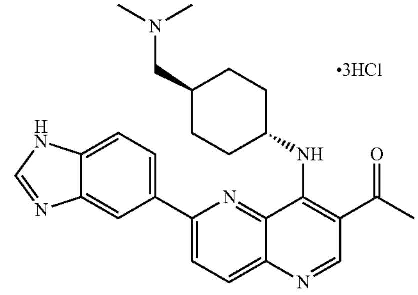 [SMILES: CC(=O)c1cnc2ccc(-c3ccc4[nH]cnc4c3)nc2c1N[C@H]1CC[C@H](CN(C)C)CC1] | 1-(6-(1H-Benzo[d]imidazol-5-yl)-4-{trans-4-[(dimethylamino)methyl]-cyclohexylamino}-1,5-naphthyridin-3-yl)ethanone trihydrochloride | 443.3 |
| 56 | 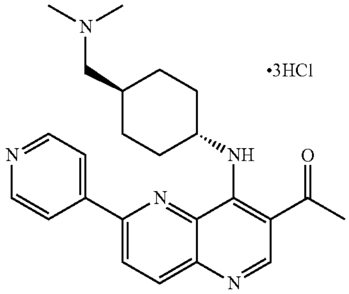 [SMILES: CC(=O)c1cnc2ccc(-c3ccncc3)nc2c1N[C@H]1CC[C@H](CN(C)C)CC1] | 1-{4-[4-(trans-4-Dimethylamino)-methylcyclohexylamino]-6-(pyridin-4-yl)-1,5-naphthyridin-3-yl} ethanone trihydrochloride | 404.2 |
| 57 | 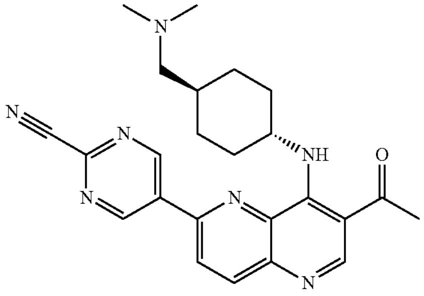 [SMILES: CC(=O)c1cnc2ccc(-c3cnc(C#N)nc3)nc2c1N[C@H]1CC[C@H](CN(C)C)CC1] | 5-(7-Acetyl-8-{trans-4-[(dimethyl-amino)methyl]cyclohexylamino}-1,5-naphthyridin-2-yl)pyrimidine-2-carbonitrile | 430.2 |
| 58 | 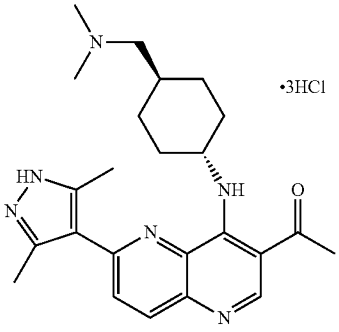 [SMILES: CC(=O)c1cnc2ccc(-c3c(C)n[nH]c3C)nc2c1N[C@H]1CC[C@H](CN(C)C)CC1] | 1-(6-(3,5-Dimethyl-1H-pyrazol-4-yl)-4-{trans-4-[(dimethylamino)methyl]-cyclohexylamino}-1,5-naphthyridin-3-yl)ethanone trihydrochloride | 421.3 |
| 59 | 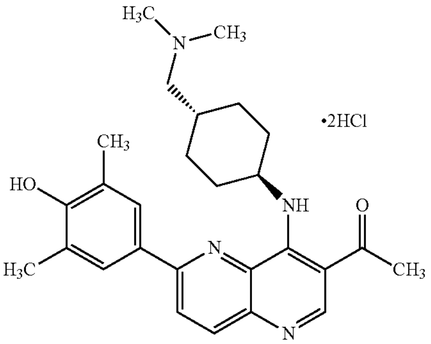 [SMILES: CC(=O)c1cnc2ccc(-c3cc(C)c(O)c(C)c3)nc2c1N[C@H]1CC[C@H](CN(C)C)CC1] | 1-(4-{trans-4-[(Dimethylamino)methyl]-cyclohexylamino}-6-(4-hydroxy-3,5-dimethylphenyl)-1,5-naphthyridin-3-yl) ethanone dihydrochloride | 447.3 |

TABLE 1-continued

| Example No. | Structure | Name | ESI MS (m/z) |
| --- | --- | --- | --- |
| 60 | 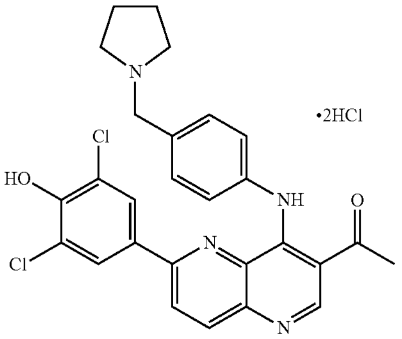 [SMILES: CC(=O)c1cnc2ccc(-c3cc(Cl)c(O)c(Cl)c3)nc2c1Nc1ccc(CN2CCCC2)cc1] •2HCl | 1-(6-(3,5-Dichloro-4-hydroxyphenyl)-4-{6-[3-(dimethylamino)pyrrolidin-1-yl]-pyridin-3-ylamino}-1,5-naphthyridin-3-yl)ethanone dihydrochloride | 507.2 |
| 61 | 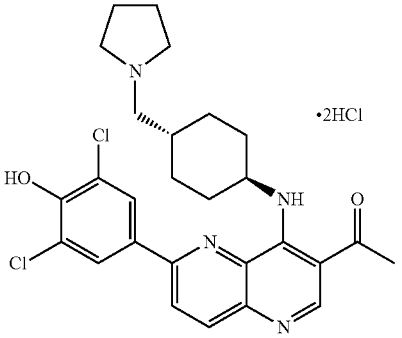 [SMILES: CC(=O)c1cnc2ccc(-c3cc(Cl)c(O)c(Cl)c3)nc2c1N[C@H]1CC[C@H](CN2CCCC2)CC1] •2HCl | 1-{6-(3,5-Dichloro-4-hydroxyphenyl)-4-[trans-4-(pyrrolidin-1-ylmethyl)-cyclohexylamino]-1,5-naphthyridin-3-yl}ethanone dihydrochloride | 513.1 |
| 62 | 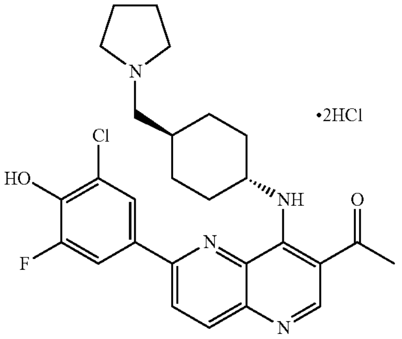 [SMILES: CC(=O)c1cnc2ccc(-c3cc(F)c(O)c(Cl)c3)nc2c1N[C@H]1CC[C@H](CN2CCCC2)CC1] •2HCl | 1-(6-(3-Chloro-5-fluoro-4-hydroxy-phenyl)-4-{[trans-4-(pyrrolidin-1-yl-methyl) cyclohexyl]amino}-1,5-naphthyridin-3-yl)ethanone dihydrochloride | 497.4 |
| 63 | 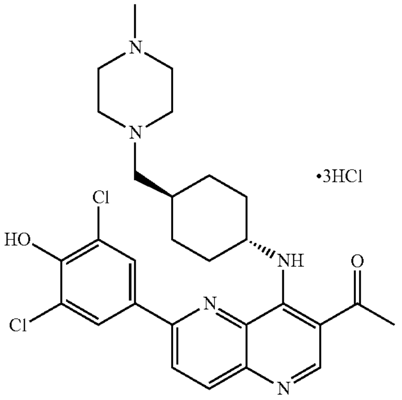 [SMILES: CC(=O)c1cnc2ccc(-c3cc(Cl)c(O)c(Cl)c3)nc2c1N[C@H]1CC[C@H](CN2CCN(C)CC2)CC1] •3HCl | 1-(6-(3,5-Dichloro-4-hydroxyphenyl)-4-{trans-4-[(4-methylpiperazin-1-yl)-methyl]cyclohexylamino}-1,5-naphthyridin-3-yl) ethanone trihydrochloride | 542.2 |

TABLE 1-continued

| Example No. | Structure | Name | ESI MS (m/z) |
|---|---|---|---|
| 64 | 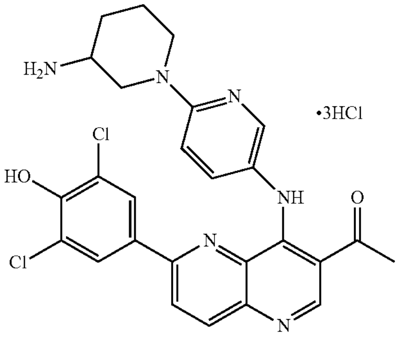 [SMILES: CC(=O)c1cnc2ccc(-c3cc(Cl)c(O)c(Cl)c3)nc2c1Nc1ccc(N2CCCC(N)C2)nc1] •3HCl | 1-(4-{[6-(3-Aminopiperidin-1-yl)pyridin-3-yl]amino}-6-(3,5-dichloro-4-hydroxyphenyl)-1,5-naphthyridin-3-yl) ethanone trihydrochloride | 523.1 |
| 65 | 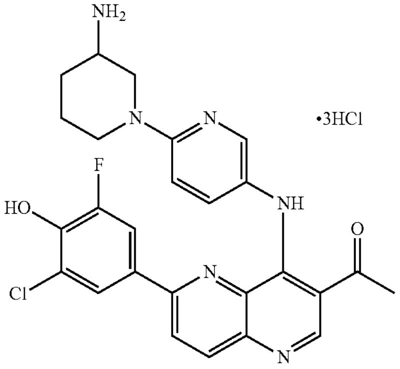 [SMILES: CC(=O)c1cnc2ccc(-c3cc(F)c(O)c(Cl)c3)nc2c1Nc1ccc(N2CCCC(N)C2)nc1] •3HCl | 1-(4-{[6-(3-Aminopiperidin-1-yl)pyridin-3-yl]amino}-6-(3-chloro-5-fluoro-4-hydroxyphenyl)-1,5-naphthyridin-3-yl)ethanone trihydrochloride | 507.0 |
| 66 | 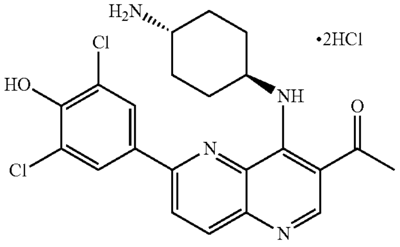 [SMILES: CC(=O)c1cnc2ccc(-c3cc(Cl)c(O)c(Cl)c3)nc2c1N[C@H]1CC[C@H](N)CC1] •2HCl | 1-{4-[trans-(4-Aminocyclohexyl)amino]-6-(3,5-dichloro-4-hydroxyphenyl)-1,5-naphthyridin-3-yl}-ethanone dihydrochloride | 445.1 |
| 67 | 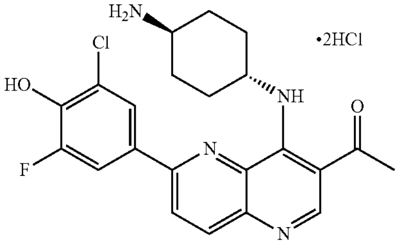 [SMILES: CC(=O)c1cnc2ccc(-c3cc(F)c(O)c(Cl)c3)nc2c1N[C@H]1CC[C@H](N)CC1] •2HCl | 1-{4-[trans-(4-Aminocyclohexyl)amino]-6-(3-chloro-5-fluoro-4-hydroxyphenyl)-1,5-naphthyridin-3-yl}ethanone dihydrochloride | 429.1 |

TABLE 1-continued

| Example No. | Structure | Name | ESI MS (m/z) |
|---|---|---|---|
| 68 | 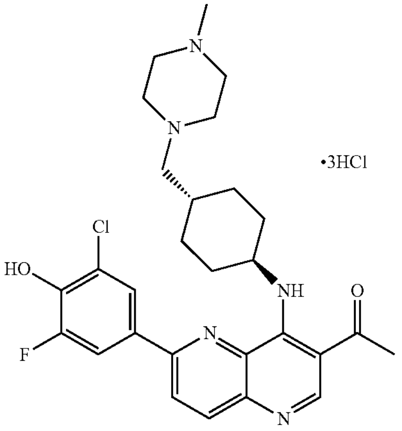 [SMILES: CC(=O)c1cnc2ccc(-c3cc(F)c(O)c(Cl)c3)nc2c1N[C@H]1CC[C@H](CN2CCN(C)CC2)CC1] | 1-(6-(3-Chloro-5-fluoro-4-hydroxy-phenyl)-4-{trans-4-[(4-methylpiperazin-1-yl)methyl]cyclohexylamino}-1,5-naphthyridin-3-yl)ethanone trihydrochloride | 526.3 |
| 69 | 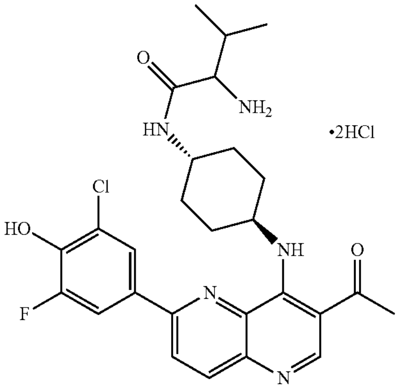 [SMILES: CC(=O)c1cnc2ccc(-c3cc(F)c(O)c(Cl)c3)nc2c1N[C@H]1CC[C@H](NC(=O)C(N)C(C)C)CC1] | N-(trans-4-{[3-Acetyl-6-(3-chloro-5-fluoro-4-hydroxyphenyl)-1,5-naphthyridin-4-yl]amino}-cyclohexyl-2-amino-3-methylbutanamide dihydrochloride | 528.2 |
| 70 | 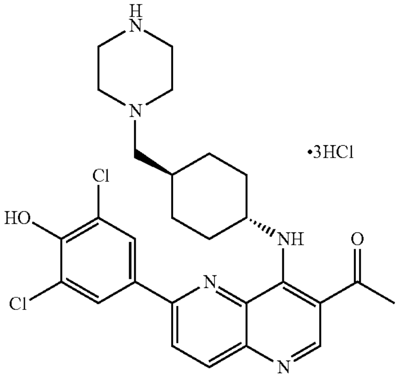 [SMILES: CC(=O)c1cnc2ccc(-c3cc(Cl)c(O)c(Cl)c3)nc2c1N[C@H]1CC[C@H](CN2CCNCC2)CC1] | 1-{6-(3,5-Dichloro-4-hydroxyphenyl)-4-[trans-4-(piperazin-1-ylmethyl)cyclo-hexylamino]-1,5-naphthyridin-3-yl} ethanone trihydrochloride | 528.1 |
| 71 | 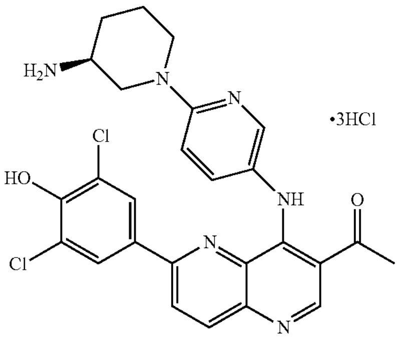 | (S)-1-(4-{[6-(3-Aminopiperidin-1-yl)-pyridin-3-yl]amino}-6-(3,5-dichloro-4-hydroxyphenyl)-1,5-naphthyridin-3-yl)ethanone trihydrochloride | 523.1 |

TABLE 1-continued

| Example No. | Structure | Name | ESI MS (m/z) |
|---|---|---|---|
| 72 | 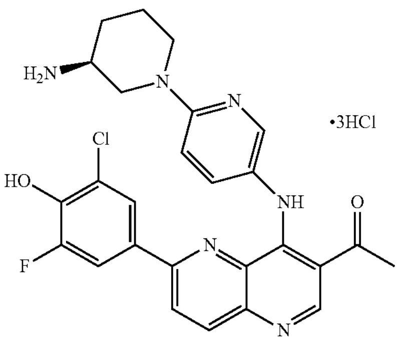 [SMILES: CC(=O)c1cnc2ccc(-c3cc(F)c(O)c(Cl)c3)nc2c1Nc1ccc(N2CCC[C@H](N)C2)nc1] •3HCl | (S)-1-(4-{[6-(3-Aminopiperidin-1-yl)-pyridin-3-yl]amino}-6-(3-chloro-5-fluoro-4-hydroxy-phenyl)-1,5-naphthyridin-3-yl)ethanone trihydrochloride | 507.1 |
| 73 | 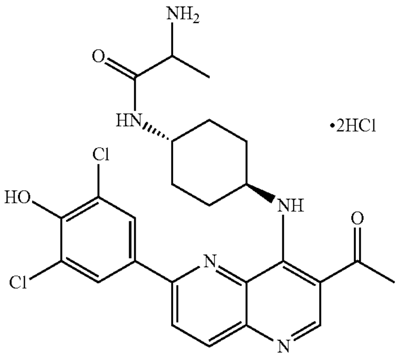 [SMILES: CC(=O)c1cnc2ccc(-c3cc(Cl)c(O)c(Cl)c3)nc2c1N[C@H]1CC[C@H](NC(=O)C(C)N)CC1] •2HCl | N-{trans-4-[3-Acetyl-6-(3,5-dichloro-4-hydroxyphenyl)-1,5-naphthyridin-4-ylamino]-cyclohexyl}-2-aminopropanamide dihydrochloride | 516.1 |
| 74 | 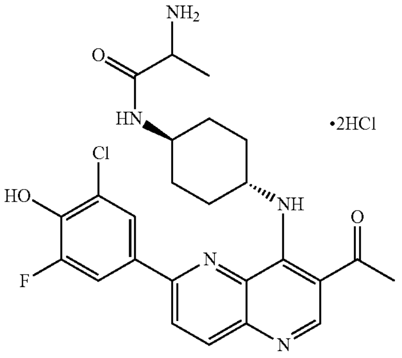 [SMILES: CC(=O)c1cnc2ccc(-c3cc(F)c(O)c(Cl)c3)nc2c1N[C@H]1CC[C@H](NC(=O)C(C)N)CC1] •2HCl | N-{4-[3-Acetyl-6-(3-chloro-5-fluoro-4-hydroxyphenyl)-1,5-naphthyridin-trans-4-ylamino]-cyclohexyl}-2-aminopropanamide dihydrochloride | 500.5 |
| 75 | 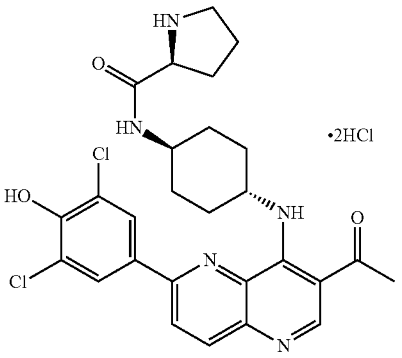 [SMILES: CC(=O)c1cnc2ccc(-c3cc(Cl)c(O)c(Cl)c3)nc2c1N[C@H]1CC[C@H](NC(=O)[C@@H]2CCCN2)CC1] •2HCl | (S)-N-{4-[3-Acetyl-6-(3,5-dichloro-4-hydroxyphenyl)-1,5-naphthyridin-trans-4-ylamino]-cyclohexyl}pyrrolidine-2-carboxamide dihydrochloride | 542.1 |

TABLE 1-continued

| Example No. | Structure | Name | ESI MS (m/z) |
|---|---|---|---|
| 76 | 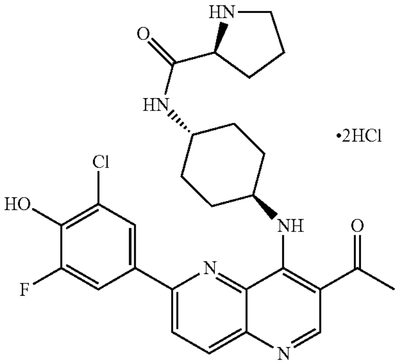 [SMILES: CC(=O)c1cnc2ccc(-c3cc(F)c(O)c(Cl)c3)nc2c1N[C@H]1CC[C@H](NC(=O)[C@@H]2CCCN2)CC1] •2HCl | (S)-N-{4-[3-Acetyl-6-(3-chloro-5-fluoro-4-hydroxyphenyl)-1,5-naphthyridin-trans-4-ylamino]cyclo-hexyl}pyrrolidine-2-carboxamide dihydrochloride | 527.1 |
| 77 | 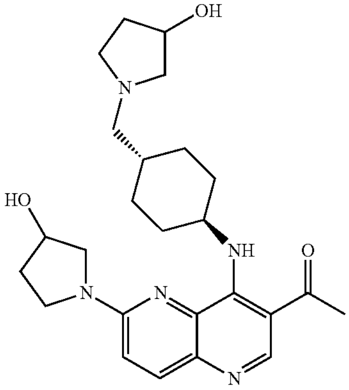 [SMILES: CC(=O)c1cnc2ccc(N3CCC(O)C3)nc2c1N[C@H]1CC[C@H](CN2CCC(O)C2)CC1] | 1-(6-(3-Hydroxypyrrolidin-1-yl)-4-{trans-4-[(3-hydroxypyrrolidin-1-yl)methyl]-cyclohexylamino}-1,5-naphthyridin-3-yl)ethanone | 454.2 |
| 78 | 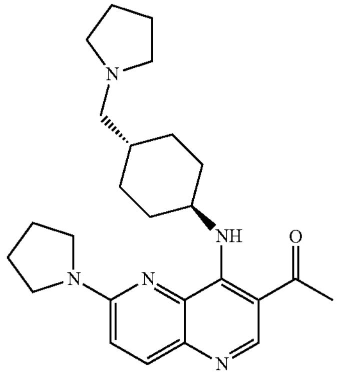 [SMILES: CC(=O)c1cnc2ccc(N3CCCC3)nc2c1N[C@H]1CC[C@H](CN2CCCC2)CC1] | 1-{6-(Pyrrolidin-1-yl)-4-[trans-4-(pyrrolidin-1-ylmethyl)cyclohexyl-amino]-1,5-naphthyridin-3-yl}ethanone | 422.2 |
| 79 | 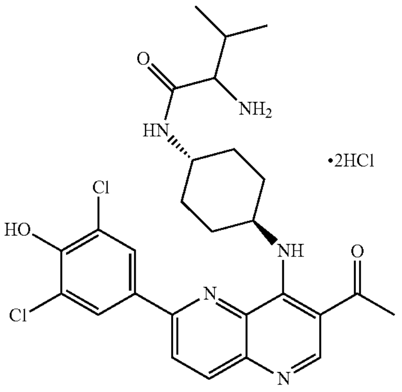 [SMILES: CC(=O)c1cnc2ccc(-c3cc(Cl)c(O)c(Cl)c3)nc2c1N[C@H]1CC[C@H](NC(=O)C(N)C(C)C)CC1] •2HCl | N-{trans-4-[3-Acetyl-6-(3,5-dichloro-4-hydroxyphenyl)-1,5-naphthyridin-4-ylamino]-cyclohexyl}-2-amino-3-methylbutanamide dihydrochloride | 544.1 |

TABLE 1-continued

| Example No. | Structure | Name | ESI MS (m/z) |
|---|---|---|---|
| 80 | 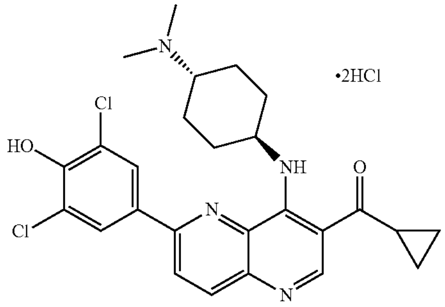 | Cyclopropyl{6-(3,5-dichloro-4-hydroxyphenyl)-4-[trans-4-(dimethylamino)-cyclohexylamino]-1,5-naphthyridin-3-yl}methanone dihydrochloride | 499.1 |
| 81 | 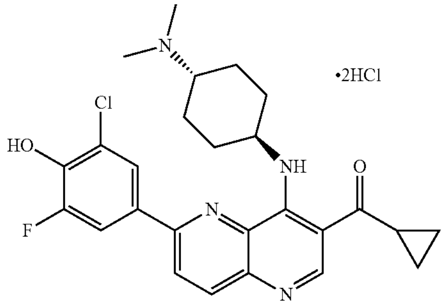 [SMILES: CN(C)[C@H]1CC[C@H](Nc2c(C(=O)C3CC3)cnc3ccc(-c4cc(Cl)c(O)c(Cl)c4)nc23)CC1] | 1-[6-(3-Chloro-5-fluoro-4-methoxyphenyl)-4-{trans-4-[(dimethylamino)methyl]-cyclohexylamino}-1,5-naphthyridin-3-yl]ethanone dihydrochloride | 483.1 |
| 82 | 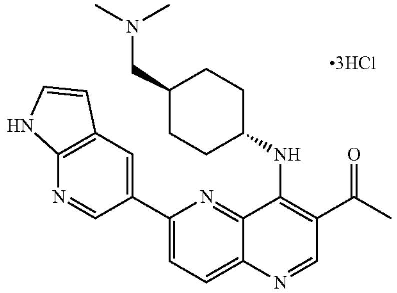 [SMILES: CC(=O)c1cnc2ccc(-c3cnc4[nH]ccc4c3)nc2c1N[C@H]1CC[C@H](CN(C)C)CC1] | 1-(4-{trans-4-[(Dimethylamino)methyl]-cyclohexylamino}-6-(1H-pyrrolo[2,3-b]-pyridin-5-yl)-1,5-naphthyridin-3-yl)ethanone trihydrochloride | 443.2 |
| 83 | 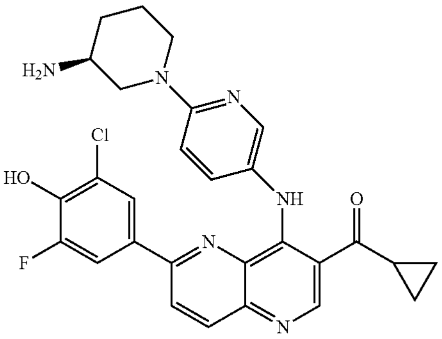 [SMILES: N[C@H]1CCCN(c2ccc(Nc3c(C(=O)C4CC4)cnc4ccc(-c5cc(F)c(O)c(Cl)c5)nc34)cn2)C1] | (S)-{4-[6-(3-Aminopiperidin-1-yl)-pyridin-3-ylamino]-6-(3-chloro-5-fluoro-4-hydroxyphenyl)-1,5-naphthyridin-3-yl}(cyclopropyl) methanone | 533.1 |
| 84 | 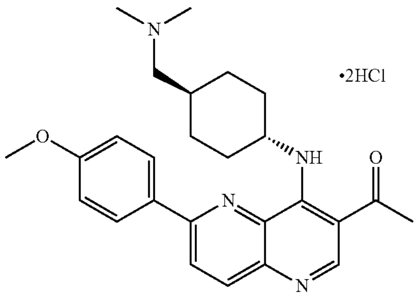 [SMILES: COc1ccc(-c2ccc3ncc(C(C)=O)c(N[C@H]4CC[C@H](CN(C)C)CC4)c3n2)cc1] | 1-(4-{trans-4-[(Dimethylamino)methyl]-cyclohexylamino}-6-(4-methoxyphenyl)-1,5-naphthyridin-3-yl)ethanone dihydrochloride | 433.2 |

TABLE 1-continued

| Example No. | Structure | Name | ESI MS (m/z) |
|---|---|---|---|
| 85 | 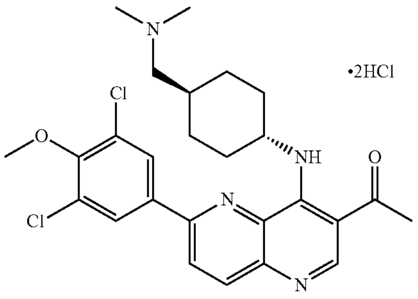 [SMILES: COc1c(Cl)cc(-c2ccc3ncc(C(C)=O)c(N[C@H]4CC[C@H](CN(C)C)CC4)c3n2)cc1Cl] | 1-[6-(3,5-Dichloro-4-methoxyphenyl)-4-{trans-4-[(dimethylamino)methyl]-cyclohexylamino}-1,5-naphthyridin-3-yl]ethanone dihydrochloride | 501.1 |
| 86 | 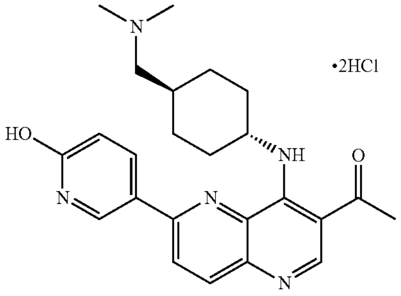 [SMILES: CC(=O)c1cnc2ccc(-c3ccc(O)nc3)nc2c1N[C@H]1CC[C@H](CN(C)C)CC1] | 1-(4-{trans-4-[(Dimethylamino)methyl]-cyclohexylamino}-6-(6-hydroxypyridin-3-yl)-1,5-naphthyridin-3-yl)ethanone dihydrochloride | 420.2 |
| 87 | 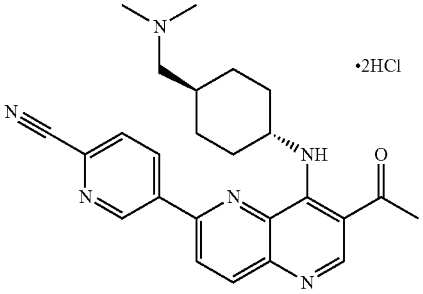 [SMILES: CC(=O)c1cnc2ccc(-c3ccc(C#N)nc3)nc2c1N[C@H]1CC[C@H](CN(C)C)CC1] | 5-(7-Acetyl-8-{trans-4-[(dimethyl-amino)methyl]cyclohexylamino}-1,5-naphthyridin-2-yl)picolinonitrile dihydrochloride | 429.3 |
| 88 | 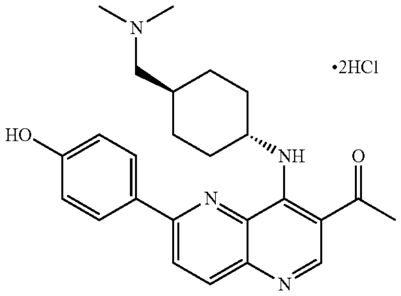 [SMILES: CC(=O)c1cnc2ccc(-c3ccc(O)cc3)nc2c1N[C@H]1CC[C@H](CN(C)C)CC1] | 1-(4-{trans-4-[(Dimethylamino)methyl]-cyclohexylamino}-6-(4-hydroxyphenyl)-1,5-naphthyridin-3-yl)ethanone dihydrochloride | 419.2 |
| 89 | 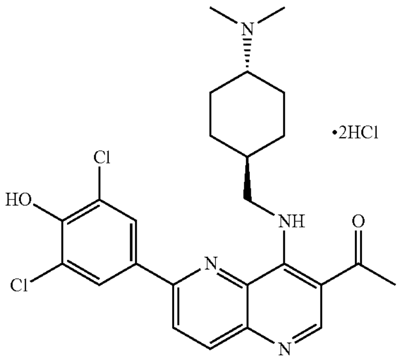 [SMILES: CC(=O)c1cnc2ccc(-c3cc(Cl)c(O)c(Cl)c3)nc2c1NC[C@H]1CC[C@H](N(C)C)CC1] | 1-[6-(3,5-Dichloro-4-hydroxyphenyl)-4-{[trans-4-(dimethylamino)cyclohexyl]-methylamino}-1,5-naphthyridin-3-yl]ethanone dihydrochloride | 487.1 |

TABLE 1-continued

| Example No. | Structure | Name | ESI MS (m/z) |
|---|---|---|---|
| 90 | 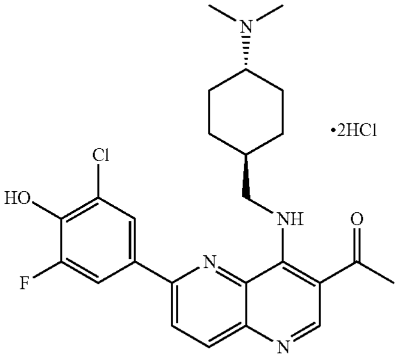 [SMILES: CC(=O)c1cnc2ccc(-c3cc(F)c(O)c(Cl)c3)nc2c1NC[C@H]1CC[C@H](N(C)C)CC1] •2HCl | 1-[6-(3-Chloro-5-fluoro-4-hydroxy-phenyl)-4-{[trans-4-(dimethyl-amino)cyclohexyl]methylamino}-1,5-naphthyridin-3-yl] ethanone dihydrochloride | 471.1 |
| 91 | 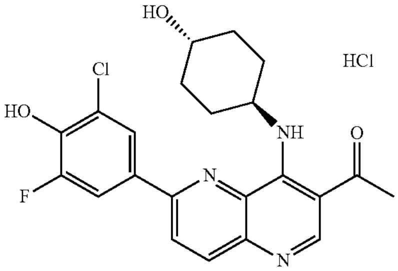 [SMILES: CC(=O)c1cnc2ccc(-c3cc(F)c(O)c(Cl)c3)nc2c1N[C@H]1CC[C@H](O)CC1 ; Cl] HCl | 1-[6-(3,5-Dichloro-4-hydroxyphenyl)-4-(trans-4-hydroxycyclohexylamino)-1,5-naphthyridin-3-yl] ethanone hydrochloride | 430.1 |
| 92 | 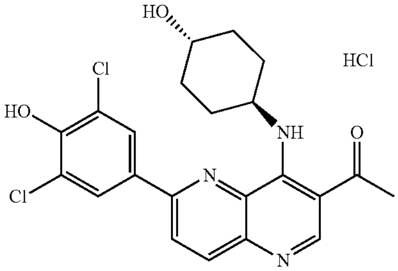 [SMILES: CC(=O)c1cnc2ccc(-c3cc(Cl)c(O)c(Cl)c3)nc2c1N[C@H]1CC[C@H](O)CC1 ; Cl] HCl | 1-[6-(3-Chloro-5-fluoro-4-hydroxy-phenyl)-4-(trans-4-hydroxycyclohexyl-amino)-1,5-naphthyridin-3-yl]ethanone hydrochloride | 446.1 |
| 93 | 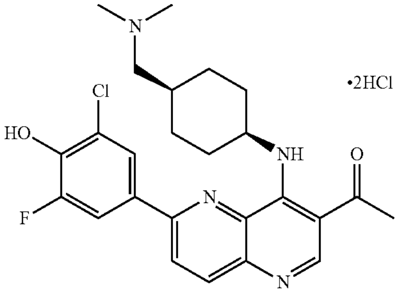 [SMILES: CC(=O)c1cnc2ccc(-c3cc(F)c(O)c(Cl)c3)nc2c1N[C@H]1CC[C@@H](CN(C)C)CC1 ; "·2HCl"] •2HCl | 1-{6-(3-Chloro-5-fluoro-4-hydroxyphenyl)-4-({cis-4-[(dimethylamino)methyl] cyclohexyl}-amino)-1,5-naphthyridin-3-yl}ethanone dihydrochloride | 471.2 |
| 94 | 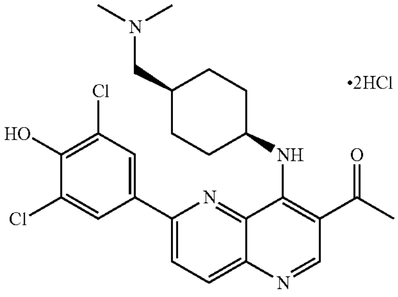 [SMILES: CC(=O)c1cnc2ccc(-c3cc(Cl)c(O)c(Cl)c3)nc2c1N[C@H]1CC[C@@H](CN(C)C)CC1 ; "·2HCl"] •2HCl | 1-{6-(3,5-Dichloro-4-hydroxyphenyl)-4-({cis-4-[(dimethylamino)methyl]-cyclohexyl}amino)-1,5-naphthyridin-3-yl}ethanone dihydrochloride | 487.1 |

TABLE 1-continued

| Example No. | Structure | Name | ESI MS (m/z) |
|---|---|---|---|
| 95 | 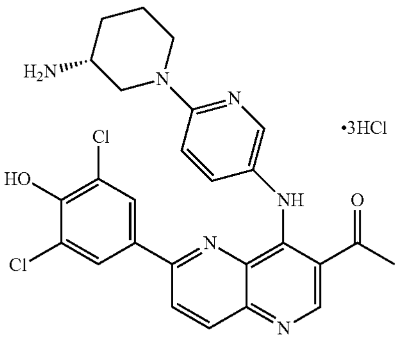 [SMILES: CC(=O)c1cnc2ccc(-c3cc(Cl)c(O)c(Cl)c3)nc2c1Nc1ccc(N2CCC[C@@H](N)C2)nc1 ; "·3HCl"] | (R)-1-{4-[6-(3-Aminopiperidin-1-yl)pyridin-3-ylamino]-6-(3,5-dichloro-4-hydroxyphenyl)-1,5-naphthyridin-3-yl}ethanone trihydrochloride | 523.3 |
| 96 | 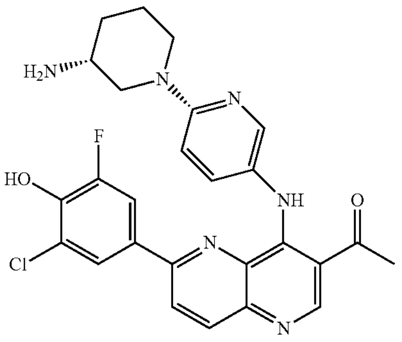 | (R)-1-{4-[6-(3-Aminopiperidin-1-yl)-pyridin-3-ylamino]-6-(3-chloro-5-fluoro-4-hydroxyphenyl)-1,5-naphthyridin-3-yl}ethanone | 507.1 |
| 201 | 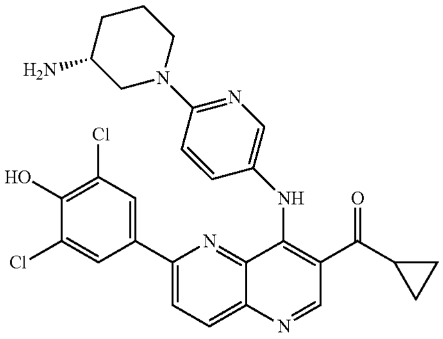 [SMILES: N[C@@H]1CCCN(c2ccc(Nc3c(C(=O)C4CC4)cnc4ccc(-c5cc(Cl)c(O)c(Cl)c5)nc34)cn2)C1] | (R)-(4-{[6-(3-aminopiperidin-1-yl)pyridin-3-yl]amino}-6-(3,5-dichloro-4-hydroxyphenyl)-1,5-naphthyridin-3-yl) (cyclopropyl)methanone | 549.1 |
| 202 | 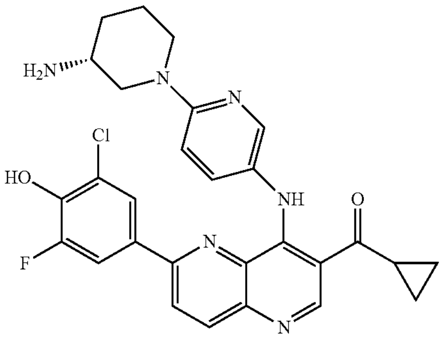 [SMILES: N[C@@H]1CCCN(c2ccc(Nc3c(C(=O)C4CC4)cnc4ccc(-c5cc(F)c(O)c(Cl)c5)nc34)cn2)C1] | (R)-(4-{[6-(3-aminopiperidin-1-yl) pyridin-3-yl]amino}-6-(3-chloro-5-fluoro-4-hydroxyphenyl)-1,5-naphthyridin-3-yl) (cyclopropyl) methanone | 533.1 |

TABLE 1-continued

| Example No. | Structure | | Name | ESI MS (m/z) |
|---|---|---|---|---|
| 203 | 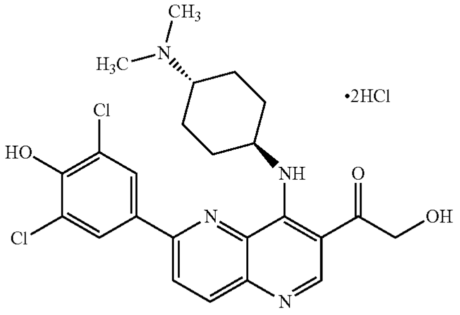 [SMILES: CN(C)[C@H]1CC[C@H](Nc2c(C(=O)CO)cnc3ccc(-c4cc(Cl)c(O)c(Cl)c4)nc23)CC1] | •2HCl | 1[6-(3,5-dichloro-4-hydroxyphenyl)-4-{[trans-4-(dimethylamino)cyclohexyl] amino}-1,5-naphthyridin-3-yl)-2-hydroxyethanone dihydrochloride | 489.1 |
| 204 | 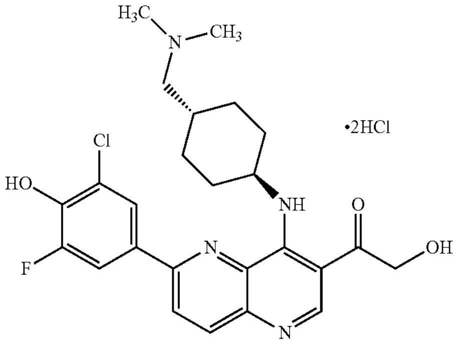 [SMILES: CN(C)C[C@H]1CC[C@H](Nc2c(C(=O)CO)cnc3ccc(-c4cc(F)c(O)c(Cl)c4)nc23)CC1] | •2HCl | 1-[6-(3-chloro-5-fluoro-4-hydroxyphenyl)-4-({trans-4-[(dimethylamino)methyl]cyclohexyl} amino)-1,5-naphthyridin-3-yl)]-2-hydroxyethanone dihydrochloride | 487.2 |
| 205 | 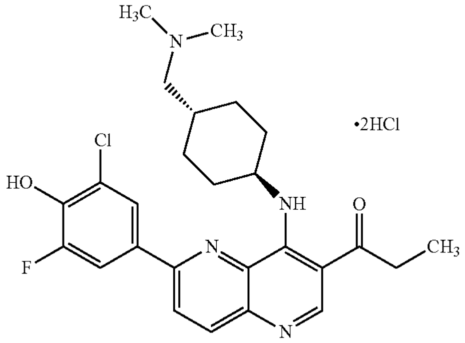 [SMILES: CCC(=O)c1cnc2ccc(-c3cc(F)c(O)c(Cl)c3)nc2c1N[C@H]1CC[C@H](CN(C)C)CC1] | •2HCl | 1-[6-(3-chloro-5-fluoro-4-hydroxyphenyl)-4-({trans-4-[(dimethylamino)methyl] cyclohexyl} amino)-1,5-naphthyridin-3-yl)]propan-1-one dihydrochloride | 484.5 |
| 206 | 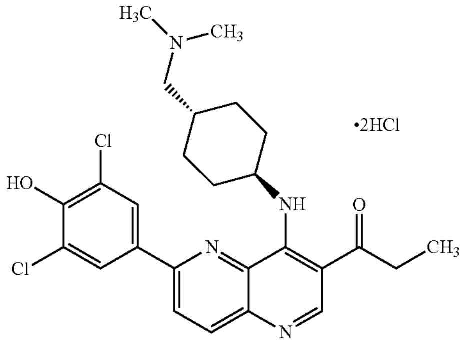 [SMILES: CCC(=O)c1cnc2ccc(-c3cc(Cl)c(O)c(Cl)c3)nc2c1N[C@H]1CC[C@H](CN(C)C)CC1] | •2HCl | 1-[6-(3,5-dichloro-4-hydroxyphenyl)-4-({trans-4-[(dimethylamino)methyl] cyclohexyl}amino)-1,5-naphthyridin-3-yl)]propan-1-one dihydrochloride | 501.2 |

TABLE 1-continued

| Example No. | Structure | Name | ESI MS (m/z) |
| --- | --- | --- | --- |
| 207 | 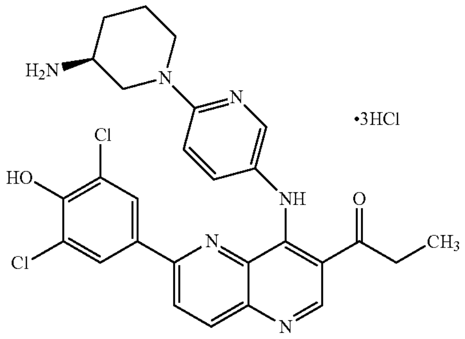 [SMILES: CCC(=O)c1cnc2ccc(-c3cc(Cl)c(O)c(Cl)c3)nc2c1Nc1ccc(N2CCC[C@H](N)C2)nc1] | (S)-1-(4-{[6-(3-aminopiperidin-1-yl)pyridin-3-yl]amino}-6-(3,5-dichloro-4-hydroxyphenyl)-1,5-naphthyridin-3-yl)propan-1-one trihydrochloride | 537.0 |
| 208 | 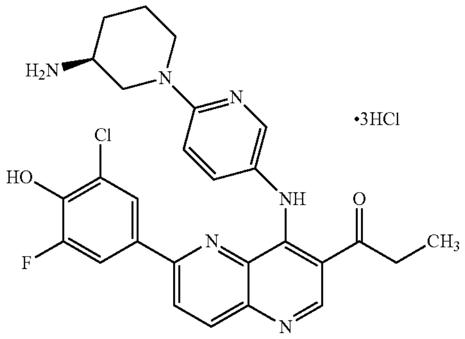 [SMILES: CCC(=O)c1cnc2ccc(-c3cc(F)c(O)c(Cl)c3)nc2c1Nc1ccc(N2CCC[C@H](N)C2)nc1] | (S)-1-(4{[6-(3-aminopiperidin-1-yl)pyridin-3-yl]amino}-6-(3-chloro-5-fluoro-4-hydroxyphenyl)-1,5-naphthyridin-3-yl)propan-1-one trihydrochloride | 521.0 |
| 209 | 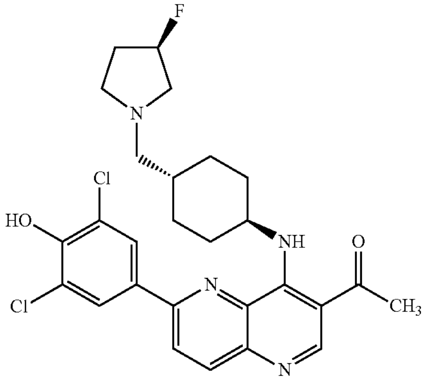 [SMILES: CC(=O)c1cnc2ccc(-c3cc(Cl)c(O)c(Cl)c3)nc2c1N[C@H]1CC[C@H](CN2CC[C@@H](F)C2)CC1] | 1-[6-(3,5-dichloro-4-hydroxyphenyl)-4-({4-[((R)-3-fluoropyrrolidin-1yl)methyl] cyclohexyl}amino)-1,5-naphthyridin-3-yl]ethanone dihydrochloride | 531.0 |
| 210 | 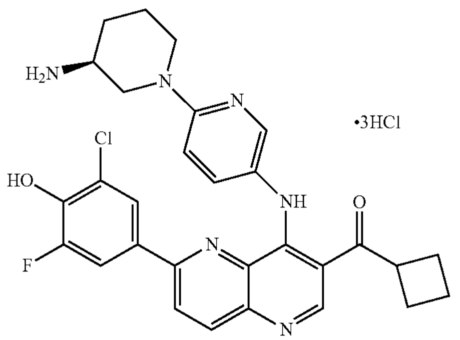 [SMILES: N[C@H]1CCCN(c2ccc(Nc3c(C(=O)C4CCC4)cnc4ccc(-c5cc(F)c(O)c(Cl)c5)nc34)cn2)C1] | (S)-(4-((6-(3-aminopiperidin-1-yl)pyridin-3-yl)amino)-6-(3-chloro-5-fluoro-4-hydroxyphenyl)-1,5-naphthyridin-3-yl)(cyclobutyl)methanone dihydrochloride | 547.2 |

TABLE 1-continued

| Example No. | Structure | Name | ESI MS (m/z) |
|---|---|---|---|
| 211 | 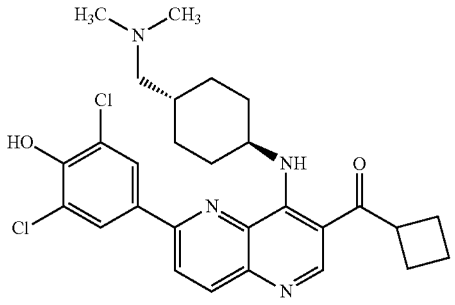 | (6-(3,5-dichloro-4-hydroxyphenyl)-4-((4-[(dimethylamino)methyl{cyclohexyl) amino)-1,5-naphthyridin-3-yl) (cyclobutyl)methanone dihydrochloride | 527.1 |
| 212 | 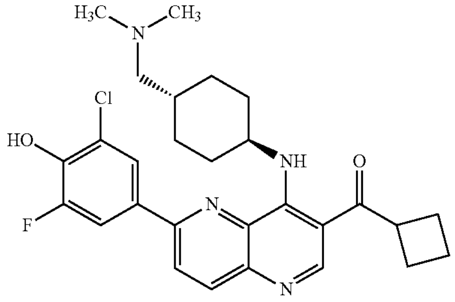 | (6-(3-chloro-5-fluoro-4-hydroxyphenyl)-4-((4-((dimethylamino)methyl) cyclo hexyl) amino)-1,5-naphthyridin-3-yl)(cyclobutyl)methanone dihydrochloride | 511.1 |
| 213 | 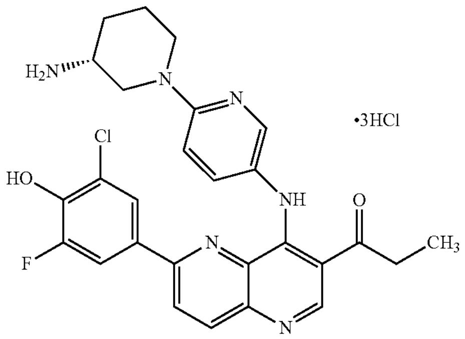 [SMILES: CCC(=O)c1cnc2ccc(-c3cc(F)c(O)c(Cl)c3)nc2c1Nc1ccc(N2CCC[C@@H](N)C2)nc1] •3HCl | (S)-(4-{[6-(3-aminopiperidin-1-yl)pyridin-3-yl]amino}-6-(3-chloro-5-fluoro-4-hydroxyphenyl)-1,5-naphthyridin-3-yl)(cyclobutyl)methanone | 521.0 |
| 214 | 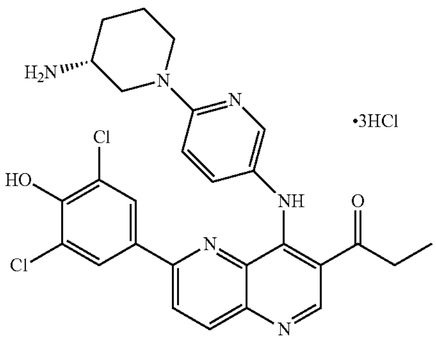 [SMILES: CCC(=O)c1cnc2ccc(-c3cc(Cl)c(O)c(Cl)c3)nc2c1Nc1ccc(N2CCC[C@@H](N)C2)nc1] •3HCl | (R)-1-(4-((6-(3-aminopiperidin-1-yl)pyridin-3-yl)amino)-6-(3,5-dichloro-4-hydroxyphenyl)-1,5-naphthyridin-3-yl)propan-1-one trihydrochloride | 537.0 |

TABLE 1-continued

| Example No. | Structure | Name | ESI MS (m/z) |
|---|---|---|---|
| 215 | 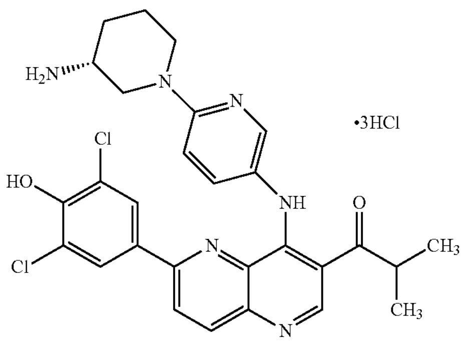 [SMILES: CC(C)C(=O)c1cnc2ccc(-c3cc(Cl)c(O)c(Cl)c3)nc2c1Nc1ccc(N2CCC[C@@H](N)C2)nc1] | (R)-1-(4-{[6-(3-aminopiperidin-1-yl)pyridin-3-yl]amino}-6-(3,5-dichloro-4-hydroxyphenyl)-1,5-naphthyridin-3-yl)-2-methylpropan-1-one trihydrochloride | 535.1 |
| 216 | 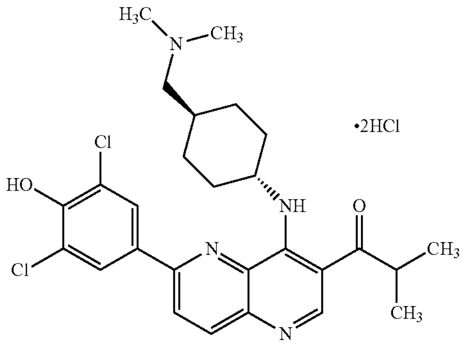 [SMILES: CC(C)C(=O)c1cnc2ccc(-c3cc(Cl)c(O)c(Cl)c3)nc2c1N[C@H]1CC[C@H](CN(C)C)CC1] | 1-[6-(3,5-dichloro-5-4-hydroxyphenyl)-4-({trans-4-[(dimethylamino)methyl]cyclohexyl}amino)-1,5-naphthyridin-3-yl]-2-methylpropan-1-one dihydrochloride | 515.1 |
| 217 | 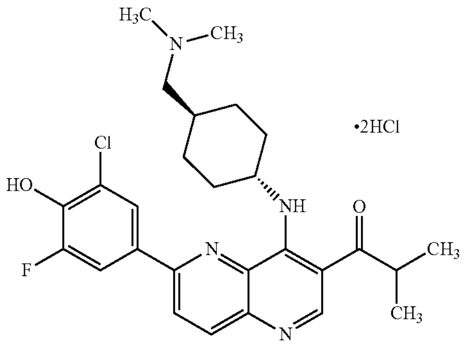 | 1-[6-chloro-4-({trans-4-[(dimethylamino)methyl]cyclohexyl}amino)-1,5-naphthyridin-3-yl]-2-methylpropan-1-one dihydrochloride | 498.9 |

Compound (I) and pharmaceutically acceptable salts thereof may be administered singly as they are; however, ordinarily, they are desirably provided as various types of pharmaceutical formulations. Such pharmaceutical formulations are used for animals or humans.

Pharmaceutical formulations of the present invention may comprise as an active ingredient compound (I) or a pharmaceutically acceptable salt thereof alone, or a mixture with any other active ingredients for treatment. Furthermore, these pharmaceutical formulations are produced by any methods well known in the technical field of drug formulation by mixing the active ingredient together with one or more types of pharmaceutically acceptable carriers (for example, diluents, solvents, and excipients).

Desirably, the route of administration most effective for the treatment is used, and examples include oral route, or parenteral route such as intravenous route.

The form of administration is, for example, tablets and injections.

Tablets are appropriate for oral administration and can be produced using excipients such as lactose, disintegrants such as starch, lubricants such as magnesium stearate, and binders such as hydroxypropylcellulose.

Injections are appropriate for parenteral administration, and can be produced using, for example, solvents or diluents such as salt solutions, glucose solutions, or a mixture of salt water and glucose solution.

The dose of compound (I) or a pharmaceutically acceptable salt thereof, and the number of doses differ depending on the form of administration, the age and body weight of the patient, the nature of the symptom to be treated or severity, and such, but ordinarily for oral administration, it is 0.01 mg to 1000 mg, preferably in the range of 0.05 mg to 100 mg for an adult, and it is administered once to several times a day. In the case of parenteral administration such as intravenous administration, 0.001 mg to 1000 mg, or preferably 0.01 mg to 100 mg is administered to an adult once to several times a day. However, these doses and the number of doses vary depending on the various conditions mentioned above.

General methods for producing the above-mentioned compounds will be indicated below.

Scheme 1

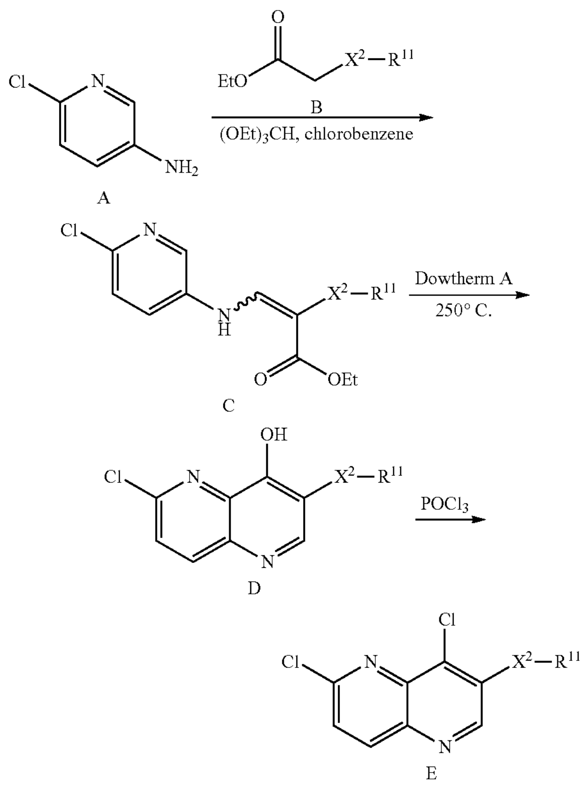

The formula —$X^2$—$R^{11}$ is defined hereinbefore, such as ($C_1$-$C_6$ alkyl)carbonyl, ($C_3$-$C_{10}$ cycloalkyl)carbonyl, ($C_1$-$C_6$ alkyl)sulfonyl, and ($C_3$-$C_{10}$ cycloalkyl)sulfonyl, wherein the alkylcarbonyl, cycloalkyl)carbonyl, alkylsulfonyl, and cycloalkylsulfonyl are optionally substituted with one or more harogen atoms. Specific examples of —$X^2$—$R^{11}$ include acetyl, ethylcarbonyl, cyclopropylcarbonyl, methylsulfonyl, ethylsulfonyl, cyclopropylsulfonyl, chloroacetyl, 1-chloroethylcarbonyl, 2-chloroethylcarbonyl, chlorocyclopropylcarbonyl, chloromethylsulfonyl, 1-chloroethylsulfonyl, 2-chloroethylsulfonyl, and chlorocyclopropylsulfonyl.

The 2-chloro-5-aminopyridine A is converted by heating in the presence of ester B and triethyl orthoformate to the condensation product C as a mixture of olefin isomers (Scheme 1). Various esters that are commercially available, known in the literature or prepared using known literature procedures are applicable to the reaction. Intermediate C is added to hot Dowtherm™ A to facilitate the ring closure and to afford the 1,5-naphthyridine D. Treatment of D with phosphorus oxychloride affords the key intermediate E (Scheme 1).

Scheme 2

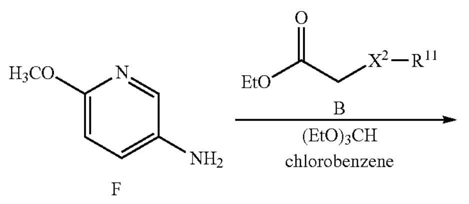

-continued

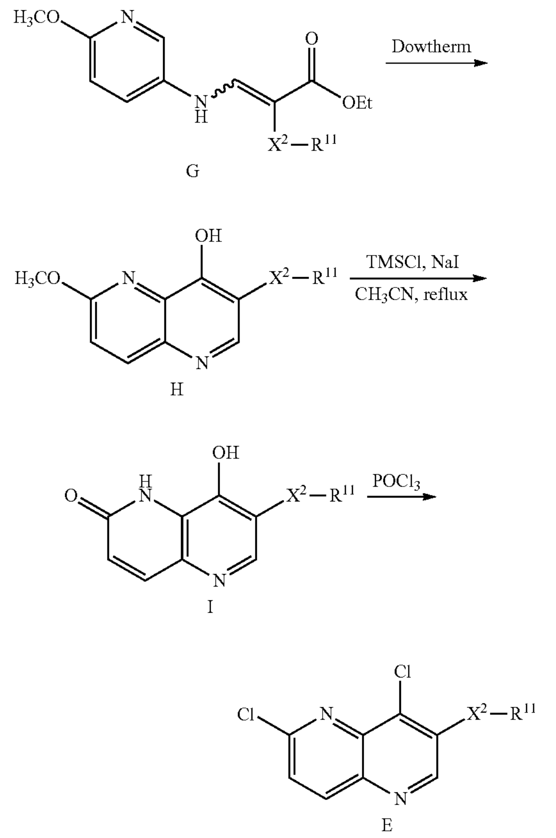

An alternative synthetic sequence to obtain the key intermediate E is described in Scheme 2. Commercially available 2-methoxy-5-aminopyridine F is converted by heating in the presence of ester B and triethyl orthoformate to the condensation product G as a mixture of olefin isomers (Scheme 2). Intermediate G is added to hot Dowtherm™ A to facilitate the ring closure and to yield the 1,5-naphthyridine H. Demethylation at the 6-position of H is conducted by treatment with trimethylsilyl chloride and sodium iodide in refluxing acetonitrile to give intermediate I, which may be used, without purification, for the reaction with phosphorus oxychloride to provide the key intermediate E (Scheme 2).

Scheme 3

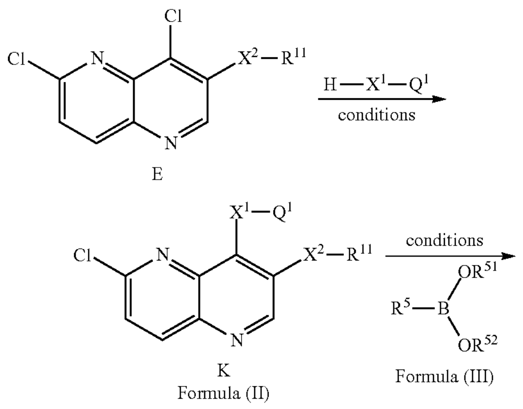

-continued

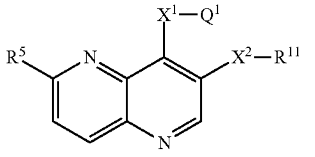

Formula (I)

The formula —$X^1$-$Q^1$ is defined hereinbefore, such as $C_5$-$C_7$ cycloalkylamino, phenylamino, pyridylamino, pyrazolylamino, pyrimidinylamino, piperidyl amino, pyrroliddin-1-yl, piperidin-1-yl, piperazin-1-yl, and morpholin-1-yl, which are optionally substituted with one or more substitutents independently selected from $A^1$ as defined hereinbefore.

The formula —$R^5$ as defined hereinbefore other than a halogen atom, such as $C_3$-$C_{10}$ cycloalkyl, $C_6$-$C_{10}$ aryl, 5- to 10-membered heteroaryl, and 3- to 10-membered non-aromatic heterocyclyl; wherein the cycloalkyl, aryl, heteroaryl, and heterocyclyl are optionally substituted with one or more substituents independently selected from $A^3$ as defined hereinbefore. Specific examples of $R^5$ include phenyl substituted with one or three substituents independently selected from $A^3$, such as 3,5-dichloro-4-hydroxyphenyl, 3,5-difluoro-4-hydroxyphenyl, and 3-chloro-5-fluoro-4-hydroxyphenyl.

The preparation of the target compounds is described in Scheme 3. Intermediate E is reacted at the 4-position with a compound defined as H—$X^1$-$Q^1$ to introduce a substituent indicated as $X^1$-$Q^1$. The resulting intermediate K, which belongs to compounds categorized by Formula (II), is reacted at the 6-position with $R^5$—B($OR^{51}$)$OR^{52}$, a compound categorized by Formula (III) to introduce a substituent indicated as $R^5$.

belonging to Formula (I). Various boronate esters that are commercially available, known in the literature or prepared using known literature procedures are applicable to the reaction. In scheme 4, the boronate ester N is prepared by reacting an aryl bromide M with bis(pinacolato)diboron in the presence of an organopalladium to provide compounds belonging to Formula (I). If necessary, a protecting group removal is conducted after the Suzuki reaction to obtain the target compound.

In Scheme 4, $A^3$ represents a optional substituent on the benzene ring as defined hereinbefore, and m represents an integer selected from 0 to 5, preferably selected from 1 to 3.

The intermediates and compounds of interest in the following Examples can be isolated and purified by subjecting them to separation and purification methods commonly used in synthetic organic chemistry unless otherwise specified, and examples include filtration, extraction, washing, drying, concentration, recrystallization, and various types of chromatographies. Alternatively, intermediates can be subjected to the next reaction without purification.

Hereinbelow, the present invention will be specifically described with reference to the Examples, but the scope of the present invention is not to be construed as being limited thereto.

Furthermore, in the Examples shown below, unless otherwise specified, if a defined group becomes altered under the conditions of the production method or is unsuitable for carrying out the method, the compound of interest can be produced by using the methods for introducing and removing protecting groups commonly used in synthetic organic chemistry (for example, "Protective Groups in Organic Synthesis", T. W. Greene, John Wiley & Sons Inc., 1999). Furthermore, the order of the reaction processes such as substituent introduction can be changed as necessary.

Scheme 4

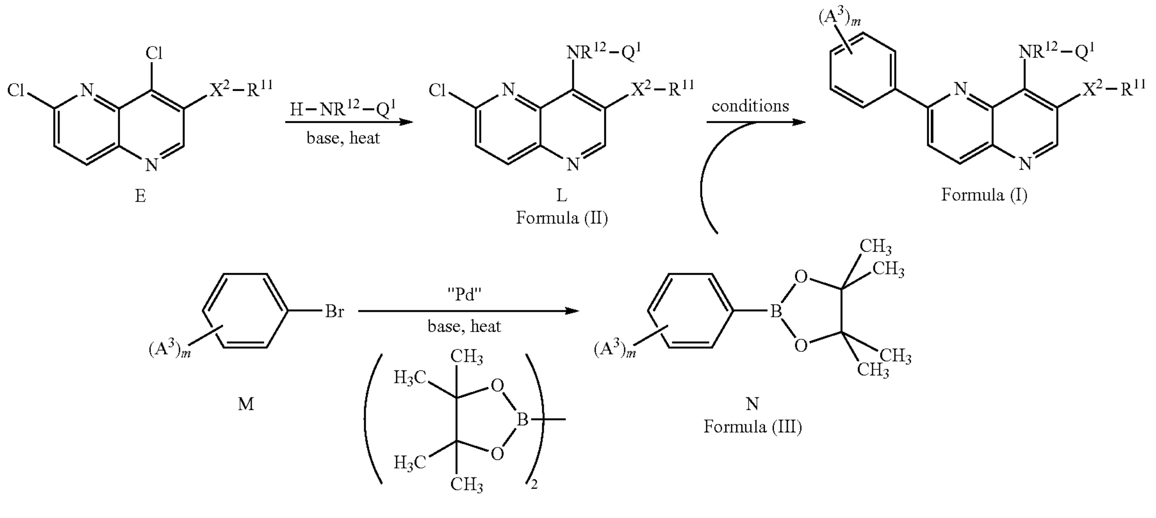

E, L Formula (II), Formula (I), M, N Formula (III)

To introduce an amino group at the 4-position of the 1,5-naphthyridine ring, E is heated with an appropriate amine in the presence of base to afford intermediate L, belonging to Formula (II) (Scheme 4). Various amines that are commercially available, known in the literature or prepared using known literature procedures are applicable to the reaction. Intermediate L is subjected to a standard Suzuki cross-coupling reaction with a boronate ester N to provide compounds

EXAMPLES

General Procedure I (Substitution at the 4-Position)

To a suspension of intermediates E (1.0 equiv) in dioxane or a mixture of dioxane and DMF (2:1) was added the requisite amine (1.0-2.0 equiv), N,N-diisopropylethylamine (2.0-5.0 equiv) and finely ground $K_2CO_3$ (2.0-3.0 equiv) and the reaction mixture was stirred with heat between 60-100° C. for 16 h or until E was consumed (monitored by LCMS analysis). The reaction mixture was cooled, diluted with satd. aq. sodium bicarbonate and extracted with ethyl acetate. The combined organic layer was dried over anhydrous sodium sulfate, filtered and the filtrate was concentrated. The residue was purified by column chromatography (silica, methanol/dichloromethane) to afford the desired product L.

General Procedure II (Substitution at the 6-Position)

To a suspension of intermediate L (1.0 equiv), the requisite boronic ester (1.5-2.0 equiv) and $Pd(dppf)Cl_2$ (0.1-0.2 equiv) in dioxane (0.1-0.2 M) was added $Cs_2CO_3$ (1.0 M in $H_2O$, 3.0-4.0 eq). The reaction mixture was degassed with nitrogen and stirred with heat at 80° C. for 2-24 h. The reaction mixture was cooled, poured onto satd. aq. sodium bicarbonate and extracted with 3:1 chloroform/isopropanol. The combined organic layers were dried over anhydrous sodium sulfate, filtered and the filtrate was concentrated. The residue was purified by chromatography (normal phase silica using methanol/dichloromethane or reverse phase silica using water/acetonitrile containing 0.025% TFA) to afford the target compound. In some instances the product was diluted in methanol followed by the addition of excess HCl (2.0-5.0 equiv as a solution in ether, methanol, dioxane or water). After 5 min the mixture was concentrated to dryness to obtain the HCl salt of the target compound.

General Procedure III (Synthesis of Boronic Esters)

To a suspension of the appropriate aryl bromide (1.0 equiv), bis(pinacolado)diboron (1.5-2.0 equiv) and KOAc (2.0-3.0 equiv) in dioxane (0.1-0.2 M) was added Pd(dppf) $Cl_2$ (0.05-0.1 equiv). The reaction mixture was degassed with nitrogen followed by stirring with heat at 80° C. for 2-16 h. The reaction mixture was cooled, filtered, and the filtrate was concentrated. The residue was purified by chromatography (silica, ethyl acetate/hexanes) to afford the desired product M.

General Procedure IV-1 (Boc-Deprotection Protocol)

To a solution of Boc-protected compound in THF, methanol or methanol/methylene chloride (0.1 M) was added excess HCl (2.0-5.0 equiv as a solution in ether, methanol, dioxane or water). The reaction was stirred at room temperature or with heat (50-70° C.) and upon completion (monitored by LCMS analysis) the reaction mixture was concentrated to obtain the HCl salt of the target compound.

General Procedure IV-2 (Boc-Deprotection Protocol)

To a solution of Boc-protected compound in THF was added excess TFA (2.0-10 equiv) and the reaction mixture was stirred at room temperature or with heat (50-70° C.) until the reaction was complete (monitored by LCMS analysis). The reaction mixture was concentrated and the residue was diluted in methanol followed by the addition of excess HCl (2.0-5.0 equiv as a solution in ether, methanol, dioxane or water). After 5 min the mixture was concentrated to dryness to obtain the HCl salt of the target compound.

General Procedure V

To a solution of {4-[(3-acetyl-6-chloro-1,5-naphthyridin-4-yl)amino]cyclohexyl}methyl methanesulfonate (1.0 mmol) in a mixture of 1,4-dioxane and N,N-dimethylformamide (2:1) was added the requisite amine (2.0-4.0 equiv), triethyl amine or N,N-diisopropylethylamine (2.0-3.0 equiv) and potassium iodide (cat.) and the reaction mixture was stirring with heat at 85° C. for 18 h. The reaction mixture was cooled and diluted with water and ethyl acetate. The layers were separated and the ethyl acetate layer was dried over sodium sulfate, filtered and the filtrate was concentrated. The residue was purified by chromatography (silica, hexanes or methylene chloride/ethyl acetate) to afford the desired product.

General Procedure VI

To a solution of 1-(4-((4-aminocyclohexyl)amino)-6-chloro-1,5-naphthyridin-3-yl)ethanone hydrochloride (1.0 mmol) in DMF (0.1 M) was added the requisite amino acid (1.2 mmol), diisopropylethylamine (5.0 equiv) and HATU (2-(7-Aza-1H-benzotriazole-1-yl)-1,1,3,3-tetramethyluronium hexafluorophosphate) (1.2 equiv) and the reaction mixture was stirred at room temperature for 18 h. The reaction mixture was diluted with water and ethyl acetate. The layers were separated and the ethyl acetate layer was dried over sodium sulfate, filtered and the filtrate was concentrated. The residue was purified by chromatography (silica, hexanes or methylene chloride/ethyl acetate) to afford the desired product.

Regarding the retention time indicated as $t_R$, HPLC analysis was performed under the following condition:

Column: Gemini-NX™ C18 column 150×4.6 mm, 5 micro 100 A (Phenomenex);
Mobile phase: [Eluent A] water w/0.05% $CF_3COOH$; [Eluent B] acetonitrile w/0.05% $CF_3COOH$;
Flow rate: 1 mL/min
Temperature: ambient
Detection wavelength: 223 nm or 254 nm
Gradient operation:

| Time | $H_2O$ w/0.05% $CF_3COOH$ | Acetonitrile w/0.05% $CF_3COOH$ |
|---|---|---|
| 00 min | 98% | 2% |
| 18 min | 10% | 90% |
| 21 min | 10% | 90% |
| 23 min | 98% | 2% |

Example 1

1-(6-Chloro-4-{trans-4-[(dimethylamino)methyl]cyclohexylamino}-1,5-naphthyridin-3-yl)-ethanone

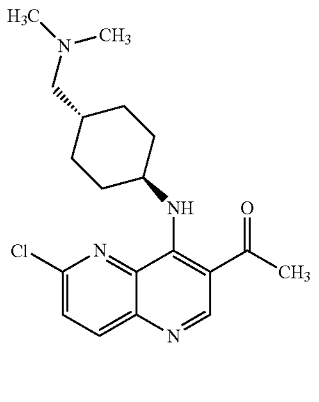 [SMILES: CC(=O)c1cnc2ccc(Cl)nc2c1N[C@H]1CC[C@H](CN(C)C)CC1]

Following general procedure I, 1-(4,6-dichloro-1,5-naphthyridin-3-yl)ethanone (360 mg, 1.5 mmol) was reacted with trans-4-[(dimethylamino)methyl]cyclohexanamine diacetic acid salt (500 mg, 1.8 mmol) to afford the desired product (340 mg, 63%) as a yellow solid: $^{1}$H NMR (500 MHz, $CDCl_3$) δ 10.89 (s, 1H), 8.93 (s, 1H), 8.07 (d, J=8.6 Hz, 1H), 7.51 (d, J=8.6 Hz, 1H), 5.16-4.96 (m, 1H), 2.67 (s, 3H), 2.34-2.24 (m, 2H), 2.22 (s, 6H), 2.14 (d, J=7.1 Hz, 2H), 1.98-1.89 (m, 2H), 1.56-1.47 (m, 1H), 1.41-1.32 (m, 2H), 1.28-1.10 (m, 2H); ESI MS m/z 361 $[M+H]^+$; HPLC 98.8% (AUC), $t_R$=8.42 min.

Example 2

1-{6-(3,5-Dichloro-4-hydroxyphenyl)-4-[trans-4-(dimethylamino)cyclohexylamino]-1,5-naphthyridin-3-yl}ethanone dihydrochloride

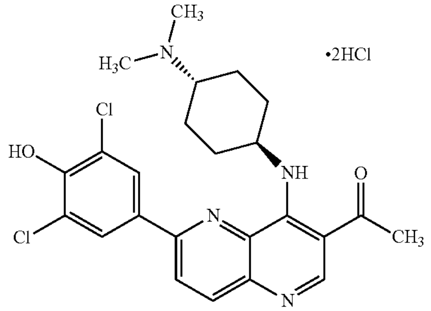 [SMILES: CC(=O)c1cnc2ccc(-c3cc(Cl)c(O)c(Cl)c3)nc2c1N[C@H]1CC[C@H](N(C)C)CC1]

Following general procedure II, 1-{6-chloro-4-[trans-4-(dimethylamino)cyclohexyl amino)-1,5-naphthyridin-3-yl) ethanone (61 mg, 0.16 mmol) was reacted with 2,6-dichloro-4-(4,4,5,5-tetramethyl-1,3,2-dioxaborolan-2-yl)phenol (65 mg, 0.23 mmol) followed by formation of the dihydrochloride salt to afford the desired product (76 mg, 90%) as an off-white solid: $^{1}$H NMR (500 MHz, $CD_3OD$) δ 9.17 (s, 1H), 8.47 (d, J=9.0 Hz, 1H), 8.36 (d, J=8.9 Hz, 1H), 8.10 (s, 2H), 5.65-5.55 (m, 1H), 3.52-3.43 (m, 1H), 2.91 (s, 6H), 2.76 (s, 3H), 2.66-2.56 (m, xH), 2.33-2.26 (m, 2H), 1.88-1.71 (m, 4H). ESI MS m/z 473 $[M+H]^+$; HPLC>99% (AUC), $t_R$=9.51 min.

Example 3

1-{6-(3-Chloro-5-fluoro-4-hydroxyphenyl)-4-[trans-4-(dimethylamino)cyclohexylamino]-1,5-naphthyridin-3-yl}ethanone dihydrochloride

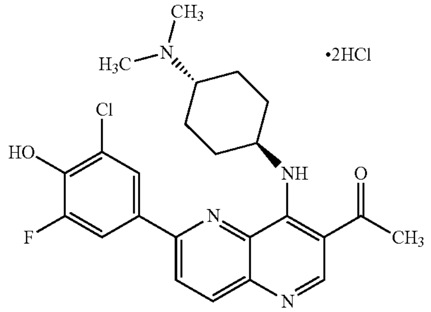 [SMILES: CC(=O)c1cnc2ccc(-c3cc(F)c(O)c(Cl)c3)nc2c1N[C@H]1CC[C@H](N(C)C)CC1]

Following general procedure II, 1-{6-chloro-4-[trans-4-(dimethylamino)cyclohexyl amino)-1,5-naphthyridin-3-yl) ethanone (45 mg, 0.12 mmol) was reacted with 2-chloro-6-fluoro-4-(4,4,5,5-tetramethyl-1,3,2-dioxaborolan-2-yl) phenol (47 mg, 0.17 mmol) followed by formation of the dihydrochloride salt to afford the desired product (6.9 mg, 11%) as an off-white solid: 1H NMR (500 MHz, $CD_3OD$) δ 9.17 (s, 1H), 8.47 (d, J=9.0 Hz, 1H), 8.34 (d, J=9.0 Hz, 1H), 8.00 (s, 1H), 7.91 (dd, J=11.4, 2.2 Hz, 1H), 5.69-5.59 (m, 1H), 3.52-3.45 (m, 1H), 2.92 (s, 6H), 2.76 (s, 3H), 2.63-2.56 (m, 2H), 2.33-2.26 (m, 2H), 1.89-1.71 (m, 4H). ESI MS m/z 457 $[M+H]^+$; HPLC>99% (AUC), $t_R$=9.32 min.

Example 4

Cyclopropyl(6-(3,5-dichloro-4-hydroxyphenyl)-4-{trans-4-[(dimethylamino)methyl]-cyclohexylamino}-1,5-naphthyridin-3-yl)methanone dihydrochloride

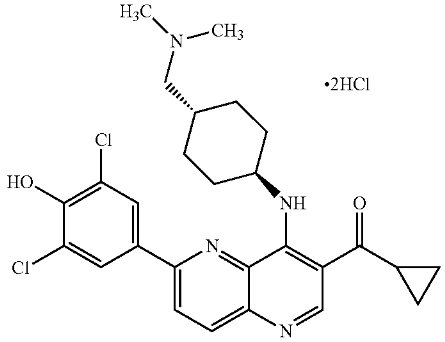 [SMILES: CN(C)C[C@H]1CC[C@H](Nc2c(C(=O)C3CC3)cnc3ccc(-c4cc(Cl)c(O)c(Cl)c4)nc23)CC1]

Following general procedure II, (6-chloro-4-{trans-4-[(dimethylamino)methyl]-cyclohexyl amino}-1,5-naphthyridin-3-yl)(cyclopropyl)methanone (60 mg, 0.16 mmol) was reacted with 2,6-dichloro-4-(4,4,5,5-tetramethyl-1,3,2-dioxaborolan-2-yl)phenol (65 mg, 0.23 mmol) followed by formation of the dihydrochloride salt to afford the desired product (66 mg, 73%) as a light yellow solid: 1H NMR (500 MHz, $CD_3OD$) δ 9.41 (s, 1H), 8.46 (d, J=8.9 Hz, 1H), 8.34 (d, J=8.9 Hz, 1H), 8.12 (s, 2H), 5.74-5.64 (m, 1H), 3.09 (d, J=6.6 Hz, 2H), 2.93 (s, 6H), 2.92-2.85 (s, 1H), 2.47-2.40 (m, 2H), 2.08-1.96 (m, 3H), 1.72-1.60 (m, 2H), 1.47-1.34 (m, 2H), 1.32-1.18 (m, 4H). ESI MS m/z 513 $[M+H]^+$; HPLC>99% (AUC), $t_R$=9.67 min.

Example 5

(6-(3-Chloro-5-fluoro-4-hydroxyphenyl)-4-{trans-4-[(dimethylamino)methyl]cyclohexyl-amino}-1,5-naphthyridin-3-yl)(cyclopropyl)methanone dihydrochloride

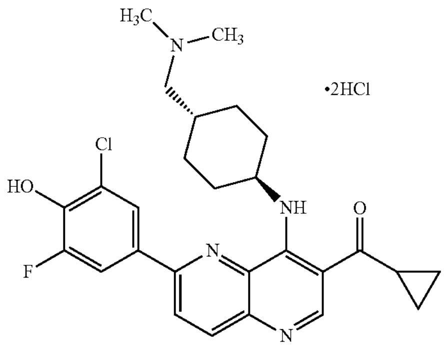 [SMILES: CN(C)C[C@H]1CC[C@H](Nc2c(C(=O)C3CC3)cnc3ccc(-c4cc(F)c(O)c(Cl)c4)nc23)CC1]

Following general procedure II, (6-chloro-4-{trans-4-[(dimethylamino)methyl]-cyclohexyl amino}-1,5-naphthyridin-3-yl)(cyclopropyl)methanone (60 mg, 0.16 mmol) was reacted with 2-chloro-6-fluoro-4-(4,4,5,5-tetramethyl-1,3,2-dioxaborolan-2-yl)phenol (61 mg, 0.23 mmol) followed by formation of the dihydrochloride salt to afford the desired product (54 mg, 61%) as a light yellow solid: $^1$H NMR (500 MHz, $CD_3OD$) δ 9.41 (s, 1H), 8.45 (d, J=8.9 Hz, 1H), 8.34 (d, J=8.9 Hz, 1H), 8.02 (t, J=1.9 Hz, 1H), 7.88 (dd, J=11.6, 2.2 Hz, 1H), 5.73-5.64 (m, 1H), 3.09 (d, J=6.6 Hz, 2H), 2.94 (s, 6H), 2.93-2.83 (m, 1H), 2.48-2.40 (m, 2H), 2.10-1.96 (m, 3H), 1.73-1.61 (m, 2H), 1.46-1.34 (m, 2H), 1.34-1.18 (m, 4H). ESI MS m/z 497 [M+H]$^+$; HPLC>99% (AUC), $t_R$=10.26 min.

Example 6

1-{6-(3,5-Dichloro-4-hydroxyphenyl)-4-({trans-4-[(dimethylamino)methyl]cyclohexyl}amino)-1,5-naphthyridin-3-yl}ethanone dihydrochloride

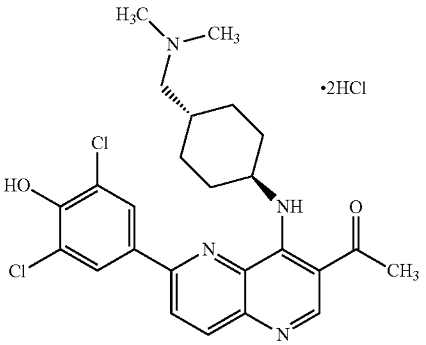 [SMILES: CC(=O)c1cnc2ccc(-c3cc(Cl)c(O)c(Cl)c3)nc2c1N[C@H]1CC[C@H](CN(C)C)CC1]

Following general procedure II, 1-(6-chloro-4-{trans-4-[(dimethylamino)methyl]cyclohexyl amino}-1,5-naphthyridin-3-yl)ethanone (20 mg, 0.055 mmol) was reacted with 2,6-dichloro-4-(4,4,5,5-tetramethyl-1,3,2-dioxaborolan-2-yl)phenol (29 mg, 0.10 mmol) followed by formation of the dihydrochloride salt to afford the desired product (18 mg, 58%) as an off-white solid: $^1$H NMR (500 MHz, $CD_3OD$) δ 9.14 (s, 1H), 8.46 (d, J=9.1 Hz, 1H), 8.33 (d, J=9.1 Hz, 1H), 8.12 (s, 2H), 5.75-5.67 (m, 1H), 3.09 (d, J=6.6 Hz, 2H), 2.94 (s, 6H), 2.76 (s, 3H), 2.48-2.41 (m, 2H), 2.09-1.98 (m, 1H), 1.75-1.63 (m, 1H), 1.48-1.36 (m, 2H). ESI MS m/z 487 [M+H]$^+$; HPLC>99% (AUC), $t_R$=9.67 min.

Example 7

1-{6-(3-Chloro-5-fluoro-4-hydroxyphenyl)-4-({trans-4-[(dimethylamino)methyl]cyclohexyl}-amino)-1,5-naphthyridin-3-yl}ethanone dihydrochloride

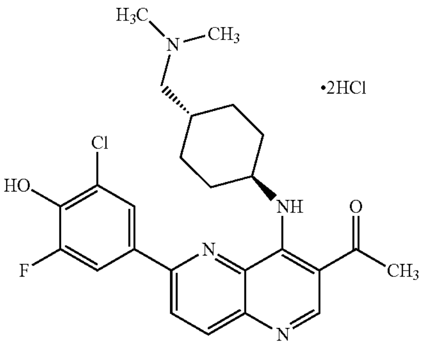 [SMILES: CC(=O)c1cnc2ccc(-c3cc(F)c(O)c(Cl)c3)nc2c1N[C@H]1CC[C@H](CN(C)C)CC1]

Following general procedure II, 1-(6-chloro-4-{trans-4-[(dimethylamino)methyl]cyclohexyl amino}-1,5-naphthyridin-3-yl)ethanone (20 mg, 0.055 mmol) was reacted with 2-chloro-6-fluoro-4-(4,4,5,5-tetramethyl-1,3,2-dioxaborolan-2-yl)phenol (27 mg, 0.10 mmol) followed by formation of the dihydrochloride salt to afford the desired product (16 mg, 52%) as a light yellow solid: $^1$H NMR (500 MHz, $CD_3OD$) δ 9.15 (s, 1H), 8.45 (d, J=9.1 Hz, 1H), 8.33 (d, J=9.0 Hz, 1H), 8.02 (t, J=1.9 Hz, 1H), 7.88 (dd, J=11.5, 2.2 Hz, 1H), 5.75-5.65 (m, 1H), 3.09 (d, J=6.6 Hz, 2H), 2.94 (s, 6H), 2.76 (s, 3H), 2.45 (d, J=12.5 Hz, 2H), 2.11-2.01 (m, 3H), 1.75-1.63 (m, 2H), 1.47-1.36 (m, 2H). ESI MS m/z 471 [M+H]$^+$; HPLC>99% (AUC), $t_R$=9.66 min.

Example 8

1-(6-(3-Chloro-4-hydroxy-5-methoxyphenyl)-4-{trans-4-[(dimethylamino)methyl]cyclohexyl-amino}-1,5-naphthyridin-3-yl)ethanone dihydrochloride

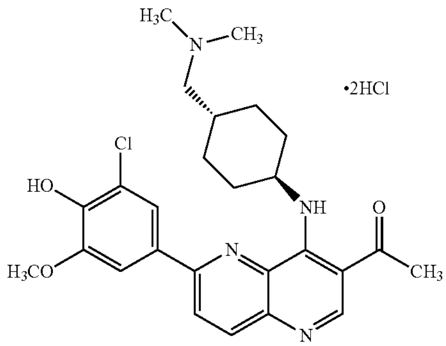 [SMILES: COc1cc(-c2ccc3ncc(C(C)=O)c(N[C@H]4CC[C@H](CN(C)C)CC4)c3n2)cc(Cl)c1O]

Following general procedure II, 1-(6-chloro-4-{trans-4-[(dimethylamino)methyl]cyclohexyl amino}-1,5-naphthyridin-3-yl)ethanone (20 mg, 0.055 mmol) was reacted with 2-chloro-6-methoxy-4-(4,4,5,5-tetramethyl-1,3,2-dioxaborolan-2-yl)phenol (28 mg, 1.0 mmol) followed by formation of the dihydrochloride salt to afford the desired product (18 mg, 59%) as a yellow solid: $^1$H NMR (500 MHz, $CD_3OD$) δ 9.13 (s, 1H), 8.49 (d, J=8.9 Hz, 1H), 8.32 (d, J=9.1 Hz, 1H), 7.81 (d, J=2.1 Hz, 1H), 7.58 (d, J=2.1 Hz, 1H), 5.80-5.70 (m, 1H), 4.03 (s, 3H), 3.08 (d, J=6.6 Hz, 2H), 2.93 (s, 6H), 2.76 (s, 3H), 2.49-2.39 (m, 2H), 2.08-1.96 (m, 3H), 1.72-1.62 (m, 2H), 1.47-1.35 (m, 2H). ESI MS m/z 483 [M+H]$^+$; HPLC>99% (AUC), $t_R$=9.62 min.

Example 9

1-[6-(3,5-Dichloro-4-hydroxyphenyl)-4-({trans-4-[2-(dimethylamino)ethyl]cyclohexyl}amino)-1,5-naphthyridin-3-yl]ethanone dihydrochloride

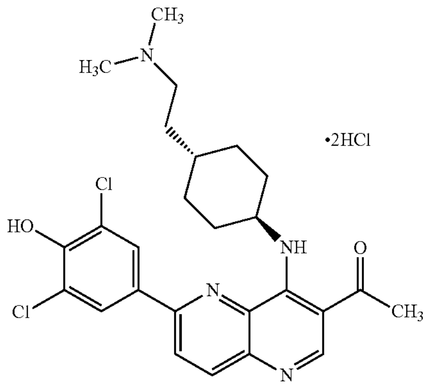 [SMILES: CC(=O)c1cnc2ccc(-c3cc(Cl)c(O)c(Cl)c3)nc2c1N[C@H]1CC[C@H](CCN(C)C)CC1]

Following general procedure II, 1-(6-chloro-4-{trans-4-[(dimethylamino)methyl]cyclohexyl amino}-1,5-naphthyridin-3-yl)ethanone (50 mg, 0.13 mmol) was reacted with 2,6-dichloro-4-(4,4,5,5-tetramethyl-1,3,2-dioxaborolan-2-yl) phenol (58 mg, 0.2 mmol) followed by formation of the dihydrochloride salt to afford the desired product (64 mg, 83%) as an off-white solid: $^1$H NMR (500 MHz, $CD_3OD$) δ 9.13 (s, 1H), 8.46 (d, J=9.1 Hz, 1H), 8.33 (d, J=9.0 Hz, 1H), 8.13 (s, 1H), 5.74-5.64 (m, 1H), 3.27-3.18 (m, 2H), 2.91 (s, 6H), 2.75 (s, 3H), 2.45-2.35 (m, 2H), 2.05-1.98 (m, 2H), 1.78-1.70 (m, 2H), 1.66-1.52 (m, 3H), 1.45-1.35 (m, 2H). ESI MS m/z 501 $[M+H]^+$; HPLC>99% (AUC), $t_R$=10.22 min.

Example 10

1-(6-(3-Chloro-5-fluoro-4-hydroxyphenyl)-4-{trans-4-[2-(dimethylamino)ethyl]-cyclohexylamino}-1,5-naphthyridin-3-yl)ethanone dihydrochloride

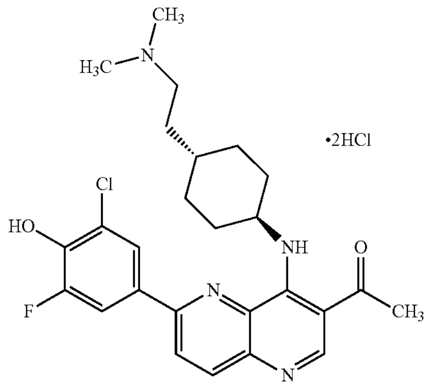 [SMILES: CC(=O)c1cnc2ccc(-c3cc(F)c(O)c(Cl)c3)nc2c1N[C@H]1CC[C@H](CCN(C)C)CC1]

Following general procedure II, 1-(6-chloro-4-(trans-4-((dimethylamino)methyl)-cyclohexylamino)-1,5-naphthyridin-3-yl)ethanone (50 mg, 0.13 mmol) was reacted with 2-chloro-6-fluoro-4-(4,4,5,5-tetramethyl-1,3,2-dioxaborolan-2-yl)phenol (55 mg, 0.2 mmol) followed by formation of the dihydrochloride salt to afford the desired product (58 mg, 78%) as an off-white solid: $^1$H NMR (500 MHz, $CD_3OD$) δ 9.13 (s, 1H), 8.45 (d, J=8.9 Hz, 1H), 8.32 (d, J=8.9 Hz, 1H), 8.04 (t, J=1.8 Hz, 1H), 7.89 (dd, J=11.6, 2.2 Hz, 1H), 5.73-5.63 (m, 1H), 3.27-3.18 (m, 2H), 2.91 (s, 6H), 2.75 (s, 3H), 2.44-2.37 (m, 2H), 2.05-1.98 (m, 2H), 1.78-1.69 (m, 2H), 1.67-1.51 (m, 3H), 1.44-1.34 (m, 2H). ESI MS m/z 485 $[M+H]^+$; HPLC>99% (AUC), $t_R$=9.91 min.

Example 11

1-(4-{trans-4-[(Dimethylamino)methyl]cyclohexylamino}-6-[4-hydroxy-3-(trifluoromethoxy)-phenyl]-1,5-naphthyridin-3-yl)ethanone dihydrochloride

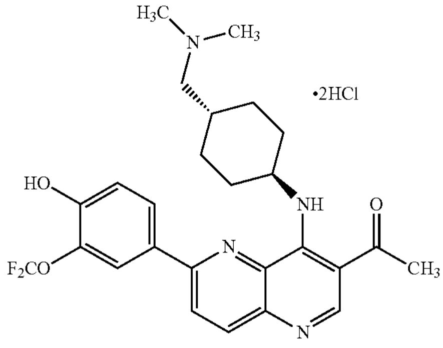

Following general procedure II, 1-(6-chloro-4-{trans-4-[(dimethylamino)methyl]cyclohexyl amino}-1,5-naphthyridin-3-yl)ethanone (55 mg, 0.15 mmol) was reacted with 4-(4,4,5,5-tetramethyl-1,3,2-dioxaborolan-2-yl)-2-(trifluoromethoxy)phenol (68 mg, 0.23 mmol) followed by formation of the dihydrochloride salt to afford the desired product (71 mg, 79%) as an off-white solid: $^1$H NMR (500 MHz, $CD_3OD$) δ 9.14 (s, 1H), 8.45 (d, J=8.9 Hz, 1H), 8.32 (d, J=9.0 Hz, 1H), 8.04-7.97 (m, 2H), 7.21 (d, J=8.6 Hz, 1H), 5.70-5.60 (m, 1H), 3.07 (d, J=6.6 Hz, 2H), 2.94 (s, 6H), 2.76 (s, 3H), 2.50-2.40 (m, 2H), 2.08-1.97 (m, 3H), 1.74-1.62 (m, 2H), 1.39-1.27 (m, 2H). ESI MS m/z 503 $[M+H]^+$; HPLC>99% (AUC), $t_R$=9.80 min.

Example 12

2,6-Dichloro-4-(8-{trans-4-[(dimethylamino)methyl]cyclohexylamino}-7-(methylsulfonyl)-1,5-naphthyridin-2-yl)phenol dihydrochloride

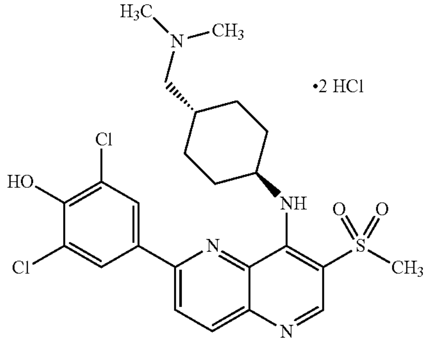 [SMILES: CN(C)C[C@H]1CC[C@H](Nc2c(S(C)(=O)=O)cnc3ccc(-c4cc(Cl)c(O)c(Cl)c4)nc23)CC1]

Following general procedure II, 6-chloro-N-{trans-4-[(dimethylamino)methyl]-cyclohexyl}-3-(methylsulfonyl)-1,5-naphthyridin-4-amine (56 mg, 0.14 mmol) was reacted with 2,6-dichloro-4-(4,4,5,5-tetramethyl-1,3,2-dioxaborolan-2-yl)phenol (61 mg, 0.21 mmol) followed by formation of the dihydrochloride salt to afford the desired product (43 mg, 51%) as a light yellow solid: $^1$H NMR (500 MHz, $CD_3OD$) δ 8.90 (s, 1H), 8.51 (d, J=9.0 Hz, 1H), 8.35 (d, J=9.0 Hz, 1H), 8.14 (s, 2H), 5.76-5.66 (m, 1H), 3.38 (s, 3H), 3.09 (d, J=6.7 Hz, 2H), 2.94 (s, 6H), 2.50-2.43 (m, 2H), 2.08-1.96 (m, 3H), 1.74-1.64 (m, 2H), 1.47-1.35 (m, 2H). ESI MS m/z 523 $[M+H]^+$; HPLC>99% (AUC), $t_R$=10.04 min.

Example 13

6-(3-Chloro-5-fluoro-4-hydroxyphenyl)-4-({trans-4-[(dimethylamino)methyl]cyclohexyl}-amino)-3-methylsulfonyl-1,5-naphthyridine dihydrochloride

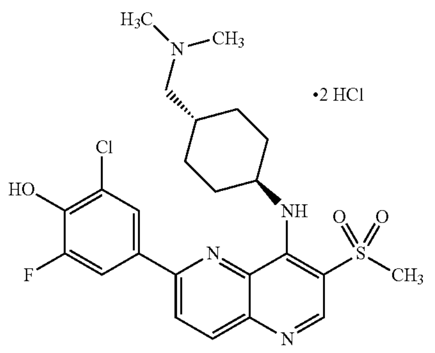 [SMILES: CN(C)C[C@H]1CC[C@H](Nc2c(S(C)(=O)=O)cnc3ccc(-c4cc(F)c(O)c(Cl)c4)nc23)CC1]

Following general procedure II, 6-chloro-N-{trans-4-[(dimethylamino)methyl]-cyclohexyl}-3-(methylsulfonyl)-1,5-naphthyridin-4-amine (61 mg, 0.15 mmol) was reacted with 2-chloro-6-fluoro-4-(4,4,5,5-tetramethyl-1,3,2-dioxaborolan-2-yl)phenol (63 mg, 0.23 mmol) followed by formation of the dihydrochloride salt to afford the desired product (52 mg, 59%) as a light yellow solid: $^1$H NMR (500 MHz, $CD_3OD$) δ 8.90 (s, 1H), 8.50 (d, J=8.9 Hz, 1H), 8.35 (d, J=9.0 Hz, 1H), 8.04 (t, J=1.8 Hz, 1H), 7.90 (dd, J=11.5, 2.2 Hz, 1H), 5.77-5.67 (m, 1H), 3.38 (s, 3H), 3.09 (d, J=6.6 Hz, 2H), 2.94 (s, 6H), 2.51-2.44 (m, 2H), 2.08-1.97 (m, 3H), 1.76-1.64 (m, 2H), 1.46-1.34 (m, 2H). ESI MS m/z 507 $[M+H]^+$; HPLC 99.0% (AUC), $t_R$=9.81 min.

Example 14

6-(3-Chloro-4-hydroxy-5-methoxyphenyl)-4-{trans-4-[(dimethylamino)methyl]-cyclohexylamino}-3-methylsulfonyl-1,5-naphthyridine-dihydrochloride

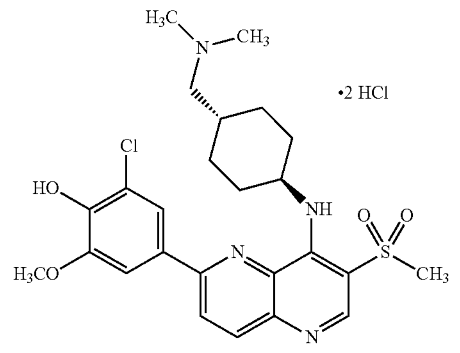 [SMILES: COc1cc(-c2ccc3ncc(S(C)(=O)=O)c(N[C@H]4CC[C@H](CN(C)C)CC4)c3n2)cc(Cl)c1O]

Following general procedure II, 6-chloro-N-{trans-4-[(dimethylamino)methyl]-cyclohexyl}-3-(methylsulfonyl)-1,5-naphthyridin-4-amine (24 mg, 0.061 mmol) was reacted with 2-chloro-6-methoxy-4-(4,4,5,5-tetramethyl-1,3,2-dioxaborolan-2-yl)phenol (28 mg, 0.10 mmol) followed by formation of the dihydrochloride salt to afford the desired product (23 mg, 64%) as a yellow solid: $^1$H NMR (500 MHz, $CD_3OD$) δ 8.89 (s, 1H), 8.54 (d, J=9.1 Hz, 1H), 8.34 (d, J=9.0 Hz, 1H), 7.83 (d, J=2.0 Hz, 1H), 7.60 (d, J=2.0 Hz, 1H), 5.83-5.73 (m, 1H), 4.04 (s, 3H), 3.38 (s, 3H), 3.08 (d, J=6.6 Hz, 2H), 2.93 (s, 6H), 2.50-2.43 (m, 2H), 2.07-1.95 (m, 3H), 1.73-1.63 (m, 2H), 1.46-1.35 (m, 2H). ESI MS m/z 519 $[M+H]^+$; HPLC>99% (AUC), $t_R$=9.77 min.

Example 15

2,6-Dichloro-4-{8-[trans-4-(dimethylamino)cyclohexylamino]-7-(methylsulfonyl)-1,5-naphthyridin-2-yl}phenol dihydrochloride

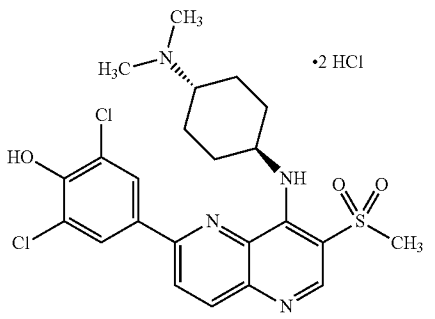 [SMILES: CN(C)[C@H]1CC[C@H](Nc2c(S(C)(=O)=O)cnc3ccc(-c4cc(Cl)c(O)c(Cl)c4)nc23)CC1]

Following general procedure II, trans-$N^1$-[6-chloro-3-(methylsulfonyl)-1,5-naphthyridin-4-yl]-$N^4$,$N^4$-dimethylcyclohexane-1,4-diamine (40 mg, 0.10 mmol) was reacted with 2,6-dichloro-4-(4,4,5,5-tetramethyl-1,3,2-dioxaborolan-2-yl)phenol (43 mg, 0.15 mmol) followed by formation of the dihydrochloride salt to afford the desired product (45 mg, 75%) as a light yellow solid: $^1$H NMR (500 MHz, $CD_3OD$) δ 8.93 (s, 1H), 8.51 (d, J=8.9 Hz, 1H), 8.37 (d, J=8.9 Hz, 1H), 8.12 (s, 2H), 5.65-5.55 (m, 1H), 3.50-3.41 (m, 1H), 3.39 (s, 3H), 2.91 (s, 6H), 2.67-2.57 (m, 2H), 2.33-2.27 (m, 2H), 1.87-1.73 (m, 4H). ESI MS m/z 509 $[M+H]^+$; HPLC 98.0% (AUC), $t_R$=9.95 min.

Example 16

2,6-Dichloro-4-(8-{4-[(dimethylamino)methyl]phenylamino}-7-(methylsulfonyl)-1,5-naphthyridin-2-yl)phenol dihydrochloride

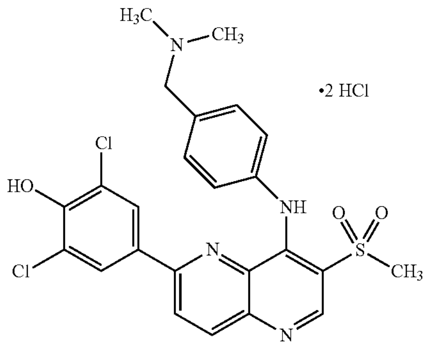 [SMILES: CN(C)Cc1ccc(Nc2c(S(C)(=O)=O)cnc3ccc(-c4cc(Cl)c(O)c(Cl)c4)nc23)cc1]

Following general procedure II, 6-chloro-N-{4-[(dimethylamino)methyl]phenyl}-3-(methylsulfonyl)-1,5-naphthyridin-4-amine (50 mg, 0.14 mmol) was reacted with 2,6-dichloro-4-(4,4,5,5-tetramethyl-1,3,2-dioxaborolan-2-yl)phenol (61 mg, 0.21 mmol) followed by formation of the dihydrochloride salt to afford the desired product (35 mg, 42%) as an orange solid: $^{1}$H NMR (500 MHz, $CD_3OD$) δ 9.12 (s, 1H), 8.47 (d, J=9.1 Hz, 1H), 8.38 (d, J=9.2 Hz, 1H), 7.63 (d, J=9.0 Hz, 2H), 7.59-7.52 (m, 2H), 7.34 (s, 2H), 4.43 (s, 2H), 3.48 (s, 3H), 2.86 (s, 6H); ESI MS m/z 517 $[M+H]^+$; HPLC>99% (AUC), $t_R$=11.03 min.

Example 17

2-Chloro-4-(8-{4-[(dimethylamino)methyl]phenylamino}-7-(methylsulfonyl)-1,5-naphthyridin-2-yl)-6-fluorophenol dihydrochloride

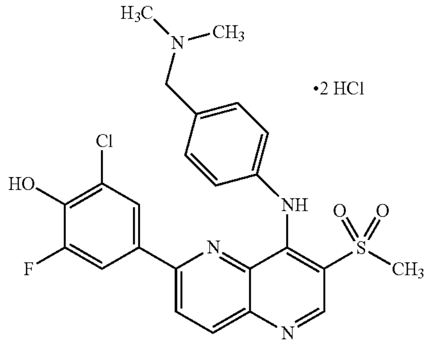 [SMILES: CN(C)Cc1ccc(Nc2c(S(C)(=O)=O)cnc3ccc(-c4cc(F)c(O)c(Cl)c4)nc23)cc1]

Following general procedure II, 6-chloro-N-{4-[(dimethylamino)methyl]phenyl}-3-(methylsulfonyl)-1,5-naphthyridin-4-amine (50 mg, 0.14 mmol) was reacted with 2-chloro-6-fluoro-4-(4,4,5,5-tetramethyl-1,3,2-dioxaborolan-2-yl)phenol (58 mg, 0.21 mmol) followed by formation of the dihydrochloride salt to afford the desired product (51 mg, 63%) as a yellow solid: 1H NMR (500 MHz, $CD_3OD$) δ 9.12 (s, 1H), 8.46 (d, J=9.0 Hz, 1H), 8.37 (d, J=9.1 Hz, $^{1}$H), 7.68-7.61 (m, 2H), 7.60-7.53 (m, 2H), 7.22 (t, J=1.8 Hz, 1H), 7.06 (dd, J=11.9, 2.2 Hz, 1H), 4.43 (s, 2H), 3.48 (s, 3H), 2.88 (s, 6H); ESI MS m/z 501 $[M+H]^+$; HPLC>99% (AUC), $t_R$=10.68 min.

Example 18

2-Chloro-4-(8-{4-[(dimethylamino)methyl]phenylamino}-7-(methylsulfonyl)-1,5-naphthyridin-2-yl)-6-methoxyphenol dihydrochloride

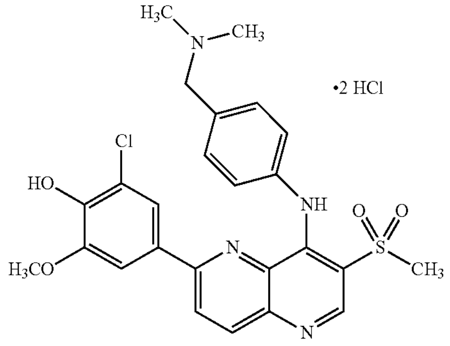 [SMILES: COc1cc(-c2ccc3ncc(S(C)(=O)=O)c(Nc4ccc(CN(C)C)cc4)c3n2)cc(Cl)c1O]

Following general procedure II, 6-chloro-N-{4-[(dimethylamino)methyl]phenyl}-3-(methylsulfonyl)-1,5-naphthyridin-4-amine (50 mg, 0.14 mmol) was reacted with 2-chloro-6-methoxy-4-(4,4,5,5-tetramethyl-1,3,2-dioxaborolan-2-yl)phenol (60 mg, 0.21 mmol) followed by formation of the dihydrochloride salt to afford the desired product (44 mg, 54%) as an orange solid: 1H NMR (500 MHz, $CD_3OD$) δ 9.11 (s, 1H), 8.50 (d, J=9.0 Hz, 1H), 8.36 (d, J=9.0 Hz, 1H), 7.62-7.50 (m, 4H), 7.34 (d, J=2.1 Hz, 1H), 6.68 (d, J=2.0 Hz, 1H), 4.40 (s, 2H), 3.92 (s, 3H), 3.47 (s, 3H), 2.83 (s, 6H); ESI MS m/z 513 $[M+H]^+$; HPLC>99% (AUC), $t_R$=10.56 min.

Example 19

1-[6-(3,5-Dichloro-4-hydroxyphenyl)-4-{3-[2-(pyrrolidin-1-yl)ethyl]phenylamino}-1,5-naphthyridin-3-yl]ethanone dihydrochloride

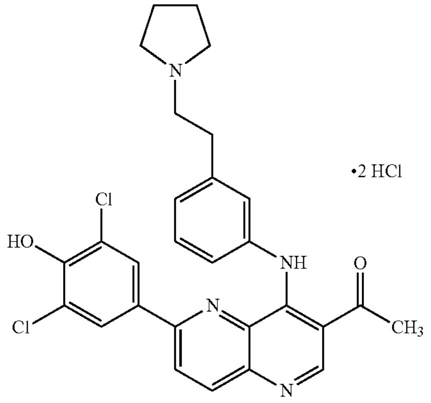 [SMILES: CC(=O)c1cnc2ccc(-c3cc(Cl)c(O)c(Cl)c3)nc2c1Nc1cccc(CCN2CCCC2)c1]

Following general procedure II, 1-(6-chloro-4-{3-[2-(pyrrolidin-1-yl)ethyl]phenylamino}-1,5-naphthyridin-3-yl)ethanone (59 mg, 0.15 mmol) was reacted with 2,6-dichloro-4-(4,4,5,5-tetramethyl-1,3,2-dioxaborolan-2-yl)phenol (65 mg, 0.23 mmol) followed by formation of the dihydrochloride salt to afford the desired product (67 mg, 75%) as a yellow solid: 1H NMR (500 MHz, $D_2O$) δ 9.13 (s, 1H), 8.13 (d, J=9.0 Hz, 1H), 8.01 (d, J=9.1 Hz, 1H), 7.64 (t, J=7.8 Hz, 1H), 7.41 (d, J=7.4 Hz, 1H), 7.32 (d, J=7.9 Hz, 1H), 6.79 (s, 1H), 6.66 (br s, 2H), 3.36-3.27 (m, 2H), 2.78 (s, 3H), 2.74-2.64 (m, 2H), 2.62-2.42 (m, 4H), 1.87-1.72 (m, 4H); ESI MS m/z 521 $[M+H]^+$; HPLC 98.9% (AUC), $t_R$=10.34 min.

Example 20

1-[6-(3-Chloro-5-fluoro-4-hydroxyphenyl)-4-{3-[2-(pyrrolidin-1-yl)ethyl]phenylamino}-1,5-naphthyridin-3-yl]ethanone dihydrochloride

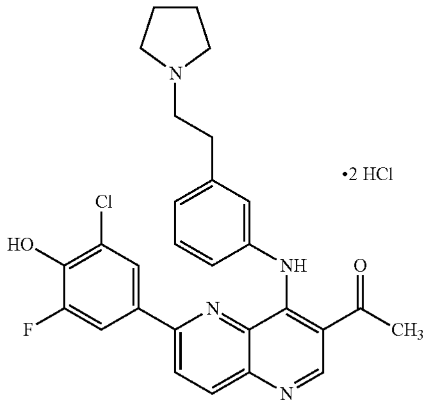 [SMILES: CC(=O)c1cnc2ccc(-c3cc(F)c(O)c(Cl)c3)nc2c1Nc1cccc(CCN2CCCC2)c1]

Following general procedure II, 1-(6-chloro-4-{3-[2-(pyrrolidin-1-yl)ethyl]phenylamino}-1,5-naphthyridin-3-yl) ethanone (59 mg, 0.15 mmol) was reacted with 2-chloro-6-fluoro-4-(4,4,5,5-tetramethyl-1,3,2-dioxaborolan-2-yl) phenol (61 mg, 0.23 mmol) followed by formation of the dihydrochloride salt to afford the desired product (63 mg, 72%) as a yellow solid: $^1$H NMR (500 MHz, $CD_3OD$) δ 9.30 (s, 1H), 8.43 (d, J=9.0 Hz, 1H), 8.34 (d, J=8.9 Hz, 1H), 7.54-7.30 (m, 4H), 7.23 (br s, 1H), 7.13 (br s, 1H), 3.68-3.60 (m, 2H), 3.35-3.23 (m, 2H), 3.11-2.99 (m, 4H), 2.80 (br s, 3H), 2.19-2.07 (m, 2H), 2.05-1.96 (m, 2H); ESI MS m/z 505 $[M+H]^+$; HPLC>99% (AUC), $t_R$=10.17 min.

Example 21

1-[6-(3,5-Dichloro-4-hydroxyphenyl)-4-{6-[2-(dimethylamino)ethoxy]pyridin-3-ylamino}-1,5-naphthyridin-3-yl)ethanone dihydrochloride

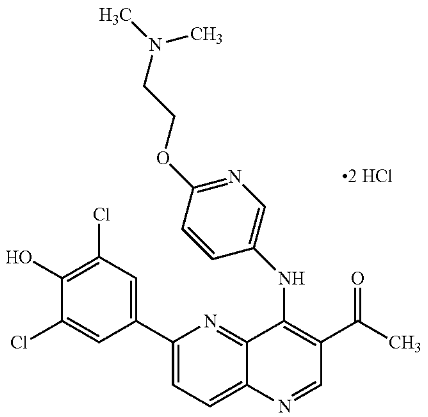 [SMILES: CC(=O)c1cnc2ccc(-c3cc(Cl)c(O)c(Cl)c3)nc2c1Nc1ccc(OCCN(C)C)nc1]

Following general procedure II, 1-(6-chloro-4-{6-[2-(dimethylamino)ethoxy]pyridin-3-ylamino}-1,5-naphthyridin-3-yl)ethanone (50 mg, 0.13 mmol) was reacted with 2,6-dichloro-4-(4,4,5,5-tetramethyl-1,3,2-dioxaborolan-2-yl) phenol (56 mg, 0.20 mmol) followed by formation of the dihydrochloride salt to afford the desired product (63 mg, 83%) as a yellow-orange solid: $^1$H NMR (500 MHz, $CD_3OD$) δ 9.35 (s, 1H), 8.46 (d, J=9.0 Hz, 1H), 8.37 (d, J=9.0 Hz, 1H), 8.24 (d, J=2.7 Hz, 1H), 7.78 (dd, J=8.8, 2.7 Hz, 1H), 7.44 (br s, 2H), 7.02 (d, J=8.8 Hz, 1H), 4.72-4.66 (m, 2H), 3.64-3.58 (m, 2H), 3.00 (s, 6H), 2.84 (s, 3H); ESI MS m/z 512 $[M+H]^+$; HPLC 99% (AUC), $t_R$=9.73 min.

Example 22

1-[6-(3-Chloro-5-fluoro-4-hydroxyphenyl)-4-{6-[2-(dimethylamino)ethoxy]pyridin-3-ylamino}-1,5-naphthyridin-3-yl)ethanone dihydrochloride

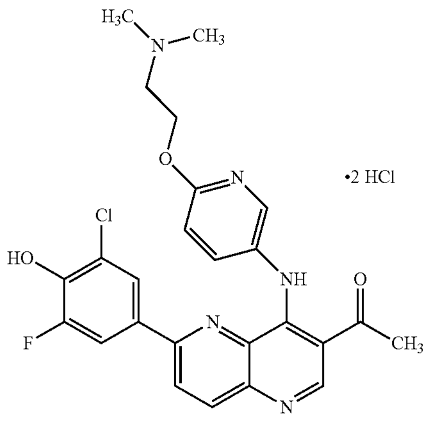 [SMILES: CC(=O)c1cnc2ccc(-c3cc(F)c(O)c(Cl)c3)nc2c1Nc1ccc(OCCN(C)C)nc1]

Following general procedure II, 1-(6-chloro-4-{6-[2-(dimethylamino)ethoxy]pyridin-3-ylamino}-1,5-naphthyridin-3-yl)ethanone (50 mg, 0.13 mmol) was reacted with 2-chloro-6-fluoro-4-(4,4,5,5-tetramethyl-1,3,2-dioxaborolan-2-yl) phenol (53 mg, 0.20 mmol) followed by formation of the dihydrochloride salt to afford the desired product (40 mg, 54%) as an orange solid: $^1$H NMR (500 MHz, $CD_3OD$) δ 9.35 (br s, 1H), 8.45 (d, J=9.0 Hz, 1H), 8.37 (d, J=8.9 Hz, 1H), 8.28 (d, J=2.6 Hz, 1H), 7.76 (dd, J=8.8, 2.7 Hz, 1H), 7.35 (br s, 1H), 7.10 (br s, 1H), 7.01 (d, J=8.8 Hz, 1H), 4.74-4.68 (m, 2H), 3.66-3.60 (m, 2H), 3.02 (s, 6H), 2.84 (s, 3H); ESI MS m/z 496 $[M+H]^+$; HPLC 98.3% (AUC), $t_R$=9.47 min.

Example 23

1-[6-(3-Chloro-4-hydroxy-5-methoxyphenyl)-4-{6-[2-(dimethylamino)ethoxy]pyridin-3-ylamino}-1,5-naphthyridin-3-yl]ethanone dihydrochloride

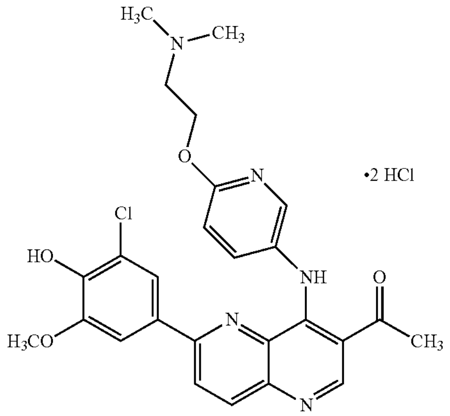 [SMILES: COc1cc(-c2ccc3ncc(C(C)=O)c(Nc4ccc(OCCN(C)C)nc4)c3n2)cc(Cl)c1O]

Following general procedure II, 1-(6-chloro-4-{6-[2-(dimethylamino)ethoxy]pyridin-3-ylamino}-1,5-naphthyridin-3-yl)ethanone (20 mg, 0.052 mmol) was reacted with 2-chloro-6-methoxy-4-(4,4,5,5-tetramethyl-1,3,2-dioxaborolan-2-yl) phenol (28 mg, 0.10 mmol) followed by formation of the dihydrochloride salt to afford the desired product (22 mg, 74%) as an orange solid: $^1H$ NMR (500 MHz, $CD_3OD$) δ 9.33 (s, 1H), 8.47 (d, J=9.0 Hz, 1H), 8.35 (d, J=9.0 Hz, 1H), 8.26 (d, J=2.7 Hz, 1H), 7.74 (dd, J=8.8, 2.7 Hz, 1H), 7.29 (br s, 1H), 6.96 (d, J=8.8 Hz, 1H), 6.85 (br s, 1H), 4.70-4.64 (m, 2H), 3.95 (s, 3H), 3.62-3.56 (m, 2H), 2.99 (s, 6H), 2.83 (s, 3H); ESI MS m/z 508 $[M+H]^+$; HPLC>99% (AUC), $t_R$=9.36 min.

Example 24

2,6-Dichloro-4-(8-{6-[2-(dimethylamino)ethoxy]pyridin-3-ylamino}-7-(methylsulfonyl)-1,5-naphthyridin-2-yl)phenol hydrochloride

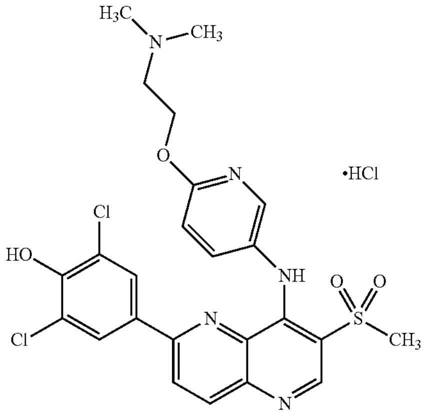 [SMILES: CN(C)CCOc1ccc(Nc2c(S(C)(=O)=O)cnc3ccc(-c4cc(Cl)c(O)c(Cl)c4)nc23)cn1 ; Cl]

Following general procedure II, 1-[6-(3-chloro-4-hydroxy-5-methoxyphenyl)-4-{6-[2-(dimethylamino)ethoxy]pyridin-3-ylamino}-1,5-naphthyridin-3-yl]ethanone (60 mg, 0.14 mmol) was reacted with 2,6-dichloro-4-(4,4,5,5-tetramethyl-1,3,2-dioxaborolan-2-yl)phenol (65 mg, 0.23 mmol) followed by formation of the dihydrochloride salt to afford the desired product (70 mg, 79%) as a yellow solid: $^1H$ NMR (500 MHz, $CD_3OD$) δ 9.11 (s, 1H), 8.49 (d, J=9.1 Hz, 1H), 8.39 (d, J=9.0 Hz, 1H), 8.28 (d, J=2.7 Hz, 1H), 7.83 (dd, J=8.8, 2.8 Hz, 1H), 7.46 (s, 2H), 7.03 (d, J=8.8 Hz, 1H), 4.71-4.65 (m, 2H), 3.63-3.57 (m, 2H), 3.49 (s, 3H), 3.00 (s, 6H); ESI MS m/z 548 $[M+H]^+$; HPLC>99% (AUC), $t_R$=10.87 min.

Example 25

2-Chloro-4-(8-{6-[2-(dimethylamino)ethoxy]pyridin-3-ylamino}-7-(methylsulfonyl)-1,5-naphthyridin-2-yl)-6-fluorophenol dihydrochloride

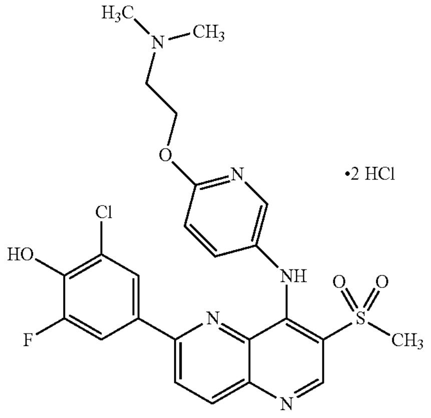 [SMILES: CN(C)CCOc1ccc(Nc2c(S(C)(=O)=O)cnc3ccc(-c4cc(F)c(O)c(Cl)c4)nc23)cn1 ; "·2 HCl"]

Following general procedure II, 1-[6-(3-chloro-4-hydroxy-5-methoxyphenyl)-4-{6-[2-(dimethylamino)ethoxy]pyridin-3-ylamino}-1,5-naphthyridin-3-yl]ethanone (50 mg, 0.16 mmol) was reacted with 2-chloro-6-fluoro-4-(4,4,5,5-tetramethyl-1,3,2-dioxaborolan-2-yl)phenol (61 mg, 0.23 mmol) followed by formation of the dihydrochloride salt to afford the desired product (58 mg, 80%) as a yellow solid: $^1H$ NMR (500 MHz, $CD_3OD$) δ 9.11 (s, 1H), 8.48 (d, J=9.1 Hz, 1H), 8.38 (d, J=9.0 Hz, 1H), 8.32 (d, J=2.7 Hz, 1H), 7.81 (dd, J=8.8, 2.7 Hz, 1H), 7.38 (t, J=1.8 Hz, 1H), 7.11 (dd, J=11.8, 2.2 Hz, 1H), 7.02 (d, J=8.7 Hz, 1H), 4.74-4.68 (m, 2H), 3.66-3.60 (m, 2H), 3.49 (s, 3H), 3.02 (s, 6H); ESI MS m/z 532 $[M+H]^+$; HPLC>99% (AUC), $t_R$=10.51 min.

Example 26

2-Chloro-4-(8-{6-[2-(dimethylamino)ethoxy]pyridin-3-ylamino}-7-(methylsulfonyl)-1,5-naphthyridin-2-yl)-6-methoxyphenol

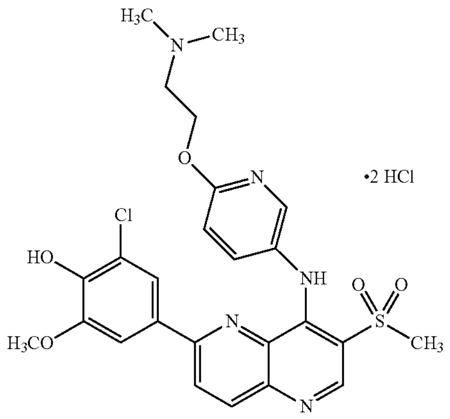 [SMILES: COc1cc(-c2ccc3ncc(S(C)(=O)=O)c(Nc4ccc(OCCN(C)C)nc4)c3n2)cc(Cl)c1O ; "·2 HCl"]

Following general procedure II, 1-[6-(3-chloro-4-hydroxy-5-methoxyphenyl)-4-{6-[2-(dimethylamino)ethoxy]pyridin-3-ylamino}-1,5-naphthyridin-3-yl]ethanone (49 mg, 0.12 mmol) was reacted with 2-chloro-6-methoxy-4-(4,4,5,5-tetramethyl-1,3,2-dioxaborolan-2-yl)phenol (50 mg, 0.18 mmol) followed by formation of the dihydrochloride salt to afford the desired product (56 mg, 78%) as an orange solid: $^1$H NMR (500 MHz, $CD_3OD$) δ 9.09 (s, 1H), 8.49 (d, J=9.0 Hz, 1H), 8.37 (d, J=9.0 Hz, 1H), 8.30 (d, J=2.6 Hz, 1H), 7.78 (dd, J=8.8, 2.8 Hz, 1H), 7.28 (d, J=2.1 Hz, 1H), 6.96 (d, J=8.8 Hz, 1H), 6.88 (d, J=2.0 Hz, 1H), 4.68-4.62 (m, 2H), 3.96 (s, 3H), 3.62-3.54 (m, 2H), 3.49 (s, 3H), 2.98 (s, 6H); ESI MS m/z 544 [M+H]$^+$; HPLC 99% (AUC), $t_R$=10.23 min.

Example 27

1-(6-(3,5-Dichloro-4-hydroxyphenyl)-4-((1-methylpiperidin-4-yl)methylamino)-1,5-naphthyridin-3-yl)ethanone dihydrochloride

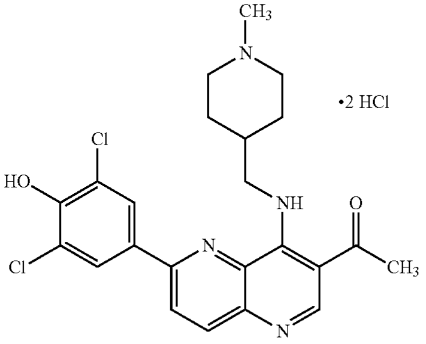 [SMILES: CC(=O)c1cnc2ccc(-c3cc(Cl)c(O)c(Cl)c3)nc2c1NCC1CCN(C)CC1]

Following general procedure II, 61-{6-chloro-4-[(1-methylpiperidin-4-yl)methylamino]-1,5-naphthyridin-3-yl}ethanone (60 mg, 0.18 mmol) was reacted with 2,6-dichloro-4-(4,4,5,5-tetramethyl-1,3,2-dioxaborolan-2-yl) phenol (78 mg, 0.27 mmol) followed by formation of the dihydrochloride salt to afford the desired product (7.3 mg, 7.6%) as an off-white solid: $^1$H NMR (500 MHz, $CD_3OD$) δ 9.18 (s, 1H), 8.48 (d, J=9.0 Hz, 1H), 8.35 (d, J=8.9 Hz, 1H), 8.11 (s, 2H), 4.60 (d, J=7.1 Hz, 2H), 3.65-3.59 (m, 2H), 3.09 (td, J=13.0, 2.8 Hz, 2H), 2.88 (s, 3H), 2.77 (s, 3H), 2.34 (br s, 1H), 2.27 (d, J=14.7 Hz, 2H), 1.80-1.67 (m, 2H); ESI MS m/z 459 [M+H]$^+$; HPLC>99% (AUC), $t_R$=9.39 min.

Example 28

1-[6-(3,5-Dichloro-4-hydroxyphenyl)-4-{trans-4-[(dimethylamino)methyl]cyclohexylamino}-1,5-naphthyridin-3-yl]ethanone dihydrochloride

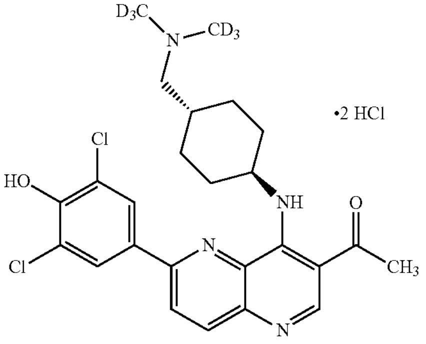 [SMILES: [2H]C([2H])([2H])N(C[C@H]1CC[C@H](Nc2c(C(C)=O)cnc3ccc(-c4cc(Cl)c(O)c(Cl)c4)nc23)CC1)C([2H])([2H])[2H]]

Following general procedure II, 1-(6-chloro-4-{trans-4-[(dimethylamino)methyl]cyclohexylamino}-1,5-naphthyridin-3-yl)ethanone (153 mg, 0.42 mmol) was reacted with 2,6-dichloro-4-(4,4,5,5-tetramethyl-1,3,2-dioxaborolan-2-yl)phenol (180 mg, 0.63 mmol) followed by formation of the dihydrochloride salt to afford the desired product (164 mg, 69%) as an off-white solid: $^1$H NMR (500 MHz, $CD_3OD$) δ 9.15 (s, 1H), 8.46 (d, J=9.0 Hz, 1H), 8.33 (d, J=9.0 Hz, 1H), 8.12 (s, 2H), 5.76-5.71 (m, 1H), 3.09 (d, J=6.6 Hz, 2H), 2.76 (s, 3H), 2.50-2.40 (m, 2H), 2.08-1.98 (m, 3H), 1.74-1.64 (m, 2H), 1.47-1.37 (m, 2H); ESI MS m/z 493 [M+H]$^+$; HPLC>99% (AUC), $t_R$=9.83 min.

Example 29

1-[6-(3,5-Dichloro-4-hydroxyphenyl)-4-{4-[2-(dimethylamino)ethyl]phenylamino}-1,5-naphthyridin-3-yl)ethanone dihydrochloride

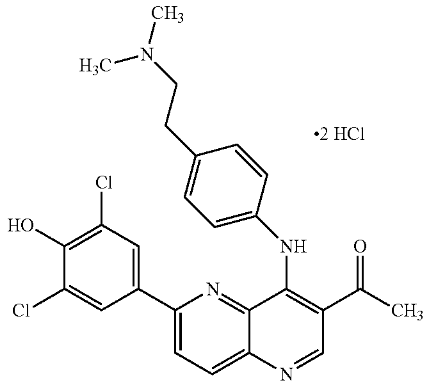 [SMILES: CC(=O)c1cnc2ccc(-c3cc(Cl)c(O)c(Cl)c3)nc2c1Nc1ccc(CCN(C)C)cc1]

Following general procedure II, 1-(6-chloro-4-{4-[2-(dimethylamino)ethyl]phenylamino}-1,5-naphthyridin-3-yl) ethanone (40 mg, 0.11 mmol) was reacted with 2,6-dichloro-4-(4,4,5,5-tetramethyl-1,3,2-dioxaborolan-2-yl)phenol (43 mg, 0.15 mmol) followed by formation of the dihydrochloride salt to afford the desired product (17 mg, 28%) as an orange solid: $^1$H NMR (500 MHz, $CD_3OD$) δ 9.30 (s, 1H), 8.43 (d, J=9.0 Hz, 1H), 8.33 (d, J=9.0 Hz, 1H), 7.52 (br s, 2H), 7.42 (d, J=8.5 Hz, 2 H), 7.37 (d, J=8.5 Hz, 2H), 3.40-3.32 (m, 2H), 3.22-3.13 (m, 2H), 2.96 (s, 6H), 2.79 (s, 3H); ESI MS m/z 495 [M+H]$^+$; HPLC>99% (AUC), $t_R$=9.91 min.

Example 30

1-[6-(3-Chloro-5-fluoro-4-hydroxyphenyl)-4-{4-[2-(dimethylamino)ethyl]phenylamino}-1,5-naphthyridin-3-yl)ethanone dihydrochloride

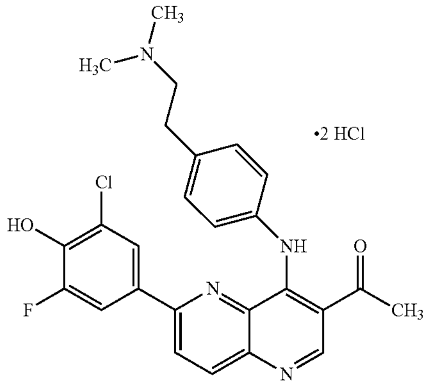 [SMILES: CC(=O)c1cnc2ccc(-c3cc(F)c(O)c(Cl)c3)nc2c1Nc1ccc(CCN(C)C)cc1]

Following general procedure II, 1-(6-chloro-4-{4-[2-(dimethylamino)ethyl]phenylamino}-1,5-naphthyridin-3-yl)

ethanone (40 mg, 0.11 mmol) was reacted with 2-chloro-6-fluoro-4-(4,4,5,5-tetramethyl-1,3,2-dioxaborolan-2-yl) phenol (41 mg, 0.15 mmol) followed by formation of the dihydrochloride salt to afford the desired product (13 mg, 22%) as an orange solid: $^1$H NMR (500 MHz, $CD_3OD$) δ 9.29 (s, 1H), 8.42 (d, J=9.1 Hz, 1H), 8.32 (d, J=9.0 Hz, 1H), 7.44 (d, J=8.5 Hz, 2 H), 7.41-7.35 (m, 3H), 7.11 (br s, 1H), 3.43-3.36 (m, 2H), 3.23-3.13 (m, 2H), 2.98 (s, 6H), 2.80 (s, 3H); ESI MS m/z 479 [M+H]$^+$; HPLC>99% (AUC), $t_R$=9.67 min.

Example 31

1-[6-(3-Chloro-4-phenol-5-methoxyphenyl)-4-{4-[2-(dimethylamino)ethyl]phenylamino}-1,5-naphthyridin-3-yl)ethanone dihydrochloride

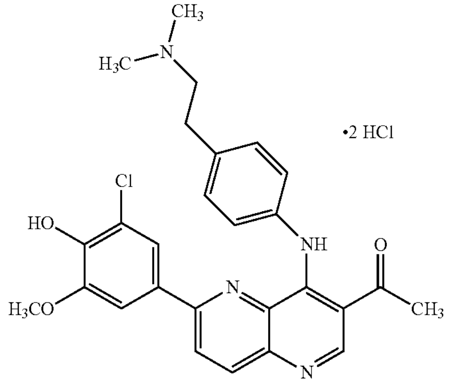 [SMILES: COc1cc(-c2ccc3ncc(C(C)=O)c(Nc4ccc(CCN(C)C)cc4)c3n2)cc(Cl)c1O]

Following general procedure II, 1-(6-chloro-4-{4-[2-(dimethylamino)ethyl]phenylamino}-1,5-naphthyridin-3-yl) ethanone (40 mg, 0.11 mmol) was reacted with 2-chloro-6-methoxy-4-(4,4,5,5-tetramethyl-1,3,2-dioxaborolan-2-yl) phenol (57 mg, 0.20 mmol) followed by formation of the dihydrochloride salt to afford the desired product (40 mg, 66%) as an orange solid: $^1$H NMR (500 MHz, $CD_3OD$) δ 9.30 (s, 1H), 8.47 (d, J=9.1 Hz, 1H), 8.35 (d, J=9.1 Hz, 1H), 7.41 (d, J=8.6 Hz, 2 H), 7.38 (d, J=8.6 Hz, 2 H), 7.33 (br s, 1 H), 6.88 (br s, 1H), 3.95 (s, 3H), 3.35-3.30 (m, 2H), 3.20-3.12 (m, 2H), 2.98 (s, 6H), 2.81 (s, 3H); ESI MS m/z 491 [M+H]$^+$; HPLC>99% (AUC), $t_R$=9.62 min.

Example 32

2-Chloro-4-{8-[trans-4-(dimethylamino)cyclohexylamino]-7-(methylsulfonyl)-1,5-naphthyridin-2-yl}-6-fluorophenol

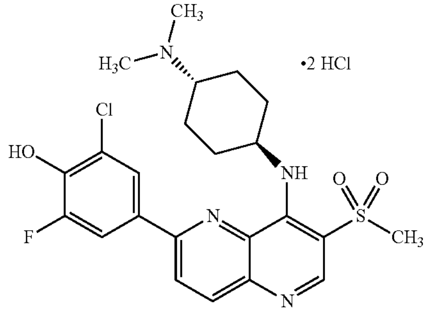 [SMILES: CN(C)[C@H]1CC[C@H](Nc2c(S(C)(=O)=O)cnc3ccc(-c4cc(F)c(O)c(Cl)c4)nc23)CC1]

Following general procedure II, trans-N$^1$-(6-chloro-3-(methylsulfonyl)-1,5-naphthyridin-4-yl)-N$^4$,N$^4$-dimethylcyclohexane-1,4-diamine (28 mg, 0.073 mmol) was reacted with 2-chloro-6-fluoro-4-(4,4,5,5-tetramethyl-1,3,2-dioxaborolan-2-yl)phenol (41 mg, 0.15 mmol) followed by formation of the dihydrochloride salt to afford the desired product (30 mg, 72%) as an off-white solid: $^1$H NMR (500 MHz, $CD_3OD$) δ 8.92 (s, 1H), 8.51 (d, J=9.0 Hz, 1H), 8.37 (d, J=8.9 Hz, 1H), 8.02 (t, J=1.7 Hz, 1H), 7.92 (dd, J=11.5, 2.2 Hz, 1H), 5.64 (br s, 1H), 3.52-3.42 (m, 1H), 3.39 (s, 3H), 2.91 (s, 6H), 2.65-2.55 (m, 2H), 2.33-2.26 (m, 2H), 1.88-1.72 (m, 4H); ESI MS m/z 493 [M+H]$^+$; HPLC 98.3% (AUC), $t_R$=9.62 min.

Example 33

1-[6-(3,5-Dichloro-4-hydroxyphenyl)-4-[1-(1-methylpiperidin-4-yl)-1H-pyrazol-4-ylamino]-1,5-naphthyridin-3-yl]ethanone dihydrochloride

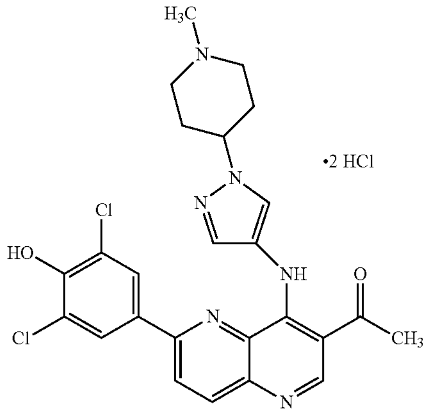 [SMILES: CC(=O)c1cnc2ccc(-c3cc(Cl)c(O)c(Cl)c3)nc2c1Nc1cnn(C2CCN(C)CC2)c1]

Following general procedure II, 1-{6-chloro-4-[1-(1-methylpiperidin-4-yl)-1H-pyrazol-4-ylamino)-1,5-naphthyridin-3-yl)]ethanone (77 mg, 0.21 mmol) was reacted with 2,6-dichloro-4-(4,4,5,5-tetramethyl-1,3,2-dioxaborolan-2-yl)phenol (87 mg, 0.30 mmol) followed by formation of the dihydrochloride salt to afford the desired product (67 mg, 57%) as a yellow solid: $^1$H NMR (500 MHz, $D_2O$) δ 9.14 (s, 1H), 8.15 (d, J=9.0 Hz, 1H), 7.99 (d, J=8.9 Hz, 1H), 7.73 (d, J=2.8 Hz, 1H), 7.51 (br s, 1H), 6.97 (br s, 2H), 4.44-4.32 (m, 1H), 3.50 (d, J=12.5 Hz, 2H), 3.07 (t, J=13.0 Hz, 2H), 2.80 (s, 3H), 2.78 (s, 3H), 2.15-1.92 (m, 4H); ESI MS m/z 511 [M+H]$^+$; HPLC>99% (AUC), $t_R$=9.37 min.

Example 34

1-(6-(3,5-Dichloro-4-hydroxyphenyl)-4-(4-((4-methylpiperazin-1-yl)methyl)-phenylamino)-1,5-naphthyridin-3-yl)ethanone trihydrochloride

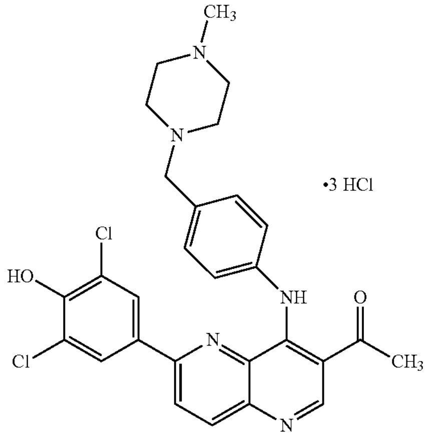 [SMILES: CC(=O)c1cnc2ccc(-c3cc(Cl)c(O)c(Cl)c3)nc2c1Nc1ccc(CN2CCN(C)CC2)cc1]

Following general procedure II, 1-(6-chloro-4-(4-((4-methylpiperazin-1-yl)methyl)-phenylamino)-1,5-naphthyridin-3-yl)ethanone (74 mg, 0.18 mmol) was reacted with 2,6-dichloro-4-(4,4,5,5-tetramethyl-1,3,2-dioxaborolan-2-yl)phenol (78 mg, 0.27 mmol) followed by formation of the dihydrochloride salt to afford the desired product (84 mg, 77%) as a yellow solid: $^1$H NMR (500 MHz, $CD_3OD$) δ 9.33 (s, 1H), 8.45 (d, J=9.1 Hz, 1H), 8.36 (d, J=9.0 Hz, 1H), 7.70 (d, J=8.1 Hz, 2H), 7.49 (d, J=8.1 Hz, 2H), 7.38 (br s, 2H), 4.45 (s, 2H), 3.55 (br s, 8H), 2.99 (s, 3H), 2.81 (s, 3H); ESI MS m/z 536 [M+H]$^+$; HPLC>99% (AUC), $t_R$=9.57 min.

Example 35

1-[6-(3-Chloro-5-fluoro-4-hydroxyphenyl)-4-{4-[(4-methylpiperazin-1-yl)methyl]phenylamino}-1,5-naphthyridin-3-yl]ethanone trihydrochloride

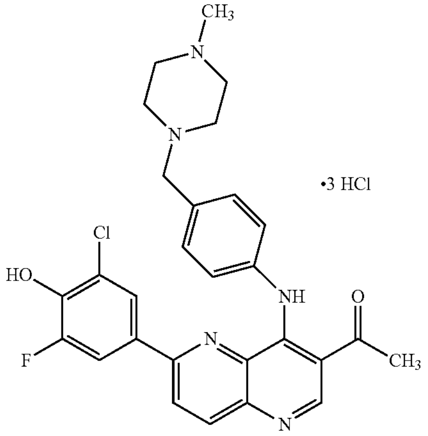 [SMILES: CC(=O)c1cnc2ccc(-c3cc(F)c(O)c(Cl)c3)nc2c1Nc1ccc(CN2CCN(C)CC2)cc1]

Following general procedure II, 1-(6-chloro-4-{4-[(4-methylpiperazin-1-yl)methyl]phenyl amino}-1,5-naphthyridin-3-yl)ethanone (74 mg, 0.18 mmol) was reacted with 2-chloro-6-fluoro-4-(4,4,5,5-tetramethyl-1,3,2-dioxaborolan-2-yl)phenol (74 mg, 0.27 mmol) followed by formation of the dihydrochloride salt to afford the desired product (96 mg, 93%) as a yellow solid: $^1$H NMR (500 MHz, $CD_3OD$) δ 9.32 (s, 1H), 8.44 (d, J=9.1 Hz, 1H), 8.34 (d, J=9.1 Hz, 1H), 7.65 (d, J=7.6 Hz, 2H), 7.48 (d, J=8.0 Hz, 2H), 7.31 (br s, 1H), 7.12 (br s, 1H), 4.26 (br s, 2H), 3.45 (br s, 8H), 2.97 (s, 3H), 2.80 (s, 3H); ESI MS m/z 520 [M+H]$^+$; HPLC>99% (AUC), $t_R$=9.37 min.

Example 36

1-[6-(3,5-Dichloro-4-hydroxyphenyl)-4-{4-[2-(pyrrolidin-1-yl)ethyl]piperidin-1-yl}-1,5-naphthyridin-3-yl]ethanone dihydrochloride

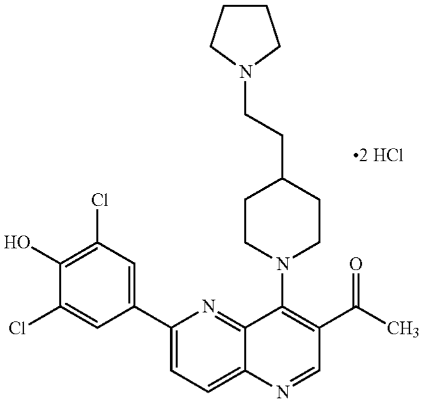 [SMILES: CC(=O)c1cnc2ccc(-c3cc(Cl)c(O)c(Cl)c3)nc2c1N1CCC(CCN2CCCC2)CC1]

Following general procedure II, 1-(6-chloro-4-{4-[2-(pyrrolidin-1-yl)ethyl]piperidin-1-yl}-1,5-naphthyridin-3-yl)ethanone (60 mg, 0.16 mmol) was reacted with 2,6-dichloro-4-(4,4,5,5-tetramethyl-1,3,2-dioxaborolan-2-yl)phenol (65 mg, 0.23 mmol) followed by formation of the dihydrochloride salt to afford the desired product (54 mg, 60%) as a yellow solid: $^1$H NMR (500 MHz, $CD_3OD$) δ 8.91 (s, 1H), 8.46 (d, J=9.1 Hz, 1H), 8.35 (d, J=8.9 Hz, 1H), 8.16 (s, 2H), 4.63 (br s, 2H), 3.70-3.54 (m, 4H), 3.32-3.24 (m, 2H), 3.13-3.03 (m, 2H), 2.67 (s, 3H), 2.22-1.96 (m, 7H), 1.82-1.69 (m, 4H);

ESI MS m/z [M+H]$^+$; HPLC>99% (AUC), $t_R$=9.75 min.

Example 37

1-[6-(3-Chloro-5-fluoro-4-hydroxyphenyl)-4-{4-[2-(pyrrolidin-1-yl)ethyl]piperidin-1-yl}-1,5-naphthyridin-3-yl]ethanone dihydrochloride

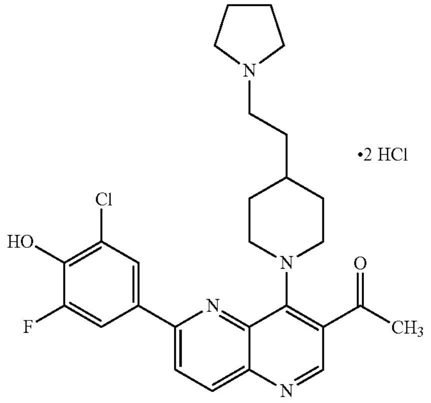 [SMILES: CC(=O)c1cnc2ccc(-c3cc(F)c(O)c(Cl)c3)nc2c1N1CCC(CCN2CCCC2)CC1]

Following general procedure II, 1-(6-chloro-4-{4-[2-(pyrrolidin-1-yl)ethyl]piperidin-1-yl}-1,5-naphthyridin-3-yl)ethanone (60 mg, 0.16 mmol) was reacted with 2-chloro-6-fluoro-4-(4,4,5,5-tetramethyl-1,3,2-dioxaborolan-2-yl)phenol (61 mg, 0.23 mmol) followed by formation of the dihydrochloride salt to afford the desired product (73 mg, 83%) as a yellow solid: $^1$H NMR (500 MHz, $CD_3OD$) δ 8.91 (s, 1H), 8.45 (d, J=9.0 Hz, 1H), 8.35 (d, J=8.9 Hz, 1H), 8.04 (t, J=1.8 Hz, 1H), 7.89 (dd, J=11.7, 2.2 Hz, 1H), 4.66 (br s, 2H), 3.69-3.54 (m, 4H), 3.33-3.23 (m, 2H), 3.13-3.03 (m, 2H), 2.67 (s, 3H), 2.22-1.96 (m, 7H), 1.81-1.68 (m, 4H); ESI MS m/z 497 [M+H]$^+$; HPLC>99% (AUC), $t_R$=9.65 min.

Example 38

1-[6-(3,5-Dichloro-4-hydroxyphenyl)-4-{6-[2-(dimethylamino)ethylamino]pyridin-3-ylamino}-1,5-naphthyridin-3-yl]ethanone trihydrochloride

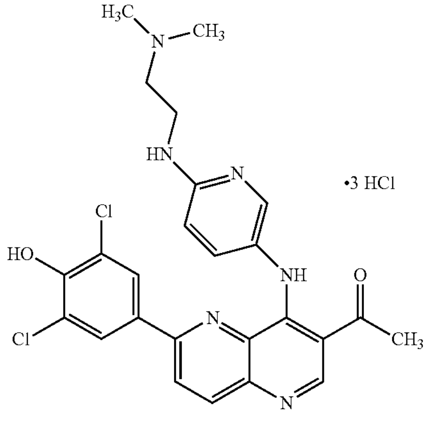 [SMILES: CC(=O)c1cnc2ccc(-c3cc(Cl)c(O)c(Cl)c3)nc2c1Nc1ccc(NCCN(C)C)nc1]

Following general procedure II, 1-[6-(3,5-dichloro-4-hydroxyphenyl)-4-{6-[2-(dimethylamino)ethylamino]pyridin-3-ylamino}-1,5-naphthyridin-3-yl]ethanone (69 mg, 0.18 mmol) was reacted with 2,6-dichloro-4-(4,4,5,5-tetramethyl-1,3,2-dioxaborolan-2-yl)phenol (78 mg, 0.27 mmol) followed by formation of the trihydrochloride salt to afford the desired product (87 mg, 78%) as a yellow-orange solid: $^1$H NMR (500 MHz, $D_2O$) δ 9.22 (s, 1H), 8.22 (d, J=8.9 Hz, 1H), 8.02 (d, J=9.1 Hz, 1H), 7.92 (d, J=2.5 Hz, 1H), 7.59-7.53 (m, 1H), 6.98 (s, 2H), 6.79 (d, J=9.4 Hz, 1H), 3.67 (t, J=6.4 Hz, 2H), 3.23 (t, J=6.4 Hz, 2H), 2.82 (s, 6H), 2.80 (s, 3H); ESI MS m/z 511 [M+H]$^+$; HPLC>99% (AUC), $t_R$=9.13 min.

Example 39

1-[6-(3-Chloro-5-fluoro-4-hydroxyphenyl)-4-{6-[2-(dimethylamino)ethylamino]pyridin-3-ylamino}-1,5-naphthyridin-3-yl]ethanone trihydrochloride

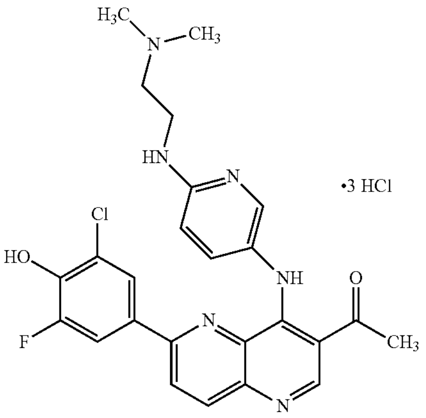 [SMILES: CC(=O)c1cnc2ccc(-c3cc(F)c(O)c(Cl)c3)nc2c1Nc1ccc(NCCN(C)C)nc1]

Following general procedure II, 1-[6-(3,5-dichloro-4-hydroxyphenyl)-4-{6-[2-(dimethylamino)ethylamino]pyridin-3-ylamino}-1,5-naphthyridin-3-yl]ethanone (69 mg, 0.18 mmol) was reacted with 2-chloro-6-fluoro-4-(4,4,5,5-tetramethyl-1,3,2-dioxaborolan-2-yl)phenol (74 mg, 0.27 mmol) followed by formation of the trihydrochloride salt to afford the desired product (71 mg, 66%) as a yellow-orange solid: $^1$H NMR (500 MHz, $CD_3OD$) δ 9.40 (s, 1H), 8.49 (d, J=9.0 Hz, 1H), 8.41 (d, J=9.1 Hz, 1H), 8.23 (d, J=2.5 Hz, 1H), 7.87 (dd, J=9.4, 2.5 Hz, 1H), 7.42 (br s, 2H), 7.06 (d, J=9.4 Hz, 1H), 3.91 (t, J=6.4 Hz, 2H), 3.47 (t, J=6.4 Hz, 2H), 2.99 (s, 6H), 2.85 (s, 3H); ESI MS m/z 495 [M+H]$^+$; HPLC 98.9% (AUC), $t_R$=8.97 min.

Example 40

(S)-{4-[6-(3-Aminopiperidin-1-yl)pyridin-3-ylamino]-6-(3,5-dichloro-4-hydroxyphenyl)-1,5-naphthyridin-3-yl}(cyclopropyl)methanone trihydrochloride

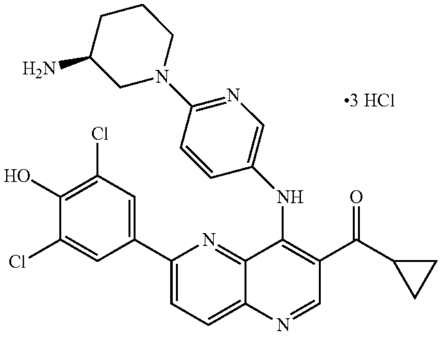 [SMILES: N[C@H]1CCCN(c2ccc(Nc3c(C(=O)C4CC4)cnc4ccc(-c5cc(Cl)c(O)c(Cl)c5)nc34)cn2)C1]

Following general procedure IV-2, (S)-tert-butyl 1-{5-[3-(cyclopropanecarbonyl)-6-(3,5-dichloro-4-hydroxyphenyl)-1,5-naphthyridin-4-ylamino]pyridin-2-yl}piperidin-3-ylcarbamate (73 mg, 0.11 mmol) was reacted with TFA (3 mL) followed by formation of the trihydrochloride salt to afford the desired product (31 mg, 42%) as an orange solid: $^1$H NMR (500 MHz, $CD_3OD$) δ 9.52 (br s, 1H), 8.51 (d, J=9.0 Hz, 1H), 8.42 (d, J=9.0 Hz, 1H), 8.23 (d, J=2.6 Hz, 1H), 7.88 (dd, J=9.4, 2.7 Hz, 1H), 7.69 (br s, 2H), 7.24 (d, J=9.5 Hz, 1H), 4.37 (d, J=10.9 Hz, 1H), 4.05-3.95 (m, 1H), 3.50-3.33 (m, 3H), 2.90 (br s, 1H), 2.27-2.17 (m, 1H), 2.06-1.96 (m, 1H), 1.86-1.74 (m, 2H), 1.37-1.18 (m, 4H); ESI MS m/z 549 [M+H]$^+$; HPLC 95.4% (AUC), $t_R$=10.09 min.

Example 41

1-{4-[2-(3-Aminopyrrolidin-1-yl)pyrimidin-5-ylamino]-6-(3,5-dichloro-4-hydroxyphenyl)-1,5-naphthyridin-3-yl}ethanone trihydrochloride

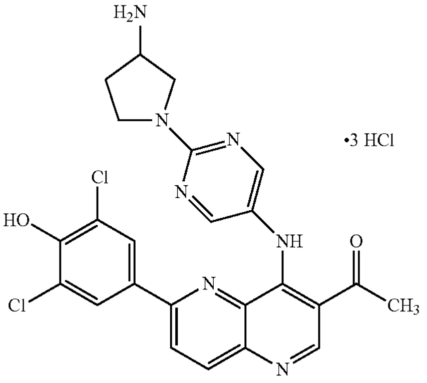 [SMILES: CC(=O)c1cnc2ccc(-c3cc(Cl)c(O)c(Cl)c3)nc2c1Nc1cnc(N2CCC(N)C2)nc1]

Following general procedure IV-1, tert-butyl 1-{5-[3-acetyl-6-(3,5-dichloro-4-hydroxyphenyl)-1,5-naphthyridin-4-ylamino]pyrimidin-2-yl}pyrrolidin-3-ylcarbamate (123 mg, 0.20 mmol) was reacted with 6 N HCl (2 mL) followed by formation of the trihydrochloride salt to afford the desired product (62 mg, 50%) as a light orange solid: $^1$H NMR (500 MHz, $CD_3OD$) δ 9.36 (br s, 1H), 8.51-8.35 (m, 3H), 7.51 (br s, 2H), 4.12-3.97 (m, 2H), 3.89-3.84 (m, 1H), 3.80-3.69 (m, 2H), 2.84 (br s, 3H), 2.58-2.48 (m, 1H), 2.28-2.17 (m, 1H); ESI MS m/z 510 [M+H]$^+$; HPLC 95.6% (AUC), $t_R$=9.18 min.

Example 42

1-(4-{trans-4-[(Dimethylamino)methyl]cyclohexylamino}-6-(1H-pyrazol-4-yl)-1,5-naphthyridin-3-yl)ethanone trihydrochloride

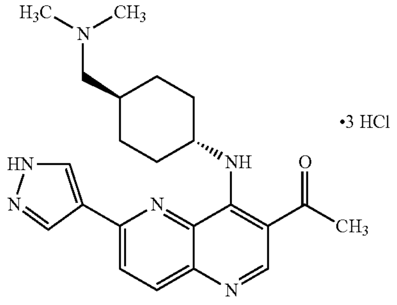 [SMILES: CC(=O)c1cnc2ccc(-c3cn[nH]c3)nc2c1N[C@H]1CC[C@H](CN(C)C)CC1 ; "·3 HCl"]

Following general procedure II, 1-(6-chloro-4-{4-[(dimethylamino)methyl]-cyclohexylamino}-1,5-naphthyridin-3-yl)ethanone (55 mg, 0.15 mmol) was reacted with tert-butyl 4-(4,4,5,5-tetramethyl-1,3,2-dioxaborolan-2-yl)-1H-pyrazole-1-carboxylate (66 mg, 0.225 mmol) followed by formation of the trihydrochloride salt to afford the desired product (32 mg, 42%) as a yellow solid: $^1$H NMR (300 MHz, $CD_3OD$) δ 9.10 (s, 1H), 8.34 (s, 2H) 8.30-8.23 (m, 2H), 5.64 (m, 1H), 3.14 (d, J=6.7 Hz, 2H), 2.94 (s, 6H), 2.75 (s, 3H), 2.47 (d, J=13.0 Hz, 2H), 2.09-1.97 (m, 3H), 1.73-1.61 (m, 2H), 1.45-1.33 (m, 2H); ESI MS m/z 393 $[M+H]^+$; HPLC 98.3% (AUC), $t_R$=8.60 min.

Example 43

1-(6-{3,5-Dichloro-4-hydroxyphenyl)-4-[trans-4-(hydroxymethyl)cyclohexyl]amino}-1,5-naphthyridin-3-yl)ethanone hydrochloride

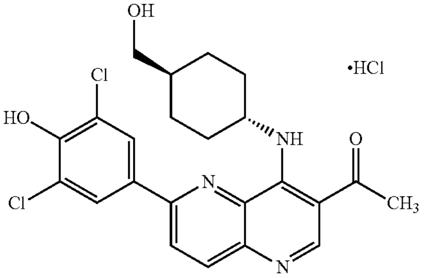 [SMILES: CC(=O)c1cnc2ccc(-c3cc(Cl)c(O)c(Cl)c3)nc2c1N[C@H]1CC[C@H](CO)CC1 ; Cl]

Following general procedure II, 1-{6-chloro-4-[4-(hydroxymethyl)cyclohexylamino]-1,5-naphthyridin-3-yl}ethanone (34 mg, 0.10 mmol) was reacted with 2,6-dichloro-4-(4,4,5,5-tetramethyl-1,3,2-dioxaborolan-2-yl) phenol (44 mg, 0.15 mmol) followed by formation of the hydrochloride salt to afford the desired product (40 mg, 80%) as an orange solid: $^1$H NMR (500 MHz, DMSO-$d_6$) δ 11.83 (d, J=8.0 Hz, 1H), 10.91 (s, 1H), 9.22 (s, 1H), 8.61 (d, J=8.9 Hz, 1H), 8.50 (d, J=9.0 Hz, 1H), 8.16 (s, 2H), 5.55-5.45 (m, 1H), 3.28 (d, J=6.5 Hz, 2H), 2.76 (s, 3H), 2.25-2.23 (m, 2H), 1.96-1.88 (m, 2H), 1.50-1.42 (m, 3H), 1.17-1.12 (m, 2H); ESI MS m/z 460 $[M+H]^+$; HPLC 96.8% (AUC), $t_R$=11.64 min.

Example 44

1-[6-(3,5-Dichloro-4-hydroxyphenyl)-4-{trans-4-[(dimethylamino)methyl]cyclohexyl-amino}-1,5-naphthyridin-3-yl]-2-hydroxyethanone dihydrochloride

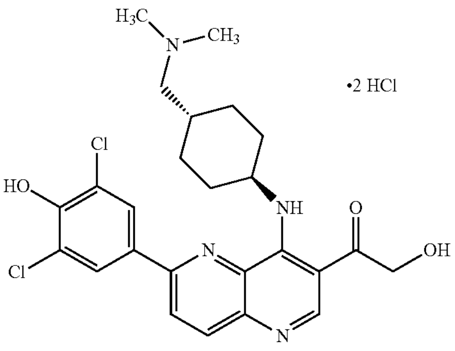 [SMILES: CN(C)C[C@H]1CC[C@H](Nc2c(C(=O)CO)cnc3ccc(-c4cc(Cl)c(O)c(Cl)c4)nc23)CC1]

Following general procedure II, 1-(6-chloro-4-{trans-4-[(dimethylamino)methyl]-cyclohexylamino}-1,5-naphthyridin-3-yl)-2-hydroxyethanone (18 mg, 0.048 mmol) was reacted with 2,6-dichloro-4-(4,4,5,5-tetramethyl-1,3,2-dioxaborolan-2-yl)phenol (18 mg, 0.062 mmol) followed by formation of the dihydrochloride salt to afford the desired product (9.1 mg, 33%) as an off-white solid. $^1$H NMR (500 MHz, $CD_3OD$) δ 9.13 (s, 1H), 8.47 (d, J=8.9 Hz, 1H), 8.33 (d, J=8.9 Hz, 1H), 8.13 (s, 2H), 5.78-5.68 (m, 1H), 4.91 (s, 2H), 3.10 (d, J=6.7 Hz, 2H), 2.94 (s, 6H), 2.49-2.42 (m, 2H), 2.10-2.00 (m, 3H), 1.76-1.66 (m, 2H), 1.48-1.36 (m, 2H).; ESI MS m/z 503 $[M+H]^+$; HPLC>99% (AUC), $t_R$=9.40 min.

Example 45

1-{6-(3,5-Dichloro-4-hydroxyphenyl)-4-[(1-methylpiperidin-4-yl)amino]-1,5-naphthyridin-3-yl}ethanone

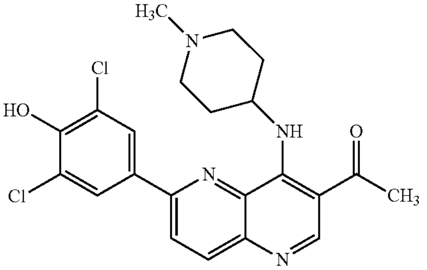 [SMILES: CC(=O)c1cnc2ccc(-c3cc(Cl)c(O)c(Cl)c3)nc2c1NC1CCN(C)CC1]

Following general procedure II, 1-{6-chloro-4-[(1-methylpiperidin-4-yl)amino]-1,5-naphthyridin-3-yl}ethanone (70 mg, 0.22 mmol) was reacted with 2,6-dichloro-4-(4,4,5,5-tetramethyl-1,3,2-dioxaborolan-2-yl)phenol (95 mg, 0.33 mmol) to afford the desired product (52 mg, 53%) as a yellow solid: $^1$H NMR (500 MHz, $CD_3OD$) δ 8.85 (s, 1H), 8.09-8.01 (m, 2H), 7.94 (s, 2H), 5.74-5.70 (m, 1H), 2.95-2.92 (m, 2H), 2.68 (s, 3H), 2.51 (t, J=11.7 Hz, 2H), 2.37 (s, 3H), 2.33-2.25 (m, 2H), 1.73-1.71 (m, 2H); ESI MS m/z 445 $[M+H]^+$; HPLC>99% (AUC), $t_R$=9.03 min.

Example 46

1-{6-(3-Chloro-5-fluoro-4-hydroxyphenyl)-4-[(1-methylpiperidin-4-yl)amino]-1,5-naphthyridin-3-yl}ethanone

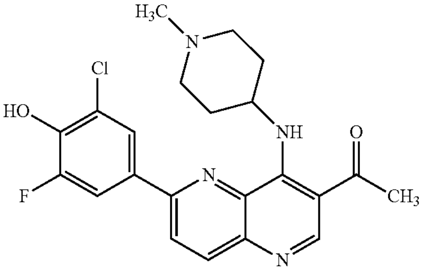 [SMILES: CC(=O)c1cnc2ccc(-c3cc(F)c(O)c(Cl)c3)nc2c1NC1CCN(C)CC1]

Following general procedure II, 1-{6-chloro-4-[(1-methylpiperidin-4-yl)amino]-1,5-naphthyridin-3-yl}ethanone (69 mg, 0.22 mmol) was reacted with 2-chloro-6-fluoro-4-(4,4,5,5-tetramethyl-1,3,2-dioxaborolan-2-yl)phenol (88 mg, 0.32 mmol) to afford the desired product (44 mg, 47%) as a yellow solid: $^1$H NMR (500 MHz, $CD_3OD+D_2O$) δ 8.94 (s, 1H), 8.15 (s, 2H), 7.92 (s, 1H), 7.74 (dd, J=12.0, 2.2 Hz, 1H), 5.70-5.62 (m, 1H), 3.17-3.12 (m, 2H), 2.71 (s, 3H), 2.69-2.64 (m, 2H), 2.53 (s, 3H), 2.37-2.35 (m, 2H), 1.85-1.82 (m, 2H); ESI MS m/z 429 [M+H]$^+$; HPLC>99% (AUC), $t_R$=8.80 min.

Example 47

1-[6-(3,5-Dichloro-4-hydroxyphenyl)-4-{[trans-4-(morpholinomethyl)cyclohexyl]amino}-1,5-naphthyridin-3-yl]ethanone

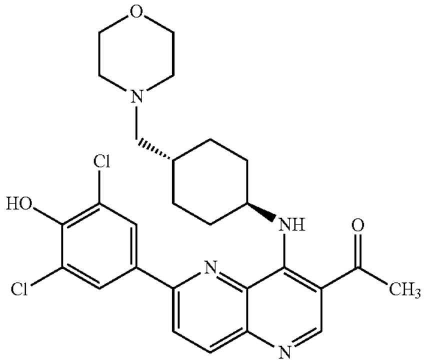 [SMILES: CC(=O)c1cnc2ccc(-c3cc(Cl)c(O)c(Cl)c3)nc2c1N[C@H]1CC[C@H](CN2CCOCC2)CC1]

Following general procedure II, 1-(6-chloro-4-{[4-(morpholinomethyl)cyclohexyl]-amino}-1,5-naphthyridin-3-yl) ethanone (85 mg, 0.21 mmol) was reacted with 2,6-dichloro-4-(4,4,5,5-tetramethyl-1,3,2-dioxaborolan-2-yl)phenol (91 mg, 0.31 mmol) to afford the desired product (59 mg, 53%) as an orange solid: $^1$H NMR (500 MHz, $CDCl_3$) δ 11.18-11.16 (m, 1H), 8.95 (s, 1H), 8.21 (d, J=8.8 Hz, 1H), 7.99 (s, 2H), 7.94 (d, J=8.8 Hz, 1H), 5.51-5.42 (m, 1H), 3.71 (t, J=4.7 Hz, 4H), 2.70 (s, 3H), 2.41-2.43 (m, 4H), 2.34-2.32 (m, 2H), 2.23-2.22 (m, 2H), 2.02-1.95 (m, 2H), 1.62-1.58 (m, 1H), 1.46-1.39 (m, 2H), 1.28-1.15 (m, 2H); ESI MS m/z 529 [M+H]$^+$; HPLC 98.2% (AUC), $t_R$=9.93 min.

Example 48

1-[6-(3,5-Dichloro-4-hydroxyphenyl)-4-(trans-4-{[(2-hydroxyethyl)(methyl)amino]methyl}-cyclohexylamino)-1,5-naphthyridin-3-yl]ethanone dihydrochloride

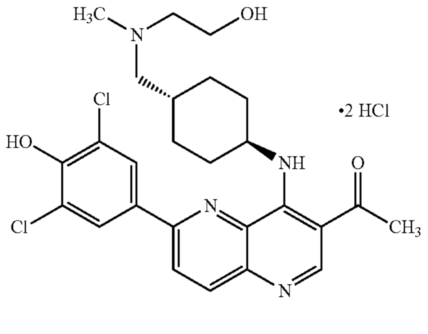 [SMILES: CC(=O)c1cnc2ccc(-c3cc(Cl)c(O)c(Cl)c3)nc2c1N[C@H]1CC[C@H](CN(C)CCO)CC1]

Following general procedure II, 1-[6-chloro-4-(4-{[(2-hydroxyethyl)(methyl)-amino]methyl}cyclohexylamino)-1,5-naphthyridin-3-yl]ethanone (70 mg, 0.18 mmol) was reacted with 2,6-dichloro-4-(4,4,5,5-tetramethyl-1,3,2-dioxaborolan-2-yl)phenol (76 mg, 0.27 mmol) followed by formation of the dihydrochloride salt to afford the desired product (68 mg, 64%) as a light yellow solid: $^1$H NMR (500 MHz, $CD_3OD$) δ 9.15 (s, 1H), 8.46 (d, J=9.0 Hz, 1H), 8.34 (d, J=9.0 Hz, 1H), 8.12 (s, 2H), 5.74-5.71 (m, 1H), 3.90 (t, J=5.0 Hz, 2H), 3.39-3.37 (m, 1H), 3.28-3.26 (m, 2H), 3.06-3.02 (m, 1H), 2.97 (s, 3H), 2.76 (m, 3H), 2.46-2.43 (m, 2H), 2.13-2.03 (m, 3H), 1.69-1.66 (m, 2H), 1.44-1.42 (m, 2H); ESI MS m/z 517 [M+H]$^+$; HPLC>99% (AUC), $t_R$=9.74 min.

Example 49

1-[6-(3-Chloro-5-fluoro-4-hydroxyphenyl)-4-(trans-4-{[(2-hydroxyethyl)(methyl)amino]-methyl}cyclohexylamino)-1,5-naphthyridin-3-yl] ethanone dihydrochloride

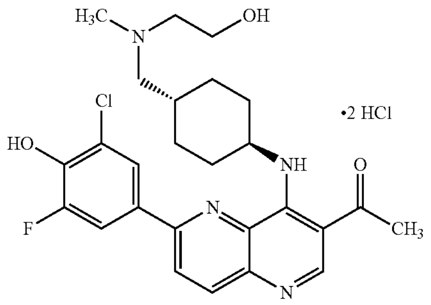 [SMILES: CC(=O)c1cnc2ccc(-c3cc(F)c(O)c(Cl)c3)nc2c1N[C@H]1CC[C@H](CN(C)CCO)CC1]

Following general procedure II, 1-[6-chloro-4-(4-{[(2-hydroxyethyl)(methyl)amino]-methyl}cyclohexylamino)-1,5-naphthyridin-3-yl]ethanone (30 mg, 0.076 mmol) was reacted with 2-chloro-6-fluoro-4-(4,4,5,5-tetramethyl-1,3,2-dioxaborolan-2-yl)phenol (31 mg, 0.11 mmol) followed by formation of the dihydrochloride salt to afford the desired product (32 mg, 73%) as a light yellow solid: $^1$H NMR (500 MHz, $CD_3OD$) δ 9.14 (s, 1H), 8.45 (d, J=9.0 Hz, 1H), 8.33 (d, J=9.0 Hz, 1H), 8.03 (s, 1H), 7.89 (d, J=11.5 Hz, 1H), 5.74-5.71 (m, 1H), 3.90 (t, J=5.1 Hz, 2H), 3.45-3.32 (m, 1H), 3.30-3.26 (m, 2H), 3.07-3.04 (m, 1H), 2.97 (s, 3H), 2.76 (s, 3H), 2.45 (s, 2H), 2.17-2.02 (m, 3H), 1.70-1.62 (m, 2H), 1.48-1.36 (m, 2H); ESI MS m/z 501 [M+H]$^+$; HPLC 98.2% (AUC), $t_R$=9.54 min.

Example 50

1-[6-(3,5-Difluoro-4-hydroxyphenyl)-4-{trans-4-[(dimethylamino)methyl]cyclohexylamino}-1,5-naphthyridin-3-yl]ethanone dihydrochloride

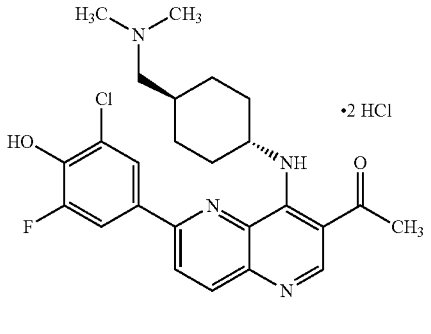 [SMILES: CC(=O)c1cnc2ccc(-c3cc(F)c(O)c(Cl)c3)nc2c1N[C@H]1CC[C@H](CN(C)C)CC1]

Following general procedure II, 1-(6-chloro-4-{4-[(dimethylamino)methyl]cyclohexyl-amino}-1,5-naphthyridin-3-yl)ethanone (65 mg, 0.18 mmol) was reacted with 2,6-difluoro-4-(4,4,5,5-tetramethyl-1,3,2-dioxaborolan-2-yl) phenol (69 mg, 0.27 mmol) followed by formation of the dihydrochloride salt to afford the desired product (87 mg, 90%) as an off-white solid: $^1$H NMR (500 MHz, $CD_3OD$) δ 9.13 (s, 1H), 8.44 (d, J=9.0 Hz, 1H), 8.35 (d, J=9.0 Hz, 1H), 7.78 (dd, J=7.8, 1.7 Hz, 2H), 5.66-5.62 (m, 1H), 3.09 (d, J=6.6 Hz, 2H), 2.94 (s, 6H), 2.76 (s, 3H), 2.47-2.44 (m, 2H), 2.08-

2.04 (m, 3H), 1.72-1.68 (m, 2H), 1.37-1.28 (m, 2H); ESI MS m/z 455 $[M+H]^+$; HPLC>99% (AUC), $t_R$=9.49 min.

Example 51

1-[6-(3,5-Dichloro-4-hydroxyphenyl)-4-{6-[3-(dimethylamino)pyrrolidin-1-yl]pyridin-3-ylamino}-1,5-naphthyridin-3-yl]ethanone trihydrochloride

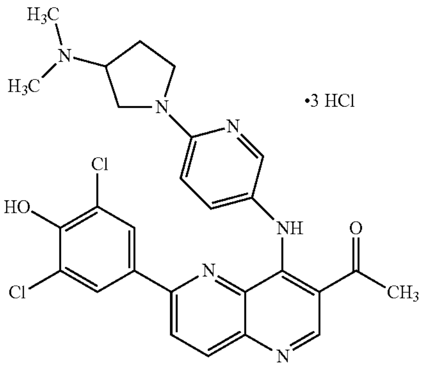 [SMILES: CC(=O)c1cnc2ccc(-c3cc(Cl)c(O)c(Cl)c3)nc2c1Nc1ccc(N2CCC(N(C)C)C2)nc1]

Following general procedure II, 1-(6-chloro-4-{6-[3-(dimethylamino)pyrrolidin-1-yl]-pyridin-3-ylamino}-1,5-naphthyridin-3-yl)ethanone (55 mg, 0.134 mmol) was reacted with 2,6-dichloro-4-(4,4,5,5-tetramethyl-1,3,2-dioxaborolan-2-yl)phenol (58 mg, 0.20 mmol) followed by formation of the trihydrochloride salt to afford the desired product (75 mg, 86%) as an orange solid: $^1$H NMR (300 MHz, $CD_3OD$) δ 9.41 (s, 1H), 8.55-8.38 (m, 2H), 8.30 (d, J=2.4 Hz, 1H), 7.97 (dd, J=9.5, 2.4 Hz, 1H), 7.54 (s, 2H), 7.05 (d, J=9.5 Hz, 1H), 4.20-4.16 (m, 2H), 4.02-3.86 (m, 2H), 3.80-3.70 (m, 1H), 3.03 (s, 6H), 2.85 (s, 3H), 2.82-2.68 (m, 1H), 2.39-2.52 (m, 1H); ESI MS m/z 537 $[M+H]^+$; HPLC>99% (AUC), $t_R$=9.08 min.

Example 52

1-[6-(3-Chloro-5-fluoro-4-hydroxyphenyl)-4-{6-[3-(dimethylamino)pyrrolidin-1-yl]pyridin-3-ylamino}-1,5-naphthyridin-3-yl]ethanone trihydrochloride

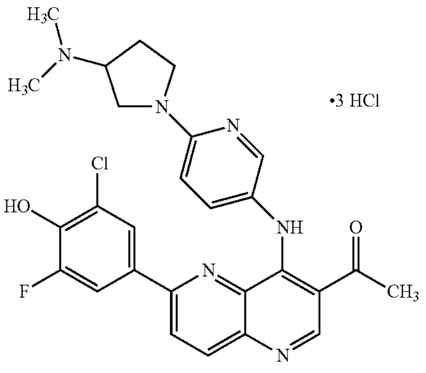 [SMILES: CC(=O)c1cnc2ccc(-c3cc(F)c(O)c(Cl)c3)nc2c1Nc1ccc(N2CCC(N(C)C)C2)nc1]

Following general procedure II, 1-(6-chloro-4-{6-[3-(dimethylamino)pyrrolidin-1-yl]pyridin-3-ylamino}-1,5-naphthyridin-3-yl)ethanone (55 mg, 0.134 mmol) was reacted with 2-chloro-6-fluoro-4-(4,4,5,5-tetramethyl-1,3,2-dioxaborolan-2-yl)phenol (55 mg, 0.20 mmol) followed by formation of the trihydrochloride salt to afford the desired product (85 mg, 99%) as a yellow solid: $^1$H NMR (300 MHz, $CD_3OD$) δ 9.41 (s, 1H), 8.54-8.37 (m, 2H), 8.29 (d, J=2.3 Hz, 1H), 7.99 (dd, J=9.5, 2.3 Hz, 1H), 7.39-7.35 (m, 2H), 7.10 (d, J=9.5 Hz, 1H), 4.29-4.11 (m, 2H), 4.03-3.85 (m, 2H), 3.75-3.71 (m, 1H), 3.03 (s, 6H), 2.85 (s, 3H), 2.71-2.82 (s, 1H); ESI MS m/z 521 $[M+H]^+$; HPLC>99% (AUC), $t_R$=8.90 min.

Example 53

1-(6-(3,5-Dichloro-4-hydroxyphenyl)-4-{6-[3-(methylamino)pyrrolidin-1-y]pyridin-3-ylamino}-1,5-naphthyridin-3-yl)ethanone trihydrochloride

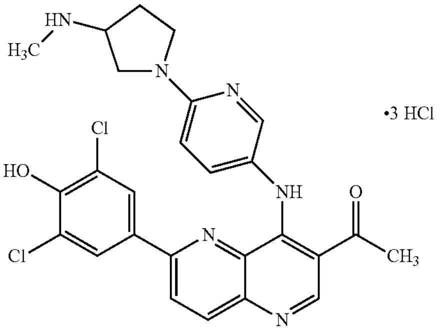 [SMILES: CNC1CCN(c2ccc(Nc3c(C(C)=O)cnc4ccc(-c5cc(Cl)c(O)c(Cl)c5)nc34)cn2)C1]

Following general procedure D-1, tert-butyl 1-{5-[3-acetyl-6-(3,5-dichloro-4-hydroxy-phenyl)-1,5-naphthyridin-4-ylamino]pyridin-2-yl}pyrrolidin-3-yl(methyl)carbamate (0.183 mmol) was reacted with TFA (2 mL) followed by formation of the trihydrochloride salt to afford the desired product (57 mg, 49% over two steps) as an orange-yellow solid: $^1$H NMR (500 MHz, $CD_3OD$) δ 9.37 (s, 1H), 8.49 (d, J=8.9 Hz, 1H), 8.40 (d, J=8.9 Hz, 1H), 8.24 (d, J=2.5 Hz, 1H), 7.88 (dd, J=9.4, 2.5 Hz, 1H), 7.57 (s, 2H), 6.96 (d, J=9.4 Hz, 1H), 4.13-4.00 (m, 2H), 3.92-3.79 (m, 2H), 3.66-3.73 (m, 1H), 2.83 (s, 6H), 2.72-2.60 (m, 1H), 2.45-2.34 (m, 1H); ESI MS m/z 523 $[M+H]^+$; HPLC>99% (AUC), $t_R$=8.97 min.

Example 54

1-(6-(3-Chloro-5-fluoro-4-hydroxyphenyl)-4-{6-[3-(methylamino)pyrrolidin-1-yl]pyridin-3-ylamino}-1,5-naphthyridin-3-yl)ethanone trihydrochloride

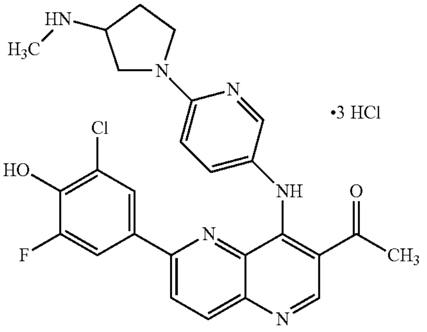 [SMILES: CNC1CCN(c2ccc(Nc3c(C(C)=O)cnc4ccc(-c5cc(F)c(O)c(Cl)c5)nc34)cn2)C1]

Following general procedure D-1, tert-butyl 1-{5-[3-acetyl-6-(3-chloro-5-fluoro-4-hydroxyphenyl]-1,5-naphthyridin-4-ylamino}pyridin-2-yl)pyrrolidin-3-yl(methyl) carbamate (0.189 mmol) was reacted with TFA (2 mL) followed by formation of the trihydrochloride salt to afford the desired product (73 mg, 63% over two steps) as an orange solid: $^1$H NMR (500 MHz, $CD_3OD$) δ 9.34 (s, 1H), 8.46 (d, J=9.0 Hz, 1H), 8.38 (d, J=9.0 Hz, 1H), 8.22 (d, J=2.5 Hz, 1H), 7.82 (dd, J=9.4, 2.5 Hz, 1H), 7.40 (s, 1H), 7.32 (d, J=11.8 Hz, 1H), 6.92 (d, J=9.4 Hz, 1H), 4.16-3.97 (m, 2H), 3.90-3.78 (m, 2H), 3.75-3.65 (m, 1H), 2.83 (s, 6H), 2.72-2.60 (m, 1H), 2.42-3.34 (m, 1H); ESI MS m/z 507 $[M+H]^+$; HPLC>99% (AUC), $t_R$=8.72 min.

Example 55

1-(6-(1H-Benzo[d]imidazol-5-yl)-4-{trans-4-[(dimethylamino)methyl]cyclohexylamino}-1,5-naphthyridin-3-yl)ethanone trihydrochloride

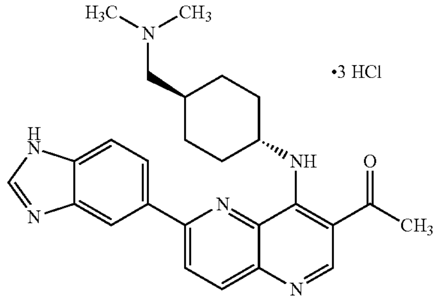 [SMILES: CC(=O)c1cnc2ccc(-c3ccc4[nH]cnc4c3)nc2c1N[C@H]1CC[C@H](CN(C)C)CC1 ; "·3 HCl"]

Following general procedure II, 1-(6-chloro-4-{trans-4-[(dimethylamino)methyl]cyclo-hexylamino}-1,5-naphthyridin-3-yl)ethanone (68 mg, 0.188 mmol) was reacted with 5-(4,4,5,5-tetramethyl-1,3,2-dioxaborolan-2-yl)-1H-benzo[d]imidazole (69 mg, 0.282 mmol) followed by formation of the trihydrochloride salt to afford the desired product (76 mg, 73%) as a yellow-brown solid: $^1$H NMR (500 MHz, $CD_3OD$) δ 9.49 (s, 1H), 9.19 (s, 1H), 8.63 (d, J=8.9 Hz, 1H), 8.56 (s, 1H), 8.46 (d, J=8.9 Hz, 1H), 8.37 (d, J=8.5 Hz, 1H), 8.19 (d, J=8.5 Hz, 1H), 5.65-5.55 (m, 1H), 3.15 (d, J=6.9 Hz, 2H), 2.93 (s, 6H), 2.78 (s, 3H), 2.52-2.48 (m, 2H), 2.07-1.95 (m, 3H), 1.76-1.64 (m, 2H), 1.43-1.31 (m, 2H); ESI MS m/z 443 $[M+H]^+$; HPLC 97.7% (AUC), $t_R$=8.20 min.

Example 56

1-{4-[4-(trans-4-Dimethylamino)methylcyclohexylamino]-6-(pyridin-4-yl)-1,5-naphthyridin-3-yl}ethanone trihydrochloride

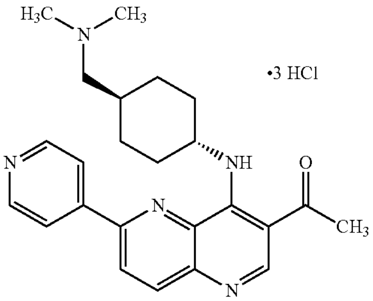 [SMILES: CC(=O)c1cnc2ccc(-c3ccncc3)nc2c1N[C@H]1CC[C@H](CN(C)C)CC1 ; "·3 HCl"]

Following general procedure II, 1-(6-chloro-4-(trans-4-((dimethylamino)methyl)cyclo-hexylamino)-1,5-naphthyridin-3-yl)ethanone (89 mg, 0.247 mmol) was reacted with 4-(4,4,5,5-tetramethyl-1,3,2-dioxaborolan-2-yl)pyridine (45 mg, 0.370 mmol) followed by formation of the trihydrochloride salt to afford the desired product (108 mg, 85%) as a yellow solid: $^1$H NMR (500 MHz, $CD_3OD$) δ 9.28-9.20 (m, 3H), 8.81 (d, J=8.9 Hz, 1H), 8.74-8.69 (m, 2H), 8.57 (d, J=8.9 Hz, 1H), 5.51-5.43 (m, 1H), 3.17 (d, J=6.7 Hz, 2H), 2.94 (s, 6H), 2.78 (s, 3H), 2.52-2.44 (m, 2H), 2.08-1.97 (m, 3H), 1.77-1.65 (m, 2H), 1.42-1.33 (m, 2H); ESI MS m/z 404 $[M+H]^+$; HPLC 95.6% (AUC), $t_R$=7.62 min.

Example 57

5-(7-Acetyl-8-{trans-4-[(dimethylamino)methyl]cyclohexylamino}-1,5-naphthyridin-2-yl)pyrimidine-2-carbonitrile

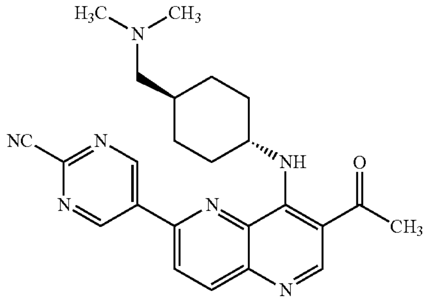 [SMILES: CC(=O)c1cnc2ccc(-c3cnc(C#N)nc3)nc2c1N[C@H]1CC[C@H](CN(C)C)CC1]

Following general procedure II, 1-(6-chloro-4-{trans-4-[(dimethylamino)methyl]cyclo-hexylamino}-1,5-naphthyridin-3-yl)ethanone (87 mg, 0.24 mmol) was reacted with 5-(4,4,5,5-tetramethyl-1,3,2-dioxaborolan-2-yl)pyrimidine-2-carbonitrile (83 mg, 0.36 mmol) to afford the desired product (24 mg, 23%) as a yellow solid: $^1$H NMR (500 MHz, $CD_3OD$+TFA-d) δ 9.62 (s, 2H), 9.23 (s, 1H), 8.68 (d, J=8.9 Hz, 1H), 8.51 (d, J=8.9 Hz, 1H), 5.52-5.41 (m, 1H), 3.12 (d, J=6.8 Hz, 2H), 2.94 (s, 6H), 2.77 (s, 3H), 2.51-2.42 (m, 2H), 2.08-1.94 (m, 3H), 1.88-1.65 (m, 2H), 1.37-1.25 (m, 2H); ESI MS m/z 430 $[M+H]^+$; HPLC>99% (AUC), $t_R$=8.73 min.

Example 58

1-(6-(3,5-Dimethyl-1H-pyrazol-4-yl)-4-{trans-4-[(dimethylamino)methyl]cyclohexylamino}-1,5-naphthyridin-3-yl)ethanone trihydrochloride

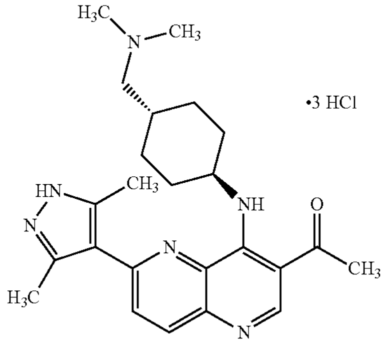 [SMILES: CC(=O)c1cnc2ccc(-c3c(C)n[nH]c3C)nc2c1N[C@H]1CC[C@H](CN(C)C)CC1]

Following general procedure D-1, tert-butyl 4-(7-acetyl-8-{trans-4-[(dimethylamino)-methyl]cyclohexyl}amino)-1,5-naphthyridin-2-yl)-3,5-dimethyl-1H-pyrazole-1-carboxylate (0.25 mmol) was reacted with TFA (2 mL) followed by formation of the trihydrochloride salt to afford the desired product (96 mg, 72% over two steps) as a yellow foam: $^1$H NMR (500 MHz, $CD_3OD$) δ 9.17 (s, 1H), 8.36 (d, J=8.8 Hz, 1H), 8.08 (d, J=8.8 Hz, 1H), 5.64-5.52 (m, 1H), 3.05 (d, J=6.7 Hz, 2H), 2.90 (s, 6H), 2.76 (s, 3H), 2.47 (s, 6H), 2.38-2.29 (m, 2H), 1.99-1.87 (m, 3H), 1.68-1.52 (m, 2H), 1.21-1.07 (m, 2H); ESI MS m/z 421 $[M+H]^+$; HPLC>99% (AUC), $t_R$=8.45 min.

Example 59

1-(4-{trans-4-[(Dimethylamino)methyl]cyclohexylamino}-6-(4-hydroxy-3,5-dimethylphenyl)-1,5-naphthyridin-3-yl)ethanone dichloride

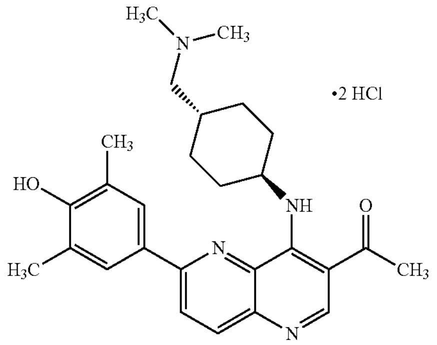 [SMILES: CC(=O)c1cnc2ccc(-c3cc(C)c(O)c(C)c3)nc2c1N[C@H]1CC[C@H](CN(C)C)CC1]

Following general procedure II, 1-(6-chloro-4-{trans-4-[(dimethylamino)methyl]cyclo-hexylamino}-1,5-naphthyridin-3-yl)ethanone (60 mg, 0.166 mmol) was reacted with 2,6-dimethyl-4-(4,4,5,5-tetramethyl-1,3,2-dioxaborolan-2-yl)phenol (62 mg, 0.25 mmol) followed by formation of the trihydrochloride salt to afford the desired product (41 mg, 48%) as a yellow solid: $^1$H NMR (500 MHz, $CD_3OD$) δ 9.10 (s, 1H), 8.39 (d, J=9.0 Hz, 1H), 8.26 (d, J=9.0 Hz, 1H), 7.72 (s, 2H), 5.82-5.73 (m, 1H), 3.06 (d, J=6.6 Hz, 2H), 2.93 (s, 6H), 2.75 (s, 3H), 2.49-2.42 (m, 2H), 2.35 (s, 6H), 2.09-1.98 (m, 3H), 1.73-1.60 (m, 2H), 1.40-1.27 (m, 2H); ESI MS m/z 447 $[M+H]^+$; HPLC 98.4% (AUC), $t_R$=9.81 min.

Example 60

1-(6-(3,5-Dichloro-4-hydroxyphenyl)-4-{6-[3-(dimethylamino)pyrrolidin-1-yl]pyridin-3-ylamino}-1,5-naphthyridin-3-yl)ethanone dihydrochloride

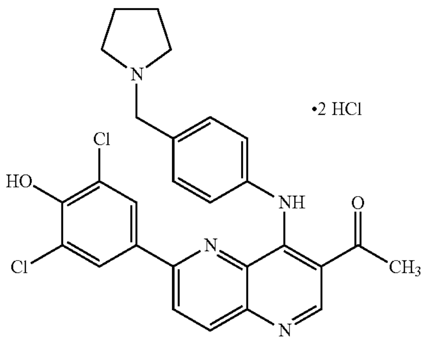 [SMILES: CC(=O)c1cnc2ccc(-c3cc(Cl)c(O)c(Cl)c3)nc2c1Nc1ccc(CN2CCCC2)cc1]

Following general procedure II, 1-{6-chloro-4-[4-(pyrrolidin-1-ylmethyl)phenylamino]-1,5-naphthyridin-3-yl}ethanone (72 mg, 0.189 mmol) was reacted with 2,6-dichloro-4-(4,4,5,5-tetramethyl-1,3,2-dioxaborolan-2-yl) phenol (82 mg, 0.284 mmol) followed by formation of the dihydrochloride salt to afford the desired product (50 mg, 45%) as a yellow solid: $^1$H NMR (500 MHz, $CD_3OD$) δ 9.34 (s, 1H), 8.44 (d, J=8.9 Hz, 1H), 8.36 (d, J=8.9 Hz, 1H), 7.68-7.62 (m, 2H), 7.54-7.47 (m, 2H), 7.40 (br s, 2H), 4.49 (s, 2H), 3.53-3.44 (m, 2H), 3.25-3.17 (m, 2H), 2.81 (s, 3H), 2.24-2.14 (m, 2H), 1.92-2.05 (m, 2H); ESI MS m/z 507 $[M+H]^+$; HPLC>99% (AUC), $t_R$=10.07 min.

Example 61

1-{6-(3,5-Dichloro-4-hydroxyphenyl)-4-[trans-4-(pyrrolidin-1-ylmethyl)cyclohexylamino]-1,5-naphthyridin-3-yl}ethanone dihydrochloride

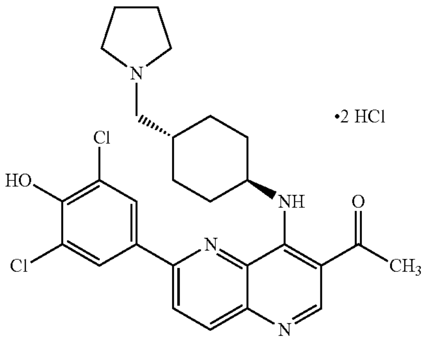 [SMILES: CC(=O)c1cnc2ccc(-c3cc(Cl)c(O)c(Cl)c3)nc2c1N[C@H]1CC[C@H](CN2CCCC2)CC1]

Following general procedure II, 1-{6-chloro-4-[trans-4-(pyrrolidin-1-ylmethyl)-cyclohexylamino]-1,5-naphthyridin-3-yl}ethanone (67 mg, 0.17 mmol) was reacted with 2,6-dichloro-4-(4,4,5,5-tetramethyl-1,3,2-dioxaborolan-2-yl) phenol (58 mg, 0.21 mmol) followed by formation of the dihydrochloride salt to afford the desired product (36 mg, 36%) as an off-white solid: $^1$H NMR (300 MHz, $CD_3OD$) δ 9.15 (s, 1H), 8.47 (d, J=9.0 Hz, 1H), 8.34 (d, J=9.0 Hz, 1H), 8.12 (s, 2H), 5.75-5.67 (m, 1H), 3.72-3.65 (m, 2H), 3.17-3.06 (m, 4H), 2.76 (s, 3H), 2.48-2.40 (m, 2H), 2.20-1.99 (m, 6H), 1.73-1.61, (m, 2H), 1.47-1.36 (m, 2H); ESI MS m/z 513 $[M+H]^+$; HPLC 95.7% (AUC), $t_R$=10.21 min.

Example 62

1-(6-(3-Chloro-5-fluoro-4-hydroxyphenyl)-4-{[trans-4-(pyrrolidin-1-ylmethyl)cyclohexyl]amino}-1,5-naphthyridin-3-yl)ethanone dihydrochloride

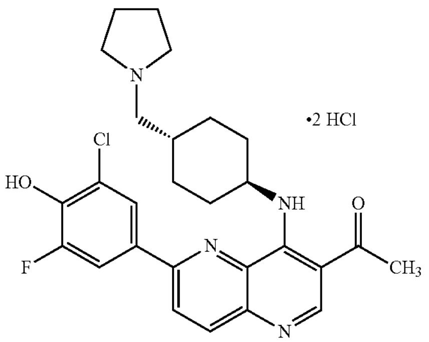 [SMILES: CC(=O)c1cnc2ccc(-c3cc(F)c(O)c(Cl)c3)nc2c1N[C@H]1CC[C@H](CN2CCCC2)CC1]

Following general procedure II, 1-(6-chloro-4-{[trans-4-(pyrrolidin-1-ylmethyl)-cyclohexyl]amino}-1,5-naphthyridin-3-yl)ethanone (86 mg, 0.22 mmol) was reacted with 2-chloro-6-fluoro-4-(4,4,5,5-tetramethyl-1,3,2-dioxaborolan-2-yl)phenol (90 mg, 0.33 mmol) followed by formation of the dihydrochloride salt to afford the desired product (75 mg, 69%) as a light brown solid: $^1$H NMR (500 MHz, $CD_3OD$) δ 9.14 (s, 1H), 8.45 (d, J=9.0 Hz, 1H), 8.34 (d, J=9.0 Hz, 1H), 8.02 (s, 1H), 7.88 (dd, J=11.5, 2.0 Hz, 1H), 5.74-5.64 (m, 1H), 3.74-3.68 (m, 2H), 3.18-3.10 (m, 4H), 2.76 (s, 3H), 2.47-2.41 (m, 2H), 2.22-1.98 (m, 7H), 1.74-1.62 (m, 2H), 1.47-1.34 (m, 2H); ESI MS m/z 497 [M+H]$^+$; HPLC 96.6% (AUC), $t_R$=9.90 min.

Example 63

1-(6-(3,5-Dichloro-4-hydroxyphenyl)-4-{trans-4-[(4-methylpiperazin-1-yl)methyl]cyclohexyl-amino}-1,5-naphthyridin-3-yl)ethanone trihydrochloride

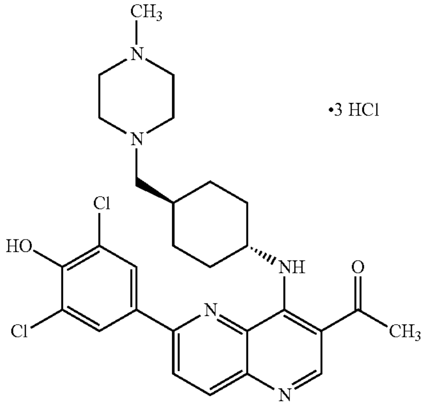 [SMILES: CC(=O)c1cnc2ccc(-c3cc(Cl)c(O)c(Cl)c3)nc2c1N[C@H]1CC[C@H](CN2CCN(C)CC2)CC1]

Following general procedure II, 1-(6-chloro-4-{4-[(4-methylpiperazin-1-yl)methyl]-cyclohexyl amino}-1,5-naphthyridin-3-yl)ethanone (32 mg, 0.076 mmol) was reacted with 2,6-dichloro-4-(4,4,5,5-tetramethyl-1,3,2-dioxaborolan-2-yl)phenol (26 mg, 0.092 mmol) followed by formation of the trihydrochloride salt to afford the desired product (31 mg, 67%) as a yellow solid: $^1$H NMR (500 MHz, $CD_3OD$) δ 9.14 (s, 1H), 8.46 (d, J=8.9 Hz, 1H), 8.33 (d, J=8.9 Hz, 1H), 8.10 (s, 2H), 5.73-5.68 (m, 1H), 3.75 (br s, 8H), 3.16 (br s, 2H), 3.02 (s, 3H), 2.76 (s, 3H), 2.46-2.42 (m, 2H), 2.22-2.14 (m, 2H), 2.10-2.00 (m, 1H), 1.72-1.63 (m, 2H), 1.46-1.37 (m, 2H); ESI MS m/z 542 [M+H]$^+$; HPLC 96.7% (AUC), $t_R$=9.37 min.

Example 64

1-(4-{[6-(3-Aminopiperidin-1-yl)pyridin-3-yl]amino}-6-(3,5-dichloro-4-hydroxyphenyl)-1,5-naphthyridin-3-yl)ethanone trihydrochloride

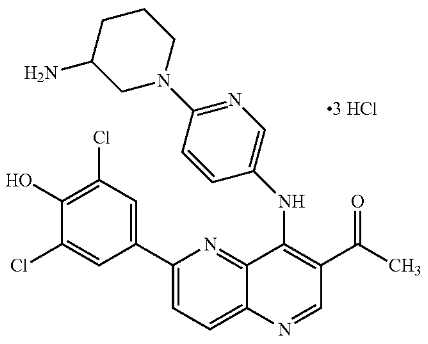 [SMILES: CC(=O)c1cnc2ccc(-c3cc(Cl)c(O)c(Cl)c3)nc2c1Nc1ccc(N2CCCC(N)C2)nc1]

Following general procedure IV-2, tert-butyl[1-(5-{[3-acetyl-6-(3,5-dichloro-4-hydroxyphenyl)-1,5-naphthyridin-4-yl]amino}pyridin-2-yl)piperidin-3-yl]carbamate (0.20 mmol) was reacted with TFA (2 mL) followed by formation of the trihydrochloride salt to afford the desired product (31 mg, 30% over two steps) as an orange solid: $^1$H NMR (500 MHz, $CD_3OD$) δ 9.38 (s, 1H), 8.49 (d, J=9.0 Hz, 1H), 8.41 (d, J=9.0 Hz, 1H), 8.25 (d, J=2.6 Hz, 1H), 7.92-7.86 (m, 1H), 7.58 (s, 2H), 7.24 (d, J=9.5 Hz, 1H), 4.41-4.34 (m, 1H), 4.03-3.96 (m, 1H), 3.53-3.32 (m, 4H), 2.84 (s, 3H), 2.24-2.21 (m, 1H), 2.05-1.97 (m, 1H), 1.84-1.76 (m, 2H); ESI MS m/z 523 [M+H]$^+$; HPLC 98.0% (AUC), $t_R$=9.48 min.

Example 65

1-(4-{[6-(3-Aminopiperidin-1-yl)pyridin-3-yl]amino}-6-(3-chloro-5-fluoro-4-hydroxyphenyl)-1,5-naphthyridin-3-yl)ethanone trihydrochloride

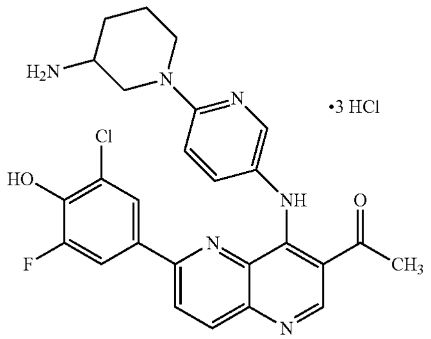 [SMILES: CC(=O)c1cnc2ccc(-c3cc(F)c(O)c(Cl)c3)nc2c1Nc1ccc(N2CCCC(N)C2)nc1]

Following general procedure IV-2, tert-butyl[1-(5-{[3-acetyl-6-(3-chloro-5-fluoro-4-hydroxyphenyl)-1,5-naphthyridin-4-yl]amino}pyridin-2-yl)piperidin-3-yl]carbamate (0.20 mmol) was reacted with TFA (2 mL) followed by formation of the trihydrochloride salt to afford the desired product (33 mg, 33% over two steps) as an orange solid: $^1$H NMR (500 MHz, $CD_3OD$) δ 9.38 (s, 1H), 8.48 (d, J=9.5 Hz, 1H), 8.41 (d, J=9.5 Hz), 8.25 (d, J=2.5 Hz, 1H), 7.91 (dd, J=9.5, 2.5 Hz, 1H), 7.41-7.37 (m, 2H), 7.28 (d, J=9.5 Hz, 1H), 4.37 (d, J=10.7 Hz, 1H), 4.03-3.99 (m, 1H), 3.52-3.32 (m, 3H), 2.84 (s, 3H), 2.28-2.20 (m, 1H), 2.08-1.98 (m, 1H), 1.84-1.78 (m, 2H); ESI MS m/z 507 [M+H]$^+$; HPLC>99% (AUC), $t_R$=9.38 min.

Example 66

1-{4-[trans-(4-Aminocyclohexyl)amino]-6-(3,5-dichloro-4-hydroxyphenyl)-1,5-naphthyridin-3-yl}-ethanone dihydrochloride

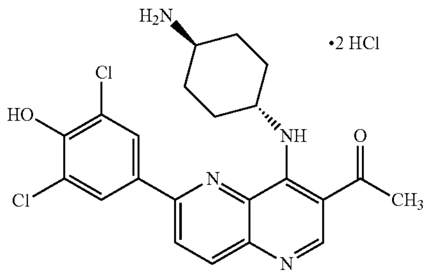 [SMILES: CC(=O)c1cnc2ccc(-c3cc(Cl)c(O)c(Cl)c3)nc2c1N[C@H]1CC[C@H](N)CC1]

Following general procedure IV-2, tert-butyl(4-{[3-acetyl-6-(3,5-dichloro-4-hydroxyphenyl)-1,5-naphthyridin-4-yl]amino}cyclohexyl)carbamate (0.23 mmol) was reacted with TFA (2 mL) followed by formation of the dihydrochloride salt to afford the desired product (32 mg, 27% over two steps) as a gray solid: $^1$H NMR (300 MHz, $D_2O$) δ 8.96 (s, 1H), 8.18-8.00 (m, 2H), 7.53 (s, 2H), 3.28-3.23 (m, 1H), 2.68 (s, 3H), 2.28-2.24 (m, 2H), 2.16-2.13 (m, 2H), 1.76-1.64 (m, 2H), 1.57-1.45 (m, 2H); ESI MS m/z 445 $[M+H]^+$; HPLC 98.4% (AUC), $t_R$=9.34 min.

Example 67

1-{4-[trans-(4-Aminocyclohexyl)amino]-6-(3-chloro-5-fluoro-4-hydroxyphenyl)-1,5-naphthyridin-3-yl}ethanone dihydrochloride

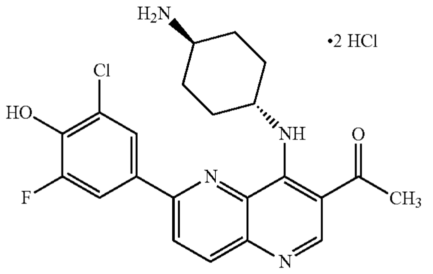 [SMILES: CC(=O)c1cnc2ccc(-c3cc(F)c(O)c(Cl)c3)nc2c1N[C@H]1CC[C@H](N)CC1]

Following general procedure IV-2, tert-butyl(4-{[3-acetyl-6-(3-chloro-5-fluoro-4-hydroxyphenyl)-1,5-naphthyridin-4-yl]amino}cyclohexyl)carbamate (0.20 mmol) was reacted with TFA (2 mL) followed by formation of the dihydrochloride salt to afford the desired product (45 mg, 45% over two steps) as a white solid: $^1$H NMR (500 MHz, $D_2O$) δ 8.99 (s, 1H), 8.13 (d, J=9.0 Hz, 1H), 8.03 (d, J=9.0 Hz, 1H), 7.40-7.34 (m, 2H), 4.91-4.94 (m, 1H), 3.35-3.28 (m, 1H), 2.72 (s, 3H), 2.30-2.22 (m, 2H), 2.21-2.14 (m, 2H), 1.75-1.68 (m, 2H), 1.56-1.48 (m, 2H); ESI MS m/z 429 $[M+H]^+$; HPLC>99% (AUC), $t_R$=9.10 min.

Example 68

1-(6-(3-Chloro-5-fluoro-4-hydroxyphenyl)-4-{trans-4-[4-methylpiperazin-1-yl)methyl]-cyclohexylamino}-1,5-naphthyridin-3-yl)ethanone trihydrochloride

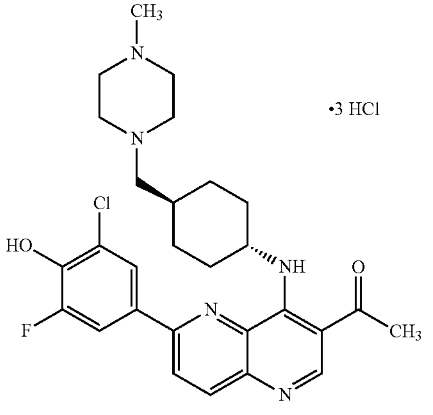 [SMILES: CC(=O)c1cnc2ccc(-c3cc(F)c(O)c(Cl)c3)nc2c1N[C@H]1CC[C@H](CN2CCN(C)CC2)CC1]

Following general procedure II, 1-(6-chloro-4-{4-[(4-methylpiperazin-1-yl)methyl]-cyclohexyl amino}-1,5-naphthyridin-3-yl)ethanone (53 mg, 0.13 mmol) was reacted with 2-chloro-6-fluoro-4-(4,4,5,5-tetramethyl-1,3,2-dioxaborolan-2-yl)phenol (41 mg, 0.152 mmol) followed by formation of the trihydrochloride salt to afford the desired product (11 mg, 14%) as a yellow solid: $^1$H NMR (500 MHz, $CD_3OD$) δ 9.14 (s, 1H), 8.45 (d, J=9.0 Hz, 1H), 8.32 (d, J=9.0 Hz, 1H), 8.02 (s, 1H), 7.88 (dd, J=11.4, 2.2 Hz, 1H), 5.75-5.65 (m, 1H), 3.70 (br s, 8H), 3.10 (br s, 2H), 3.01 (s, 3H), 2.75 (s, 3H), 2.46-2.42 (m, 2H), 2.16-2.13 (m, 2H), 2.05-2.02 (m, 1H), 1.73-1.61 (m, 2H), 1.46-1.35 (m, 2H); ESI MS m/z 526 $[M+H]^+$; HPLC>99% (AUC), $t_R$=9.14 min.

Example 69

N-(trans-4-{[3-Acetyl-6-(3-chloro-5-fluoro-4-hydroxyphenyl)-1,5-naphthyridin-4-yl]amino}-cyclohexyl)-2-amino-3-methylbutanamide dihydrochloride

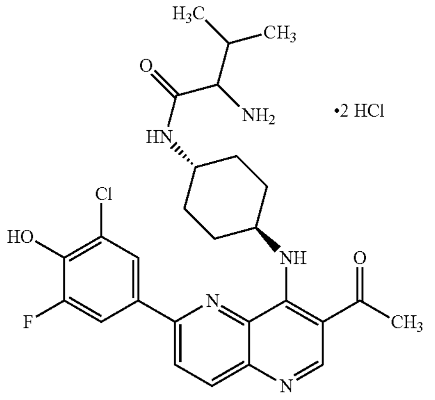 [SMILES: CC(=O)c1cnc2ccc(-c3cc(F)c(O)c(Cl)c3)nc2c1N[C@H]1CC[C@H](NC(=O)C(N)C(C)C)CC1]

Following general procedure IV-2, tert-butyl[1-(trans-4-{[3-acetyl-6-(3-chloro-5-fluoro-4-hydroxyphenyl)-1,5-naphthyridin-4-yl]amino}cyclohexylamino)-3-methyl-1-oxobutan-2-yl]carbamate (0.19 mmol) was reacted with TFA (2 mL) followed by formation of the dihydrochloride salt to afford the desired product (35 mg, 30% over two steps) as an off-white solid: $^1$H NMR (500 MHz, $CD_3OD$) δ 9.14 (s, 1H), 8.44 (d, J=9.0 Hz, 1H), 8.33 (d, J=9.0 Hz, 1H), 8.00 (s, 1H), 7.87 (dd, J=11.4, 2.2 Hz, 1H), 5.63-5.57 (m, 1H), 3.88-3.83 (m, 1H), 3.62 (d, J=6.0 Hz, 1H), 2.76 (s, 3H), 2.51-2.40 (m, 2H), 2.10-2.12 (m, 3H), 1.81-1.53 (m, 4H), 1.08 (t, J=7.4 Hz, 6H); ESI MS m/z 528 $[M+H]^+$; HPLC 98.9% (AUC), $t_R$=9.99 min.

Example 70

1-{6-(3,5-Dichloro-4-hydroxyphenyl)-4-[trans-4-(piperazin-1-ylmethyl)cyclohexylamino]-1,5-naphthyridin-3-yl}ethanone trihydrochloride

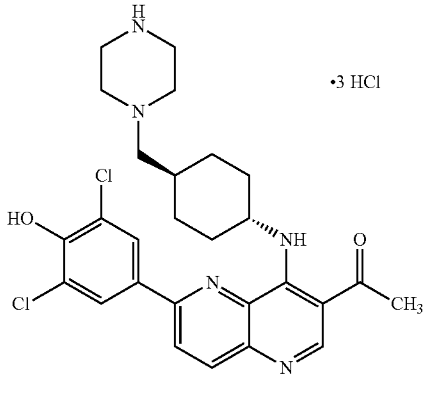 [SMILES: CC(=O)c1cnc2ccc(-c3cc(Cl)c(O)c(Cl)c3)nc2c1N[C@H]1CC[C@H](CN2CCNCC2)CC1]

Following general procedure IV-2, tert-butyl 4-((4-((3-acetyl-6-(3,5-dichloro-4-hydroxy-phenyl)-1,5-naphthyridin-4-yl)amino)cyclohexyl)methyl)piperazine-1-carboxylate (0.298 mmol) was reacted with TFA (2 mL) followed by formation of the trihydrochloride salt to afford the desired product (84 mg, 47% over two steps) as a yellow solid: $^1$H NMR (500 MHz, $D_2O$) δ 9.00 (s, 1H), 8.22-8.11 (m, 2H), 7.59 (s, 2H), 5.06 (m, 1H), 4.76-4.71 (m, 1H), 4.66 (s, 1H), 3.60 (s, 8H), 3.15 (d, J=6.7 Hz, 2H), 2.74 (s, 3H), 2.25-2.23 (m, 2H), 2.02-1.97 (m, 2H), 1.60-1.58 (m, 2H), 1.24-1.20 (m, 2H); ESI MS m/z 528 [M+H]$^+$; HPLC 98.0% (AUC), $t_R$=9.29 min.

Example 71

(S)-1-(4-{[6-(3-Aminopiperidin-1-yl)pyridin-3-yl]amino}-6-(3,5-dichloro-4-hydroxyphenyl)-1,5-naphthyridin-3-yl)ethanone trihydrochloride

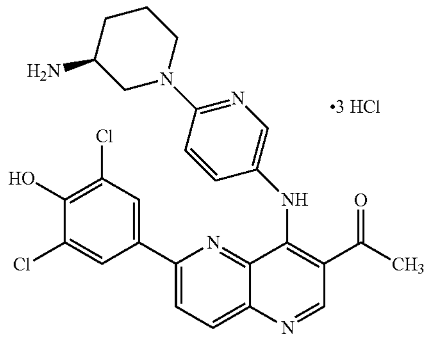 [SMILES: CC(=O)c1cnc2ccc(-c3cc(Cl)c(O)c(Cl)c3)nc2c1Nc1ccc(N2CCC[C@H](N)C2)nc1]

Following general procedure IV-2, (S)-tert-butyl[1-(5-{[3-acetyl-6-(3,5-dichloro-4-hydroxy-phenyl)-1,5-naphthyridin-4-yl]amino}pyridin-2-yl)piperidin-3-yl]carbamate (0.197 mmol) was reacted with TFA (2 mL) followed by formation of the trihydrochloride salt to afford the desired product (42 mg, 33% over two steps) as a yellow solid: $^1$H NMR (500 MHz, $CD_3OD$) δ 9.39 (s, 1H), 8.49 (d, J=9.0 Hz, 1H), 8.41 (d, J=9.0 Hz, 1H), 8.25 (d, J=2.6 Hz, 1H), 7.92 (dd, J=9.5, 2.6 Hz, 1H), 7.57 (s, 2H), 7.27 (d, J=9.5 Hz, 1H), 4.37 (d, J=10.9 Hz, 1H), 4.02-3.99 (m, 1H), 3.52-3.32 (m, 3H), 2.84 (s, 3H), 2.24-2.22 (m, 1H), 2.07-1.95 (m, 1H), 1.82-1.77 (m, 2H); ESI MS m/z 523 [M+H]$^+$; HPLC 97.5% (AUC), $t_R$=9.56 min.

Example 72

(S)-1-(4-{[6-(3-Aminopiperidin-1-yl)pyridin-3-yl]amino}-6-(3-chloro-5-fluoro-4-hydroxy-phenyl)-1,5-naphthyridin-3-yl)ethanone trihydrochloride

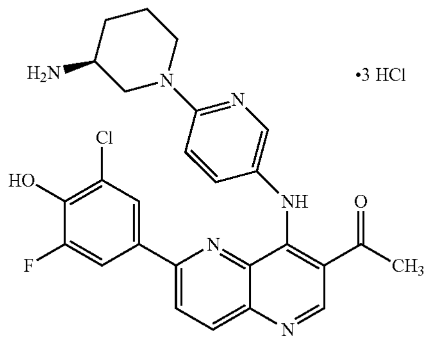 [SMILES: CC(=O)c1cnc2ccc(-c3cc(F)c(O)c(Cl)c3)nc2c1Nc1ccc(N2CCC[C@H](N)C2)nc1]

Following general procedure IV-2, (S)-tert-butyl[1-(5-{[3-acetyl-6-(3-chloro-5-fluoro-4-hydroxyphenyl)-1,5-naphthyridin-4-yl]amino}pyridin-2-yl)piperidin-3-yl]carbamate (0.20 mmol) was reacted with TFA (2 mL) followed by formation of the trihydrochloride salt to afford the desired product (42 mg, 34% over two steps) as an orange-yellow solid: $^1$H NMR (500 MHz, $CD_3OD$) δ 9.30 (s, 1H), 8.45 (d, J=9.0 Hz, 1H), 8.35 (d, J=9.0 Hz, 1H), 8.19 (d, J=2.6 Hz, 1H), 7.68 (dd, J=9.2, 2.6 Hz, 1H), 7.45 (br s, 1H), 7.27 (br s, 1H), 7.05 (d, J=9.2 Hz, 1H), 4.43-4.36 (m, 1H), 3.94-3.92 (m, 1H), 3.44-3.32 (m, 3H), 2.81 (s, 3H), 2.23-2.15 (m, 1H), 2.05-1.91 (m, 1H), 1.77-1.73 (m, 2H); ESI MS m/z 507 [M+H]$^+$; HPLC>99% (AUC), $t_R$=9.57 min.

Example 73

N-{trans-4-[3-Acetyl-6-(3,5-dichloro-4-hydroxyphenyl)-1,5-naphthyridin-4-ylamino]-cyclohexyl}-2-aminopropanamide dihydrochloride

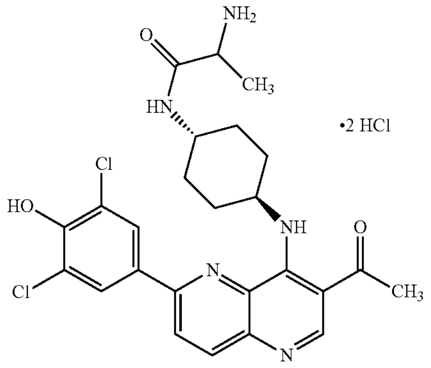 [SMILES: CC(=O)c1cnc2ccc(-c3cc(Cl)c(O)c(Cl)c3)nc2c1N[C@H]1CC[C@H](NC(=O)C(C)N)CC1]

Following general procedure IV-1, crude tert-butyl 1-{trans-4-[3-acetyl-6-(3,5-dichloro-4-hydroxyphenyl)-1,5-naphthyridin-4-ylamino]cyclohexylamino}-1-oxopropan-2-ylcarbamate (0.13 mmol) was reacted with HCl (5 mL, 2 M in ether) to afford the desired product (32 mg, 41% over two steps) as a brown solid: $^1$H NMR (500 MHz, $CD_3OD$) δ 9.14 (s, 1H), 8.45 (d, J=8.5 Hz, 1H), 8.34 (d, J=8.5 Hz, 1H), 8.10 (s, 2H), 5.65-5.55 (m, 1H), 3.90 (q, J=6.9 Hz, 1H), 3.85-3.76 (m, 1H), 2.76 (s, 3H), 2.50-2.39 (m, 2H), 2.21-2.10 (m, 2H), 1.78-1.69 (m, 2H), 1.65-1.52 (m, 2H), 1.51 (d, J=6.9 Hz, 3H); ESI MS m/z 516 [M+H]$^+$; HPLC>99% (AUC), $t_R$=9.65 min.

Example 74

N-{4-[3-Acetyl-6-(3-chloro-5-fluoro-4-hydroxyphenyl)-1,5-naphthyridin-trans-4-ylamino]-cyclohexyl}-2-aminopropanamide dihydrochloride

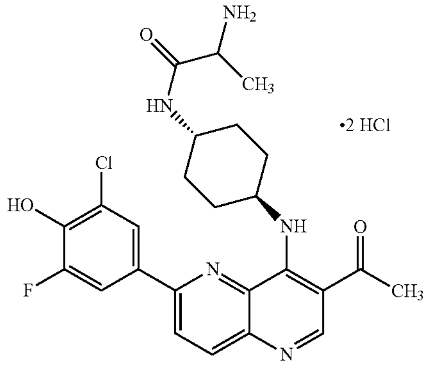 [SMILES: CC(=O)c1cnc2ccc(-c3cc(F)c(O)c(Cl)c3)nc2c1N[C@H]1CC[C@H](NC(=O)C(C)N)CC1]

Following general procedure IV-1, tert-butyl 1-{4-[3-acetyl-6-(3-chloro-5-fluoro-4-hydroxyphenyl)-1,5-naphthyridin-trans-4-ylamino]cyclohexylamino}-1-oxopropan-2-ylcarbamate (0.13 mmol) was reacted was reacted with HCl (5 mL, 2 M in ether) to afford the desired product (6.0 mg, 8% over two steps) as a white solid: $^1$H NMR (500 MHz, $CD_3OD$) δ 9.14 (s, 1H), 8.44 (d, J=8.9 Hz, 1H), 8.33 (d, J=8.9 Hz, 1H), 8.00 (t, J=1.8 Hz, 1H), 7.87 (dd, J=11.6, 1.8 Hz, 1H), 5.65-5.57 (m, 2H), 3.94-3.77 (m, 2H), 2.76 (s, 3H), 2.50-2.40 (s, 2H), 2.20-2.12 (m, 2H), 1.78-1.58 (m, 2H), 1.61-1.52 (m, 2H), 1.51 (d, J=7.1 Hz, 3H); ESI MS m/z 500 [M+H]$^+$; HPLC 99.0% (AUC), $t_R$=9.59 min.

Example 75

(S)—N-{4-[3-Acetyl-6-(3,5-dichloro-4-hydroxyphenyl)-1,5-naphthyridin-trans-4-ylamino]-cyclohexyl}pyrrolidine-2-carboxamide dihydrochloride

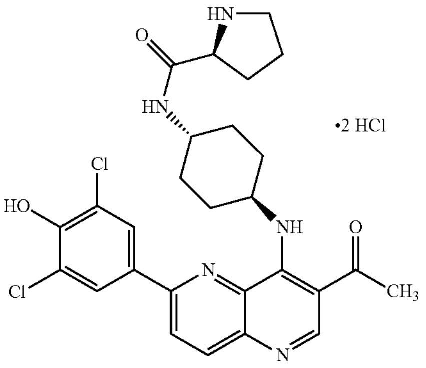 [SMILES: CC(=O)c1cnc2ccc(-c3cc(Cl)c(O)c(Cl)c3)nc2c1N[C@H]1CC[C@H](NC(=O)[C@@H]2CCCN2)CC1]

Following general procedure IV-1, (S)-tert-butyl 2-{4-[3-acetyl-6-(3,5-dichloro-4-hydroxyphenyl)-1,5-naphthyridin-trans-4-ylamino]cyclohexylcarbamoyl}pyrrolidine-1-carboxylate (0.19 mmol) was reacted was reacted with HCl (5 mL, 2 M in ether) to afford the desired product (70 mg, 58% over two steps) as an off-white solid: $^1$H NMR (500 MHz, $CD_3OD$) δ 9.14 (s, 1H), 8.45 (d, J=9.0 Hz, 1H), 8.34 (d, J=9.0 Hz, 1H), 8.09 (s, 2H), 5.66-5.53 (m, 1H), 4.24 (dd, J=8.5, 6.9 Hz, 1H), 3.90-3.77 (m, 1H), 3.46-3.30 (m, 2H), 2.76 (s, 3H), 2.51-2.40 (m, 3H), 2.22-1.94 (m, 5H), 1.80-1.53 (m, 4H); ESI MS m/z 542 [M+H]$^+$; HPLC 98.9% (AUC), $t_R$=9.88 min.

Example 76

(S)—N-{4-[3-Acetyl-6-(3-chloro-5-fluoro-4-hydroxyphenyl)-1,5-naphthyridin-trans-4-ylamino]-cyclohexyl}pyrrolidine-2-carboxamide dihydrochloride

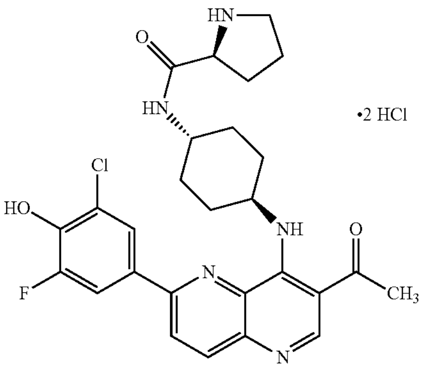 [SMILES: CC(=O)c1cnc2ccc(-c3cc(F)c(O)c(Cl)c3)nc2c1N[C@H]1CC[C@H](NC(=O)[C@@H]2CCCN2)CC1]

Following general procedure IV-1, tert-butyl 1-{4-[3-acetyl-6-(3-chloro-5-fluoro-4-hydroxy-phenyl)-1,5-naphthyridin-4-ylamino]cyclohexylamino}-1-oxopropan-2-ylcarbamate (0.19 mmol) was reacted with HCl (5 mL, 2 M in ether) to afford the desired product (46 mg, 45% over two steps) as an off-white solid: $^1$H NMR (500 MHz, $CD_3OD$) δ 9.14 (s, 1H), 8.44 (d, J=8.9 Hz, 1H), 8.33 (d, J=8.9 Hz, 1H), 8.00 (t, J=1.8 Hz, 1H), 7.87 (dd, J=11.4, 1.8 Hz, 1H), 5.69-5.52 (m, 1H), 4.23 (dd, J=8.5, 6.9 Hz, 1H), 3.80-3.88 (m, 1H), 3.47-3.32 (m, 2H), 2.75 (s, 3H), 2.51-2.39 (m, 3H), 2.20-2.13 (m, 2H), 2.12-1.95 (m, 3H), 1.81-1.68 (m, 2H), 1.67-1.52 (m, 2H); ESI MS m/z 527 [M+H]$^+$; HPLC>99% (AUC), $t_R$=9.69 min.

Example 77

1-(6-(3-Hydroxypyrrolidin-1-yl)-4-{trans-4-[(3-hydroxypyrrolidin-1-yl)methyl]-cyclohexylamino}-1,5-naphthyridin-3-yl)ethanone

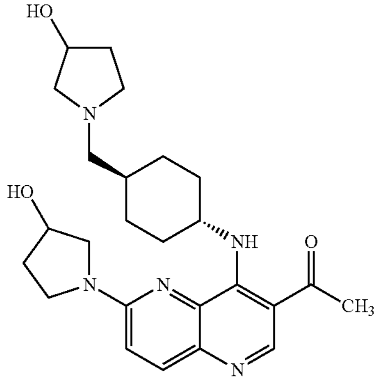 [SMILES: CC(=O)c1cnc2ccc(N3CCC(O)C3)nc2c1N[C@H]1CC[C@H](CN2CCC(O)C2)CC1]

Following general procedure V, {4-[(3-acetyl-6-chloro-1,5-naphthyridin-trans-4-yl)-amino]cyclohexylmethyl methanesulfonate (170 mg, 0.41 mmol) was reacted with pyrrolidin-3-ol (680 mg, 7.8 mmol) to afford the product (33 mg, 17%) as an orange-brown solid: $^1$H NMR (500 MHz, $CD_3OD$) δ 8.64 (s, 1H), 7.85 (d, J=9.2 Hz, 1H), 7.04 (d, J=9.2 Hz, 1H), 5.63-5.55 (m, 1H), 4.61-4.54 (m, 1H), 4.40-4.30 (m, 1H), 3.79-3.65 (m, 3H), 3.60-3.52 (m, 1H), 2.88-2.80 (m, 1H), 2.79-2.70 (m, 1H), 2.63 (s, 2H), 2.63-2.53 (m, 1H), 2.53-2.48 (m, 1H), 2.47-2.35 (m, 2H), 2.30-2.05 (m, 6H), 2.00-1.89 (m, 2H), 1.75-1.70 (m, 1H), 1.62-1.52 (m, 1H), 1.40-1.31 (m, 2H), 1.21-1.10 (m, 2H); ESI MS m/z 454 [M+H]$^+$; HPLC 98.1% (AUC), $t_R$=8.66 min.

Example 78

1-{6-(Pyrrolidin-1-yl)-4-[trans-4-(pyrrolidin-1-ylmethyl)cyclohexylamino]-1,5-naphthyridin-3-yl}ethanone

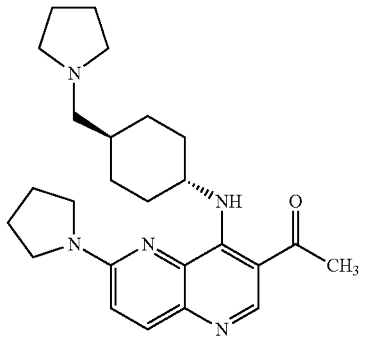 [SMILES: CC(=O)c1cnc2ccc(N3CCCC3)nc2c1N[C@H]1CC[C@H](CN2CCCC2)CC1]

Following general procedure V, {4-[(3-acetyl-6-chloro-1,5-naphthyridin-4-yl)amino]-cyclohexyl}methyl methanesulfonate (180 mg, 0.437 mmol) was reacted with pyrrolidine (34 mg, 0.48 mmol) to afford the desired product (34 mg, 18%) as a brown solid: $^1$H NMR (500 MHz, $CD_3OD$) δ 8.63 (s, 1H), 7.83 (d, J=9.2 Hz, 1H), 7.02 (d, J=9.2 Hz, 1H), 5.57 (br s, 1H), 3.61-3.53 (m, 4H), 2.63 (s, 6H), 2.45 (d, J=7.0 Hz, 2H), 2.30-2.18 (m, 2H), 2.14-2.04 (m, 4H), 1.98-1.91 (m, 2H), 1.89-1.80 (m, 4H), 1.68-1.55 (m, 1H), 1.40-1.28 (m, 2H), 1.18-1.08 (m, 2H); ESI MS m/z 422 [M+H]$^+$; HPLC 97.5% (AUC), $t_R$=9.68 min.

Example 79

N-{trans-4-[3-Acetyl-6-(3,5-dichloro-4-hydroxyphenyl)-1,5-naphthyridin-4-ylamino]-cyclohexyl}-2-amino-3-methylbutanamide dihydrochloride

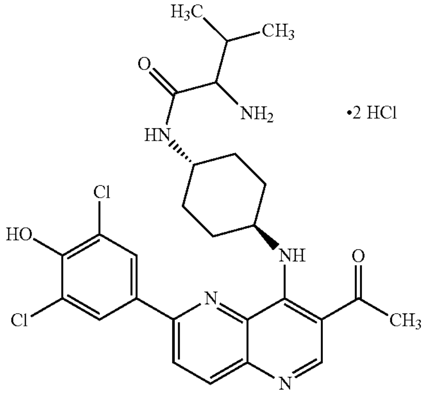 [SMILES: CC(=O)c1cnc2ccc(-c3cc(Cl)c(O)c(Cl)c3)nc2c1N[C@H]1CC[C@H](NC(=O)C(N)C(C)C)CC1]

Following general procedure IV-2, tert-butyl 1-(4-(3-acetyl-6-(3,5-dichloro-4-hydroxy-phenyl)-1,5-naphthyridin-4-ylamino)cyclohexylamino)-3-methyl-1-oxobutan-2-ylcarbamate (0.19 mmol) was reacted with HCl (5 mL, 2 M in ether) to afford the desired product (55 mg, 47% over two steps) as an off-white solid: $^1$H NMR (500 MHz, $CD_3OD$) δ 9.14 (s, 1H), 8.45 (d, J=9.0 Hz, 1H), 8.33 (d, J=9.0 Hz, 1H), 8.10 (s, 2H), 5.67-5.53 (m, 1H), 3.91-3.80 (m, 1H), 3.62 (d, J=6.0 Hz, 1H), 2.76 (s, 3H), 2.49-2.40 (m, 2H), 2.25-2.10 (m, 3H), 1.81-1.54 (m, 4H), 1.07 (dd, J=9.0, 6.9 Hz, 6H); ESI MS m/z 544 [M+H]$^+$; HPLC 99.0% (AUC), $t_R$=10.15 min.

Example 80

Cyclopropyl {6-(3,5-dichloro-4-hydroxyphenyl)-4-[trans-4-(dimethylamino)-cyclohexylamino]-1,5-naphthyridin-3-yl}methanone dihydrochloride

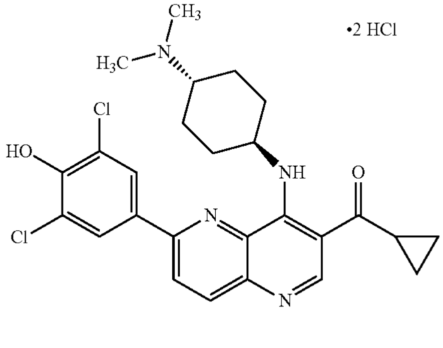 [SMILES: CN(C)[C@H]1CC[C@H](Nc2c(C(=O)C3CC3)cnc3ccc(-c4cc(Cl)c(O)c(Cl)c4)nc23)CC1]

Following general procedure II, {6-chloro-4-[trans-4-(dimethylamino)cyclohexyl-amino]-1,5-naphthyridin-3-yl}(cyclopropyl)methanone (50 mg, 0.13 mmol) was reacted with 2,6-dichloro-4-(4,4,5,5-tetramethyl-1,3,2-dioxaborolan-2-yl)phenol (65 g, 0.23 mmol) followed by formation of the dihydrochloride salt to afford the desired product (65 g, 84%) as an off-white solid: $^1$H NMR (500 MHz, $CD_3OD$) δ 9.43 (s, 1H), 8.46 (d, J=9.0 Hz, 1H), 8.36 (d, J=9.0 Hz, 1H), 8.11 (s, 2H), 5.64-5.54 (m, 1H), 3.51-3.44 (m, 1H), 2.91 (s, 6H), 2.93-2.89 (m, 1H), 2.63-2.56 (m, 2H), 2.32-2.24 (m, 2H), 1.87-1.68 (m, 4H), 1.33-1.18 (m, 4H).; ESI MS m/z 499 [M+H]$^+$; HPLC>99% (AUC), $t_R$=10.12 min.

Example 81

1-[6-(3-Chloro-5-fluoro-4-methoxyphenyl)-4-{trans-4-[(dimethylamino)methyl]-cyclohexylamino}-1,5-naphthyridin-3-yl]ethanone dihydrochloride

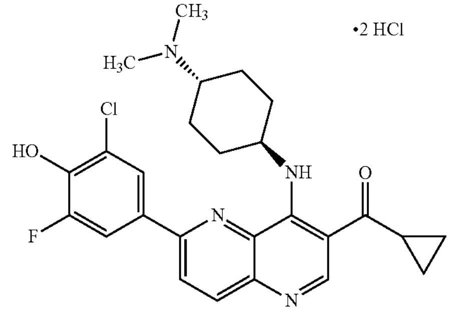 [SMILES: CN(C)[C@H]1CC[C@H](Nc2c(C(=O)C3CC3)cnc3ccc(-c4cc(F)c(O)c(Cl)c4)nc23)CC1]

Following general procedure II, {6-chloro-4-[trans-4-(dimethylamino)cyclohexyl-amino]-1,5-naphthyridin-3-yl}(cyclopropyl)methanone (50 mg, 0.13 mmol) was reacted with 2-chloro-6-fluoro-4-(4,4,5,5-tetramethyl-1,3,2-dioxaborolan-2-yl)phenol (61 mg, 0.23 mmol) followed by formation of the dihydrochloride salt to afford the desired product (58 g, 78%) as an off-white solid: $^1$H NMR (500 MHz, $CD_3OD$) δ 9.43 (s, 1H), 8.46 (d, J=8.9 Hz, 1H), 8.36 (d, J=9.0 Hz, 1H), 8.00 (t, J=1.9 Hz, 1H), 7.91 (dd, J=11.6, 2.2 Hz, 1H), 5.66-5.56 (m, 1H), 3.53-3.43 (m, 1H), 2.91 (s, 6H), 2.93-2.86 (m, 1H), 2.62-2.54 (m, 2H), 2.33-2.23 (m, 2H), 1.88-1.69 (m, 4H), 1.33-1.18 (m, 4H). ESI MS m/z 483 [M+H]$^+$; HPLC>99% (AUC), $t_R$=9.84 min.

Example 82

1-(4-{trans-4-[(Dimethylamino)methyl]cyclohexylamino}-6-(1H-pyrrolo[2,3-b]pyridin-5-yl)-1,5-naphthyridin-3-yl)ethanone trihydrochloride

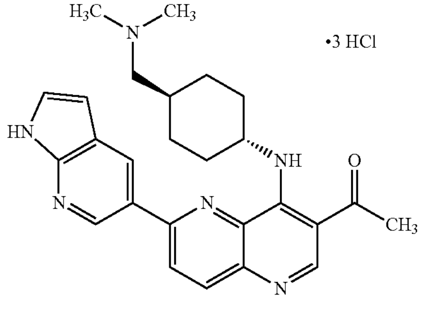 [SMILES: CC(=O)c1cnc2ccc(-c3cnc4[nH]ccc4c3)nc2c1N[C@H]1CC[C@H](CN(C)C)CC1]

Following general procedure II, 1-(6-chloro-4-{trans-4-[(dimethylamino)methyl]-cyclohexylamino}-1,5-naphthyridin-3-yl)ethanone (60 mg, 0.17 mmol) was reacted with 5-(4, 4,5,5-tetramethyl-1,3,2-dioxaborolan-2-yl)-1H-pyrrolo[2,3-b]pyridine (60 mg, 0.25 mmol) followed by formation of the trihydrochloride salt to afford the desired product (7.5 mg, 9%) as an off-white solid: $^1$H NMR (500 MHz, $CD_3OD$) δ 9.19 (s, 1H), 9.08 (s, 2H), 8.65 (d, J=8.9 Hz, 1H), 8.44 (d, J=8.9 Hz, 1H), 7.72 (d, J=3.7 Hz, 1H), 6.91 (d, J=3.6 Hz, 1H), 5.69-5.59 (m, 1H), 3.18 (d, J=6.8 Hz, 2H), 2.94 (s, 6H), 2.77 (s, 3H), 2.55-2.45 (m, 2H), 2.08-1.98 (m, 3H), 1.76-1.64 (m, 2H), 1.48-1.36 (m, 2H). ESI MS m/z 443 [M+H]$^+$; HPLC>99% (AUC), $t_R$=9.25 min.

Example 83

(S)-{4-[6-(3-Aminopiperidin-1-yl)pyridin-3-ylamino]-6-(3-chloro-5-fluoro-4-hydroxyphenyl)-1,5-naphthyridin-3-yl}(cyclopropyl)methanone

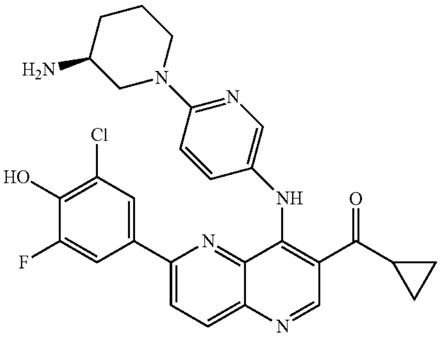 [SMILES: N[C@H]1CCCN(c2ccc(Nc3c(C(=O)C4CC4)cnc4ccc(-c5cc(F)c(O)c(Cl)c5)nc34)cn2)C1]

Following general procedure IV-2, (S)-tert-Butyl 1-{5-[6-(3-chloro-5-fluoro-4-hydroxy-phenyl)-3-(cyclopropanecarbonyl)-1,5-naphthyridin-4-ylamino)pyridin-2-yl]piperidin-3-ylcarbamate (100 mg, 0.16 mmol) was reacted with TFA (3 mL) to afford the desired product (33 mg, 40%) as an orange-red solid: $^1$H NMR (500 MHz, $CD_3OD$) δ 9.15 (s, 1H), 8.06 (d, J=9.0 Hz, 1H), 8.01 (d, J=9.0 Hz, 1H), 7.94 (d, J=2.7 Hz, 1H), 7.40 (s, 1H), 7.33 (dd, J=9.0, 2.8 Hz, 1H), 6.94 (dd, J=12.6, 2.3 Hz, 1H), 6.69 (d, J=8.9 Hz, 1H), 4.20-4.10 (m, 1H), 3.87-3.77 (m, 1H), 3.30-3.21 (m, 1H), 3.13-3.03 (m, 2H), 2.91-2.83 (m, 1H), 2.17-2.06 (m, 1H), 1.90-1.82 (m, 1H), 1.77-1.51 (m, 2H), 1.43-1.04 (m, 4H); ESI MS m/z 533 [M+H]$^+$; HPLC>99% (AUC), $t_R$=9.97 min.

Example 84

1-(4-{trans-4-[(Dimethylamino)methyl]cyclohexylamino}-6-(4-methoxyphenyl)-1,5-naphthyridin-3-yl)ethanone dihydrochloride

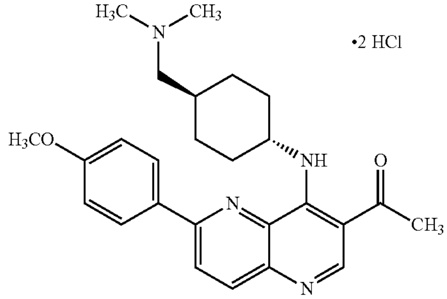 [SMILES: COc1ccc(-c2ccc3ncc(C(C)=O)c(N[C@H]4CC[C@H](CN(C)C)CC4)c3n2)cc1]

Following general procedure II, 1-(6-chloro-4-{trans-4-[(dimethylamino)methyl]-cyclohexylamino}-1,5-naphthyridin-3-yl)ethanone (72 g, 0.20 mmol) was reacted with (4-methoxyphenyl)boronic acid (45 g, 0.30 mmol) followed by formation of the dihydrochloride salt to afford the desired product (80 mg, 79%) as an orange solid: $^1$H NMR (300 MHz, $CD_3OD$) δ 9.13 (s, 1H), 8.45 (d, J=9.0 Hz, 1H), 8.31 (d, J=9.0 Hz, 1H), 8.15-8.03 (m, 2H), 7.24-7.12 (m, 2H), 5.73-5.59 (m, 1H), 3.91 (s, 3H), 3.13 (d, J=6.7 Hz, 2H), 2.94 (s, 6H), 2.75 (s, 3H), 2.50-2.42 (m, 2H), 2.09-1.96 (m, 3H), 1.77-1.60 (m, 2H), 1.45-1.25 (m, 2H); ESI MS m/z 433 [M+H]$^+$; HPLC>99% (AUC), $t_R$=9.83 min.

Example 85

1-[6-(3,5-Dichloro-4-methoxyphenyl)-4-{trans-4-[(dimethylamino)methyl]-cyclohexylamino}-1,5-naphthyridin-3-yl]ethanone dihydrochloride

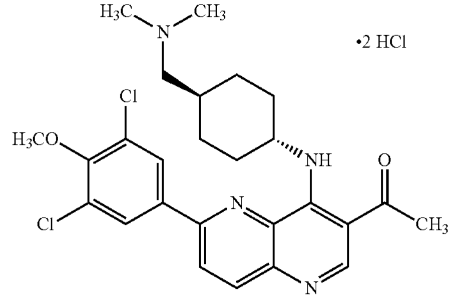 [SMILES: COc1c(Cl)cc(-c2ccc3ncc(C(C)=O)c(N[C@H]4CC[C@H](CN(C)C)CC4)c3n2)cc1Cl]

Following general procedure II, 1-(6-chloro-4-{trans-4-[(dimethylamino)methyl]-cyclohexylamino}-1,5-naphthyridin-3-yl)ethanone (77 g, 0.21 mmol) was reacted with (3,5-dichloro-4-methoxyphenyl)boronic acid (70 g, 0.32 mmol) followed by formation of the dihydrochloride salt to afford the desired product (80 g, 66%) as a brown solid: $^1$H NMR (300 MHz, $CD_3OD$) δ 9.18 (s, 1H), 8.52 (d, J=9.0 Hz, 1H), 8.39 (d, J=9.0 Hz, 1H), 8.20 (s, 2H), 5.74-5.59 (m, 1H), 3.99 (s, 3H), 3.09 (d, J=6.6 Hz, 2H), 2.94 (s, 6H), 2.76 (s, 3H), 2.48-2.40 (m, 2H), 2.10-2.00 (m, 3H), 1.79-1.61 (m, 2H), 1.50-1.31 (m, 2H);

ESI MS m/z 501 [M+H]$^+$; HPLC>99% (AUC), $t_R$=10.49 min.

Example 86

1-(4-{trans-4-[(Dimethylamino)methyl]cyclohexylamino}-6-(6-hydroxypyridin-3-yl)-1,5-naphthyridin-3-yl)ethanone dihydrochloride

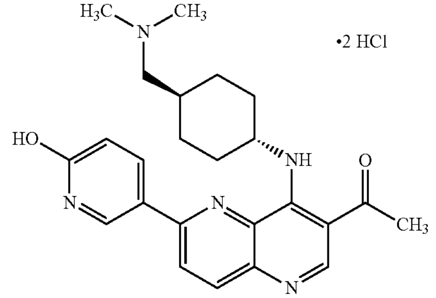 [SMILES: CC(=O)c1cnc2ccc(-c3ccc(O)nc3)nc2c1N[C@H]1CC[C@H](CN(C)C)CC1]

Following general procedure II, 1-(6-Chloro-4-{trans-4-[(dimethylamino)methyl]cyclohexylamino}-1,5-naphthyridin-3-yl)ethanone (74 g, 0.21 mmol) was reacted with (6-hydroxypyridin-3-yl)boronic acid (43 g, 0.31 mmol) followed by formation of the dihydrochloride salt to afford the desired product (49 g, 48%) as a yellow solid: $^1$H NMR (500 MHz, $CD_3OD$) δ 9.14 (s, 1H), 8.41-8.29 (m, 4H), 6.76 (d, J=9.5 Hz, 1H), 5.58-5.50 (m, 1H), 3.13 (d, J=6.7 Hz, 2H), 2.94 (s, 6H), 2.75 (s, 3H), 2.49-2.40 (m, 2H), 2.08-2.00 (m, 3H), 1.73-1.61 (m, 2H), 1.39-1.27 (m, 2H); ESI MS m/z 420 $[M+H]^+$; HPLC>99% (AUC), $t_R$=8.43 min.

Example 87

5-(7-Acetyl-8-{trans-4-[(dimethylamino)methyl] cyclohexylamino}-1,5-naphthyridin-2-yl)picolinonitrile dihydrochloride

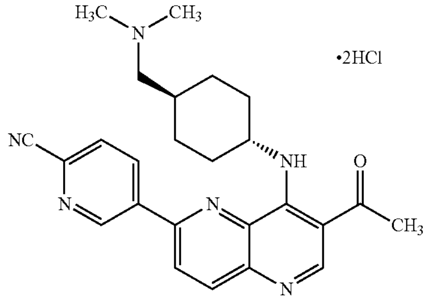

Following general procedure II, 1-(6-chloro-4-{trans-4-[(dimethylamino)methyl]cyclo-hexylamino}-1,5-naphthyridin-3-yl)ethanone (77 g, 0.21 mmol) was reacted with 5-(4,4,5,5-tetramethyl-1,3,2-dioxaborolan-2-yl)picolinonitrile (72 g, 0.32 mmol) followed by formation of the dihydrochloride salt to afford the desired product (100 g, 95%) as a light brown solid: $^1$H NMR (500 MHz, $CD_3OD$) δ 9.46 (d, J=2.2 Hz, 1H), 9.21 (s, 1H), 8.70 (dd, J=8.2, 2.2 Hz, 1H), 8.63 (d, J=8.9 Hz, 1H), 8.47 (d, J=8.9 Hz, 1H), 8.17 (d, J=8.2 Hz, 1H), 5.58-5.50 (m, 1H), 3.14 (d, J=6.8 Hz, 2H), 2.94 (s, 6H), 2.77 (s, 3H), 2.49-2.42 (m, 2H), 2.05-1.97 (m, 3H), 1.75-1.65 (m, 2H), 1.39-1.27 (m, 2H); ESI MS m/z 429 $[M+H]^+$; HPLC 96.2% (AUC), $t_R$=8.88 min.

Example 88

1-(4-{trans-4-[(Dimethylamino)methyl]cyclohexylamino}-6-(4-hydroxyphenyl)-1,5-naphthyridin-3-yl) ethanone dihydrochloride

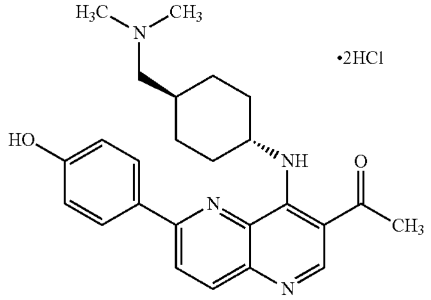 [SMILES: CC(=O)c1cnc2ccc(-c3ccc(C#N)nc3)nc2c1N[C@H]1CC[C@H](CN(C)C)CC1]

Following general procedure II, 1-(6-chloro-4-{trans-4-[(dimethylamino)methyl]-cyclohexylamino}-1,5-naphthyridin-3-yl)ethanone (76 g, 0.21 mmol) was reacted with (4-hydroxyphenyl)boronic acid (43 g, 0.32 mmol) followed by formation of the dihydrochloride salt to afford the desired product (35 g, 34%) as a yellow solid: $^1$H NMR (500 MHz, $CD_3OD$) δ 9.11 (s, 1H), 8.41 (d, J=8.9 Hz, 1H), 8.28 (d, J=8.9 Hz, 1H), 8.03-7.97 (m, 2H), 7.04-6.98 (m, 2H), 5.73-5.62 (m, 1H), 3.11 (d, J=6.8 Hz, 2H), 2.94 (s, 6H), 2.75 (s, 3H), 2.50-2.42 (m, 2H), 2.06-1.99 (m, 3H), 1.73-1.61 (m, 2H), 1.40-1.27 (m, 2H); ESI MS m/z 419 $[M+H]^+$; HPLC>99% (AUC), $t_R$=9.24 min.

Example 89

1-[6-(3,5-Dichloro-4-hydroxyphenyl)-4-{[trans-4-(dimethylamino)cyclohexyl]-methylamino}-1,5-naphthyridin-3-yl]ethanone dihydrochloride

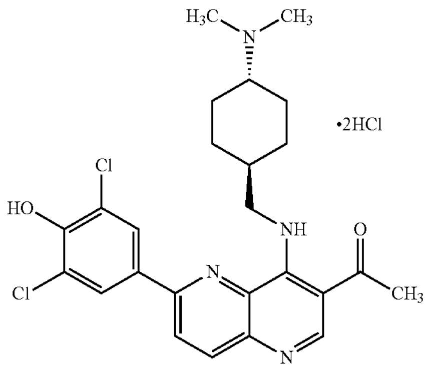 [SMILES: CC(=O)c1cnc2ccc(-c3cc(Cl)c(O)c(Cl)c3)nc2c1NC[C@H]1CC[C@H](N(C)C)CC1]

Following general procedure II, 1-(6-chloro-4-{[trans-4-(dimethylamino)cyclohexyl]methylamino}-1,5-naphthyridin-3-yl)ethanone (100 mg, 0.27 mmol) was reacted with 2,6-dichloro-4-(4,4,5,5-tetramethyl-1,3,2-dioxaborolan-2-yl)phenol (86 g, 0.30 mmol) followed by formation of the dihydrochloride salt to afford the desired product (50 mg, 38%) as a pale yellow solid: $^1$H NMR (500 MHz, $CD_3OD$) δ 9.14 (s, 1H), 8.45 (dd, J=9.0, 1.5 Hz, 1H), 8.37 (d, J=9.1 Hz, 1H), 8.08 (d, J=2.1 Hz, 2H), 4.51 (dd, J=7.2, 1.9 Hz, 2H), 3.33-3.24 (m, 1H), 2.87 (s, 6H), 2.78 (s, 3H), 2.30-2.20 (m, 4H), 2.03 (dtd, J=18.7, 7.3, 6.9, 3.4 Hz, 1H), 1.65 (qd, J=13.2, 12.3, 3.8 Hz, 2H), 1.42 (qd, J=14.6, 13.8, 3.6 Hz, 2H), 0.14-0.06 (m, 2H); ESI MS m/z 487 $[M+H]^+$; HPLC 95.0% (AUC), $t_R$=9.74 min.

Example 90

1-[6-(3-Chloro-5-fluoro-4-hydroxyphenyl)-4-{[trans-4-(dimethylamino)-cyclohexyl]methylamino}-1,5-naphthyridin-3-yl]ethanone dihydrochloride

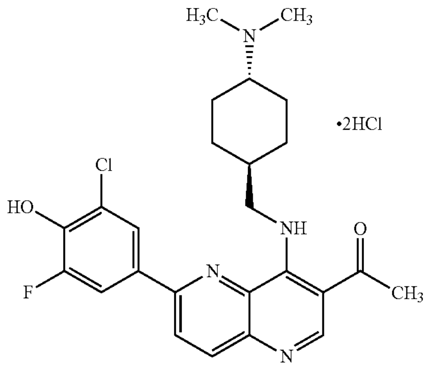 [SMILES: CC(=O)c1cnc2ccc(-c3cc(F)c(O)c(Cl)c3)nc2c1NC[C@H]1CC[C@H](N(C)C)CC1]

Following general procedure II, 1-(6-chloro-4-{[trans-4-(dimethylamino)cyclohexyl]-methylamino}-1,5-naphthyridin-3-yl)ethanone (100 g, 0.27 mmol) was reacted with 2-chloro-6-fluoro-4-(4,4,5,5-tetramethyl-1,3,2-dioxaborolan-2-yl)phenol (85 g, 0.30 mmol) followed by formation of the dihydrochloride salt to afford the desired product (50 g, 38%) as a white solid: $^1$H NMR (500 MHz, $CD_3OD$) δ 9.12 (s, 1H), 8.43 (d, J=9.0 Hz, 1H), 8.36 (d, J=8.9 Hz, 1H), 8.01-7.95 (m, 1H), 7.87 (dd, J=11.5, 2.2 Hz, 1H), 4.51 (d, J=7.0 Hz, 2H), 4.25 (d, J=6.7 Hz, 1H), 3.27 (dt, J=12.2, 3.3 Hz, 1H), 2.87 (s, 3H), 2.77 (d, J=16.7 Hz, 6H), 2.28-2.19 (m, 1H), 2.09-1.95 (m, 1H), 1.84 (s, 1H), 1.64 (qd, J=12.8, 12.1, 3.7 Hz, 1H), 1.41 (qd, J=14.0, 13.3, 3.4 Hz, 1H), 1.27 (dd, J=23.6, 12.3 Hz, 1H); ESI MS m/z 471 $[M+H]^+$; HPLC 98.9% (AUC), $t_R$=8.55 min.

Example 91

1-[6-(3,5-Dichloro-4-hydroxyphenyl)-4-(trans-4-hydroxycyclohexylamino)-1,5-naphthyridin-3-yl]-ethanone hydrochloride

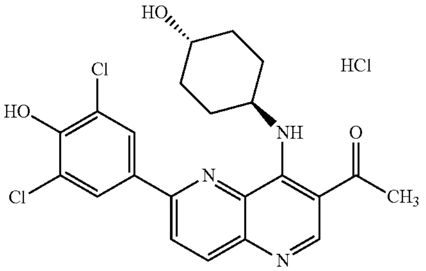 [SMILES: CC(=O)c1cnc2ccc(-c3cc(Cl)c(O)c(Cl)c3)nc2c1N[C@H]1CC[C@H](O)CC1 ; Cl]

Following general procedure II, 1-[6-chloro-4-(trans-4-hydroxycyclohexylamino)-1,5-naphthyridin-3-yl]ethanone (160 mg, 0.50 mmol) was reacted with 2,6-dichloro-4-(4,4,5,5-tetramethyl-1,3,2-dioxaborolan-2-yl)phenol (165 mg, 0.60 mmol) followed by formation of the hydrochloride salt to afford the desired product (120 mg, 56%) as a pale yellow solid: $^1$H NMR (500 MHz, $CD_3OD$) δ 9.11 (s, 1H), 8.44 (d, J=9.0 Hz, 1H), 8.30 (d, J=9.0 Hz, 1H), 8.00 (t, J=1.9 Hz, 1H), 7.87 (dd, J=11.5, 2.3 Hz, 1H), 5.60 (tt, J=10.5, 4.2 Hz, 1H), 3.75 (tt, J=9.6, 4.2 Hz, 1H), 2.75 (s, 3H), 2.42-2.35 (m, 2H), 2.14-2.06 (m, 2H), 1.74-1.54 (m, 4H); ESI MS m/z 430 $[M+H]^+$; HPLC>99% (AUC), $t_R$=10.9 min.

Example 92

1-[6-(3-Chloro-5-fluoro-4-hydroxyphenyl)-4-(trans-4-hydroxycyclohexylamino)-1,5-naphthyridin-3-yl] ethanone hydrochloride

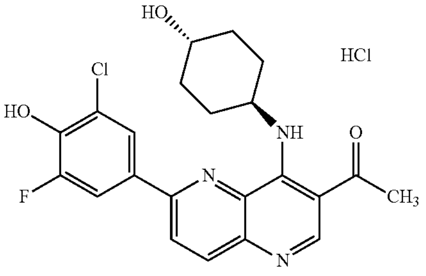 [SMILES: CC(=O)c1cnc2ccc(-c3cc(F)c(O)c(Cl)c3)nc2c1N[C@H]1CC[C@H](O)CC1 ; Cl]

Following general procedure II, 1-[6-chloro-4-(trans-4-hydroxycyclohexylamino)-1,5-naphthyridin-3-yl]ethanone (160 mg, 0.50 mmol) was reacted with 2-chloro-6-fluoro-4-(4,4,5,5-tetramethyl-1,3,2-dioxaborolan-2-yl)phenol (160 g, 0.60 mmol) followed by formation of the hydrochloride salt to afford the desired product (120 mg, 57%) as an off-white solid: $^1$H NMR (500 MHz, $CD_3OD$) δ 9.11 (s, 1H), 8.45 (d, J=9.1 Hz, 1H), 8.30 (d, J=9.0 Hz, 1H), 8.11 (s, 2H), 5.60 (dq, J=10.1, 4.5 Hz, 1H), 4.94-4.83 (m, 1H), 3.75 (tt, J=7.6, 3.9 Hz, 1H), 3.66 (s, 2H), 3.41-3.31 (m, 1H), 2.75 (s, 3H), 2.38 (dd, J=9.0, 5.3 Hz, 2H), 2.14-2.07 (m, 2H), 2.03 (s, 1H), 1.74-1.57 (m, 4H); ESI MS m/z 446 $[M+H]^+$; HPLC 96.7% (AUC), $t_R$=11.1 min.

Example 93

1-{6-(3-Chloro-5-fluoro-4-hydroxyphenyl)-4-({cis-4-[(dimethylamino)methyl]cyclohexyl}-amino)-1,5-naphthyridin-3-yl}ethanone dihydrochloride

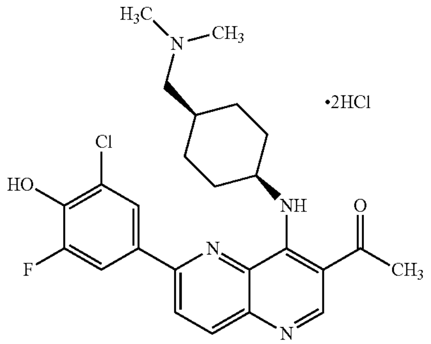 [SMILES: CC(=O)c1cnc2ccc(-c3cc(F)c(O)c(Cl)c3)nc2c1N[C@H]1CC[C@@H](CN(C)C)CC1 ; "·2HCl"]

Following general procedure II, 1-(6-chloro-4-{cis-4-[(dimethylamino)methyl]-cyclohexyl amino}-1,5-naphthyridin-3-yl)ethanone (120 mg, 0.30 mmol) was reacted with 2-chloro-6-fluoro-4-(4,4,5,5-tetramethyl-1,3,2-dioxaborolan-2-yl)phenol (100 mg, 0.30 mmol) followed by formation of the dihydrochloride salt to afford the desired product (150 mg, 81%) as an off-white solid: $^1$H NMR (500 MHz, $CD_3OD$) δ 9.17 (s, 1H), 8.46 (d, J=9.0 Hz, 1H), 8.45-8.30 (m, 1H), 7.99 (q, J=2.7, 1.7 Hz, 1H), 7.90-7.82 (m, 1H), 5.93 (p, J=4.2 Hz, 1H), 3.20 (d, J=7.1 Hz, 2H), 2.95 (s, 6H), 2.78 (s, 3H), 2.15 (dddt, J=44.4, 14.7, 11.4, 4.1 Hz, 3H), 2.01-1.86 (m, 2H), 1.61 (dtd, J=14.3, 10.8, 3.6 Hz, 3H), 1.20 (s, 1H); ESI MS m/z 471 $[M+H]^+$; HPLC 95.7% (AUC), $t_R$=9.9 min.

Example 94

1-{6-(3,5-Dichloro-4-hydroxyphenyl)-4-({cis-4-[(dimethylamino)methyl]-cyclohexyl}amino)-1,5-naphthyridin-3-yl}ethanone dihydrochloride

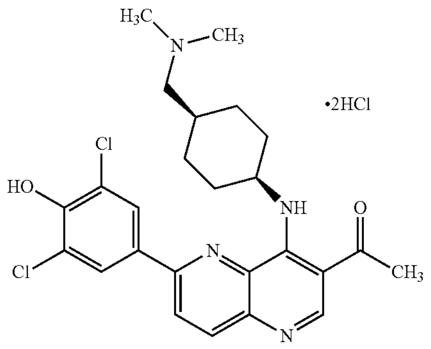 [SMILES: CC(=O)c1cnc2ccc(-c3cc(Cl)c(O)c(Cl)c3)nc2c1N[C@H]1CC[C@@H](CN(C)C)CC1 ; "·2HCl"]

Following general procedure II, 1-(6-chloro-4-{cis-4-[(dimethylamino)methyl]-cyclohexyl amino}-1,5-naphthyridin-3-yl)ethanone (120 mg, 0.30 mmol) was reacted with 2,6-dichloro-4-(4,4,5,5-tetramethyl-1,3,2-dioxaborolan-2-yl)phenol (100 mg, 0.30 mmol) followed by formation of the dihydrochloride salt to afford the desired product (150 mg, 81%) as an off-white solid: $^1$H NMR (500 MHz, $CD_3OD$) δ 9.17 (s, 1H), 8.47 (d, J=9.0 Hz, 1H), 8.34 (d, J=8.9 Hz, 1H), 8.11 (s, 2H), 5.92 (p, J=4.4 Hz, 1H), 3.21 (d, J=7.2 Hz, 2H), 2.96 (s, 6H), 2.78 (s, 3H), 2.25-2.05 (m, 3H), 1.99-1.88 (m, 2H), 1.62 (dtd, J=14.1, 11.2, 10.8, 3.7 Hz, 3H), 1.20 (s, 1H); ESI MS m/z 487 [M+H]$^+$; HPLC 96.5% (AUC), $t_R$=9.9 min.

Example 95

(R)-1-{4-[6-(3-Aminopiperidin-1-yl)pyridin-3-ylamino]-6-(3,5-dichloro-4-hydroxyphenyl)-1,5-naphthyridin-3-yl}ethanone trihydrochloride

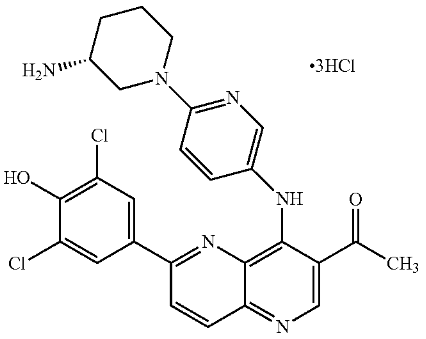 [SMILES: CC(=O)c1cnc2ccc(-c3cc(Cl)c(O)c(Cl)c3)nc2c1Nc1ccc(N2CCC[C@@H](N)C2)nc1 ; "·3HCl"]

Following general procedure IV-2, (R)-tert-butyl 1-(5-(3-acetyl-6-(3,5-dichloro-4-hydroxyphenyl)-1,5-naphthyridin-4-ylamino)pyridin-2-yl)piperidin-3-ylcarbamate (60 mg, 0.10 mmol) was reacted with TFA (1.5 mL) to afford the desired product (37 mg, 74%) as a yellow-brown solid: $^1$H NMR (500 MHz, $CD_3OD$) δ 9.28 (s, 1H), 8.49-8.31 (m, 2H), 8.16 (d, J=2.7 Hz, 1H), 7.63 (dd, J=9.1, 2.8 Hz, 1H), 7.51 (s, 2H), 6.98 (d, J=9.1 Hz, 1H), 4.40 (dd, J=12.7, 3.6 Hz, 1H), 3.93 (d, J=13.4 Hz, 1H), 3.41-3.19 (m, 3H), 2.80 (s, 3H), 2.16 (m, 1H), 1.97-1.89 (m, 1H), 1.78-1.65 (m, 2H); ESI MS m/z 523 [M+H]$^+$; HPLC 98.1% (AUC), $t_R$=9.87 min.

Example 96

(R)-1-{4-[6-(3-Aminopiperidin-1-yl)pyridin-3-ylamino]-6-(3-chloro-5-fluoro-4-hydroxyphenyl)-1,5-naphthyridin-3-yl}ethanone

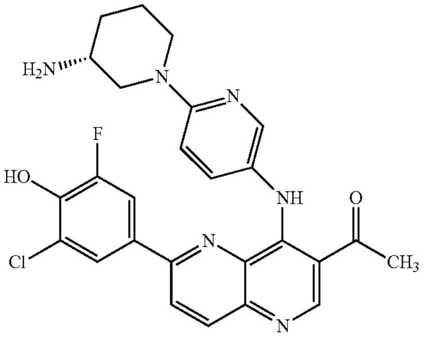 [SMILES: CC(=O)c1cnc2ccc(-c3cc(F)c(O)c(Cl)c3)nc2c1Nc1ccc(N2CCC[C@@H](N)C2)nc1]

Following general procedure IV-2, (R)-tert-butyl 1-(5-(3-acetyl-6-(3-chloro-5-fluoro-4-hydroxyphenyl)-1,5-naphthyridin-4-ylamino)pyridin-2-yl)piperidin-3-ylcarbamate (100 mg, 0.16 mmol) was reacted with TFA (2.0 mL) to afford the desired product (56 mg, 67%) as a yellow-brown solid: $^1$H NMR (500 MHz, $CD_3OD$) δ 9.27 (s, 1H), 8.40 (d, J=9.0 Hz, 1H), 8.33 (d, J=9.0 Hz, 1H), 8.16 (d, J=2.7 Hz, 1H), 7.59 (dd, J=9.1, 2.8 Hz, 1H), 7.44 (s, 1H), 7.20 (d, J=11.7 Hz, 1H), 6.97 (d, J=9.1 Hz, 1H), 4.39 (dd, J=12.6, 3.4 Hz, 1H), 3.38-3.94 (m, 2H), 3.43-3.21 (m, 5H), 2.79 (s, 3H), 2.17 (m, 2H), 1.93 (m, 1H), 1.80-1.66 (m, 2H).; ESI MS m/z 507 [M+H]$^+$; HPLC 98.8% (AUC), $t_R$=9.34 min.

Example 97

Ethyl 2-(ethoxymethylene)-3-oxobutanoate

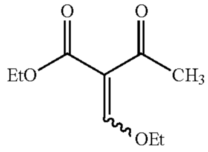

A mixture of ethyl acetoacetate (100 g, 0.77 mol), triethyl orthoformate (130 g, 0.92 mol), and acetic anhydride (150 g, 1.5 mol) was heated at 135° C. for 6-18 h in a round bottomed flask that was equipped with a distillation apparatus to collect the ethanol generated during the reaction. The reaction was cooled, concentrated and the residue was distilled under high vacuum to obtain the desired product (100 g, 70%) as a pale yellow oil:

ESI MS m/z 187 [M+H]$^+$.

Example 98

Ethyl 2-[(6-chloropyridin-3-ylamino)methylene)]-3-oxobutanoate

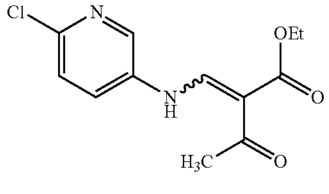 [SMILES: CCOC(=O)C(=CNc1ccc(Cl)nc1)C(C)=O]

A mixture of ethyl 2-(ethoxymethylene)-3-oxobutanoate (48 g, 0.26 mol) and 2-chloro-5-aminopyridine (33 g, 0.26 mol) in chlorobenzene (150 mL) was heated at 135° C. for 4 h in a round bottomed flask that was equipped with a distillation apparatus to collect the ethanol generated during the reaction. The reaction mixture was cooled and concentrated and the residue was triturated in diethylether and filtered to obtain the desired product (55 g, 79%) as an off-white solid: $^1$H NMR (500 MHz, $CDCl_3$) δ 12.76 (d, 12.3 Hz, 1H), 8.42 (s, 1H), 8.38 (s, 1H), 8.31 (d, J=2.8 Hz, 1H), 7.52-7.48 (m, 1H), 7.37-7.34 (m, 1H), 4.30 (q, J=7.1 Hz, 2H), 2.56 (s, 1H), 1.35 (t, J=7.1 Hz, 3H); ESI MS m/z 269 [M+H]$^+$.

Example 99

Ethyl 2-[(6-methoxypyridin-3-ylamino)methylene]-3-oxobutanoate

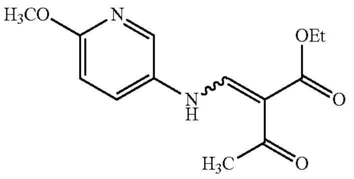 [SMILES: CCOC(=O)C(=CNc1ccc(OC)nc1)C(C)=O]

A mixture of ethyl 2-(ethoxymethylene)-3-oxobutanoate (100 g, 0.54 mol) and 2-methoxy-5-aminopyridine (67 g, 0.54 mol) in chlorobenzene (500 mL) was heated at 135° C. for 4 h in a round bottomed flask that was equipped with a distillation apparatus to collect the ethanol generated during the reaction. The reaction mixture was cooled and concentrated and the residue was triturated in diethylether and filtered to obtain the desired product (120 g, 84%) as an off-white solid: $^1$H NMR (500 MHz, $CDCl_3$) δ 12.74 (d, 12.3 Hz, 1H), 8.35 (d, J=13.0 Hz, 1H), 8.07 (d, J=2.8 Hz, 1H), 7.55 (d, J=8.8, 2.9 Hz, 1H), 6.79 (d, J=8.8 Hz, 1H), 4.30 (q, J=7.1 Hz, 2H), 2.55 (s, 3H), 1.33 (t, J=7.1 Hz, 1H); ESI MS m/z 265 $[M+H]^+$.

Example 100

1-(4-Hydroxy-6-methoxy-1,5-naphthyridin-3-yl)ethanone

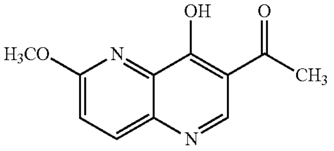 [SMILES: COc1ccc2ncc(C(C)=O)c(O)c2n1]

To a flask containing Dowtherm™ A (500 mL) at 250° C. was added ethyl 2-[(6-methoxypyridin-3-ylamino)methylene]-3-oxobutanoate (75 g, 0.28 mol) portion wise over 3 to 5 min and the reaction mixture was stirred for an additional 30 to 60 min. The reaction mixture was removed from the heat source, cooled to room temperature and diluted with hexanes to facilitate precipitation. The solids were filtered, washed with hexanes and acetonitrile and dried under vacuum to afford the desired product (60 g, 46%) as an off-white solid: $^1$H NMR (500 MHz, DMSO-$d_6$) δ 12.48 (bs, 1H), 8.45 (d, J=5.2 Hz, 1H), 8.00 (d, J=8.9 Hz, 1H), 7.40-7.37 (m, 1H), 7.21 (d, J=8.9 Hz, 1H), 7.01-6.99 (m, 1H), 3.96 (s, 3H), 2.61 (s, 3H); ESI MS m/z 219 $[M+H]^+$.

Example 101

1-(4,6-Dichloro-1,5-naphthyridin-3-yl)ethanone

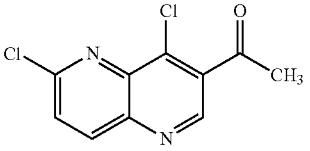

Preparation Following the Synthetic Route Outlined in Scheme 1:

To a flask containing Dowtherm™ A (500 mL) at 250° C. was added ethyl 2-[(6-chloropyridin-3-ylamino)methylene]-

3-oxobutanoate (10 g, 27 mmol) portion wise over 3 to 5 min and the reaction mixture was stirred for an additional 30 to 45 min. The reaction mixture was removed from the heat source, cooled to room temperature and diluted with hexanes to facilitate precipitation. The solids were filtered, washed with hexanes and dried under vacuum to afford the intermediate 1-(6-chloro-4-hydroxy-1,5-naphthyridin-3-yl)ethanone which was heated in neat phosphorus oxychloride with catalytic N,N-dimethylformamide for 4 h at 70° C. The reaction was cooled and poured slowly into a vigorously stirring mixture of ice-cold satd. aq. sodium bicarbonate and ethyl acetate. The layers were separated and the organic layer was dried over sodium sulfate, filtered and the filtrate was concentrated. The residue was purified by column chromatography (silica, hexanes/ethyl acetate) to provide the desired product (3 g, 46% over two steps) as a brown solid: ESI MS m/z 241 $[M+H]^+$.

Preparation Following the Synthetic Route Outlined in Scheme 2:

To a suspension of ethyl 2-[(6-methoxypyridin-3-ylamino)methylene]-3-oxobutanoate (70 g, 0.32 mol) in acetonitrile (800 ml) was added trimethylsilylchloride (173 g, 1.6 mol) and sodium iodide (140 g, 0.96 mol) and the reaction mixture was heated at reflux for 2 h. The reaction mixture was cooled to room temperature and satd. aq. sodium thiosulfate was added. The mixture was concentrated to remove acetonitrile, diluted with brine and the solids were filtered and dried to provide the intermediate 1-(4,6-dihydroxy-1,5-naphthyridin-3-yl)ethanone. This intermediate was suspended in dichloroethane (350 mL) followed by the addition of phosphorus oxychloride (200 mL) and catalytic N,N-dimethylformamide and the reaction mixture was stirred with heat at 80° C. for 3 h. The reaction mixture was cooled to room temperature and quenched by pouring slowly into ice-cold satd. aq. sodium bicarbonate or 3 N sodium hydroxide. The quenched reaction mixture was concentrated to remove the dichloroethane and the resulting solids were collected by filtration and purified by chromatography (silica, hexanes/ethyl acetate) to provide the desired product (50 g, 74% over 2 steps) as a brown solid: $^1$H NMR (300 MHz, $CDCl_3$) δ 9.00 (s, 1H), 8.38 (d, J=8.8 Hz, 1H), 7.74 (d, J=8.8 Hz, 1H), 4.30 (q, J=7.1 Hz, 2H), 3.28-3.18 (m, 1H), 1.36 (t, J=7.1 Hz, 3H), ESI MS m/z 241 $[M+H]^+$.

Example 102

Methyl 3-(6-chloropyridin-3-ylamino)-2-(cyclopropanecarbonyl)acrylate

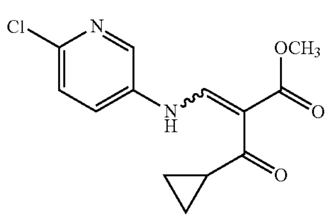 [SMILES: COC(=O)C(=CNc1ccc(Cl)nc1)C(=O)C1CC1]

A mixture of methyl 3-cyclopropyl-3-oxopropanoate (7.2 g, 50 mmol), triethyl orthoformate (13 mL, 75 mmol) and 2-chloro-5-aminopyridine (6.4 g, 50 mmol) was heated at 145° C. for 3 h in a round bottomed flask that was equipped with a short path distillation apparatus to collect the ethanol generated during the reaction. The reaction was cooled, concentrated and the residue was purified by chromatography (silica, hexanes/ethyl acetate) to afford the desired product (4.2 g, 28%) as a pale yellow oil: $^1$H NMR (300 MHz, $CDCl_3$) δ 12.78 (d, 12.5 Hz, 1H), 8.40-8.34 (m, 1H), 8.28 (d, J=2.9 Hz, 1H), 7.51-7.44 (m, 1H), 7.35 (d, J=8.6 Hz, 1H), 4.30 (q, J=7.1 Hz, 2H), 3.28-3.18 (m, 1H), 1.36 (t, J=7.1 Hz, 3H), 1.17-1.09 (m, 2H), 1.02-0.86 (m, 2H). ESI MS m/z 281 $[M+H]^+$.

Example 103

Cyclopropyl(4,6-dichloro-1,5-naphthyridin-3-yl) methanone

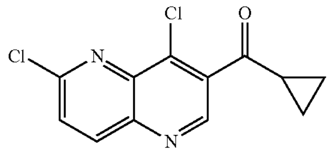 [SMILES: O=C(c1cnc2ccc(Cl)nc2c1Cl)C1CC1]

To a flask containing Dowtherm™ A (500 mL) at 250° C. was added methyl 3-(6-chloropyridin-3-ylamino)-2-(cyclopropanecarbonyl)acrylate (4.2 g, 15 mmol) portion wise over 3 to 5 min and the reaction mixture was stirred for an additional 30 to 45 min. The reaction mixture was removed from the heat source, cooled to room temperature and diluted with hexanes to facilitate precipitation. The solids were filtered, washed with hexanes and dried under vacuum to afford the intermediate (6-chloro-4-hydroxy-1,5-naphthyridin-3-yl)(cyclopropyl)methanone which was stirred with heat at 70° C. in neat phosphorus oxychloride (10 mL) with catalytic N,N-dimethylformamide for 4 h. The reaction was cooled and poured slowly into a vigorously stirring mixture of ice-cold satd. aq. sodium bicarbonate and ethyl acetate. The layers were separated and the organic layer was dried over sodium sulfate, filtered and concentrated. The residue was purified by chromatography (silica, methylene chloride/ethyl acetate) to provide the desired product (0.78 g, 20% over two steps) as a brown solid: $^1$H NMR (500 MHz, $CDCl_3$) δ 8.93 (s, 1H), 8.39 (d, J=8.7 Hz, 1H), 7.74 (d, J=8.8 Hz, 1H), 2.65 (t, J=7.7, 4.5 Hz, 1H), 1.52-1.42 (m, 2H), 1.32-1.22 (m, 2H); ESI MS m/z 268 $[M+H]^+$.

Example 104

Ethyl 3-(6-chloropyridin-3-ylamino)-2-(methylsulfonyl)acrylate

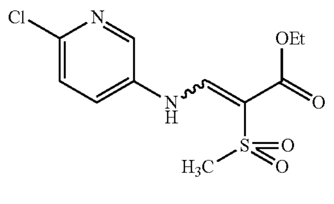 [SMILES: CCOC(=O)C(=CNc1ccc(Cl)nc1)S(C)(=O)=O]

A mixture of ethyl 3-ethoxy-2-(methylsulfonyl)acrylate (7.0 g, 32 mmol) and 2-chloro-5-aminopyridine (4.1 g, 32 mmol) in chlorobenzene (16 mL) was stirred with heat at 135° C. for 3 h in a round bottomed flask that was equipped with a short path distillation apparatus to collect the ethanol generated during the reaction. The reaction was cooled, concentrated and the residue was purified by chromatography (silica, methylene chloride/ethyl acetate) to afford the desired product (8.2 g, 84%) as a pale yellow oil: $^1$H NMR (500 MHz, $CDCl_3$) δ 10.61 (d, 13.4 Hz, 1H), 8.34 (d, J=13.4 Hz, 1H), 8.27 (d, J=2.9 Hz, 1H), 7.50 (dd, J=8.6, 3.0 Hz, 1H), 7.37 (d, J=8.6 Hz, 1H), 4.41 (q, J=7.2 Hz, 2H), 3.18 (s, 3H), 1.42 (t, J=7.2 Hz, 3H); ESI MS m/z 305 $[M+H]^+$.

Example 105

2,8-Dichloro-7-(methylsulfonyl)-1,5-naphthyridine

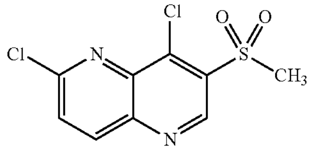 [SMILES: CS(=O)(=O)c1cnc2ccc(Cl)nc2c1Cl]

To a flask containing Dowtherm™ A (500 mL) at 250° C. was added ethyl 3-(6-chloropyridin-3-ylamino)-2-(methylsulfonyl)acrylate (8.2 g, 30 mmol) portion wise over 3 to 5 min and the reaction mixture was stirred for an additional 30 to 45 min. The reaction mixture was removed from the heat source, cooled to room temperature and diluted with hexanes to facilitate precipitation. The solids were collected by filtration, filtered, washed with hexanes and dried under vacuum to afford the intermediate 6-chloro-3-(methylsulfonyl)-1,5-naphthyridin-4-ol which was stirred with heat at 70° C. in neat phosphorus oxychloride (31 mL) with catalytic N,N-dimethylformamide for 4 h. The reaction was cooled and poured slowly into a vigorously stirring mixture of ice-cold satd. aq. sodium bicarbonate and ethyl acetate. The layers were separated and the organic layer was dried over sodium sulfate, filtered and concentrated. The residue was purified by chromatography (silica, hexanes/ethyl acetate) to provide the desired product (2.7 g, 33% over two steps) as a brown solid: $^1$H NMR (500 MHz, $CDCl_3$) δ 9.50 (s, 1H), 8.46 (d, J=8.8 Hz, 1H), 7.83 (d, J=8.8 Hz, 1H), 3.41 (s, 3H); ESI MS m/z 278 $[M+H]^+$.

Example 106

2-Chloro-1-(4,6-dichloro-1,5-naphthyridin-3-yl)ethanone

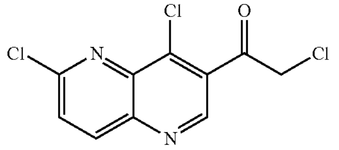 [SMILES: O=C(CCl)c1cnc2ccc(Cl)nc2c1Cl]

To a solution of 1-(4,6-dichloro-1,5-naphthyridin-3-yl) ethanone (3.0 g, 12 mmol) in THF (120 mL) was added benzyltrimethylammonium dichloroiodate (4.3 g, 12 mmol) and the reaction mixture was stirred at 70° C. for 5 h. The reaction mixture was cooled, diluted with satd. aq. sodium bicarbonate and extracted with dichloromethane. The combined organic layers were dried over anhydrous sodium sulfate, filtered and the filtrate was concentrated. The residue was purified by column chromatography (silica, dichloromethane/ethyl acetate) to afford the desired product (1.1 g, 32%) as an off-white solid. ESI MS m/z 275 $[M+H]^+$.

Example 107

2-(4,6-Dichloro-1,5-naphthyridin-3-yl)-2-oxoethyl acetate

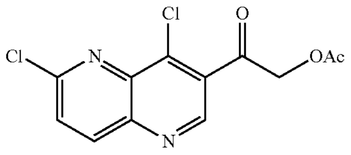 [SMILES: CC(=O)OCC(=O)c1cnc2ccc(Cl)nc2c1Cl]

To a solution of acetic acid (0.32 mL, 5.5 mmol) and N,N-diisopropylethylamine (0.87 mL, 5.0 mmol) in acetone (20 mL) was added 2-chloro-1-(4,6-dichloro-1,5-naphthyridin-3-yl)ethanone (0.26 g, 0.96 mmol) and the reaction mixture was stirred at room temperature for 4 h. The reaction mixture was diluted with satd. aq. sodium bicarbonate and extracted with dichloromethane. The combined organic layers were dried over anhydrous sodium sulfate, filtered and the filtrate was concentrated. The residue was purified by column chromatography (silica, dichloromethane/ethyl acetate) to afford the desired product (0.12 g, 42%) as a white solid. ESI MS m/z 299 $[M+H]^+$.

Example 108

Benzyl 4-[(dimethylamino)methyl]cyclohexylcarbamate

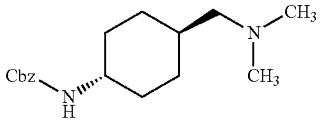 [SMILES: CN(C)C[C@H]1CC[C@H](NC(=O)OCc2ccccc2)CC1]

To a suspension of commercially available benzyl 4-(aminomethyl)cyclohexylcarbamate (15 g, 57 mmol) in water (150 mL) was added formaldehyde (14 mL, 0.17 mol, 37% solution) and formic acid (6.5 mL, 0.17 mol). The mixture was heated to reflux for 2 h, cooled to rt, neutralized with 2 N NaOH, and extracted with $CH_2Cl_2$. The organic extract was dried over anhydrous sodium sulfate, filtered, and concentrated to give desired product (16 g, 96%) as a tan, waxy solid.: APCI MS m/z 291 $[C_{12}H_{26}N_2O_2+H]^+$.

Example 109 trans-4-[(Dimethylamino)methyl]cyclohexanamine diacetic salt

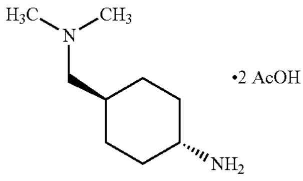

•2 AcOH

To a flask containing Pd/C (1.5 g, Degussa type E101) in methanol/acetic acid (100 mL, 3:1) was added benzyl 4-[(dimethylamino)methyl]cyclohexylcarbamate (16 g, 54 mmol) in methanol/acetic acid (300 mL, 3:1) and the reaction mixture was stirred under an atmosphere of $H_2$ (1 atm) at room temperature for 6 h. The reaction mixture was filtered through diatomaceous, the filtrate was concentrated, and azeotroped with toluene. The thick oil was dried under vacuum to give desired product (18 g, crude) as a waxy solid which was used without any purification: $^1H$ NMR (300 MHz, $CD_3OD$) δ 3.11-2.98 (m, 1H), 2.78 (d, J=7.0 Hz, 2H), 2.69 (s, 6H), 2.07 (br d, J=13.9 Hz, 4H), 2.02-1.86 (m, 2H), 1.92 (s, 6H), 1.79-1.67 (m, 1H), 1.53-1.35 (m, 2H), 1.20-1.05 (m, 2H).

Example 110 tert-Butyl[trans-4-(pyrrolidin-1-ylmethyl)cyclohexyl]carbamate

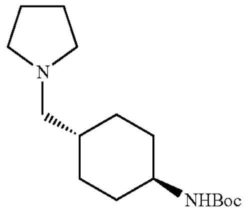 [SMILES: CC(C)(C)OC(=O)N[C@H]1CC[C@H](CN2CCCC2)CC1]

To a suspension of trans-4-((tert-butoxycarbonyl)amino)cyclohexyl)methyl methanesulfonate (1.8 g, 6.0 mmol), $K_2CO_3$ (1.7 g, 12 mmol) and KI (600 mg, 3.6 mmol) in acetonitrile (30 mL) was added pyrrolidine (5.0 mL, 60 mmol) dropwise and the reaction mixture was heated at 85° C. for 16 h. The solution was cooled to room temperature, diluted with a saturated $NaHCO_3$ solution and extracted with a mixture of $CHCl_3$/isopropanol (3:1). The combined organic layers were dried over sodium sulfate, filtered and the filtrate was concentrated. The residue was purified by chromatography (silica, methanol/dichloromethane) to afford the desired product (1.3 g, 76%) as a white solid. ESI MS m/z 283 $[C_{16}H_{30}N_2O_2+H]^+$ Example 111 trans-4-(Pyrrolidin-1-ylmethyl)cyclohexanamine dihydrochloride

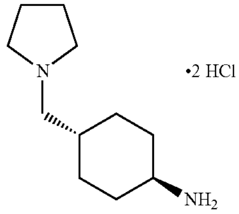 [SMILES: N[C@H]1CC[C@H](CN2CCCC2)CC1]

•2 HCl

To a solution of tert-butyl(trans-4-(pyrrolidin-1-ylmethyl)cyclohexyl)carbamate (1.3 g, 4.5 mmol) in THF (15 mL) was added aqueous 6 N HCl (6 mL) and water (6 mL) and the reaction mixture was stirred with heat at 65° C. for 3 h. The reaction mixture was cooled to room temperature and concentrated to afford the desired product (1.2 g, >99%) as an off-white solid. ESI MS m/z 183 $[C_{11}H_{22}FN_2+H]^+$ Example 112 tert-Butyl(trans-4-[2-(dimethylamino)ethyl] cyclohexyl}carbamate

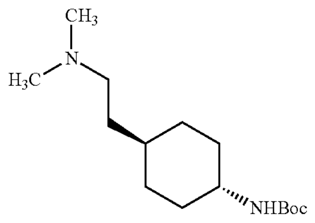 [SMILES: CN(C)CC[C@H]1CC[C@H](NC(=O)OC(C)(C)C)CC1]

To a suspension of tert-butyl[trans-4-(2-aminoethyl)cyclohexyl]carbamate (970 mg, 4.0 mmol) and paraformaldehyde (360 mg, 12 mmol) in methanol (40 mL) was added sodium cyanoborohydride (750 mg, 12 mmol) and acetic acid (1 drop). The resultant suspension was stirred at room temperature for 16 h, diluted with a saturated $NaHCO_3$ solution and extracted with a mixture of $CHCl_3$/isopropanol (3:1). The combined organic layers were dried over anhydrous sodium sulfate, filtered and the filtrate was concentrated. The residue was purified by chromatography (silica, methanol/dichloromethane) to afford the desired product (340 mg, 31%) as a white solid. ESI MS m/z 271 $[C_{15}H_{30}N_2O_2+H]^+$ Example 113 trans-4-[2-(Dimethylamino)ethyl]cyclohexanamine dihydrochloride

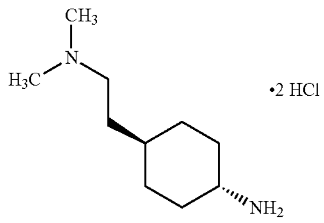

Following general procedure IV-1, tert-butyl {trans-4-[2-(dimethylamino)ethyl]-cyclohexyl}carbamate (330 mg, 1.2 mmol) was reacted with 6 N HCl (2 mL) to afford the desired product as a viscous colorless oil that was used without purification.

Example 114

$N^2$-[2-(Dimethylamino)ethyl)pyridine-2,5-diamine

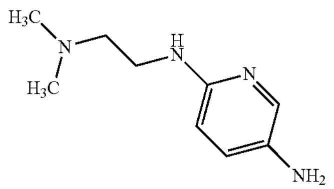

To a solution of 2-chloro-5-nitropyridine (500 mg, 3.1 mmol) in THF (30 mL) was added $N^1$,$N^1$-dimethylethane-1,2-diamine (310 mg, 3.5 mmol) and triethylamine (0.64 mL, 4.6 mmol) and the reaction mixture was stirred at room temperature for 16 h. The reaction mixture was concentrated, the residue was dissolved in dichloromethane and washed with 1 N HCl aq and water. The organic layer was dried over anhydrous sodium sulfate, filtered and the filtrate was concentrated. The residue was dissolved in tetrahydrofuran (30 mL), degassed with nitrogen, charged with catalytic 10 wt. % Pd/C (0.3 g) and the reaction mixture was placed under an atmosphere of hydrogen (40 Psi) until the reduction was complete as indicated by LCMS analysis. The reaction mixture was filtered over diatomaceous earth and the filtrate was concentrated to provide the desired product (280 mg, 50%) as a purple solid: ESI MS m/z 181 $[C_9H_{16}N_4+H]^+$.

Example 115

6-[2-(Dimethylamino)ethoxy]pyridin-3-amine

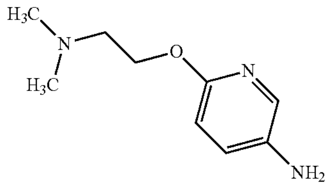

To a solution of 2-chloro-5-nitropyridine (500 mg, 3.1 mmol) in dioxane (30 mL) at room temperature was added 2-(dimethylamino)ethanol (309 mg, 3.5 mmol) and 60 wt. % NaH (0.15 g, 3.7 mmol) and the reaction mixture was stirred at room temperature until the reaction was complete by LCMS analysis. The reaction mixture was poured onto ice-cold water and the product was extracted with dichloromethane. The organic layer was dried over sodium sulfate, filtered and the filtrate was concentrated. The residue was dissolved in tetrahydrofuran (30 mL), degassed with nitrogen, charged with catalytic 10 wt. % Pd/C (0.3 g) and the reaction mixture was placed under an atmosphere of hydrogen (40 Psi) until the reduction was complete by LCMS analysis. The reaction mixture was filtered over diatomaceous earth and the filtrate was concentrated to provide the desired product (340 mg, 61%) as a purple solid: ESI MS m/z 182 $[C_9H_{15}N_3O+H]^+$.

Example 116 tert-Butyl[1-(5-aminopyridin-2-yl)pyrrolidin-3-yl] (methyl)carbamate

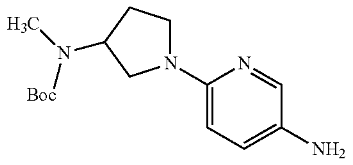 [SMILES: CN(C(=O)OC(C)(C)C)C1CCN(c2ccc(N)cn2)C1]

To a solution of commercially available tert-butyl methyl (pyrrolidin-3-yl)carbamate (1.0 g, 5.0 mmol) in THF (25 mL) was added triethylamine (0.70 mL, 5.0 mmol) and 2-chloro- 5-nitropyridine (500 mg, 3.1 mmol) and the reaction mixture was stirred at room temperature for 16 h. The reaction mixture was diluted with a satd. aq. $NaHCO_3$ and extracted with ethyl acetate. The organic layer was dried over sodium sulfate, filtered and the filtrate was concentrated. The residue was purified by chromatography (silica, ethyl acetate/hexanes) to afford the desired product (1.0 g, quant.) as a yellow solid. The solid was dissolved in tetrahydrofuran (50 mL), degassed with nitrogen, charged with catalytic 10 wt. % Pd/C (0.5 g) and the reaction mixture was placed under an atmosphere of hydrogen (1 atm) until the reduction was complete by LCMS analysis. The reaction mixture was filtered over diatomaceous earth and the filtrate was concentrated to provide the desired product (940 mg, 100%) as a red oil. ESI MS m/z 293 $[C_{15}H_{24}N_4O_2+H]^+$ Example 117 tert-Butyl {trans-4-[(dimethyl-$d_6$-amino)methyl] cyclohexyl}carbamate

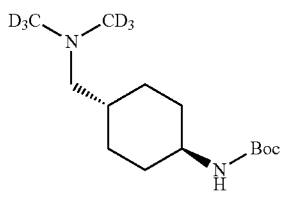 [SMILES: [2H]C([2H])([2H])N(C[C@H]1CC[C@H](NC(=O)OC(C)(C)C)CC1)C([2H])([2H])[2H]]

To a suspension of trans-4-[(tert-butoxycarbonyl)amino) cyclohexyl]methyl methanesulfonate (310 mg, 1.0 mmol), KI (330 mg, 2.0 mmol) and N,N-diisopropylethylamine (1.8 mL, 10 mmol) in acetonitrile (4 mL) was added dimethyl-$d_6$-amine hydrochloride (350 mg, 4.0 mmol) and the reaction vessel was heated in a CEM® microwave at 100° C. for 1 h. The reaction mixture was cooled, diluted with a satd. aq. $NaHCO_3$ and extracted with ethyl acetate. The organic layer was dried over sodium sulfate, filtered and the filtrate was concentrated to afford the product (240 mg, 90%) as a light brown solid. ESI MS m/z 263 $[C_{14}H_{22}D_6N_2O_2+H]^+$ Example 118 trans-4-[(Dimethylamino-$d_6$)methyl]cyclohexanamine dihydrochloride

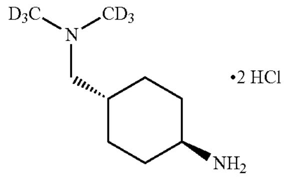

To a solution of tert-butyl {trans-4-[(dimethyl-$d_6$-amino) methyl]cyclohexyl}carbamate (750 mg, 2.9 mmol) in THF (10 mL) was added water (5 mL) and HCl (6.0 M in $H_2O$, 5.0 mL, 30 mmol). The resultant solution was stirred with heat at 65° C. for 2 h, concentrated and dried to obtain a white semisolid that was used without further purification or characterization.

Example 119 tert-Butyl trans-4-(dimethylamino)cyclohexylcarbamate

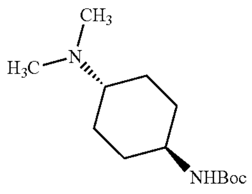 [SMILES: CN(C)[C@H]1CC[C@H](NC(=O)OC(C)(C)C)CC1]

To a solution of tert-butyl trans-4-aminocyclohexylcarbamate (750 mg, 3.5 mmol), paraformaldehyde (320 mg, 10 mmol), and sodium cyanoborohydride (660 mg, 13 mmol) in methanol (30 mL) was added acetic acid (catalytic) and the reaction was stirred at room temperature for 18 h. The reaction mixture was diluted with water and methylene chloride the layers were separated. The aqueous layer was adjusted to pH 10 using 1 M sodium hydroxide followed by extraction with methylene chloride. The combined organic layers were dried over sodium sulfate, filtered and the filtrate was concentrated to afford the desired product (800 mg, 95%) as a white solid: ESI MS m/z 243 $[C_{13}H_{26}N_2O_2+H]^+$.

Example 120 trans-$N^1$,$N^1$-Dimethylcyclohexane-1,4-diamine

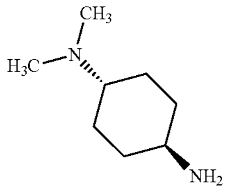

To a solution of tert-butyl trans-4-(dimethylamino)cyclohexylcarbamate (800 mg, 3.3 mmol) was added TFA (5 mL) and the reaction mixture was stirred with heat at 75° C. for 18 h. The reaction mixture was concentrated, the residue was loaded onto an SCX® ion-exchange column, flushed with methanol and then 7 N ammonia in methanol to obtain the desired product. The fractions containing the product were concentrated to dryness to obtain the desired product as the free base (400 mg, 85%) as an orange oil: ESI MS m/z 143 $[C_8H_{18}N_2+H]^+$.

Example 121

6-[3-(Dimethylamino)pyrrolidin-1-yl]pyridin-3-amine

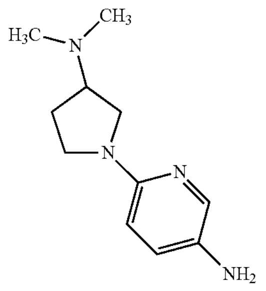

To a solution of 2-chloro-5-nitropyridine (500 mg, 3.1 mmol) in THF (30 mL) was added N,N-dimethylpyrrolidin-3-amine (400 mg, 3.5 mmol) and triethylamine (0.64 mL, 4.6 mmol) and the reaction mixture was stirred at room temperature for 16 h. The reaction mixture was concentrated to dryness, the residue was dissolved in dichloromethane and washed with 1 N HCl aq. and water. The organic layer was dried over anhydrous sodium sulfate, filtered and the filtrate was concentrated to dryness. The residue was dissolved in tetrahydrofuran (30 mL), degassed with nitrogen, charged with catalytic 10 wt. % Pd/C (0.3 g) and the reaction mixture was placed under an atmosphere of hydrogen (40 Psi) until the reduction was complete as indicated by LCMS analysis. The reaction mixture was filtered over diatomaceous earth and the filtrate was concentrated to provide the desired product (360 mg, 56%) as a purple solid: ESI MS m/z 207 $[C_{11}H_{18}N_4+H]^+$.

Example 122 tert-Butyl 1-(5-aminopyridin-2-yl)piperidin-3-ylcarbamate

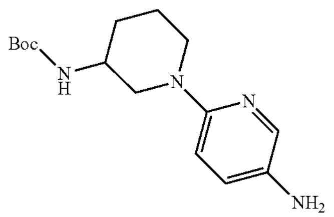 [SMILES: CC(C)(C)OC(=O)NC1CCCN(c2ccc(N)cn2)C1]

To a solution of 2-chloro-5-nitropyridine (500 mg, 3.1 mmol) in THF (30 mL) was added tert-butyl piperidin-3-ylcarbamate (700 mg, 3.5 mmol) and triethylamine (0.64 mL, 4.6 mmol) and the reaction mixture was stirred at room temperature for 16 h. The reaction mixture was concentrated to dryness, the residue was dissolved in dichloromethane and washed with 1 N HCl aq. and water. The organic layer was dried over anhydrous sodium sulfate, filtered and the filtrate was concentrated to dryness. The residue was dissolved in tetrahydrofuran (30 mL), degassed with nitrogen, charged with catalytic 10 wt. % Pd/C (0.3 g) and the reaction mixture was placed under an atmosphere of hydrogen (40 Psi) until the reduction was complete as indicated by LCMS analysis.

The reaction mixture was filtered over diatomaceous earth and the filtrate was concentrated to provide the desired product (850 mg, 93%) as a purple solid: ESI MS m/z 293 $[C_{15}H_{24}N_4O_2+H]^+$.

Example 123

(S)-tert-Butyl 1-(5-aminopyridin-2-yl)piperidin-3-ylcarbamate

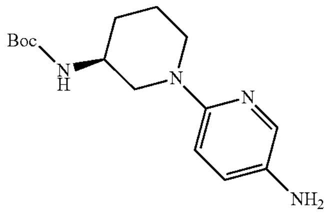 [SMILES: CC(C)(C)OC(=O)N[C@H]1CCCN(c2ccc(N)cn2)C1]

To a solution of 2-chloro-5-nitropyridine (500 mg, 3.1 mmol) in THF (30 mL) was added (S)-tert-butyl piperidin-4-ylcarbamate (700 mg, 3.5 mmol) and triethylamine (0.64 mL, 4.6 mmol) and the reaction mixture was stirred at room temperature for 16 h. The reaction mixture was concentrated to dryness, the residue was dissolved in dichloromethane and washed with 1 N HCl aq. and water. The organic layer was dried over anhydrous sodium sulfate, filtered and the filtrate was concentrated to dryness. The residue was dissolved in tetrahydrofuran (30 mL), degassed with nitrogen, charged with catalytic 10 wt. % Pd/C (0.3 g) and the reaction mixture was placed under an atmosphere of hydrogen (40 Psi) until the reduction was complete as indicated by LCMS analysis. The reaction mixture was filtered over diatomaceous earth and the filtrate was concentrated to provide the desired product (945 mg, quant.) as a purple solid: ESI MS m/z 293 $[C_{15}H_{24}N_4O_2+H]^+$.

Example 124 tert-Butyl 4-(4-nitro-1H-pyrazol-1-yl)piperidine-1-carboxylate

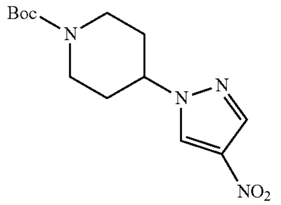

To a solution of nitropyrazole (3.0 g, 25 mmol), tert-butyl 4-hydroxypiperidine-1-carboxylate (6.0 g, 30 mmol) and triphenylphosphine (7.9 g, 30 mmol) in THF (200 mL) at room temperature was added diisopropyl azodicarboxylate (6.0 g, 30 mmol) and the reaction mixture was stirred for 16 h. The reaction mixture was concentrated and the residue was purified by chromatography (silica, hexanes/ethyl acetate) to provide the desired product (4.2 g, 57%) as a white solid:

Example 125

1-(1-Methylpiperidin-4-yl)-1H-pyrazol-4-amine

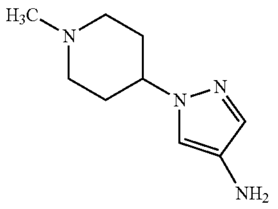 [SMILES: CC(C)(C)OC(=O)N1CCC(n2cc([N+](=O)[O-])cn2)CC1]

To a suspension of lithium aluminum hydride (0.32 g, 8.4 mmol) in THF (15 mL) was added a solution of tert-butyl 4-(4-nitro-1H-pyrazol-1-yl)piperidine-1-carboxylate (500 mg, 1.7 mmol) in THF (10 mL) and the reaction mixture was stirred with heat at 60° C. for 16 h. The reaction mixture was cooled to 0° C. and quenched by the slow addition of ethanol (0.3 mL) then water (0.3 mL) and finally 3 N NaOH aq. (0.3 mL). The resulting mixture was stirred for 30 min, filtered and the filtrate was concentrated and dried to obtain the desired product (280 mg) which was used without any purification: ESI MS m/z 181 $[M+H]^+$.

Example 126

2,6-Dichloro-4-(4,4,5,5-tetramethyl-1,3,2-dioxaborolan-2-yl)phenol

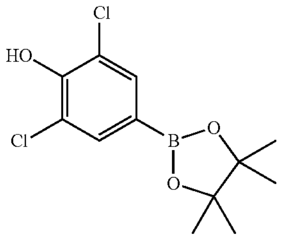 [SMILES: CC1(C)OB(c2cc(Cl)c(O)c(Cl)c2)OC1(C)C]

A flask was charged with 4-bromo-2,6-dichlorophenol (45 g, 0.20 mol), KOAc (39 g, 0.40 mol), bis(pinacolato)diboron (61 g, 0.22 mol) and Pd(dppf)$Cl_2$ (8.1 g, 0.010 mol) followed by the addition of 1,4-dioxane (1200 mL). The reaction mixture was degassed with nitrogen and stirred with heat at 90° C. for 16 h. The reaction mixture was cooled, diluted with methylene chloride, filtered and the filtrate was concentrated to dryness. The residue was purified by chromatography (silica, hexanes/ethyl acetate) to obtain a yellow oil which was treated with hexanes and the resulting solids were filtered to obtain the desired product (24 g, 44%) as a white solid: $^1H$ NMR (500 MHz, $CDCl_3$) δ 7.57 (t, J=1.3 Hz, 1H), 7.42 (dd, J=10.2, 1.3 Hz, 1H), 1.33 (s, 12H).

Example 127

2-Chloro-6-fluoro-4-(4,4,5,5-tetramethyl-1,3,2-dioxaborolan-2-yl)phenol

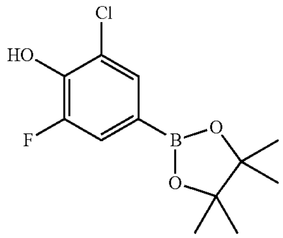 [SMILES: CC1(C)OB(c2cc(F)c(O)c(Cl)c2)OC1(C)C]

Following the procedure outlined in Example 106, 4-bromo-2-chloro-6-fluorophenol (270 mg, 1.2 mmol) was reacted with bis(pinacolato)diboron (305 mg, 1.2 mmol) and Pd(dppf)$Cl_2$ (98 mg, 0.12 mmol) to afford the desired product (340 mg, quant.) as a colorless oil: $^1H$ NMR (500 MHz, $CDCl_3$) δ 7.57 (t, J=1.3 Hz, 1H), 7.42 (dd, J=10.2, 1.3 Hz, 1H), 1.33 (s, 12H).

Example 128

1-{6-Chloro-4-[trans-4-(dimethylamino)cyclohexylamino]-1,5-naphthyridin-3-yl}ethanone

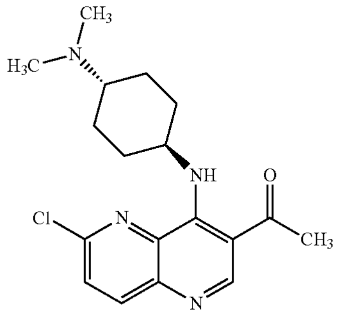 [SMILES: CC(=O)c1cnc2ccc(Cl)nc2c1N[C@H]1CC[C@H](N(C)C)CC1]

Following general procedure I, 1-(4,6-dichloro-1,5-naphthyridin-3-yl)ethanone (250 mg, 1.0 mmol) was reacted with trans-$N^1$,$N^1$-dimethylcyclohexane-1,4-diamine dihydrochloride (336 mg, 1.6 mmol) to afford the desired product (156 mg, 38%) as a light brown solid. $^1H$ NMR (500 MHz, $CDCl_3$) δ 10.88 (br s, 1H), 8.94 (s, 1H), 8.08 (d, J=8.7 Hz, 1H), 7.53 (d, J=8.8 Hz, 1H), 5.07-4.92 (m, 1H), 2.67 (s, 3H), 2.34 (s, 6H), 2.39-2.32 (m, 2H), 2.31-2.22 (m, 1 H), 2.07-1.99 (m, 2H), 1.56-1.35 (m, 4H); ESI MS m/z 347 $[M+H]^+$ Example 129

(6-Chloro-4-{trans-4-[(dimethylamino)methyl]cyclohexylamino}-1,5-naphthyridin-3-yl)(cyclopropyl)methanone

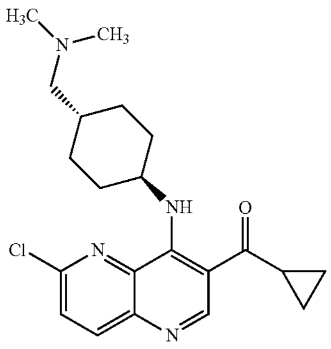 [SMILES: CN(C)C[C@H]1CC[C@H](Nc2c(C(=O)C3CC3)cnc3ccc(Cl)nc23)CC1]

Following general procedure I, cyclopropyl(4,6-dichloro-1,5-naphthyridin-3-yl)-methanone (267 mg, 1.0 mmol) was reacted with trans-4-[(dimethylamino)methyl]cyclohexanamine diacetic acid salt (270 mg, 1.0 mmol) to afford the desired product (150 mg, 39%) as an off-white solid: $^1$H NMR (500 MHz, $CDCl_3$) δ 10.85 (br s, 1H), 9.19 (s, 1H), 8.08 (d, J=8.7 Hz, 1H), 7.51 (d, J=8.7 Hz, 1H), 4.97 (br s, 1H), 2.72-2.62 (m, 1H), 2.31-2.24 (m, 2H), 2.22 (s, 6H), 2.13 (d, J=7.2 Hz, 2H), 1.96-1.89 (m, 2H), 1.55-1.46 (m, 1 H), 1.36 (qd, J=12.4, 3.3 Hz, 2H), 1.28-1.22 (m, 2H), 1.21-1.09 (m, 2H), 1.08-1.02 (m, 2H); ESI MS m/z 387 $[M+H]^+$.

Example 130

1-(6-Chloro-4-{trans-4-[2-(dimethylamino)ethyl]cyclohexylamino}-1,5-naphthyridin-3-yl)ethanone

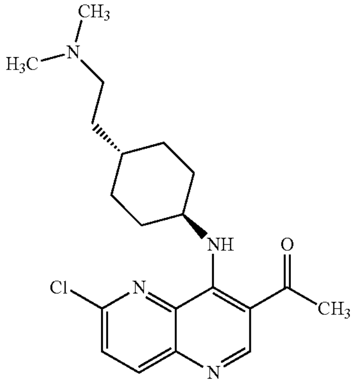 [SMILES: CC(=O)c1cnc2ccc(Cl)nc2c1N[C@H]1CC[C@H](CCN(C)C)CC1]

Following general procedure I, 1-(4,6-dichloro-1,5-naphthyridin-3-yl)ethanone (250 mg, 1.0 mmol) was reacted with trans-4-[2-(dimethylamino)ethyl]cyclohexanamine dihydrochloride (300 mg, 1.2 mmol) to afford the desired product (140 mg, 36%) as an off-white solid: $^1$H NMR (500 MHz, $CDCl_3$) δ 10.88 (br s, 1H), 8.93 (s, 1H), 8.07 (d, J=8.7 Hz, 1H), 7.52 (d, J=8.8 Hz, 1H), 5.04-4.96 (m, 1H), 2.67 (s, 3H), 2.36-2.22 (m, 4H), 2.24 (s, 6 H), 1.93-1.83 (dd, J=13.9, 3.5 Hz, 2H), 1.49-1.31 (m, 5H), 1.27-1.15 (m, 2H); ESI MS m/z 375 $[M+H]^+$ Example 131

1-(6-Chloro-4-{cis-4-[(dimethylamino)methyl]cyclohexylamino}-1,5-naphthyridin-3-yl)ethanone

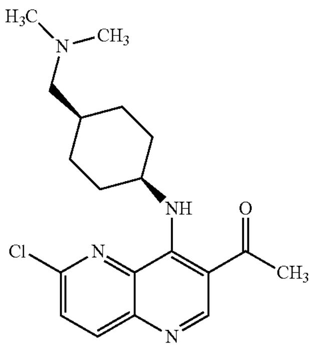 [SMILES: CC(=O)c1cnc2ccc(Cl)nc2c1N[C@H]1CC[C@@H](CN(C)C)CC1]

Following general procedure I, 1-(4,6-dichloro-1,5-naphthyridin-3-yl)ethanone (500 mg, 2.1 mmol) was reacted with cis-4-[(dimethylamino)methyl]cyclohexanamine (300 mg, 2.0 mmol) to afford the desired product (400 mg, 55%) as a yellow solid: ESI MS m/z 361 $[M+H]^+$;

Example 132

6-Chloro-N-{trans-4-[(dimethylamino)methyl]cyclohexyl}-3-(methylsulfonyl)-1,5-naphthyridin-4-amine

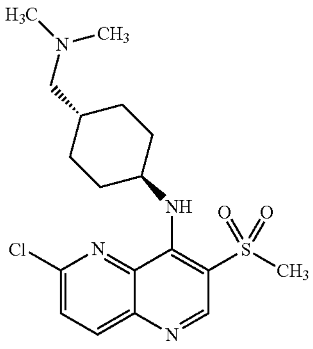 [SMILES: CN(C)C[C@H]1CC[C@H](Nc2c(S(C)(=O)=O)cnc3ccc(Cl)nc23)CC1]

Following general procedure I, 2,8-dichloro-7-(methylsulfonyl)-1,5-naphthyridine (150 mg, 0.54 mmol) was reacted with trans-4-[(dimethylamino)methyl]cyclohexanamine diacetic acid salt (190 mg, 0.68 mmol) to afford the desired product (150 mg, 68%) as a light yellow solid: $^1$H NMR (500 MHz, $CDCl_3$) δ 8.84 (s, 1H), 8.14 (d, J=8.8 Hz, 1H), 7.70-7.60 (m, 1H), 7.57 (d, J=8.8 Hz, 1H), 5.05-4.95 (m, 1H), 3.09 (s, 3H), 2.34-2.24 (m, 8H), 2.18 (d, J=7.0 Hz, 2H), 2.00-1.92

(m, 2H), 1.57-1.50 (m, 1H), 1.42-1.30 (m, 2H), 1.24-1.12 (m, 2H); ESI MS m/z 397 $[M+H]^+$

Example 133 trans-$N^1$-[6-Chloro-3-(methylsulfonyl)-1,5-naphthyridin-4-yl]-$N^4$,$N^4$-dimethylcyclohexane-1,4-diamine

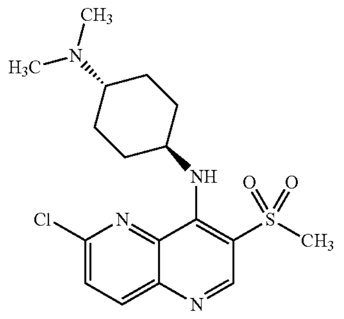

Following general procedure I, 2,8-dichloro-7-(methylsulfonyl)-1,5-naphthyridine (140 mg, 0.52 mmol) was reacted with trans-$N^1$,$N^1$-dimethylcyclohexane-1,4-diamine dihydrochloride (140 mg, 0.65 mmol) to afford the desired product (68 mg, 34%) as an off-white solid: $^1$H NMR (500 MHz, $CDCl_3$) δ 8.85 (s, 1H), 8.15 (d, J=8.8 Hz, 1H), 7.66 (d, J=7.7 Hz, 1H), 7.58 (d, J=8.8 Hz, 1H), 5.06-4.96 (m, 1H), 3.09 (s, 3H), 2.33 (s, 6H), 2.33-2.28 (m, 2 H), 2.27-2.17 (m, 1 H), 2.06-1.99 (m, 2H), 1.56-1.32 (m, 4H); ESI MS m/z 383 $[M+H]^+$ Example 134

6-Chloro-N-{4-[(dimethylamino)methyl]phenyl}-3-(methylsulfonyl)-1,5-naphthyridin-4-amine

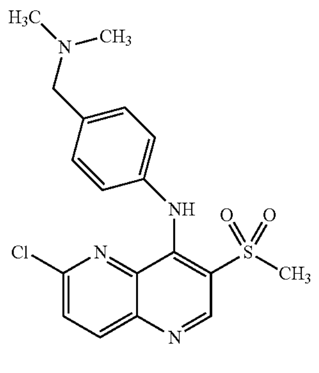 [SMILES: CN(C)Cc1ccc(Nc2c(S(C)(=O)=O)cnc3ccc(Cl)nc23)cc1]

Following general procedure I, 2,8-dichloro-7-(methylsulfonyl)-1,5-naphthyridine (150 mg, 0.53 mmol) was acted with 4-[(dimethylamino)methyl]aniline (120 mg, 0.80 mmol) to afford the desired product (150 mg, 80%) as a yellow solid: $^1$H NMR (500 MHz, $CDCl_3$) δ 9.05 (s, 1H), 8.95 (s, 1H), 8.18 (d, J=8.8 Hz, 1H), 7.52 (d, J=8.7 Hz, 1H), 7.34-7.27 (m, 2H), 7.12-7.04 (m, 2H), 3.49 (s, 2H), 3.17 (s, 3H), 2.30 (s, 6H); ESI MS m/z 391 $[M+H]^+$ Example 135

1-(6-Chloro-4-{3-[2-(pyrrolidin-1-yl)ethyl]phenylamino}-1,5-naphthyridin-3-yl)ethanone

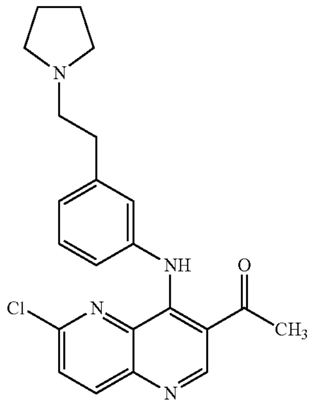 [SMILES: CC(=O)c1cnc2ccc(Cl)nc2c1Nc1cccc(CCN2CCCC2)c1]

Following general procedure I, 1-(4,6-dichloro-1,5-naphthyridin-3-yl)ethanone (250 mg, 1.0 mmol) was reacted with 3-[2-(pyrrolidin-1-yl)ethyl]aniline (240 mg, 1.3 mmol) to afford the desired product (230 mg, 57%) as a yellow solid: $^1$H NMR (500 MHz, $CDCl_3$) δ 10.79 (br s, 1H), 8.99 (s, 1H), 8.16 (d, J=8.7 Hz, 1H), 7.52 (d, J=8.8 Hz, 1H), 7.29-7.20 (m, 1H), 7.07 (d, J=7.7 Hz, 1H), 7.03-6.96 (m, 2H), 2.85-2.77 (m, 2H), 2.72-2.66 (m, 2H), 2.59-2.49 (m, 4H), 2.53 (s, 3 H), 1.84-1.74 (m, 4H); ESI MS m/z 395 $[M+H]^+$ Example 136

1-(6-Chloro-4-{6-[2-(dimethylamino)ethoxy]pyridin-3-ylamino}-1,5-naphthyridin-3-yl)ethanone

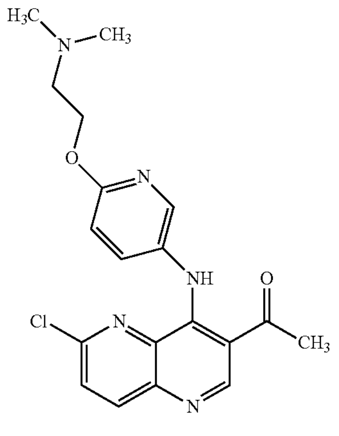 [SMILES: CC(=O)c1cnc2ccc(Cl)nc2c1Nc1ccc(OCCN(C)C)nc1]

Following general procedure I, 1-(4,6-dichloro-1,5-naphthyridin-3-yl)ethanone (170 mg, 0.71 mmol) was reacted with 6-[2-(dimethylamino)ethoxy]pyridin-3-amine (160 mg, 0.90 mmol) to afford the desired product (120 mg, 44%) as a light brown solid: $^1$H NMR (500 MHz, $CDCl_3$) δ 11.63 (br s, 1H), 9.08 (s, 1H), 8.11 (d, J=8.8 Hz, 1H), 7.99 (d, J=2.7 Hz, 1H), 7.47 (d, J=8.7 Hz, 1H), 7.41 (dd, J=8.8, 2.8 Hz, 1H), 6.80 (d, J=8.7 Hz, 1H), 4.46 (t, J=5.6 Hz, 2H), 2.76 (t, J=5.6 Hz, 2H), 2.74 (s, 3H), 2.36 (s, 6H); ESI MS m/z 386 [M+H]$^+$ Example 137

6-Chloro-N-(6-(2-(dimethylamino)ethoxy)pyridin-3-yl)-3-(methylsulfonyl)-1,5-naphthyridin-4-amine

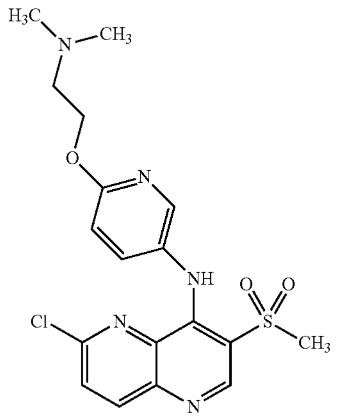

Following general procedure I, 2,8-dichloro-7-(methylsulfonyl)-1,5-naphthyridine (150 mg, 0.54 mmol) was reacted with 6-[2-(dimethylamino)ethoxy]pyridin-3-amine (120 mg, 0.65 mmol) to afford the desired product (160 mg, 70%) as a light yellow solid. 1H NMR (500 MHz, $CDCl_3$) δ 9.03 (s, 1H), 8.98 (s, 1H), 8.17 (d, J=8.8 Hz, 1H), 7.98 (d, J=2.8 Hz, 1H), 7.52 (d, J=8.8 Hz, 1H), 7.42 (dd, J=8.8, 2.8 Hz, 1H), 6.82 (d, J=8.8 Hz, 1H), 4.46 (t, J=5.5 Hz, 2H), 3.20 (s, 3H), 2.76 (t, J=5.6 Hz, 2H), 2.37 (s, 6H); ESI MS m/z 422 [M+H]$^+$ Example 138

1-[6-Chloro-4-(trans-4-hydroxycyclohexylamino)-1,5-naphthyridin-3-yl]ethanone

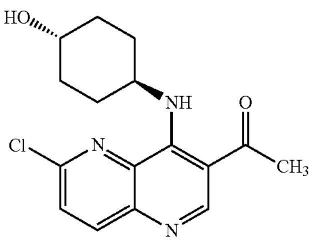 [SMILES: CC(=O)c1cnc2ccc(Cl)nc2c1N[C@H]1CC[C@H](O)CC1]

Following general procedure I, 1-(4,6-dichloro-1,5-naphthyridin-3-yl)ethanone (480 mg, 2.0 mmol) was reacted with trans-4-aminocyclohexanol (287 mg, 2.5 mmol) to afford the desired product (500 mg, 78%) as an orange-red solid: $^1$H NMR (500 MHz, $CDCl_3$) δ 10.90 (s, 1H), 8.95 (s, 1H), 8.09 (d, J=8.7 Hz, 1H), 7.53 (d, J=8.7 Hz, 1H), 5.10 (tdt, J=11.2, 8.0, 3.9 Hz, 1H), 3.76 (tt, J=10.0, 4.3 Hz, 1H), 2.68 (s, 3H), 2.33-2.24 (m, 2H), 2.13-2.04 (m, 2H), 1.63-1.41 (m, 8H); ESI MS m/z 320 [M+H]$^+$ Example 139

1-(6-Chloro-4-{[trans-4-(dimethylamino)cyclohexyl]methylamino}-1,5-naphthyridin-3-yl)ethanone

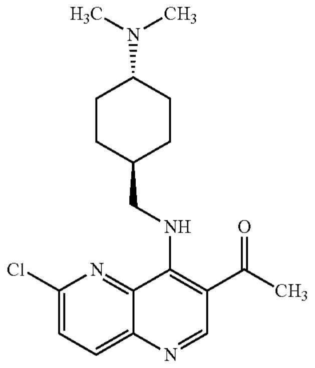 [SMILES: CC(=O)c1cnc2ccc(Cl)nc2c1NC[C@H]1CC[C@H](N(C)C)CC1]

Following general procedure I, 1-(4,6-dichloro-1,5-naphthyridin-3-yl)ethanone (300 mg, 1.2 mmol) was reacted with trans-4-(aminomethyl)-N,N-dimethylcyclohexanamine (350 mg, 1.5 mmol) to afford the desired product (400 mg, 86%) as an orange-red solid: $^1$H NMR (300 MHz, $CD_3OD$) δ 8.95 (s, 1H), 8.11 (d, J=8.8 Hz, 1H), 7.69 (d, J=8.8 Hz, 1H), 4.07 (d, J=6.5 Hz, 2H), 2.69 (s, 3H), 2.32 (s, 6H), 2.13-1.95 (m, 4H), 1.43-1.08 (m, 4H); ESI MS m/z 361 [M+H]$^+$ Example 140

1-{6-Chloro-4-[(1-methylpiperidin-4-yl)methylamino]-1,5-naphthyridin-3-yl}ethanone

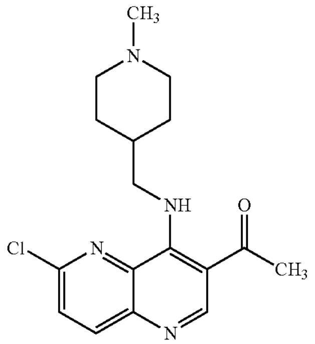 [SMILES: CC(=O)c1cnc2ccc(Cl)nc2c1NCC1CCN(C)CC1]

Following general procedure I, 1-(4,6-dichloro-1,5-naphthyridin-3-yl)ethanone (250 mg, 1.0 mmol) was reacted with (1-methylpiperidin-4-yl)methanamine (160 mg, 1.3 mmol) to afford the desired product (170 mg, 49%) as a light yellow-brown solid: $^1$H NMR (500 MHz, $CDCl_3$) δ 11.06 (br s, 1H), 8.95 (s, 1H), 8.10 (d, J=8.8 Hz, 1H), 7.53 (d, J=8.7 Hz, 1H), 4.13 (t, J=6.4 Hz, 2H), 2.99-2.92 (m, 2H), 2.69 (s, 3H), 2.32

(s, 3H), 2.07-1.98 (m, 2H), 1.97-1.89 (m, 2H), 1.85-1.75 (m, 1H), 1.57-1.47 (m, 2H); ESI MS m/z 333 $[M+H]^+$

Example 141

(S)-tert-Butyl 1-{5-[3-(cyclopropanecarbonyl)-6-(3,5-dichloro-4-hydroxyphenyl)-1,5-naphthyridin-4-ylamino]pyridin-2-yl}piperidin-3-ylcarbamate

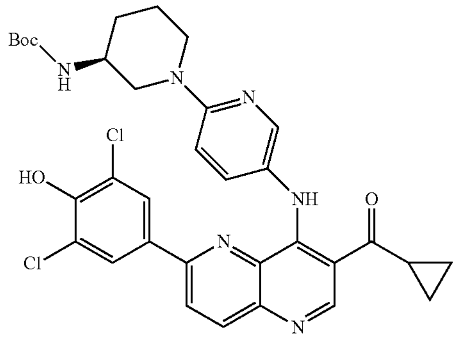 [SMILES: CC(C)(C)OC(=O)N[C@H]1CCCN(c2ccc(Nc3c(C(=O)C4CC4)cnc4ccc(-c5cc(Cl)c(O)c(Cl)c5)nc34)cn2)C1]

Following general procedure II, (S)-tert-butyl 1-{5-[6-chloro-3-(cyclopropanecarbonyl)-1,5-naphthyridin-4-ylamino]pyridin-2-yl}piperidin-3-ylcarbamate (98 mg, 0.19 mmol) was reacted with 2,6-dichloro-4-(4,4,5,5-tetramethyl-1,3,2-dioxaborolan-2-yl)phenol (87 mg, 0.30 mmol) to afford the desired product (73 mg, 60%) as a red-brown solid: $^1$H NMR (500 MHz, $CDCl_3$) δ 11.55 (br s, 1H), 9.29 (s, 1H), 8.25 (d, J=8.8 Hz, 1H), 8.03 (d, J=2.7 Hz, 1H), 7.92 (d, J=8.8 Hz, 1H), 7.46 (s, 2H), 7.32 (dd, J=9.0, 2.8 Hz, 1H), 6.67 (d, J=9.0 Hz, 1H), 4.78-4.72 (m, 1H), 3.87-3.69 (m, 3H), 3.29-3.07 (m, 2H), 2.79-2.71 (m, 1H), 1.98-1.69 (m, 2H), 1.45 (s, 9H), 1.31-1.22 (m, 2H), 1.16-1.06 (m, 2H); ESI MS m/z 649 $[M+H]^+$ Example 142

(S)-tert-Butyl 1-{5-[6-chloro-3-(cyclopropanecarbonyl)-1,5-naphthyridin-4-ylamino]-pyridin-2-yl}piperidin-3-ylcarbamate

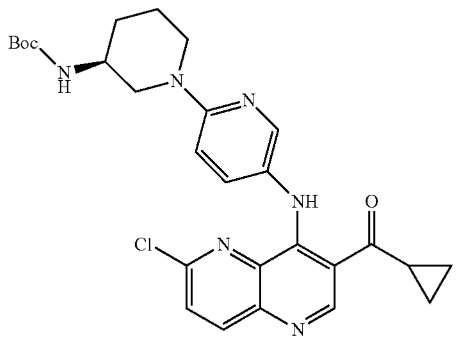 [SMILES: CC(C)(C)OC(=O)N[C@H]1CCCN(c2ccc(Nc3c(C(=O)C4CC4)cnc4ccc(Cl)nc34)cn2)C1]

Following general procedure I, cyclopropyl(4,6-dichloro-1,5-naphthyridin-3-yl)-methanone (267 mg, 1.0 mmol) was reacted with (S)-tert-butyl 1-(5-aminopyridin-2-yl)-piperidin-3-ylcarbamate (340 mg, 1.2 mmol) to afford the desired product (329 mg, 63%) as a brown solid: $^1$H NMR (500 MHz, $CDCl_3$) δ 10.19 (br s, 1H), 9.03 (s, 1H), 8.17 (d, J=8.8 Hz, 1H), 8.04 (d, J=2.8 Hz, 1H), 7.53 (d, J=8.8 Hz, 1H), 7.31-7.25 (m, 1H), 6.70 (d, J=9.1 Hz, 1H), 4.78 (br s, 1H), 3.83-3.62 (m, 3H), 3.47-3.25 (m, 2H), 2.55-2.47 (m, 1H), 1.97-1.83 (m, 2H), 1.73-1.58 (m, 1H), 1.45 (s, 9H), 1.12-1.04 (m, 2H), 1.00-0.90 (m, 2H); ESI MS m/z 523 $[M+H]^+$ Example 143

1-(6-Chloro-4-(trans-4-((dimethylamino-$d_6$)methyl)cyclohexylamino)-1,5-naphthyridin-3-yl)ethanone

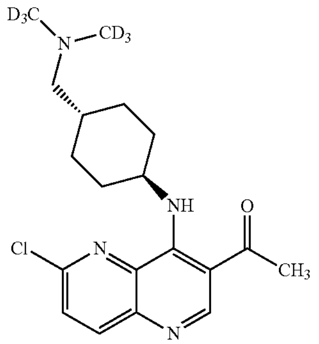

Following general procedure I, 1-(4,6-dichloro-1,5-naphthyridin-3-yl)ethanone (100 mg, 0.42 mmol) was reacted with trans-4-[(dimethylamino-$d_6$)methyl]cyclohexanamine (87 mg, 0.37 mmol) to afford the desired product (85 mg, 63%) as a light brown solid: $^1$H NMR (500 MHz, $CD_3OD$) δ 8.96 (s, 1H), 8.11 (d, J=8.8 Hz, 1H), 7.70 (d, J=8.7 Hz, 1H), 5.08-4.98 (m, 1H), 2.68 (s, 3H), 2.34-2.24 (m, 4H), 2.00-1.91 (m, 2H), 1.68-1.53 (m, 1H), 1.46-1.36 (m, 2H), 1.25-1.15 (m, 2H); ESI MS m/z 367 $[M+H]^+$ Example 144

1-(6-Chloro-4-{4-[2-(dimethylamino)ethyl]phenylamino}-1,5-naphthyridin-3-yl)ethanone

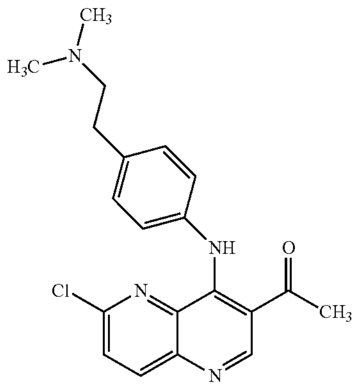 [SMILES: CC(=O)c1cnc2ccc(Cl)nc2c1Nc1ccc(CCN(C)C)cc1]

Following general procedure I, 1-(4,6-dichloro-1,5-naphthyridin-3-yl)ethanone (150 mg, 0.64 mmol) was reacted with 4-[2-(dimethylamino)ethyl)aniline (110 mg, 0.64 mmol) to afford the desired product (143 mg, 60%) as a yellow solid: $^1$H NMR (500 MHz, $CDCl_3$) δ 10.86 (br s, 1H), 8.99 (s, 1H), 8.14 (d, J=8.8 Hz, 1H), 7.50 (d, J=8.8 Hz, 1H), 7.22-7.15 (m, 2H), 7.11-7.04 (m, 2H), 2.87 (t, J=8.1 Hz, 2H), 2.70-2.60 (m, 2H), 2.55 (s, 3H), 2.39 (s, 6H); ESI MS m/z 369 $[M+H]^+$ Example 145 trans-$N^1$-[6-Chloro-3-(methylsulfonyl)-1,5-naphthyridin-4-yl]-$N^4$,$N^4$-dimethylcyclohexane-1,4-diamine

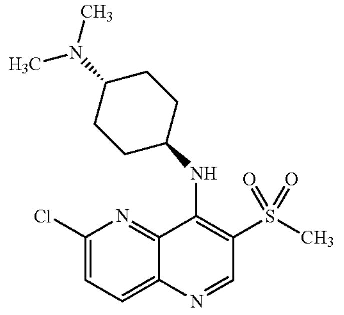

Following general procedure I, 2,8-dichloro-7-(methylsulfonyl)-1,5-naphthyridine (140 mg, 0.52 mmol) was reacted with trans-$N^1$,$N^1$-dimethylcyclohexane-1,4-diamine dihydrochloride (140 mg, 0.65 mmol) to afford the desired product (68 mg, 34%) as an off-white solid: ESI MS m/z 383 $[M+H]^+$ Example 146

1-{6-Chloro-4-[1-(1-methylpiperidin-4-yl)-1H-pyrazol-4-ylamino]-1,5-naphthyridin-3-yl}ethanone

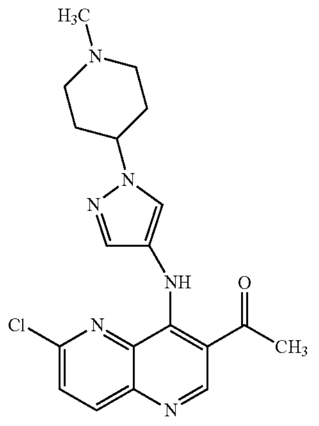 [SMILES: CC(=O)c1cnc2ccc(Cl)nc2c1Nc1cnn(C2CCN(C)CC2)c1]

Following general procedure I, 1-(4,6-dichloro-1,5-naphthyridin-3-yl)ethanone (250 mg, 1.0 mmol) was reacted with 1-(1-methylpiperidin-4-yl)-1H-pyrazol-4-amine (216 mg, 1.2 mmol) to afford the desired product (304 mg, 76%) as a light orange solid: $^1$H NMR (500 MHz, $CDCl_3$) δ 8.99 (s, 1H), 8.12 (d, J=8.7 Hz, 1H), 7.56-7.48 (m, 2H), 7.42 (d, J=0.6 Hz, 1H), 4.18-4.11 (m, 1H), 3.00 (d, J=11.4 Hz, 2H), 2.67 (s, 3H), 2.34 (s, 3H), 2.26-2.02 (m, 6H); ESI MS m/z 385 $[M+H]^+$ Example 147 tert-Butyl 1-{5-[3-acetyl-6-(3,5-dichloro-4-hydroxyphenyl)-1,5-naphthyridin-4-ylamino]pyrimidin-2-yl}pyrrolidin-3-ylcarbamate

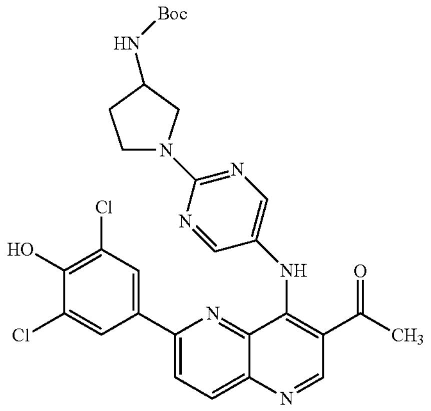 [SMILES: CC(=O)c1cnc2ccc(-c3cc(Cl)c(O)c(Cl)c3)nc2c1Nc1cnc(N2CCC(NC(=O)OC(C)(C)C)C2)nc1]

Following general procedure II, tert-butyl 1-[5-(3-acetyl-6-chloro-1,5-naphthyridin-4-ylamino)pyrimidin-2-yl]pyrrolidin-3-ylcarbamate (120 mg, 0.25 mmol) was reacted with 2,6-dichloro-4-(4,4,5,5-tetramethyl-1,3,2-dioxaborolan-2-yl)phenol (110 mg, 0.38 mmol) to afford the product (120 mg, 80%) as an orange solid: $^1$H NMR (500 MHz, $CDCl_3$) δ 12.02 (s, 1H), 9.12 (s, 1H), 8.28-8.20 (m, 3H), 7.93 (d, J=8.8 Hz, 1H), 7.39 (s, 2H), 4.72 (br s, 1H), 4.36 (br s, 1H), 3.86 (br s, 1H), 3.65 (br s, 2H), 3.40 (br s, 1H), 2.80 (s, 3H), 2.28 (br s, 1H), 2.03-1.93 (m, 1H), 1.48 (s, 9H); ESI MS m/z 610 $[M+H]^+$ Example 148 tert-Butyl 1-[5-(3-acetyl-6-chloro-1,5-naphthyridin-4-ylamino) pyrimidin-2-yl]pyrrolidin-3-ylcarbamate

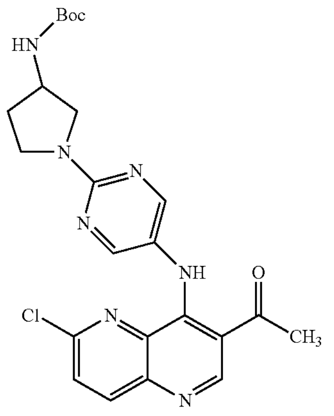 [SMILES: CC(=O)c1cnc2ccc(Cl)nc2c1Nc1cnc(N2CCC(NC(=O)OC(C)(C)C)C2)nc1]

Following general procedure I, 1-(4,6-dichloro-1,5-naphthyridin-3-yl)ethanone (300 mg, 1.2 mmol) was reacted with tert-butyl 1-(5-aminopyrimidin-2-yl)pyrrolidin-3-ylcarbamate (380 mg, 1.4 mmol) to afford the desired product (468 mg, 78%) as a yellow-orange solid: $^1$H NMR (500 MHz, $CDCl_3$) δ 11.72 (s, 2H), 9.09 (s, 2H), 8.21 (s, 3H), 8.11 (d, J=8.7 Hz, 2H), 7.48 (d, J=8.8 Hz, 2H), 7.26 (s, 2H), 4.70 (s, 2H), 4.38 (s, 2H), 3.90 (dd, J=11.6, 6.1 Hz, 2H), 3.78-3.66 (m, 4H), 3.52 (dd, J=11.6, 4.3 Hz, 2H), 2.77 (s, 5H), 2.31 (dq, J=13.4, 7.2 Hz, 2H), 1.57 (s, 2H), 1.47 (s, 17H), 1.19 (s, 1H); ESI MS m/z 484 [M+H]$^+$ Example 149

1-(6-Chloro-4-{4-[(4-methylpiperazin-1-yl)methyl] phenylamino}-1,5-naphthyridin-3-yl)ethanone

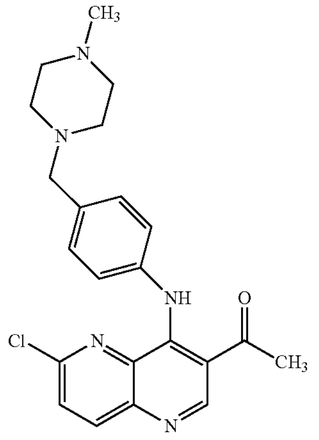 [SMILES: CC(=O)c1cnc2ccc(Cl)nc2c1Nc1ccc(CN2CCN(C)CC2)cc1]

Following general procedure I, 1-(4,6-dichloro-1,5-naphthyridin-3-yl)ethanone (250 mg, 1.0 mmol) was reacted with 4-[(4-methylpiperazin-1-yl)methyl]aniline (260 mg, 1.3 mmol) to afford the desired product (250 mg, 58%) as a yellow solid: $^1$H NMR (500 MHz, $CDCl_3$) δ 11.04 (br s, 1H), 9.01 (s, 1H), 8.14 (d, J=8.7 Hz, 1H), 7.49 (d, J=8.7 Hz, 1H), 7.30 (d, J=8.0 Hz, 2H), 7.10 (d, J=8.0 Hz, 2H), 3.52 (s, 2H), 2.58 (s, 3H), 2.48 (br s, 8H), 2.30 (s, 3H); ESI MS m/z 410 [M+H]$^+$ Example 150

1-(6-Chloro-4-{4-[2-(pyrrolidin-1-yl)ethyl]piperidin-1-yl}-1,5-naphthyridin-3-yl)ethanone

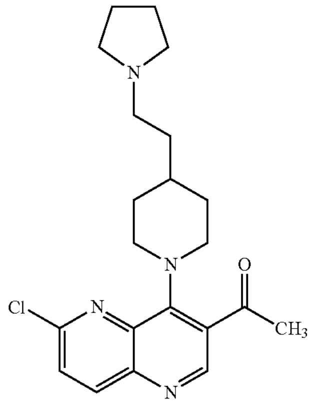 [SMILES: CC(=O)c1cnc2ccc(Cl)nc2c1N1CCC(CCN2CCCC2)CC1]

Following general procedure I, 1-(4,6-dichloro-1,5-naphthyridin-3-yl)ethanone (250 mg, 1.0 mmol) was reacted with 4-[2-(pyrrolidin-1-yl)ethyl]piperidine (230 mg, 1.3 mmol) to afford the desired product (190 mg, 47%) as a yellow solid: $^1$H NMR (500 MHz, $CDCl_3$) δ 8.74 (s, 1 H), 8.18 (d, J=8.8 Hz, 1H), 7.53 (d, J=8.7 Hz, 1H), 3.98-3.90 (m, 2H), 3.32-3.23 (m, 2H), 2.58-2.50 (m, 6H), 2.55 (s, 3H), 1.86-1.53 (m, 11H); ESI MS m/z 387 [M+H]$^+$ Example 151

1-(6-Chloro-4-{6-[2-(dimethylamino)ethylamino] pyridin-3-ylamino}-1,5-naphthyridin-3-yl)ethanone

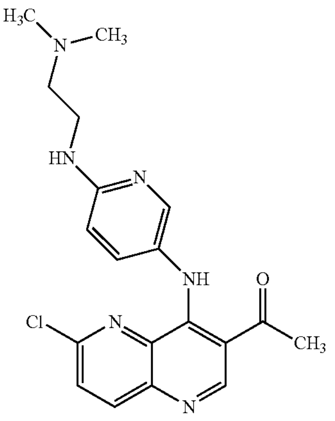 [SMILES: CC(=O)c1cnc2ccc(Cl)nc2c1Nc1ccc(NCCN(C)C)nc1]

Following general procedure I, 1-(4,6-dichloro-1,5-naphthyridin-3-yl)ethanone (300 mg, 1.2 mmol) was reacted with N$^2$-[2-(dimethylamino)ethyl]pyridine-2,5-diamine (320 mg, 1.5 mmol) to afford the desired product (210 mg, 37%) as an orange solid: $^1$H NMR (500 MHz, $CDCl_3$) δ 11.41 (br s, 1H), 9.02 (s, 1H), 8.13-8.07 (m, 1H), 7.95 (d, J=2.5 Hz, 1H), 7.47 (dd, J=8.7, 1.1 Hz, 1H), 7.29-7.23 (m, 1H), 6.44 (d, J=8.8 Hz, 1H), 5.12 (t, J=5.1 Hz, 1H), 3.41 (q, J=5.7 Hz, 2H), 2.69 (s, 3H), 2.60 (t, J=6.0 Hz, 2H), 2.30 (s, 6H); ESI MS m/z 385 [M+H].$^+$ Example 152

1-[6-Chloro-4-(1-methylpiperidin-4-ylamino)-1,5-naphthyridin-3-yl]ethanone

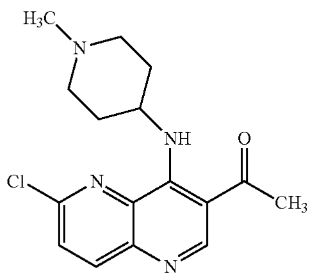 [SMILES: CC(=O)c1cnc2ccc(Cl)nc2c1NC1CCN(C)CC1]

Following general procedure I, 1-(4,6-dichloro-1,5-naphthyridin-3-yl)ethanone (220 mg, 0.91 mmol) was reacted with 1-methylpiperidin-4-amine (160 mg, 1.4 mmol) to afford the desired product (200 mg, 69%) as a light brown solid: $^1$H NMR (500 MHz, $CDCl_3$) δ 10.98 (s, 1H), 8.96 (s, 1H), 8.10 (d, J=8.7 Hz, 1H), 7.53 (d, J=8.7 Hz, 1H), 5.11 (br s, 1H), 2.98-2.870 (m, 2H), 2.69 (s, 3H), 2.41-2.28 (m, 5H), 2.28-2.20 (m, 2H), 1.85-1.73 (m, 2H); ESI MS m/z 319 $[M+H]^+$; ESI MS m/z 319 $[M+H]^+$ Example 153

(S)-tert-Butyl 1-[5-(3-acetyl-6-chloro-1,5-naphthyridin-4-ylamino) pyridin-2-yl]piperidin-3-ylcarbamate

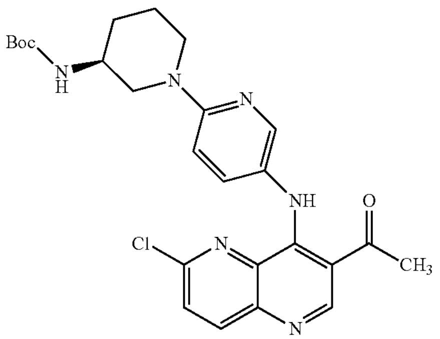 [SMILES: CC(=O)c1cnc2ccc(Cl)nc2c1Nc1ccc(N2CCC[C@H](NC(=O)OC(C)(C)C)C2)nc1]

Following general procedure I, 1-(4,6-dichloro-1,5-naphthyridin-3-yl)ethanone (260 mg, 1.1 mmol) was reacted with (S)-tert-butyl 1-(5-aminopyridin-2-yl)piperidin-3-ylcarbamate (470 mg, 1.6 mmol) to afford the desired product (350 mg, 65%) as an orange-red solid: $^1$H NMR (300 MHz, $CDCl_3$) δ 11.48 (s, 1H), 9.04 (s, 1H), 8.10 (d, J=8.7 Hz, 1H), 8.01 (d, J=2.8 Hz, 1H), 7.46 (d, J=8.7 Hz, 1H), 7.31 (dd, J=9.0, 2.8 Hz, 1H), 6.73 (d, J=9.0 Hz, 1H), 4.80 (br s, 1H), 3.85-3.62 (m, 3H), 3.55-3.25 (m, 3H), 2.71 (s, 3H), 1.96-1.84 (m, 1H), 1.82-1.70 (m, 1H), 1.72-1.55 (m, 1H), 1.45 (s, 9H); ESI MS m/z 497 $[M+H]^+$ Example 154

1-{6-Chloro-4-[trans-4-(hydroxymethyl)cyclohexylamino]-1,5-naphthyridin-3-yl}ethanone

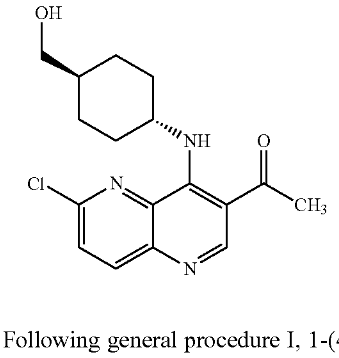

Following general procedure I, 1-(4,6-dichloro-1,5-naphthyridin-3-yl)ethanone (200 mg, 0.83 mmol) was reacted with (trans-4-aminocyclohexyl)methanol (130 mg, 1.0 mmol) to afford the desired product (180 mg, 65%) as an orange-yellow solid: $^1$H NMR (500 MHz, $CDCl_3$) δ 10.90 (s, 1H), 8.94 (s, 1H), 8.08 (d, J=8.7 Hz, 1H), 7.52 (d, J=8.7 Hz, 1H), 5.10-4.92 (m, 1H), 3.58-3.47 (m, 2H), 2.68 (s, 3H), 2.37-2.23 (m, 2H), 2.01-1.89 (m, 2H), 1.65-1.51 (m, 1H), 1.42-1.30 (m, 2H), 1.29-1.18 (m, 2H); ESI MS m/z 334 $[M+H]^+$ Example 155

{6-Chloro-4-[trans-4-(dimethylamino)cyclohexylamino]-1,5-naphthyridin-3-yl}(cyclopropyl)methanone

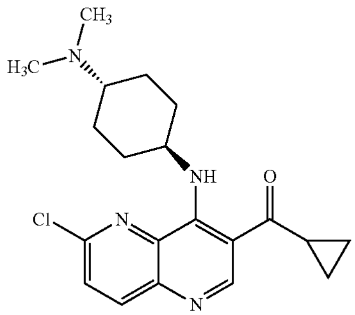 [SMILES: CN(C)[C@H]1CC[C@H](Nc2c(C(=O)C3CC3)cnc3ccc(Cl)nc23)CC1]

Following general procedure I, cyclopropyl(4,6-dichloro-1,5-naphthyridin-3-yl) methanone (243 mg, 0.91 mmol) was reacted with trans-$N^1$,$N^1$-dimethylcyclohexane-1,4-diamine (168 mg, 1.2 mmol) to afford the desired product (150 mg, 44%) as a light yellow solid. 1H NMR (500 MHz, Chloroform-d) δ 10.83 (br s, 1H), 9.20 (s, 1H), 8.09 (d, J=8.7 Hz, 1H), 7.52 (d, J=8.8 Hz, 1H), 4.98 (br s, 1H), 2.71-2.63 (m, 1H), 2.33 (s, 6H), 2.34-2.29 (m, 2H), 2.28-2.19 (m, 1H), 2.06-1.97 (m, 2H), 1.54-1.33 (m, 4H), 1.31-1.22 (m, 2H), 1.11-1.01 (m, 2H). ESI MS m/z 373 $[M+H]^+$.

Example 156

{trans-4-[(3-Acetyl-6-chloro-1,5-naphthyridin-4-yl)amino]cyclohexyl}methyl methanesulfonate

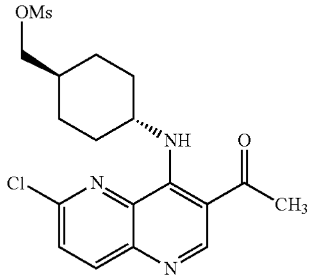 [SMILES: CC(=O)c1cnc2ccc(Cl)nc2c1N[C@H]1CC[C@H](COS(C)(=O)=O)CC1]

To a solution of 1-{6-chloro-4-[trans-4-(hydroxymethyl)cyclohexylamino]-1,5-naphthyridin-3-yl}ethanone (140 mg, 0.42 mmol) in methylene chloride (10 mL) was added triethylamine (0.12 mL, 0.84 mmol) and methanesulfonyl chloride (65 μL, 0.84 mmol) and the reaction mixture was stirred at room temperature for 4 h. The reaction mixture was diluted with satd. aq. sodium bicarbonate, the layers were separated and the organic layer was concentrated to afford the crude product (180 mg) as a yellow solid which was used without further purification: $^1$H NMR (500 MHz, $CDCl_3$) δ 10.90 (br s, 1H), 8.95 (s, 1H), 8.09 (d, J=8.7 Hz, 1H), 7.53 (d, J=8.7 Hz, 1H), 5.10-4.95 (m, 1H), 4.11 (d, J=6.5 Hz, 2H), 3.03 (s, 3H), 2.68 (s, 3H), 2.39-2.26 (m, 2H), 2.01-1.92 (m, 2H), 1.90-1.78 (m, 1H), 1.47-1.24 (m, 4H); ESI MS m/z 412 $[M+H]^+$

Example 157 tert-Butyl 4-{[trans-4-(3-acetyl-6-chloro-1,5-naphthyridin-4-ylamino)cyclohexyl]methyl}piperazine-1-carboxylate

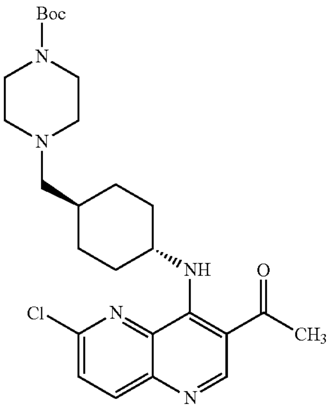 [SMILES: CC(=O)c1cnc2ccc(Cl)nc2c1N[C@H]1CC[C@H](CN2CCN(C(=O)OC(C)(C)C)CC2)CC1]

Following general procedure V, {4-[(3-acetyl-6-chloro-1,5-naphthyridin-4-yl)amino]-cyclohexyl}methyl methanesulfonate (170 mg, 0.42 mmol) was reacted with tert-butyl 4-[(trans-4-aminocyclohexyl)methyl]piperazine-1-carboxylate (93 mg, 0.50 mmol) to afford the desired product (150 mg, 73%) as a yellow solid. ESI MS m/z 502 $[M+H]^+$

Example 158

1-{6-Chloro-4-[trans-4-(morpholinomethyl)cyclohexylamino]-1,5-naphthyridin-3-yl}ethanone

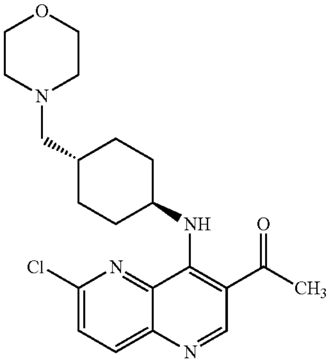 [SMILES: CC(=O)c1cnc2ccc(Cl)nc2c1N[C@H]1CC[C@H](CN2CCOCC2)CC1]

Following general procedure V, {trans-4-[(3-acetyl-6-chloro-1,5-naphthyridin-4-yl)-amino]cyclohexyl}methyl methanesulfonate (230 mg, 0.56 mmol) was reacted with morpholine (72 mg, 0.84 mmol) to afford the desired product (85 mg, 38%) as a yellow solid: $^1H$ NMR (300 MHz, $CDCl_3$) δ 10.90 (br s, 1H), 8.94 (s, 1H), 8.08 (d, J=8.7 Hz, 1H), 7.52 (d, J=8.7 Hz, 1H), 5.11-4.88 (m, 1H), 3.77-3.65 (m, 4H), 2.68 (s, 3H), 2.46-2.38 (m, 4H), 2.36-2.21 (m, 2H), 2.21-2.15 (m, 2H), 2.01-1.89 (m, 2H), 1.64-1.50 (m, 1H), 1.46-1.07 (m, 4H); ESI MS m/z 403 $[M+H]^+$

Example 159

1-[6-Chloro-4-(trans-4-{[(2-hydroxyethyl)(methyl)amino]methyl]cyclohexylamino)-1,5-naphthyridin-3-yl]ethanone

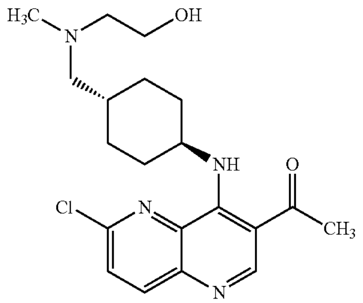 [SMILES: CC(=O)c1cnc2ccc(Cl)nc2c1N[C@H]1CC[C@H](CN(C)CCO)CC1]

Following general procedure V, {trans-4-[(3-acetyl-6-chloro-1,5-naphthyridin-4-yl)-amino]cyclohexyl}methyl methanesulfonate (240 mg, 0.58 mmol) was reacted with 2-methylamino ethanol (88 mg, 1.2 mmol) to afford the desired product (110 mg, 47%) as a yellow solid: $^1H$ NMR (300 MHz, $CDCl_3$) δ 10.89 (s, 1H), 8.94 (s, 1H), 8.08 (d, J=8.8 Hz, 1H), 7.52 (d, J=8.8 Hz, 1H), 5.09-4.88 (m, 1H), 3.63 (t, J=5.3 Hz, 2H), 2.68 (s, 3H), 2.59 (br s, 2H), 2.31 (br s, 7H), 2.04-1.91 (m, 2H), 1.68-1.50 (m, 1H), 1.48-1.07 (m, 4H; ESI MS m/z 391 $[M+H]^+$

Example 160

1-{6-Chloro-4-[trans-4-(pyrrolidin-1-ylmethyl)cyclohexylamino]-1,5-naphthyridin-3-yl}ethanone

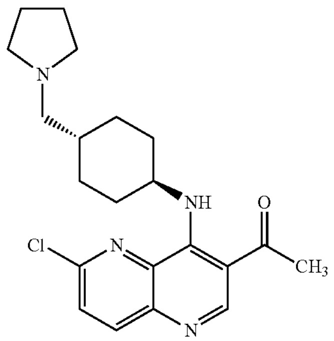 [SMILES: CC(=O)c1cnc2ccc(Cl)nc2c1N[C@H]1CC[C@H](CN2CCCC2)CC1]

Following general procedure I, 1-(4,6-dichloro-1,5-naphthyridin-3-yl)ethanone (220 mg, 0.92 mmol) was reacted with 4-(pyrrolidin-1-ylmethyl)cyclohexanamine (200 mg, 1.1 mmol) to afford the desired product (67 mg, 19%) as a brown solid. $^1H$ NMR (300 MHz, $CDCl_3$) δ 10.88 (br s, 1H), 8.93 (s, 1H), 8.07 (d, J=8.7 Hz, 1H), 7.51 (d, J=8.7 Hz, 1H), 5.09-4.88 (m, 1H), 2.66 (br s, 7H), 2.46 (d, J=7.1 Hz, 2H), 2.37-2.25 (m, 2H), 2.08-1.76 (m, 6H), 1.72-1.55 (m, 1H), 1.51-1.12 (m, 4H); ESI MS m/z 387 [M+H]$^+$ Example 161 tert-Butyl 1-[5-(3-acetyl-6-chloro-1,5-naphthyridin-4-ylamino)pyridin-2-yl]-piperidin-3-ylcarbamate

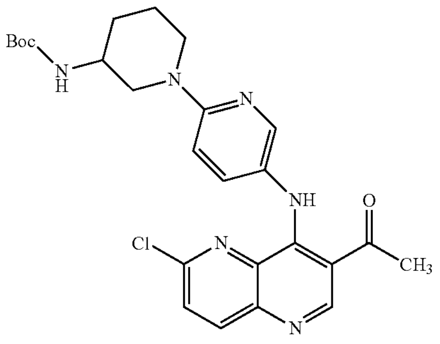 [SMILES: CC(=O)c1cnc2ccc(Cl)nc2c1Nc1ccc(N2CCCC(NC(=O)OC(C)(C)C)C2)nc1]

Following general procedure I, 1-(4,6-dichloro-1,5-naphthyridin-3-yl)ethanone (610 mg, 2.5 mmol) was reacted with tert-butyl 1-(5-aminopyridin-2-yl)piperidin-3-ylcarbamate (590 mg, 3.0 mmol) to afford the desired product (420 mg, 35%) as an orange-red solid: $^1$H NMR (500 MHz, $CDCl_3$) δ 11.47 (s, 1H), 9.01 (s, 1H), 8.09 (d, J=8.7 Hz, 1H), 8.01 (d, J=2.6 Hz, 1H), 7.45 (d, J=8.7 Hz, 1H), 7.34-7.28 (m, 1H), 6.72 (d, J=9.1 Hz, 1H), 4.95-4.90 (m, 1H), 3.85-3.67 (m, 3H), 3.47-3.27 (m, 2H), 2.69 (s, 3H), 1.97-1.88 (m, 1H), 1.86-1.75 (m, 1H), 1.73-1.59 (m, 2H), 1.45 (s, 9H); ESI MS m/z 497 [M+H]$^+$ Example 162

1-(6-Chloro-4-{trans-4-[(4-methylpiperazin-1-yl)methyl]cyclohexylamino}-1,5-naphthyridin-3-yl)ethanone

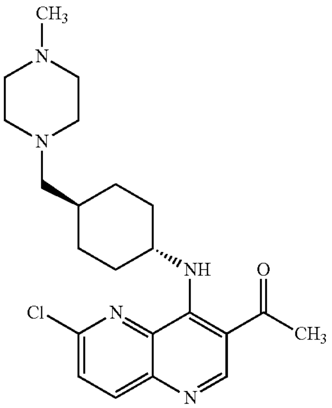 [SMILES: CC(=O)c1cnc2ccc(Cl)nc2c1N[C@H]1CC[C@H](CN2CCN(C)CC2)CC1]

Following general procedure I, 1-(4,6-dichloro-1,5-naphthyridin-3-yl)ethanone (250 mg, 1.0 mmol) was reacted with trans-4-[(4-methylpiperazin-1-yl)methyl]cyclohexanamine (330 mg, 1.6 mmol) to afford the desired product (32 mg, 7%) as a yellow solid: $^1$H NMR (300 MHz, $CDCl_3$) δ 10.93-10.89 (m, 1H), 8.95 (s, 1H), 8.11 (d, J=8.7 Hz, 1H), 7.53 (d, J=8.7 Hz, 1H), 5.09-4.90 (m, 1H), 3.31 (br s, 4H), 2.90 (br s, 4H), 2.75 (s, 3H), 2.68 (s, 3H), 2.43-2.24 (m, 4H), 1.99-1.87 (m, 2H), 1.62-1.46 (m, 1H), 1.47-1.07 (m, 4H); ESI MS m/z 416 [M+H]$^+$ Example 163 tert-Butyl {trans-4-[(3-acetyl-6-chloro-1,5-naphthyridin-4-yl)amino]cyclohexyl}carbamate

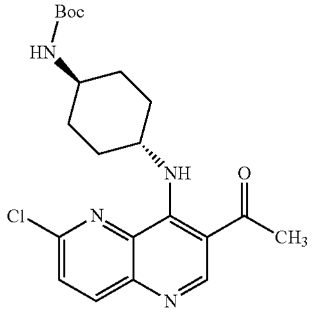 [SMILES: CC(=O)c1cnc2ccc(Cl)nc2c1N[C@H]1CC[C@H](NC(=O)OC(C)(C)C)CC1]

Following general procedure I, 1-(4,6-dichloro-1,5-naphthyridin-3-yl)ethanone (480 mg, 2.0 mmol) was reacted with tert-butyl(trans-4-aminocyclohexyl)carbamate (430 mg, 2.0 mmol) to afford the desired product (600 mg, 71%) as a light orange solid: $^1$H NMR (500 MHz, $CDCl_3$) δ 10.91 (br s, 1H), 8.96 (s, 1H), 8.10 (d, J=8.8 Hz, 1H), 7.54 (d, J=8.8 Hz, 1H), 5.10-4.99 (m, 1H), 4.48 (br s, 1H), 3.55 (br s, 1H), 2.69 (s, 3H), 2.34-2.25 (m, 2H), 2.19-2.10 (m, 2H), 1.56-1.45 (m, 2H), 1.47 (s, 9H), 1.44-1.33 (m, 2H);

ESI MS m/z 419 [M+H]$^+$

Example 164

2-(6-Chloro-4-{trans-4-[(dimethylamino)methyl]cyclohexylamino}-1,5-naphthyridin-3-yl)-2-oxoethyl acetate

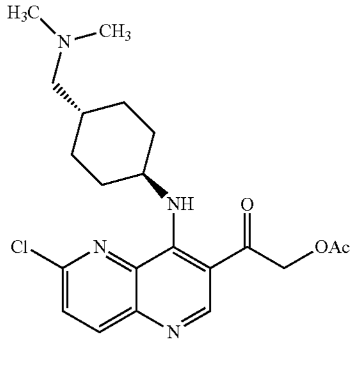 [SMILES: CC(=O)OCC(=O)c1cnc2ccc(Cl)nc2c1N[C@H]1CC[C@H](CN(C)C)CC1]

Following general procedure I, 2-(4,6-dichloro-1,5-naphthyridin-3-yl)-2-oxoethyl acetate (101 mg, 0.33 mmol) was reacted with trans-4-[(dimethylamino)methyl]cyclohexan amine (67 mg, 0.43 mmol) to afford the desired product (90 mg, 65%) as an off-white solid.

ESI MS m/z 419 [M+H]$^+$.

Example 165

1-(6-Chloro-4-{trans-4-[(dimethylamino)methyl]cyclohexylamino}-1,5-naphthyridin-3-yl)-2-hydroxyethanone

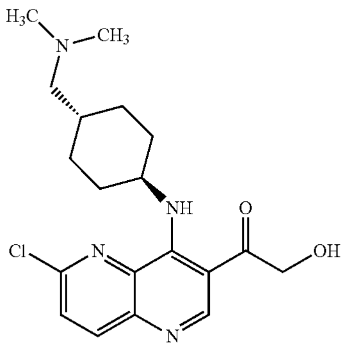 [SMILES: CN(C)C[C@H]1CC[C@H](Nc2c(C(=O)CO)cnc3ccc(Cl)nc23)CC1]

To a solution of 2-(6-chloro-4-{trans-4-[(dimethylamino)methyl]cyclohexylamino}-1,5-naphthyridin-3-yl)-2-oxoethyl acetate (90 mg, 0.22 mmol) in methanol was added freshly ground potassium carbonate (90 mg, 0.65 mmol) and the reaction mixture was stirred at room temperature for 30 minutes. The reaction mixture was diluted with satd. aq. sodium bicarbonate and extracted with ethyl acetate. The combined organic layers were dried over anhydrous sodium sulfate, filtered and the filtrate was concentrated. The residue was purified by column chromatography (silica, dichloromethane/methanol) to afford the desired product (18 mg, 22%) as a yellow solid. ESI MS m/z 377 $[M+H]^+$.

Example 166

1-{4-[(4-Aminocyclohexyl)amino]-6-chloro-1,5-naphthyridin-3-yl}ethanone dihydrochloride

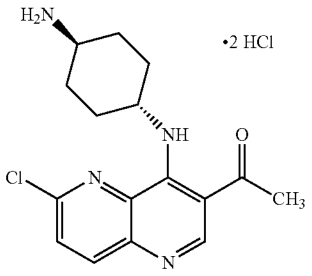 [SMILES: CC(=O)c1cnc2ccc(Cl)nc2c1N[C@H]1CC[C@H](N)CC1]

Following general procedure IV-1, tert-butyl {trans-4-[(3-acetyl-6-chloro-1,5-naphthyridin-4-yl)amino]cyclohexyl}carbamate (360 mg, 0.86 mmol) was reacted with HCl (5 mL, 2 M in ether) to afford the desired product (190 mg, 56%) as a white solid. ESI MS m/z 318 $[M+H]^+$ Example 167

1-{6-Chloro-4-[4-(pyrrolidin-1-ylmethyl)phenylamino]-1,5-naphthyridin-3-yl}ethanone

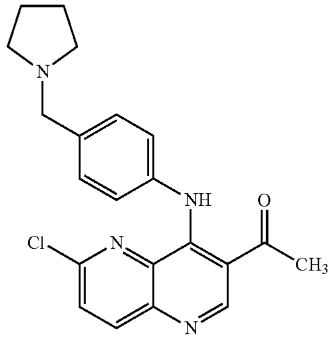 [SMILES: CC(=O)c1cnc2ccc(Cl)nc2c1Nc1ccc(CN2CCCC2)cc1]

Following general procedure I, 1-(4,6-dichloro-1,5-naphthyridin-3-yl)ethanone (200 mg, 0.83 mmol) was reacted with 4-(pyrrolidin-1-ylmethyl)aniline (310 mg, 1.24 mmol) to afford the desired product (78 mg, 25%) as a brown-orange solid: $^1$H NMR (300 MHz, $CDCl_3$) δ 11.06 (s, 1H), 9.03 (s, 1H), 8.15 (d, J=8.7 Hz, 1H), 7.50 (d, J=8.7 Hz, 1H), 7.41 (d, J=8.3 Hz, 2H), 7.13 (d, J=8.3 Hz, 2H), 3.85 (br s, 2H), 2.80 (br s, 4H), 2.60 (s, 3H), 1.92 (br s, 4H); ESI MS m/z 381 $[M+H]^+$ Example 168 tert-Butyl 1-[5-(3-acetyl-6-chloro-1,5-naphthyridin-4-ylamino)pyridin-2-yl]-pyrrolidin-3-yl(methyl)carbamate

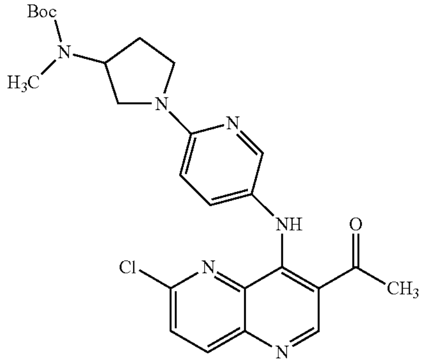 [SMILES: CC(=O)c1cnc2ccc(Cl)nc2c1Nc1ccc(N2CCC(N(C)C(=O)OC(C)(C)C)C2)nc1]

Following general procedure I, 1-(4,6-dichloro-1,5-naphthyridin-3-yl)ethanone (200 mg, 0.83 mmol) was reacted with tert-butyl 1-(5-aminopyridin-2-yl)pyrrolidin-3-yl(methyl) carbamate (360 mg, 1.2 mmol) to afford the desired product (360 mg, 85%) as a dark red solid: $^1$H NMR (500 MHz, $CDCl_3$) δ 11.39 (s, 1H), 9.02 (s, 1H), 8.10 (d, J=8.7 Hz, 1H), 8.02 (d, J=2.6 Hz, 1H), 7.47 (d, J=8.7 Hz, 1H), 7.32 (dd, J=8.8, 2.6 Hz, 1H), 6.37 (d, J=8.8 Hz, 1H), 4.91 (br s, 1H), 3.73-3.62 (m, 2H), 3.51-3.38 (m, 2H), 2.83 (s, 3H), 2.68 (s, 3H), 2.28-2.06 (m, 2H), 1.49 (s, 9H); ESI MS m/z 497 $[M+H]^+$ Example 169

1-(6-Chloro-4-{6-[3-(dimethylamino)pyrrolidin-1-yl]pyridin-3-ylamino}-1,5-naphthyridin-3-yl)ethanone

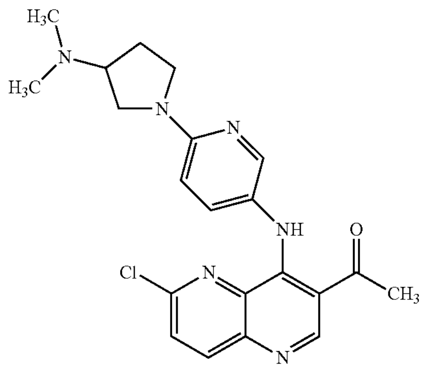 [SMILES: CC(=O)c1cnc2ccc(Cl)nc2c1Nc1ccc(N2CCC(N(C)C)C2)nc1]

Following general procedure I, 1-(4,6-dichloro-1,5-naphthyridin-3-yl)ethanone (250 mg, 1.0 mmol) was reacted with N,N-dimethylpyrrolidin-3-amine (260 mg, 1.2 mmol) to afford the desired product (380 mg, 89%) as an orange solid: $^{1}H$ NMR (300 MHz, $CDCl_3$) δ 11.35 (s, 1H), 9.00 (s, 1H), 8.10 (d, J=8.7 Hz, 1H), 8.02 (dd, J=2.7, 0.7 Hz, 1H), 7.47 (d, J=8.7 Hz, 1H), 7.30 (dd, J=8.9, 2.7 Hz, 1H), 6.35 (d, J=8.9 Hz, 1H), 3.88-3.77 (m, 1H), 3.62-3.72 (m, 1H), 3.49-3.37 (m, 1H), 3.33-3.22 (m, 1H), 2.94-2.76 (m, 1H), 2.68 (s, 3H), 2.34 (s, 6H), 2.34-2.18 (m, 1H), 2.06-1.89 (m, 1H); ESI MS m/z 411 $[M+H]^+$ Example 170 tert-Butyl 4-[7-acetyl-8-({trans-4-[(dimethylamino)methyl]cyclohexyl}amino)-1,5-naphthyridin-2-yl]-3,5-dimethyl-1H-pyrazole-1-carboxylate

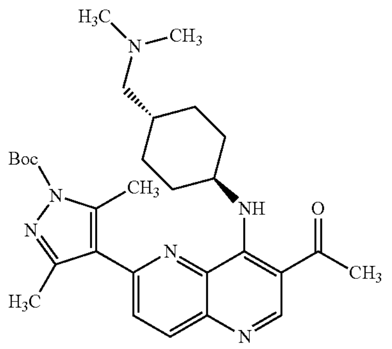 [SMILES: CC(=O)c1cnc2ccc(-c3c(C)nn(C(=O)OC(C)(C)C)c3C)nc2c1N[C@H]1CC[C@H](CN(C)C)CC1]

Following general procedure II, 1-(6-chloro-4-{trans-4-[(dimethylamino)methyl]-cyclohexylamino}-1,5-naphthyridin-3-yl)ethanone (92 mg, 0.25 mmol) was reacted with tert-butyl 3,5-dimethyl-4-(4,4,5,5-tetramethyl-1,3,2-dioxaborolan-2-yl)-1H-pyrazole-1-carboxylate (120 mg, 0.37 mmol) to afford crude product (100 mg) as a brown solid which was carried forward without any purification: ESI MS m/z 521 $[M+H]^+$ Example 171 tert-Butyl 1-(5-(3-acetyl-6-(3,5-dichloro-4-hydroxyphenyl)-1,5-naphthyridin-4-ylamino)-pyridin-2-yl)pyrrolidin-3-yl(methyl)carbamate

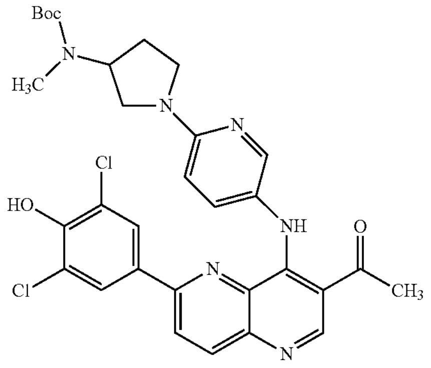 [SMILES: CC(=O)c1cnc2ccc(-c3cc(Cl)c(O)c(Cl)c3)nc2c1Nc1ccc(N2CCC(N(C)C(=O)OC(C)(C)C)C2)nc1]

Following general procedure II, tert-butyl 1-(5-(3-acetyl-6-chloro-1,5-naphthyridin-4-ylamino)-pyridin-2-yl)pyrrolidin-3-yl(methyl) carbamate (91 mg, 0.183 mmol) was reacted with 2,6-dichloro-4-(4,4,5,5-tetramethyl-1,3,2-dioxaborolan-2-yl)phenol (79 mg, 0.273 mmol) to afford crude product (72 mg) as an orange solid which was carried forward without any purification: ESI MS m/z 623 $[M+H]^+$ Example 172 tert-Butyl 1-(5-(3-acetyl-6-(3-chloro-5-fluoro-4-hydroxyphenyl)-1,5-naphthyridin-4-ylamino)pyridin-2-yl)pyrrolidin-3-yl(methyl)carbamate

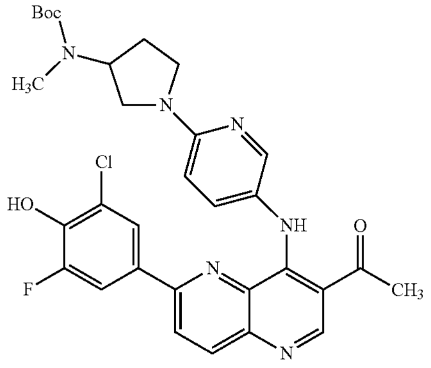 [SMILES: CC(=O)c1cnc2ccc(-c3cc(F)c(O)c(Cl)c3)nc2c1Nc1ccc(N2CCC(N(C)C(=O)OC(C)(C)C)C2)nc1]

Following general procedure II, tert-butyl 1-[5-(3-acetyl-6-chloro-1,5-naphthyridin-4-ylamino)-pyridin-2-yl]pyrrolidin-3-yl(methyl)carbamate (94 mg, 0.19 mmol) was reacted with 2-chloro-6-fluoro-4-(4,4,5,5-tetramethyl-1,3,2-dioxaborolan-2-yl)phenol (77 mg, 0.28 mmol) to afford crude product (79 mg) as an orange solid which was carried forward without any purification: ESI MS m/z 607 $[M+H]^+$ Example 173 tert-Butyl(1-{trans-4-[(3-acetyl-6-chloro-1,5-naphthyridin-4-yl)amino]cyclohexyl-amino}-3-methyl-1-oxobutan-2-yl)carbamate

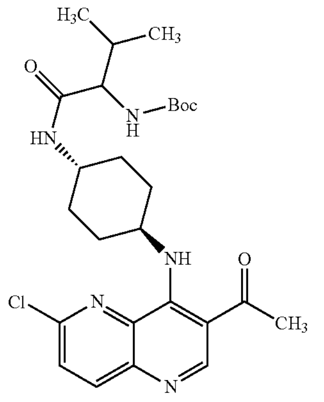 [SMILES: CC(=O)c1cnc2ccc(Cl)nc2c1N[C@H]1CC[C@H](NC(=O)C(NC(=O)OC(C)(C)C)C(C)C)CC1]

Following general procedure VI, 1-{4-[(4-aminocyclohexyl)amino]-6-chloro-1,5-naphthyridin-3-yl}ethanone dihydrochloride (300 mg, 0.94 mmol) was reacted with 2-[(tert-butoxycarbonyl)amino]-3-methylbutanoic acid (310 mg, 1.4 mmol) to afford the desired product (320 mg, 65%) as a white solid. ESI MS m/z 518 $[M+H]^+$ Example 174 tert-Butyl 1-{trans-4-[3-acetyl-6-(3-chloro-5-fluoro-4-hydroxyphenyl)-1,5-naphthyridin-4-ylamino]cyclohexylamino}-3-methyl-1-oxobutan-2-ylcarbamate

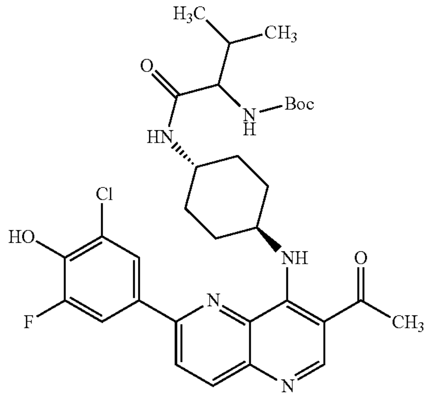 [SMILES: CC(=O)c1cnc2ccc(-c3cc(F)c(O)c(Cl)c3)nc2c1N[C@H]1CC[C@H](NC(=O)C(NC(=O)OC(C)(C)C)C(C)C)CC1]

Following general procedure II, tert-Butyl(1-{trans-4-[(3-acetyl-6-chloro-1,5-naphthyridin-4-yl)amino]cyclohexylamino}-3-methyl-1-oxobutan-2-yl)carbamates (100 mg, 0.19 mmol) was reacted with 2-chloro-6-fluoro-4-(4,4,5,5-tetramethyl-1,3,2-dioxaborolan-2-yl)phenol (50 mg, 0.23 mmol) to afford the crude product (115 mg) as an off-white solid: ESI MS m/z 628 $[M+H]^+$.

Example 175 tert-Butyl trans-4-{[3-acetyl-6-(3,5-dichloro-4-hydroxyphenyl)-1,5-naphthyridin-4-yl]aminocyclohexyl}carbamate

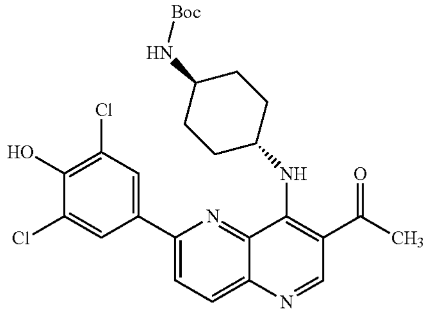 [SMILES: CC(=O)c1cnc2ccc(-c3cc(Cl)c(O)c(Cl)c3)nc2c1N[C@H]1CC[C@H](NC(=O)OC(C)(C)C)CC1]

Following general procedure II, tert-butyl trans-4-[(3-acetyl-6-chloro-1,5-naphthyridin-4-yl)-aminocyclohexyl]carbamate (100 mg, 0.23 mmol) was reacted with 2,6-dichloro-4-(4,4,5,5-tetramethyl-1,3,2-dioxaborolan-2-yl)phenol (81 mg, 0.28 mmol) to afford crude product which was carried forward without any purification: ESI MS m/z 545 $[M+H]^+$.

Example 176

(R)-tert-Butyl 1-(5-(3-acetyl-6-chloro-1,5-naphthyridin-4-ylamino)pyridin-2-yl) piperidin-3-ylcarbamate

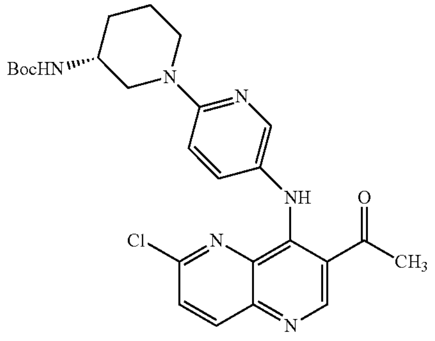 [SMILES: CC(=O)c1cnc2ccc(Cl)nc2c1Nc1ccc(N2CCC[C@@H](NC(=O)OC(C)(C)C)C2)nc1]

Following general procedure I, 1-(4,6-dichloro-1,5-naphthyridin-3-yl)ethanone (340 mg, 1.4 mmol) was reacted with (R)-tert-butyl 1-(5-aminopyridin-2-yl)piperidin-3-ylcarbamate (500 mg, 1.7 mmol) to afford the desired product (410 mg, 58%) as a brown-orange solid. ESI MS m/z 497 $[M+H]^+$ Example 177

(R)-tert-Butyl 1-(5-(3-acetyl-6-(3,5-dichloro-4-hydroxyphenyl)-1,5-naphthyridin-4-ylamino)pyridin-2-yl)piperidin-3-ylcarbamate

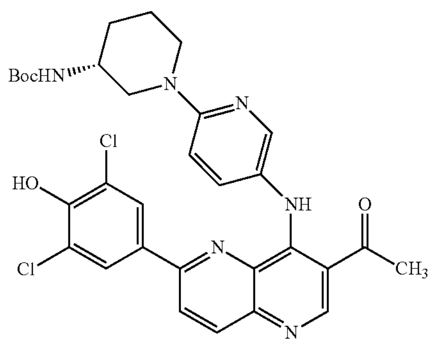 [SMILES: CC(=O)c1cnc2ccc(-c3cc(Cl)c(O)c(Cl)c3)nc2c1Nc1ccc(N2CCC[C@@H](NC(=O)OC(C)(C)C)C2)nc1]

Following general procedure II, (R)-tert-butyl 1-(5-(3-acetyl-6-chloro-1,5-naphthyridin-4-ylamino)pyridin-2-yl)piperidin-3-ylcarbamate (200 mg, 0.40 mmol) was reacted with 2,6-dichloro-4-(4,4,5,5-tetramethyl-1,3,2-dioxaborolan-2-yl)phenol (170 mg, 0.60 mmol) to afford the desired product (210 mg, 85%) as a orange solid. ESI MS m/z 623 $[M+H]^+$ Example 178

(R)-tert-Butyl 1-(5-(3-acetyl-6-(3-chloro-5-fluoro-4-hydroxyphenyl)-1,5-naphthyridin-4-ylamino)pyridin-2-yl)piperidin-3-ylcarbamate

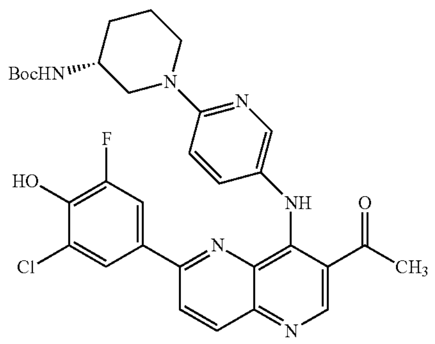 [SMILES: CC(=O)c1cnc2ccc(-c3cc(F)c(O)c(Cl)c3)nc2c1Nc1ccc(N2CCC[C@@H](NC(=O)OC(C)(C)C)C2)nc1]

Following general procedure II, (R)-tert-butyl 1-(5-(3-acetyl-6-chloro-1,5-naphthyridin-4-ylamino)pyridin-2-yl)piperidin-3-ylcarbamate (200 mg, 0.40 mmol) was reacted with 2-chloro-6-fluoro-4-(4,4,5,5-tetramethyl-1,3,2-dioxaborolan-2-yl)phenol (165 mg, 0.60 mmol) to afford the desired product (125 g, 51%) as a yellow-orange solid. ESI MS m/z 607 $[M+H]^+$ Example 179 tert-Butyl[1-(5-{[3-acetyl-6-(3-chloro-5-fluoro-4-hydroxyphenyl)-1,5-naphthyridin-4-yl]amino}pyridin-2-yl)piperidin-3-yl]carbamate

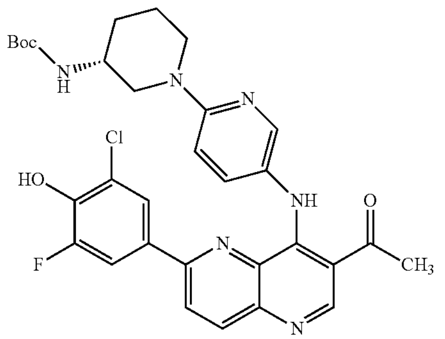 [SMILES: CC(=O)c1cnc2ccc(-c3cc(F)c(O)c(Cl)c3)nc2c1Nc1ccc(N2CCC[C@@H](NC(=O)OC(C)(C)C)C2)nc1]

Following general procedure II, tert-butyl(1-{5-[(3-acetyl-6-chloro-1,5-naphthyridin-4-yl)amino]pyridin-2-yl}piperidin-3-yl)carbamate (100 mg, 0.20 mmol) was reacted with 2-chloro-6-fluoro-4-(4,4,5,5-tetramethyl-1,3,2-dioxaborolan-2-yl)phenol (65 mg, 0.24 mmol) to afford crude product which was carried forward without any purification: ESI MS m/z 607 $[M+H]^+$.

Example 180 tert-Butyl[1-(5-{[3-acetyl-6-(3,5-dichloro-4-hydroxyphenyl)-1,5-naphthyridin-4-yl]amino}pyridin-2-yl)piperidin-3-yl]carbamate

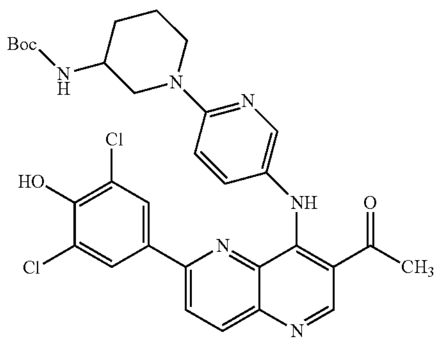 [SMILES: CC(=O)c1cnc2ccc(-c3cc(Cl)c(O)c(Cl)c3)nc2c1Nc1ccc(N2CCCC(NC(=O)OC(C)(C)C)C2)nc1]

Following general procedure II, tert-butyl(1-{5-[(3-acetyl-6-chloro-1,5-naphthyridin-4-yl)amino]pyridin-2-yl}piperidin-3-yl)carbamate (100 mg, 0.20 mmol) was reacted with 2,6-dichloro-4-(4,4,5,5-tetramethyl-1,3,2-dioxaborolan-2-yl)phenol (68 mg, 0.24 mmol) to afford crude product (45 mg) which was carried forward without any purification: ESI MS m/z 623 $[M+H]^+$.

Example 181 tert-Butyl 1-{4-[3-acetyl-6-(3,5-dichloro-4-hydroxyphenyl)-1,5-naphthyridin-trans-4-ylamino]cyclohexylamino}-3-methyl-1-oxobutan-2-ylcarbamate

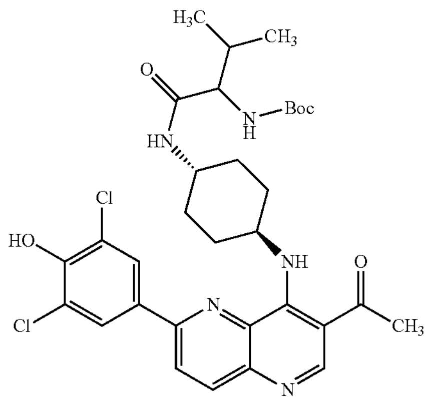 [SMILES: CC(=O)c1cnc2ccc(-c3cc(Cl)c(O)c(Cl)c3)nc2c1N[C@H]1CC[C@H](NC(=O)C(NC(=O)OC(C)(C)C)C(C)C)CC1]

Following general procedure II, tert-butyl[1-({4-[(3-acetyl-6-chloro-1,5-naphthyridin-trans-4-yl)amino]cyclohexyl}amino)-3-methyl-1-oxobutan-2-yl]carbamate (100 mg, 0.19 mmol) was reacted with 2,6-dichloro-4-(4,4,5,5-tetramethyl-1,3,2-dioxaborolan-2-yl)phenol (65 mg, 0.23 mmol) to afford crude product (80 mg) as a brown solid which was carried forward without any purification: ESI MS m/z 644 $[M+H]^+$ Example 182 tert-Butyl 1-{trans-4-[3-acetyl-6-(3,5-dichloro-4-hydroxyphenyl)-1,5-naphthyridin-4-ylamino]cyclohexylamino}-1-oxopropan-2-ylcarbamate

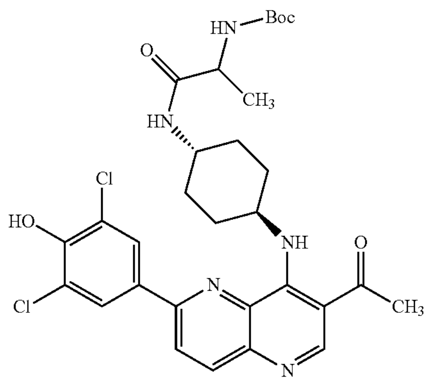 [SMILES: CC(=O)c1cnc2ccc(-c3cc(Cl)c(O)c(Cl)c3)nc2c1N[C@H]1CC[C@H](NC(=O)C(C)NC(=O)OC(C)(C)C)CC1]

Following general procedure II, tert-butyl 1-[trans-4-(3-acetyl-6-chloro-1,5-naphthyridin-trans-4-ylamino)cyclohexylamino]-1-oxopropan-2-ylcarbamate (65 mg, 0.13 mmol) was reacted with 2,6-dichloro-4-(4,4,5,5-tetramethyl- 1,3,2-dioxaborolan-2-yl)phenol (45 mg, 0.16 mmol) to afford crude product that was carried forward without any purification.

Example 183 tert-Butyl 1-{4-[3-acetyl-6-(3-chloro-5-fluoro-4-hydroxyphenyl)-1,5-naphthyridin-trans-4-ylamino]cyclohexylamino}-1-oxopropan-2-ylcarbamate

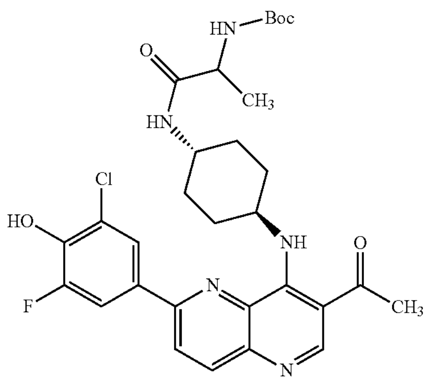 [SMILES: CC(=O)c1cnc2ccc(-c3cc(F)c(O)c(Cl)c3)nc2c1N[C@H]1CC[C@H](NC(=O)C(C)NC(=O)OC(C)(C)C)CC1]

Following general procedure II, tert-butyl 1-[4-(3-acetyl-6-chloro-1,5-naphthyridin-trans-4-ylamino)cyclohexylamino]-1-oxopropan-2-ylcarbamate (68 mg, 0.13 mmol) was reacted with 2-chloro-6-fluoro-4-(4,4,5,5-tetramethyl-1,3,2-dioxaborolan-2-yl)phenol (43 mg, 0.16 mmol) to afford crude product that was carried forward without any purification.

Example 184

(S)-tert-Butyl 2-{4-[3-acetyl-6-(3-chloro-5-fluoro-4-hydroxyphenyl)-1,5-naphthyridin-trans-4-ylamino]cyclohexylcarbamoyl}pyrrolidine-1-carboxylate

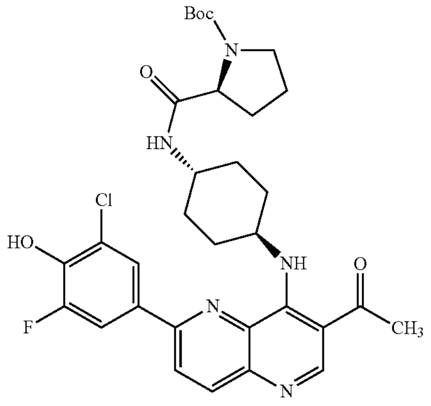 [SMILES: CC(=O)c1cnc2ccc(-c3cc(F)c(O)c(Cl)c3)nc2c1N[C@H]1CC[C@H](NC(=O)[C@@H]2CCCN2C(=O)OC(C)(C)C)CC1]

Following general procedure II, (S)-tert-butyl 2-[4-(3-acetyl-6-chloro-1,5-naphthyridin-trans-4-ylamino)cyclohexylcarbamoyl]pyrrolidine-1-carboxylate (100 mg, 0.19 mmol) was reacted with 2-chloro-6-fluoro-4-(4,4,5,5-tetramethyl-1,3,2-dioxaborolan-2-yl)phenol (63 mg, 0.23 mmol) to afford crude product (75 mg) as an brown solid that was carried forward without any purification: ESI MS m/z 626 $[M+H]^+$ Example 185

(S)-tert-butyl 2-{4-[3-acetyl-6-(3,5-dichloro-4-hydroxyphenyl)-1,5-naphthyridin-trans-4-ylamino]-cyclohexylcarbamoyl}pyrrolidine-1-carboxylate

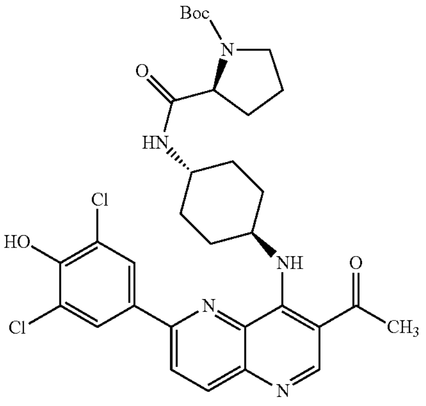 [SMILES: CC(=O)c1cnc2ccc(-c3cc(Cl)c(O)c(Cl)c3)nc2c1N[C@H]1CC[C@H](NC(=O)[C@@H]2CCCN2C(=O)OC(C)(C)C)CC1]

Following general procedure II, (S)-tert-butyl 2-[4-(3-acetyl-6-chloro-1,5-naphthyridin-trans-4-ylamino)cyclohexylcarbamoyl]pyrrolidine-1-carboxylate (100 mg, 0.195 mmol) was reacted with 2,6-dichloro-4-(4,4,5,5-tetramethyl-1,3,2-dioxaborolan-2-yl)phenol (66 mg, 0.234 mmol) to afford crude product (113 mg) as a yellow solid product that was carried forward without any purification.

Example 186

(S)-tert-butyl 2-[4-(3-acetyl-6-chloro-1,5-naphthyridin-trans-4-ylamino)-cyclohexylcarbamoyl]pyrrolidine-1-carboxylate

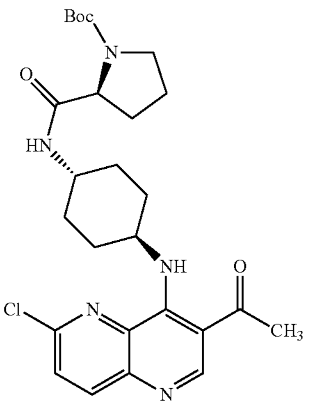 [SMILES: CC(=O)c1cnc2ccc(Cl)nc2c1N[C@H]1CC[C@H](NC(=O)[C@@H]2CCCN2C(=O)OC(C)(C)C)CC1]

Following general procedure V, 1-[4-(trans-4-aminocyclohexyl)amino)-6-chloro-1,5-naphthyridin-3-yl]ethanone dihydrochloride (220 mg, 0.564 mmol) was reacted with (S)-1-(tert-butoxycarbonyl)pyrrolidine-2-carboxylic acid (145 mg, 0.676 mmol) to afford the desired product (290 mg, 99%) as an off-white solid. ESI MS m/z 518 $[M+H]^+$ Example 187 tert-Butyl 1-[4-(3-acetyl-6-chloro-1,5-naphthyridin-4-ylamino)cyclohexyl amino]-1-oxopropan-2-ylcarbamate

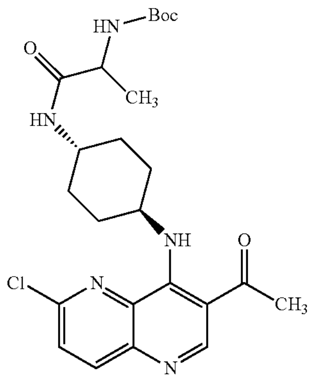 [SMILES: CC(=O)c1cnc2ccc(Cl)nc2c1N[C@H]1CC[C@H](NC(=O)C(C)NC(=O)OC(C)(C)C)CC1]

Following general procedure V, {1-[4-(trans-4-aminocyclohexyl)amino]-6-chloro-1,5-naphthyridin-3-yl}ethanone dihydrochloride (130 mg, 0.35 mmol) was reacted with 2-(tert-butoxycarbonylamino)propanoic acid (78 mg, 0.42 mmol) to afford the desired product (130 mg, 79%) as a yellow solid. ESI MS m/z 490 $[M+H]^+$ Example 188

(S)-tert-Butyl[1-(5-{[3-acetyl-6-(3-chloro-5-fluoro-4-hydroxyphenyl)-1,5-naphthyridin-4-yl]amino}pyridin-2-yl)piperidin-3-yl]carbamate

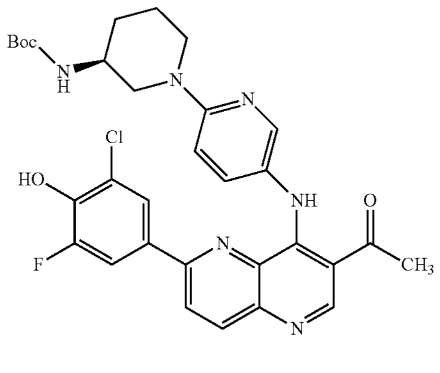 [SMILES: CC(=O)c1cnc2ccc(-c3cc(F)c(O)c(Cl)c3)nc2c1Nc1ccc(N2CCC[C@H](NC(=O)OC(C)(C)C)C2)nc1]

Following general procedure II, (S)-tert-butyl(1-{5-[(3-acetyl-6-chloro-1,5-naphthyridin-4-yl)amino]pyridin-2-yl}piperidin-3-yl)carbamate (100 mg, 0.20 mmol) was reacted with 2-chloro-6-fluoro-4-(4,4,5,5-tetramethyl-1,3,2-dioxaborolan-2-yl)phenol (82 mg, 0.30 mmol) to afford the crude product (72 mg) which was carried forward without any purification: ESI MS m/z 607 [M+H]$^+$.

Example 189

(S)-tert-Butyl[1-(5-{[3-acetyl-6-(3,5-dichloro-4-hydroxyphenyl)-1,5-naphthyridin-4-yl]amino}pyridin-2-yl)piperidin-3-yl]carbamate

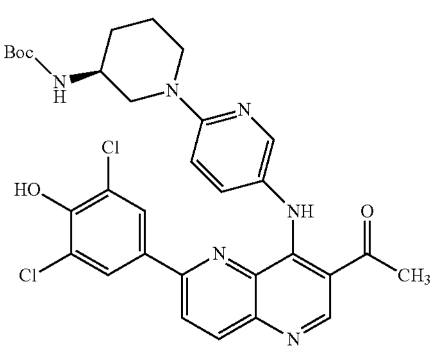 [SMILES: CC(=O)c1cnc2ccc(-c3cc(Cl)c(O)c(Cl)c3)nc2c1Nc1ccc(N2CCC[C@H](NC(=O)OC(C)(C)C)C2)nc1]

Following general procedure II, (S)-tert-butyl(1-{5-[(3-acetyl-6-chloro-1,5-naphthyridin-4-yl)-amino]pyridin-2-yl}piperidin-3-yl)carbamate (98 mg, 0.20 mmol) was reacted with 2,6-dichloro-4-(4,4,5,5-tetramethyl-1,3,2-dioxaborolan-2-yl)phenol (85 mg, 0.30 mmol) to afford the product (56 mg) which was carried forward without any purification: ESI MS m/z 625 [M+H]$^+$.

Example 190

(S)-tert-Butyl[1-(5-{[3-(cyclopropylcarbonyl)-6-(3-chloro-5-fluoro-4-hydroxyphenyl)-1,5-naphthyridin-4-yl]amino}pyridin-2-yl)piperidin-3-yl]carbamate

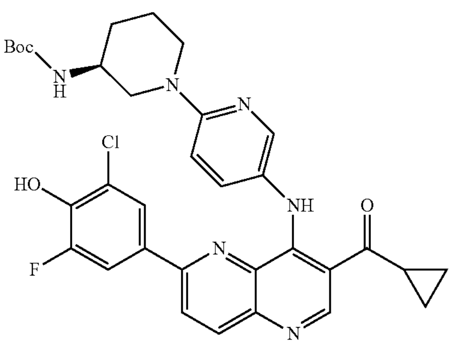

Following general procedure II, (S)-tert-Butyl 1-{5-[6-chloro-3-(cyclopropanecarbonyl)-1,5-naphthyridin-4-ylamino]pyridin-2-yl}piperidin-3-ylcarbamate (131 mg, 0.25 mmol) was reacted with 2-chloro-6-fluoro-4-(4,4,5,5-tetramethyl-1,3,2-dioxaborolan-2-yl)phenol (102 mg, 0.38 mmol) to afford the desired product (100 mg, 63%) as an orange red solid. ESI MS m/z 633 [M+H]$^+$.

Example 191 tert-Butyl 4-({trans-4-[3-acetyl-6-(3,5-dichloro-4-hydroxyphenyl)-1,5-naphthyridin-4-ylamino]cyclohexyl}methyl)piperazine-1-carboxylate

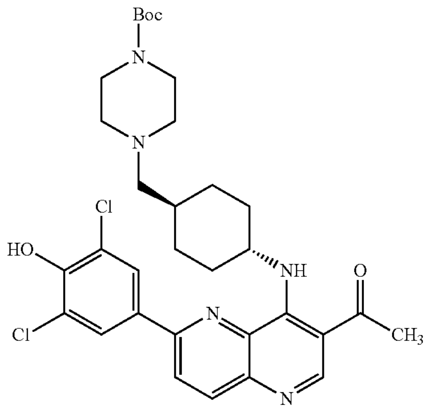 [SMILES: CC(=O)c1cnc2ccc(-c3cc(Cl)c(O)c(Cl)c3)nc2c1N[C@H]1CC[C@H](CN2CCN(C(=O)OC(C)(C)C)CC2)CC1]

Following general procedure II, tert-butyl 4-{[trans-4-(3-acetyl-6-chloro-1,5-naphthyridin-4-ylamino)cyclohexyl]methyl}piperazine-1-carboxylate (150 mg, 0.30 mmol) was reacted with 2,6-dichloro-4-(4,4,5,5-tetramethyl-1,3,2-dioxaborolan-2-yl)phenol (130 mg, 0.45 mmol) to afford the product (170 mg) which was carried forward without any purification: ESI MS m/z 628 [M+H]$^+$.

Example 192 tert-Butyl 1-{4-[3-acetyl-6-(3,5-dichloro-4-hydroxyphenyl)-1,5-naphthyridin-trans-4-ylamino]cyclohexylamino}-3-methyl-1-oxobutan-2-ylcarbamate

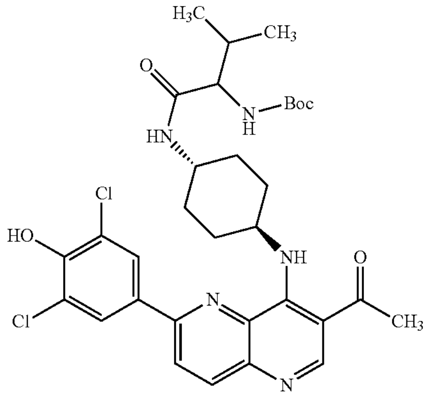

Following general procedure B, tert-butyl(1-{4-[(3-acetyl-6-chloro-1,5-naphthyridin-trans-4-yl)aminocyclohexy]amino}-3-methyl-1-oxobutan-2-yl)carbamate (100 mg, 0.19 mmol) was reacted with 2,6-dichloro-4-(4,4,5,5-tetramethyl- 1,3,2-dioxaborolan-2-yl)phenol (65 mg, 0.23 mmol) to afford crude product (80 mg) as a brown solid. ESI MS m/z 644 $[M+H]^+$ Example 193 tert-Butyl 1-{trans-4-[3-acetyl-6-(3,5-dichloro-4-hydroxyphenyl)-1,5-naphthyridin-4-ylamino]cyclohexylamino}-1-oxopropan-2-ylcarbamate

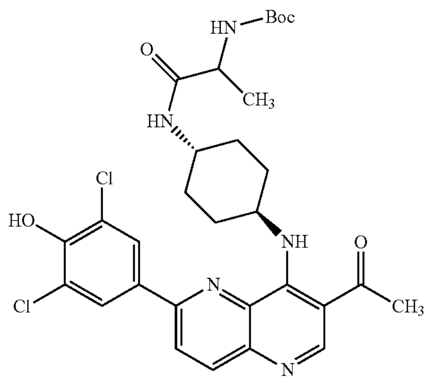 [SMILES: CC(=O)c1cnc2ccc(-c3cc(Cl)c(O)c(Cl)c3)nc2c1N[C@H]1CC[C@H](NC(=O)C(C)NC(=O)OC(C)(C)C)CC1]

Following general procedure B, tert-butyl 1-[trans-4-(3-acetyl-6-chloro-1,5-naphthyridin-trans-4-ylamino)cyclohexylamino]-1-oxopropan-2-ylcarbamate (65 mg, 0.13 mmol) was reacted with 2,6-dichloro-4-(4,4,5,5-tetramethyl-1,3,2-dioxaborolan-2-yl)phenol (45 mg, 0.16 mmol) to afford crude product.

Example 194 tert-Butyl 1-{4-[3-acetyl-6-(3-chloro-5-fluoro-4-hydroxyphenyl)-1,5-naphthyridin-trans-4-ylamino]cyclohexylamino}-1-oxopropan-2-ylcarbamate

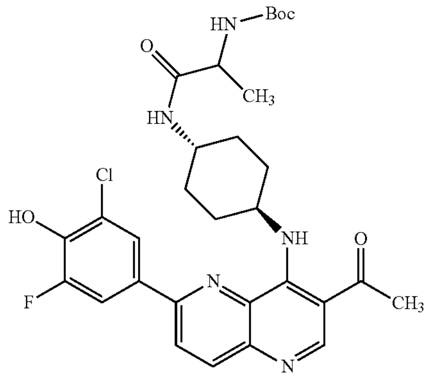 [SMILES: CC(=O)c1cnc2ccc(-c3cc(F)c(O)c(Cl)c3)nc2c1N[C@H]1CC[C@H](NC(=O)C(C)NC(=O)OC(C)(C)C)CC1]

Following general procedure B, tert-butyl 1-[4-(3-acetyl-6-chloro-1,5-naphthyridin-trans-4-ylamino)cyclohexylamino]-1-oxopropan-2-ylcarbamate (68 mg, 0.13 mmol) was reacted with 2-chloro-6-fluoro-4-(4,4,5,5-tetramethyl-1,3,2-dioxaborolan-2-yl)phenol (43 mg, 0.16 mmol) to afford crude product which was carried forward without further purification or characterization.

Example 195

(S)-tert-Butyl 2-[4-(3-acetyl-6-chloro-1,5-naphthyridin-trans-4-ylamino)-cyclohexylcarbamoyl]pyrrolidine-1-carboxylate

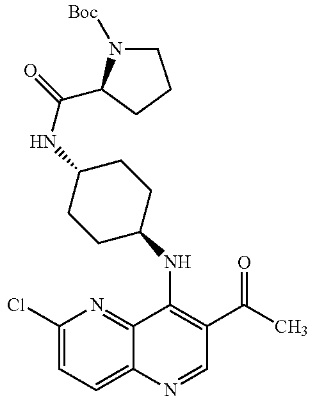 [SMILES: CC(=O)c1cnc2ccc(Cl)nc2c1N[C@H]1CC[C@H](NC(=O)[C@@H]2CCCN2C(=O)OC(C)(C)C)CC1]

Following general procedure D, 1-[4-(trans-4-aminocyclohexyl)amino]-6-chloro-1,5-naphthyridin-3-yl)ethanone dihydrochloride (220 mg, 0.564 mmol) was reacted with (S)-1-(tert-butoxycarbonyl)pyrrolidine-2-carboxylic acid (145 mg, 0.676 mmol) to afford the desired product (290 mg, 99%) as an off-white solid. ESI MS m/z 518 $[M+H]^+$ Example 196

(S)-tert-Butyl 2-{4-[3-acetyl-6-(3-chloro-5-fluoro-4-hydroxyphenyl)-1,5-naphthyridin-trans-4-ylamino]cyclohexylcarbamoyl}pyrrolidine-1-carboxylate

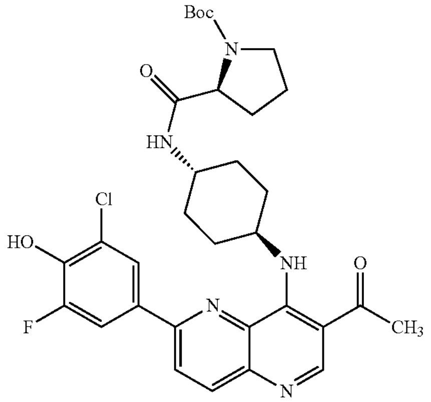

Following general procedure B, (S)-tert-butyl 2-[4-(3-acetyl-6-chloro-1,5-naphthyridin-trans-4-ylamino)cyclohexylcarbamoyl]pyrrolidine-1-carboxylate (100 mg, 0.19 mmol) was reacted with 2-chloro-6-fluoro-4-(4,4,5,5-tetramethyl-1,3,2-dioxaborolan-2-yl)phenol (63 mg, 0.23 mmol) to afford crude product (75 mg) as an brown solid which was carried forward without further purification or characterization: ESI MS m/z 626 $[M+H]^+$ Example 197 tert-Butyl 1-[4-(3-acetyl-6-chloro-1,5-naphthyridin-4-ylamino)cyclohexylamino]-1-oxopropan-2-ylcarbamate

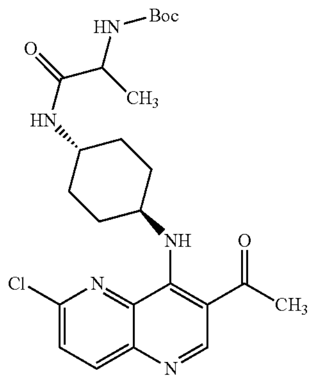 [SMILES: CC(=O)c1cnc2ccc(Cl)nc2c1N[C@H]1CC[C@H](NC(=O)C(C)NC(=O)OC(C)(C)C)CC1]

Following general procedure C, 1-[4-(trans-4-aminocyclohexyl)amino]-6-chloro-1,5-naphthyridin-3-yl)ethanone dihydrochloride (130 mg, 0.35 mmol) was reacted with 2-(tert-butoxycarbonylamino)propanoic acid (78 mg, 0.42 mmol) to afford the desired product (130 mg, 79%) as a yellow solid. ESI MS m/z 490 $[M+H]^+$ Example 198

(S)-tert-Butyl 2-(4-(3-acetyl-6-(3,5-dichloro-4-hydroxyphenyl)-1,5-naphthyridin-trans-4-ylamino) cyclohexylcarbamoyl)pyrrolidine-1-carboxylate

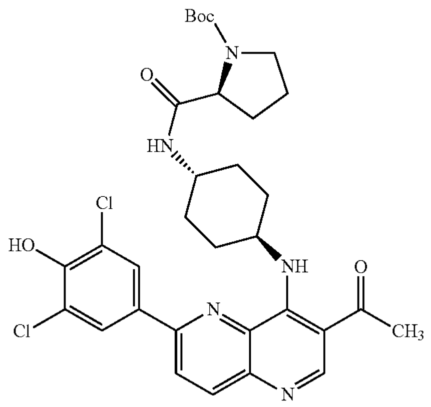

Following general procedure B, (S)-tert-butyl 2-[4-(3-acetyl-6-chloro-1,5-naphthyridin-trans-4-ylamino)cyclohexylcarbamoyl]pyrrolidine-1-carboxylate (100 mg, 0.19 mmol) was reacted with 2,6-dichloro-4-(4,4,5,5-tetramethyl-1,3,2-dioxaborolan-2-yl)phenol (66 mg, 0.23 mmol) to afford crude product (113 mg) as a yellow solid which was carried forward without further purification or characterization.

Example 199 tert-Butyl[trans-4-(dimethylamino)cyclohexyl]methylcarbamate

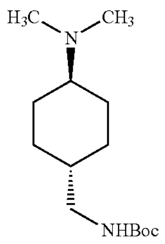

To a solution of tert-butyl[trans-4-aminocyclohexyl]methylcarbamate (1.15 g, 5.00 mmol), paraformaldehyde (454 mg, 15.0 mmol), and sodium cyanoborohydride (940 mg, 15.0 mmol) in methanol (40 mL) was added acetic acid (catalytic) and the reaction mixture stirred at room temperature for 18 h. The reaction mixture was quenched with water and concentrated to remove methanol. The pH of the aqueous layer was adjusted to 10 with 1 M aqueous sodium hydroxide followed by extraction with methylene chloride. The organic layers were dried over anhydrous sodium sulfate, filtered, and concentrated to afford the desired product (1.2 g, 96%) as a thick oil: ESI MS m/z 257 $[C_{14}H_{28}N_2O_2+H]^+$.

Example 200 trans-4-(Aminomethyl)-N,N-dimethylcyclohexanamine

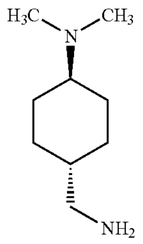

Following general procedure IV-1, tert-butyl[trans-4-(dimethylamino)cyclohexyl]methyl carbamate (1.2 g, 4.8 mmol) was reacted with 3 M hydrochloric acid (10 mL) to afford the dihydrochloride salt as the desired product (1.2 g, >99%) as white solid: ESI MS m/z 230 $[C_9H_{20}N_2+H]^+$.

Example 201

(R)-(4-{[6-(3-aminopiperidin-1-yl)pyridin-3-yl]amino}-6-(3,5-dichloro-4-hydroxyphenyl)-1,5-naphthyridin-3-yl)(cyclopropyl)methanone

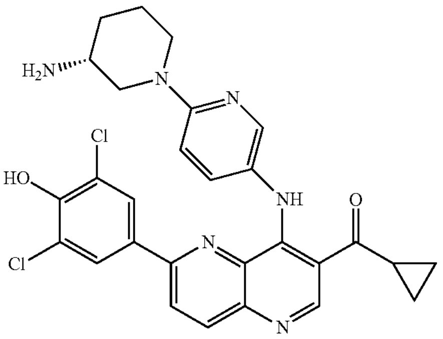 [SMILES: N[C@@H]1CCCN(c2ccc(Nc3c(C(=O)C4CC4)cnc4ccc(-c5cc(Cl)c(O)c(Cl)c5)nc34)cn2)C1]

Following general procedure IV-2, (R)-tert-butyl[1-(5-{[3-(cyclopropanecarbonyl)-6-(3,5-dichloro-4-hydroxyphenyl)-1,5-naphthyridin-4-yl}amino)pyridin-2-yl)piperidin-3-yl) carbamate (0.12 g, 0.18 mmol,) was reacted with TFA (2 mL). The resulting trifluoroacetate salt of the product was converted to the free base to afford the desired product (67 mg, 67%) as an orange solid: $^1$H NMR (500 MHz, $CD_3OD$) δ 9.17 (s, 1H), 8.09 (d, J=9.0 Hz, 1H), 8.03 (d, J=9.0 Hz, 1H), 7.92 (d, J=2.5 Hz, 1H), 7.44 (s, 2H), 7.37 (dd, J=9.0, 2.5 Hz, 1H), 6.70 (d, J=9.0 Hz, 1H), 4.16-4.13 (m, 1H), 3.87-3.84 (m, 1H), 3.27-3.21 (m, 1H), 3.09-3.05 (m, 2H), 2.89-2.86 (m, 1H), 2.18-2.08 (m, 1H), 1.90-1.81 (m, 1H), 1.73-1.58 (m, 2H), 1.21-1.08 (m, 4H); ESI MS m/z 549 [M+H]$^+$; HPLC>99% (AUC), $t_R$=10.15 min.

Example 202

(R)-(4-{[6-(3-aminopiperidin-1-yl)pyridin-3-yl]amino}-6-(3-chloro-5-fluoro-4-hydroxyphenyl)-1,5-naphthyridin-3-yl)(cyclopropyl)methanone

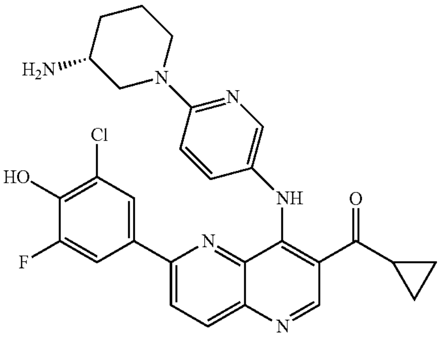 [SMILES: N[C@@H]1CCCN(c2ccc(Nc3c(C(=O)C4CC4)cnc4ccc(-c5cc(F)c(O)c(Cl)c5)nc34)cn2)C1]

Following general procedure IV-2, (R)-tert-butyl[1-(5-{[3-(cyclopropanecarbonyl)-6-(3-chloro-5-fluoro-4-hydroxyphenyl)-1,5-naphthyridin-4-yl)amino)pyridin-2-yl)piperidin-3-yl)arbamate (0.98 g, 0.16 mmol) was reacted with TFA (2 mL). The resulting trifluoroacetate salt of the product was converted to the free base to afford the desired product (58 mg, 71%) as an orange solid: $^1$H NMR (500 MHz, $CD_3OD$) δ 9.18 (s, 1H), 8.09 (d, J=9.0 Hz, 1H), 8.04 (d, J=9.0 Hz, 1H), 7.97 (d, J=2.0 Hz, 1H), 7.37 (dd, J=9.0, 2.0 Hz, 1H), 6.97 (d, J=13.0 Hz, 1H), 6.75 (d, J=9.0 Hz, 1H), 4.18-4.15 (m, 1H), 3.83-3.81 (m, 1H), 3.31-3.22 (m, 1H), 3.15-3.05 (m, 2H), 2.91-2.85 (m, 1H), 2.12-2.08 (m, 1H), 1.91-1.83 (m, 1H), 1.71-1.58 (m, 2H), 1.25-1.08 (m, 4H); ESI MS m/z 533 [M+H]$^+$; HPLC 99.0% (AUC), $t_R$=9.18 min.

Example 203

1-[6-(3,5-dichloro-4-hydroxyphenyl)-4-{[trans-4-(dimethylamino)cyclohexyl]amino}-1,5-naphthyridin-3-yl)-2-hydroxyethanone dihydrochloride

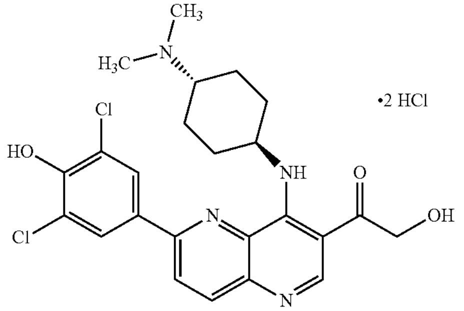 [SMILES: CN(C)[C@H]1CC[C@H](Nc2c(C(=O)CO)cnc3ccc(-c4cc(Cl)c(O)c(Cl)c4)nc23)CC1]

Following general procedure II, 2-[(tert-butyldimethylsilyl)oxy)]-1-{6-chloro-4-[(trans-4-(dimethylamino) cyclohexyl}amino)-1,5-naphthyridin-3-yl)ethanone (44 mg, 0.093 mmol) was reacted with 2,6-dichloro-4-(4,4,5,5-tetramethyl-1,3,2-dioxaborolan-2-yl)phenol (43 mg, 0.15 mmol) followed by formation of the dihydrochloride salt to afford the product (10 mg, 20%) as a yellow solid: solid: $^1$H NMR (500 MHz, $CD_3OD$) δ 9.15 (s, 1H), 8.47 (d, J=9.0 Hz, 1H), 8.35 (d, J=9.0 Hz, 1H), 8.11 (s, 2H), 5.68-5.60 (m, 1H), 4.92 (s, 2H), 3.51-3.42 (m, 1H), 2.92 (s, 6H), 2.63-2.59 (m, 2H), 2.33-2.28 (m, 2H), 1.88-1.73 (m, 4H); ESI MS m/z 489 [M+H]$^+$; HPLC>99% (AUC), $t_R$=9.16 min.

Example 204

1-[6-(3-chloro-5-fluoro-4-hydroxyphenyl)-4-({trans-4-[(dimethylamino)methyl]cyclohexyl}amino)-1,5-naphthyridin-3-yl)]-2-hydroxyethanone dihydrochloride

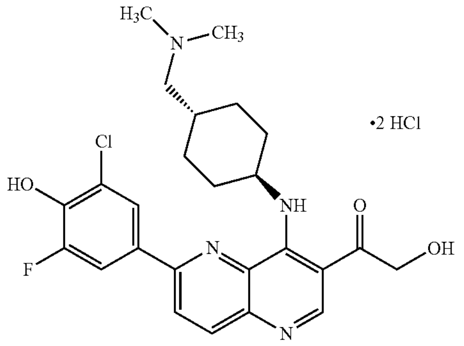 [SMILES: CN(C)C[C@H]1CC[C@H](Nc2c(C(=O)CO)cnc3ccc(-c4cc(F)c(O)c(Cl)c4)nc23)CC1]

Following general procedure II, 1-(6-chloro-4-{trans-4-[(dimethylamino)methyl]cyclohexylamino}-1,5-naphthyridin-3-yl)-2-hydroxyethanone (49 mg, 0.13 mmol) was reacted with 2-chloro-6-fluoro-4-(4,4,5,5-tetramethyl-1,3,2-dioxaborolan-2-yl)phenol (53 mg, 0.12 mmol) followed by formation of the dihydrochloride salt to afford the product (31 mg, 42%) as an off-white solid: $^1$H NMR (500 MHz, $CD_3OD$)

δ 9.12 (s, 1H), 8.45 (d, J=9.0 Hz, 1H), 8.32 (d, J=9.0 Hz, 1H), 8.03 (s, 1H), 7.89 (d, J=11.0 Hz, 1H), 5.80-5.65 (m, 1H), 4.91 (s, 2H), 3.13-3.05 (m, 2H), 2.94 (s, 6H), 2.50-2.43 (m, 2H), 2.12-1.98 (m, 2H), 1.78-1.65 (m, 2H), 1.48-1.35 (m, 2H); ESI MS m/z 487 $[M+H]^+$; HPLC>99% (AUC), $t_R$=9.26 min.

Example 205

1-[6-(3-chloro-5-fluoro-4-hydroxyphenyl)-4-({trans-4-[(dimethylamino)methyl]cyclohexyl}amino)-1,5-naphthyridin-3-yl)]propan-1-one dihydrochloride

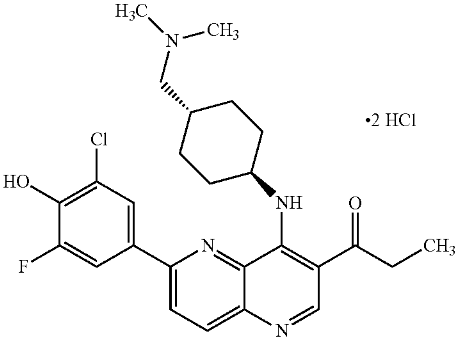 [SMILES: CCC(=O)c1cnc2ccc(-c3cc(F)c(O)c(Cl)c3)nc2c1N[C@H]1CC[C@H](CN(C)C)CC1]

Following general procedure II, 1-(6-chloro-4-{trans-4-[(dimethylamino)methyl]cyclohexylamino}-1,5-naphthyridin-3-yl)-2-hydroxyethanone (170 mg, 0.50 mmol) was reacted with 2-chloro-6-fluoro-4-(4,4,5,5-tetramethyl-1,3,2-dioxaborolan-2-yl)phenol (170 mg, 0.60 mmol). After work up and purification the dihydrochloride salt was obtained (31 mg, 42%) as an off-white solid: $^1$H NMR (500 MHz, $CD_3OD$) δ 9.17 (s, 1H), 8.44 (d, J=9.0 Hz, 1H), 8.33 (d, J=9.0 Hz, 1H), 8.02 (d, J=2.0 Hz, 1H), 7.88 (dd, J=11.5, 2.0 Hz, 1H), 5.72-5.53 (m, 1H), 3.20 (q, J=7.0 Hz, 2H), 3.13-3.08 (m, 2H), 2.94 (s, 6H), 2.50-2.43 (m, 2H), 2.12-2.00 (m, 3H), 1.78-1.65 (m, 2H), 1.48-1.35 (m, 2H), 1.25 (t, J=7.0 Hz, 3H); ESI MS m/z 485 $[M+H]^+$; HPLC>99% (AUC), $t_R$=9.96 min.

Example 206

1-[6-(3,5-dichloro-4-hydroxyphenyl)-4-({trans-4-[(dimethylamino)methyl]cyclohexyl}amino)-1,5-naphthyridin-3-yl)]propan-1-one dihydrochloride

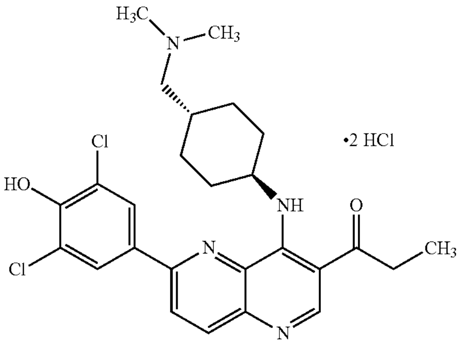 [SMILES: CCC(=O)c1cnc2ccc(-c3cc(Cl)c(O)c(Cl)c3)nc2c1N[C@H]1CC[C@H](CN(C)C)CC1]

Following general procedure II, 1-(6-chloro-4-{trans-4-[(dimethylamino)methyl]cyclo hexylamino}-1,5-naphthyridin-3-yl)-2-hydroxyethanone (170 mg, 0.50 mmol) was reacted with 2,6-dichloro-4-(4,4,5,5-tetramethyl-1,3,2-dioxaborolan-2-yl)phenol (170 mg, 0.60 mmol). After work up and purification the dihydrochloride salt was obtained (45 mg, 14%) as a white solid: $^1$H NMR (500 MHz, $CD_3OD$) δ

9.17 (s, 1H), 8.45 (d, J=9.0 Hz, 1H), 8.34 (d, J=9.0 Hz, 1H), 8.11 (s, 2H), 5.75-5.66 (m, 1H), 3.20 (q, J=7.0 Hz, 2H), 3.13-3.08 (m, 2H), 2.94 (s, 6H), 2.50-2.41 (m, 2H), 2.10-2.00 (m, 3H), 1.74-1.62 (m, 2H), 1.48-1.36 (m, 2H), 1.25 (t, J=7.0 Hz, 3H); ESI MS m/z 501 $[M+H]^+$; HPLC>99% (AUC), $t_R$=10.17 min.

Example 207

(S)-1-(4-{[6-(3-aminopiperidin-1-yl)pyridin-3-yl]amino}-6-(3,5-dichloro-4-hydroxyphenyl)-1,5-naphthyridin-3-yl)propan-1-one trihydrochloride

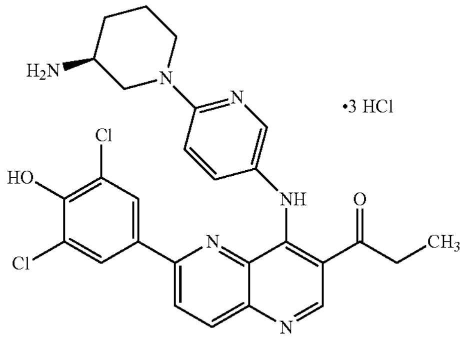 [SMILES: CCC(=O)c1cnc2ccc(-c3cc(Cl)c(O)c(Cl)c3)nc2c1Nc1ccc(N2CCC[C@H](N)C2)nc1]

Following general procedure IV-2, (S)-tert-butyl(1-(5-((6-(3,5-dichloro-4-hydroxyphenyl)-3-propionyl-1,5-naphthyridin-4-yl)amino)pyridin-2-yl)piperidin-3-yl)carbamate (0.195 mmol) was reacted with TFA (2 mL) followed by formation of the trihydrochloride salt to afford the desired product (78 mg, 62% over two steps) as an orange-brown solid: $^1$H NMR (500 MHz, $CD_3OD$) δ 9.32 (s, 1H), 8.47 (d, J=9.0 Hz, 1H), 8.37 (d, J=9.0 Hz, 1H), 8.20 (d, J=2.5 Hz, 1H), 7.76 (dd, J=9.0, 2.5 Hz, 1H), 7.61 (s, 2H), 7.11 (d, J=9.0 Hz, 1H), 4.41-4.38 (m, 1H), 3.97-3.95 (m, 1H), 3.48-3.16 (m, 5H), 2.24-2.15 (m, 1H), 2.03-1.91 (m, 1H), 1.82-1.74 (m, 2H), 1.32-1.19 (m, 3H); ESI MS m/z 537 $[M+H]^+$; HPLC>99% (AUC), $t_R$=9.92 min.

Example 208

(S)-1-(4{[6-(3-aminopiperidin-1-yl)pyridin-3-yl]amino}-6-(3-chloro-5-fluoro-4-hydroxyphenyl)-1,5-naphthyridin-3-yl)propan-1-one trihydrochloride

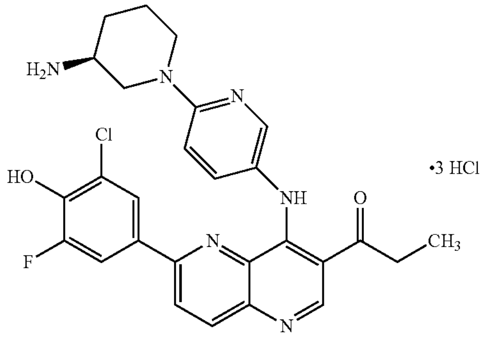 [SMILES: CCC(=O)c1cnc2ccc(-c3cc(F)c(O)c(Cl)c3)nc2c1Nc1ccc(N2CCC[C@H](N)C2)nc1]

Following general procedure IV-2, (S)-tert-butyl[1-(5-{[6-(3-chloro-5-fluoro-4-hydroxyphenyl)-3-propionyl-1,5-naphthyridin-4-yl]amino]pyridin-2-yl)piperidin-3-yl]carbamate (0.21 mmol) was reacted with TFA (2 mL) followed by formation of the trihydrochloride salt to afford the desired product (67 mg, 52%) as a green-brown solid: $^1$H NMR (500 MHz, $CD_3OD$) δ 9.32 (s, 1H), 8.46 (d, J=9.0 Hz, 1H), 8.37 (d, J=9.0 Hz, 1H), 8.21 (d, J=2.5 Hz, 1H), 7.75 (dd, J=9.3, 2.5 Hz, 1H), 7.63-7.26 (m, 2H), 7.12 (d, J=9.3 Hz, 1H), 4.39 (d, J=10.5 Hz, 1H), 4.01-3.96 (m, 1H), 3.48-3.16 (m, 5H), 2.25-2.15 (m, 1H), 2.04-1.93 (m, 1H), 1.82-1.71 (m, 2H), 1.32-1.19 (m, 3H); ESI MS m/z 521 [M+H]$^+$; HPLC>99% (AUC), $t_R$=9.75 min.

Example 209

1-[6-(3,5-dichloro-4-hydroxyphenyl)-4-({4-[((R)-3-fluoropyrrolidin-1yl)methyl]cyclohexyl}amino)-1,5-naphthyridin-3-yl]ethanone

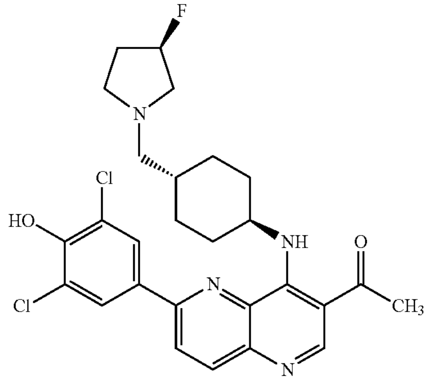 [SMILES: CC(=O)c1cnc2ccc(-c3cc(Cl)c(O)c(Cl)c3)nc2c1N[C@H]1CC[C@H](CN2CC[C@@H](F)C2)CC1]

Following general procedure II, 1-(6-chloro-4-((4-(((R)-3-fluoropyrrolidin-1-yl)methyl)cyclohexyl)amino)-1,5-naphthyridin-3-yl)ethanone (58 mg, 0.143 mmol) was reacted with 2,6-dichloro-4-(4,4,5,5-tetramethyl-1,3,2-dioxaborolan-2-yl)phenol (62 mg, 0.21 mmol) to afford the desired product (52 mg, 60%) as an orange solid: $^1$H NMR (500 MHz, $CD_3OD$) δ 9.15 (s, 1H), 8.46 (d, J=9.0 Hz, 1H), 8.33 (d, J=9.0 Hz, 1H), 8.12 (s, 2H), 5.74-5.69 (m, 1H), 5.53-5.43 (m, 1H), 4.12-3.84 (m, 2H), 3.31-3.17 (m, 2H), 2.76 (s, 3H), 2.50-2.43 (m, 2H), 2.18-1.96 (m, 3H), 1.74-1.62 (m, 2H), 1.50-1.38 (m, 2H); ESI MS m/z 531 [M+H]$^+$; HPLC 96.7% (AUC), tR=10.05 min.

Example 210

(S)-(4-{[6-(3-aminopiperidin-1-yl)pyridin-3-yl]amino}-6-(3-chloro-5-fluoro-4-hydroxyphenyl)-1,5-naphthyridin-3-yl)(cyclobutyl)methanone trihydrochloride

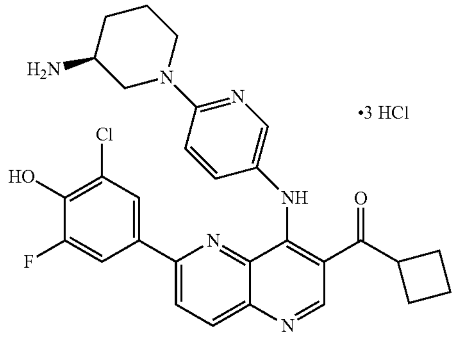 [SMILES: N[C@H]1CCCN(c2ccc(Nc3c(C(=O)C4CCC4)cnc4ccc(-c5cc(F)c(O)c(Cl)c5)nc34)cn2)C1]

Following general procedure IV-2, (S)-tert-butyl[1-(5-{[6-(3-chloro-5-fluoro-4-hydroxyphenyl)-3-(cyclobutanecarbonyl)-1,5-naphthyridin-4-yl]amino}pyridin-2-yl)piperidin-3-yl]carbamate (0.20 mmol) was reacted with TFA (2 mL) followed by formation of the trihydrochloride salt to afford the desired product (94 mg, 72% over two steps) as a orange-brown solid: $^1$H NMR (500 MHz, $CD_3OD$) δ 9.10 (s, 1H), 8.45 (d, J=9.0 Hz, 1H), 8.36 (d, J=9.0 Hz, 1H), 8.22 (d, J=3.0 Hz, 1H), 7.74 (dd, J=9.3, 3.0 Hz, 1H), 7.63-7.23 (m, 2H), 7.10 (d, J=9.3 Hz, 1H), 4.40 (d, J=10.5 Hz, 1H), 4.38-4.23 (m, 1H), 4.03-3.92 (m, 1H), 3.45-3.36 (m, 2H), 2.60-2.36 (m, 4H), 2.26-2.13 (m, 2H), 2.03-1.90 (m, 2H), 1.81-1.70 (m, 2H); ESI MS m/z 547 [M+H]$^+$; HPLC 98.2% (AUC), $t_R$=10.33 min.

Example 211

(6-(3,5-dichloro-4-hydroxyphenyl)-4-((4-[(dimethylamino)methyl{cyclohexyl)amino)-1,5-naphthyridin-3-yl)(cyclobutyl)methanone

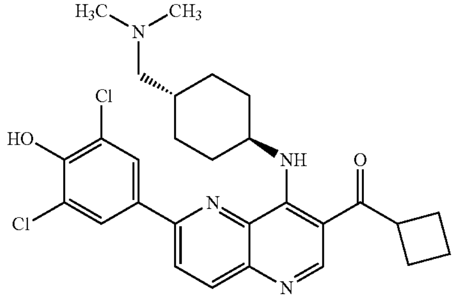 [SMILES: CN(C)C[C@H]1CC[C@H](Nc2c(C(=O)C3CCC3)cnc3ccc(-c4cc(Cl)c(O)c(Cl)c4)nc23)CC1]

Following general procedure II, (6-chloro-4-((4-((dimethylamino)methyl)cyclohexyl)amino)-1,5-naphthyridin-3-yl)(cyclobutyl)methanone (40 mg, 0.10 mmol) was reacted with 2,6-dichloro-4-(4,4,5,5-tetramethyl-1,3,2-dioxaborolan-2-yl)phenol (43 mg, 0.15 mmol) to afford the desired product (53 mg, 68%) as light yellow solid: $^1$H NMR (500 MHz, $CD_3OD$) δ 8.93 (s, 1H), 8.45 (d, J=9.0 Hz, 1H), 8.33 (d, J=9.0 Hz, 1H), 8.12 (s, 2H), 5.76-5.65 (m, 1H), 4.30-4.20 (m, 1H), 3.12-3.07 (m, 2H), 2.95 (s, 6H), 2.52-2.41 (m, 4H), 2.39-2.34 (m, 2H), 2.22-2.12 (m, 1H), 2.09-2.00 (m, 2H), 1.98-1.90 (m, 1H), 1.76-1.64 (m, 2H), 1.49-1.36 (m, 2H); ESI MS m/z 527 [M+H]$^+$; HPLC>99% (AUC), tR=10.72 min.

Example 212

(6-(3-chloro-5-fluoro-4-hydroxyphenyl)-4-((4-((dimethylamino)methyl)cyclohexyl)amino)-1,5-naphthyridin-3-yl)(cyclobutyl)methanone

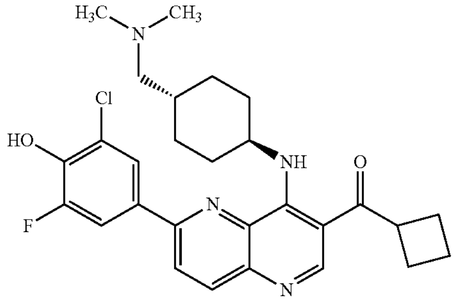 [SMILES: CN(C)C[C@H]1CC[C@H](Nc2c(C(=O)C3CCC3)cnc3ccc(-c4cc(F)c(O)c(Cl)c4)nc23)CC1]

Following general procedure II, (6-chloro-4-((4-((dimethylamino)methyl)cyclohexyl)amino)-1,5-naphthyridin-3-yl)(cyclobutyl)methanone (65 mg, 0.16 mmol) was reacted with 2-chloro-6-fluoro-4-(4,4,5,5-tetramethyl-1,3,2-dioxaborolan-2-yl)phenol (65 mg, 0.24 mmol) to afford the desired product (72 mg, 77%) as light yellow solid: $^1H$ NMR (500 MHz, $CD_3OD$) δ 8.93 (s, 1H), 8.44 (d, J=9.0 Hz, 1H), 8.33 (d, J=9.0 Hz, 1H), 8.02 (s, 1H), 7.88 (dd, J=11.5, 2.0 Hz, 1H), 5.74-5.64 (m, 1H), 4.29-4.19 (m, 1H), 3.12-3.07 (m, 2H), 2.95 (s, 6H), 2.52-2.41 (m, 4H), 2.39-2.34 (m, 2H), 2.24-2.12 (m, 1H), 2.09-1.98 (m, 2H), 1.98-1.89 (m, 1H), 1.78-1.66 (m, 2H), 1.49-1.35 (m, 2H); ESI MS m/z 511 $[M+H]^+$; HPLC>99% (AUC), tR=10.52 min.

Example 213

(R)-1-(4-((6-(3-aminopiperidin-1-yl)pyridin-3-yl)amino)-6-(3-chloro-5-fluoro-4-hydroxyphenyl)-1,5-naphthyridin-3-yl)propan-1-one trichloride

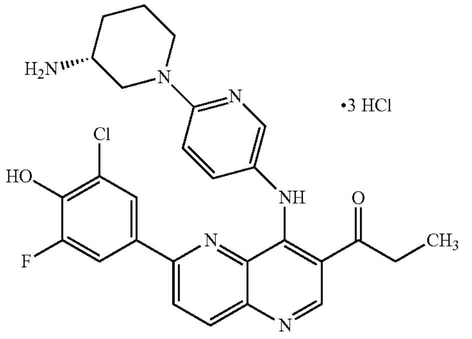 [SMILES: CCC(=O)c1cnc2ccc(-c3cc(F)c(O)c(Cl)c3)nc2c1Nc1ccc(N2CCC[C@@H](N)C2)nc1]

Following general procedure IV-2, (R)-tert-butyl(1-(5-((6-(3-chloro-5-fluoro-4-hydroxyphenyl)-3-propionyl-1,5-naphthyridin-4-yl)amino)pyridin-2-yl)piperidin-3-yl)carbamate (120 mg, 0.19 mmol) was reacted with TFA (2 mL) followed by formation of the trihydrochloride salt to afford the desired product (78 mg, 65%) as a orange-brown solid: $^1H$ NMR (500 MHz, $CD_3OD$) δ 9.38 (s, 1H), 8.48 (d, J=9.0 Hz, 1H), 8.41 (d, J=9.0 Hz, 1H), 8.25 (d, J=2.5 Hz, 1H), 7.90 (dd, J=9.5, 2.5 Hz, 1H), 7.56-7.30 (m, 2H), 7.27 (d, J=9.5 Hz, 1H), 4.43-4.32 (m, 1H), 4.08-3.96 (m, 1H), 3.53-3.38 (m, 3H), 3.29-3.20 (m, 2H), 2.29-2.20 (m, 1H), 2.09-1.98 (m, 1H), 1.88-1.74 (m, 2H), 1.38-1.21 (m, 3H); ESI MS m/z 521 $[M+H]^+$; HPLC 97.6% (AUC), $t_R$=9.86 min.

Example 214

(R)-1-(4-((6-(3-aminopiperidin-1-yl)pyridin-3-yl)amino)-6-(3,5-dichloro-4-hydroxyphenyl)-1,5-naphthyridin-3-yl)propan-1-one trihydrochloride

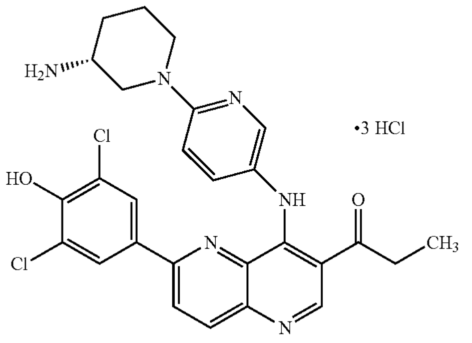 [SMILES: CCC(=O)c1cnc2ccc(-c3cc(Cl)c(O)c(Cl)c3)nc2c1Nc1ccc(N2CCC[C@@H](N)C2)nc1]

Following general procedure IV-2, (R)-tert-butyl[1-(5-{[3-(cyclopropanecarbonyl)-6-(3,5-dichloro-4-hydroxyphenyl)-1,5-naphthyridin-4-yl]amino}pyridin-2-yl)piperidin-3-yl] carbamate (80 mg, 0.12 mmol) was reacted with TFA (2 mL) followed by formation of the trihydrochloride salt to afford the desired product (48 mg, 62%) as an orange solid: $^1H$ NMR (500 MHz, $CD_3OD$) δ 9.39 (s, 1H), 8.49 (d, J=9.5 Hz, 1H), 8.42 (d, J=9.0 Hz, 1H), 8.26 (d, J=2.0 Hz, 1H), 7.92 (dd, J=9.5, 2.0 Hz, 1H), 7.58 (s, 2H), 7.28 (d, J=9.5 Hz, 1H), 4.42-4.32 (m, 1H), 4.16-3.96 (m, 1H), 3.52-3.22 (m, 5H), 2.29-2.18 (m, 1H), 2.08-1.98 (m, 1H), 1.88-1.75 (m, 2H), 1.37-1.20 (m, 3H); ESI MS m/z 537 $[M+H]^+$; HPLC 98.0% (AUC), $t_R$=9.92 min Example 215

(R)-1-(4-((6-(3-aminopiperidin-1-yl)pyridin-3-yl)amino)-6-(3-chloro-5-fluoro-4-hydroxyphenyl)-1,5-naphthyridin-3-yl)-2-methylpropan-1-one trihydrochloride

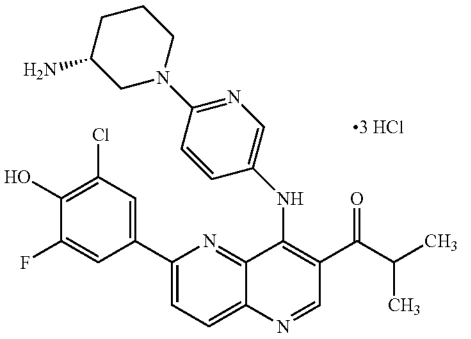 [SMILES: CC(C)C(=O)c1cnc2ccc(-c3cc(F)c(O)c(Cl)c3)nc2c1Nc1ccc(N2CCC[C@@H](N)C2)nc1]

Following general procedure IV-2, (R)-tert-butyl(1-(5-((6-(3-chloro-5-fluoro-4-hydroxyphenyl)-3-isobutyryl-1,5-naphthyridin-4-yl)amino)pyridin-2-yl)piperidin-3-yl)carbamate (168 mg, 0.26 mmol) was reacted with TFA (2 mL) followed by formation of the trihydrochloride salt to afford the desired product (110 mg, 78%) as an orange solid: $^1H$ NMR (500 MHz, $CD_3OD$) δ 9.31 (s, 1H), 8.35 (s, 2H), 8.18 (d, J=2.5 Hz, 1H), 7.64 (d, J=9.0, 2.5 Hz, 1H), 7.38 (bs, 1H), 7.22-7.12 (m, 1H), 7.02 (d, J=9.0 Hz, 1H), 4.44-4.32 (m, 1H), 3.98-3.90 (m, 1H), 3.82-3.70 (m, 1H), 3.46-3.22 (m, 3H), 2.22-2.12 (m, 1H), 2.01-1.88 (m, 1H), 1.80-1.68 (m, 2H), 1.36-1.20 (m, 6H); ESI MS m/z 535 $[M+H]^+$; HPLC>99% (AUC), $t_R$=10.07 min.

Example 216

1-[6-(3,5-dichloro-5-4-hydroxyphenyl)-4-({trans-4-[(dimethylamino)methyl]cyclohexyl}amino)-1,5-naphthyridin-3-yl]-2-methylpropan-1-one dihydrochloride

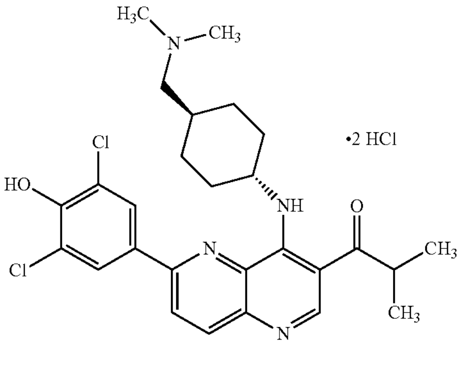 [SMILES: CC(C)C(=O)c1cnc2ccc(-c3cc(Cl)c(O)c(Cl)c3)nc2c1N[C@H]1CC[C@H](CN(C)C)CC1]

Following general procedure II, 1-[6-chloro-4-({trans-4-[(dimethylamino)methyl]cyclo hexyl}amino)-1,5-naphthyridin-3-yl)-2-methylpropan-1-one (0.25 g, 0.64 mmol) was reacted with 2,6-dichloro-4-(4,4,5,5-tetramethyl-1,3,2-dioxaborolan-2-yl)phenol (0.28 g, 0.96 mmol). After work up and purification the dihydrochloride salt was formed to afford the desired product (150 mg, 41%) as a yellow solid: $^1$H NMR (500 MHz, $CD_3OD$) δ 9.23 (s, 1H), 8.45 (d, J=9.0 Hz, 1H), 8.35 (d, J=9.0 Hz, 1H), 8.10 (s, 2H), 5.77-5.63 (m, 1H), 3.83-3.71 (m, 1H), 3.11-3.04 (m, 2H), 2.94 (s, 6H), 2.47-2.42 (m, 1H), 2.08-2.00 (m, 3H), 1.73-1.65 (m, 2H), 1.50-1.37 (m, 2H), 1.36-1.24 (m, 6H); ESI MS m/z 515 [M+H]$^+$; HPLC 98.7% (AUC), $t_R$=10.57 min.

Example 217

1-[6-chloro-4-({trans-4-[(dimethylamino)methyl]cyclohexyl}amino)-1,5-naphthyridin-3-yl]-2-methylpropan-1-one

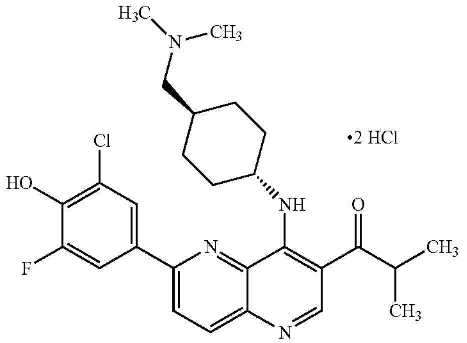 [SMILES: CC(C)C(=O)c1cnc2ccc(-c3cc(F)c(O)c(Cl)c3)nc2c1N[C@H]1CC[C@H](CN(C)C)CC1]

Following general procedure II, 1-[6-chloro-4-({trans-4-[(dimethylamino)methyl]cyclo hexyl}amino)-1,5-naphthyridin-3-yl]-2-methylpropan-1-one (0.25 g, 0.64 mmol) was reacted with 3,5-dichloro-4-(4,4,5,5-tetramethyl-1,3,2-dioxaborolan-2-yl)phenol (0.26 g, 0.96 mmol). After work up and purification the dihydrochloride salt was formed to afford the desired product (175 mg, 46%) as a light brown solid: $^1$H NMR (500 MHz, $CD_3OD$) δ 9.22 (s, 1H), 8.45 (d, J=9.0 Hz, 1H), 8.34 (d, J=9.0 Hz, 1H), 8.03 (d, J=2.0, 2H), 7.88 (dd, J=11.5, 2.0 Hz, 1H), 5.75-5.68 (m, 1H), 3.83-3.74 (m, 1H), 3.13-3.08 (m, 2H), 2.94 (s, 6H), 2.50-2.38 (m, 2H), 2.12-1.99 (m, 3H), 1.78-1.65 (m, 2H), 1.49-1.37 (m, 2H), 1.33-1.25 (m, 6H); ESI MS m/z 499 [M+H]$^+$; HPLC 97.5% (AUC), $t_R$=10.24 min.

Example 218

(R)-tert-butyl[1-(5-{[3-(cyclopropanecarbonyl)-6-(3,5-dichloro-4-hydroxyphenyl)-1,5-naphthyridin-4-yl]amino}pyridin-2-yl)piperidin-3-yl]carbamate

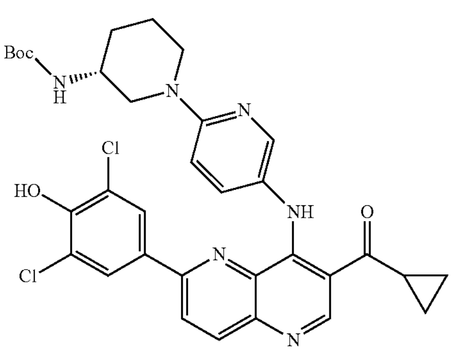 [SMILES: CC(C)(C)OC(=O)N[C@@H]1CCCN(c2ccc(Nc3c(C(=O)C4CC4)cnc4ccc(-c5cc(Cl)c(O)c(Cl)c5)nc34)cn2)C1]

Following general procedure II, (R)-tert-butyl[1-(5-{[6-chloro-3-(cyclopropanecarbonyl)-1,5-naphthyridin-4-yl]amino}pyridin-2-yl)piperidin-3-yl]carbamate (150 mg, 0.29 mmol) was reacted with 2,6-dichloro-4-(4,4,5,5-tetramethyl-1,3,2-dioxaborolan-2-yl)phenol (120 mg, 0.43 mmol) to afford the product (119 mg, 64%) as an orange solid: ESI MS m/z 649 [M+H]$^+$.

Example 219

(R)-tert butyl[1-(5-{[6-chloro-3-(cyclopropanecarbonyl)-1,5-naphthyridin-4-yl]amino}pyridin-2-yl)piperidin-3-yl]carbamate

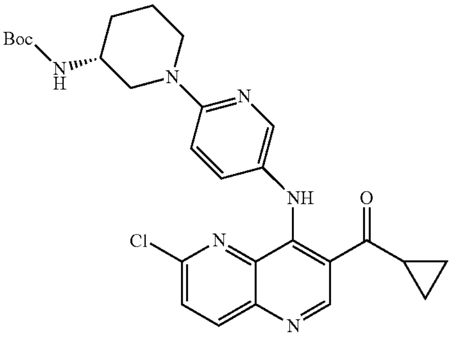 [SMILES: CC(C)(C)OC(=O)N[C@@H]1CCCN(c2ccc(Nc3c(C(=O)C4CC4)cnc4ccc(Cl)nc34)cn2)C1]

Following general procedure I, 4,6-dichloro-1,5-naphthyridin-3-yl(cyclopropyl) methanone (400 mg, 1.5 mmol) was reacted with (R)-tert-butyl[1-(5-aminopyridin-2-yl) piperidine-3-yl]carbamate (550 mg, 1.9 mmol) to afford the product (600 mg, 76%) as an orange foam: ESI MS m/z 523 [M+H]$^+$.

Example 220

(R)-tert-butyl[1-(5-{[3-(cyclopropanecarbonyl)-6-(3-chloro-5-fluoro-4-hydroxyphenyl)-1,5-naphthyridin-4-yl]amino}pyridin-2-yl)piperidin-3-yl]carbamate

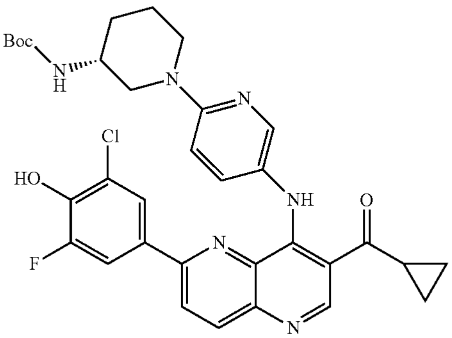 [SMILES: CC(C)(C)OC(=O)N[C@@H]1CCCN(c2ccc(Nc3c(C(=O)C4CC4)cnc4ccc(-c5cc(F)c(O)c(Cl)c5)nc34)cn2)C1]

Following general procedure II, (R)-tert-butyl[1-(5-{[6-chloro-3-(cyclopropanecarbonyl)-1,5-naphthyridin-4-yl]amino}pyridin-2-yl)piperidin-3-yl]carbamate (150 mg, 0.29 mmol) was reacted with 2-chloro6-fluro-4-(4,4,5,5-tetramethyl-1,3,2-dioxaborolan-2-yl)phenol (120 mg, 0.43 mmol) to afford the product (100 mg, 54%) as an orange-red solid: ESI MS m/z 633 $[M+H]^+$.

Example 221

2-((tert-butyldimethylsilyl)oxy)-1-(6-chloro-4-((trans-4-(dimethylamino)cyclohexyl)amino)-1,5-naphthyridin-3-yl)ethanone

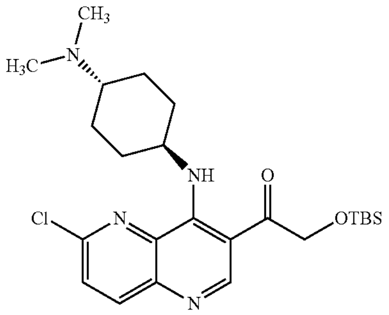 [SMILES: CN(C)[C@H]1CC[C@H](Nc2c(C(=O)CO[Si](C)(C)C(C)(C)C)cnc3ccc(Cl)nc23)CC1]

Following general procedure I, 2-((tert-butyldimethylsilyl)oxy)-1-(4,6-dichloro-1,5-naphthyridin-3-yl)ethanone (87 mg, 0.23 mmol) was reacted with trans-dimethylcyclohexane-1,4-diamine (50 mg, 0.35 mmol) to afford the product (44 mg, 40%) as a light yellow oil: ESI MS m/z 477 $[M+H]^+$.

Example 222

2-((tert-butyldimethylsilyl)oxy)-1-(4,6-dichloro-1,5-naphthyridin-3-yl)ethanone

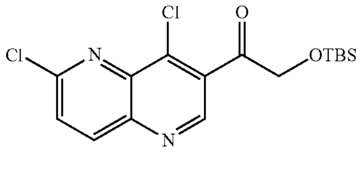 [SMILES: CC(C)(C)[Si](C)(C)OCC(=O)c1cnc2ccc(Cl)nc2c1Cl]

To a solution of 1-(4,6-dichloro-1,5-naphthyridin-3-yl)-2-hydroxyethanone (128 mg, 0.5 mmol) in DMF (5 mL) was added imidazole (68 mg, 1.0 mmol) and tert-butyldimethylsilyl chloride (90 mg, 0.6 mmol) at 0° C. The mixture was stirred for 3 h, poured into $NaHCO_3$ (saturated), and extracted with ethyl acetate. The organic layer was dried over $Na_2SO_4$, concentrated, and purified by chromatography to afford product (87 mg, 47%) as a light yellow oil: ESI MS m/z 371 $[M+H]^+$.

Example 223

1-(6-chloro-4-((4-((dimethylamino)methyl)cyclohexyl)amino)-1,5-naphthyridin-3-yl)propan-1-one

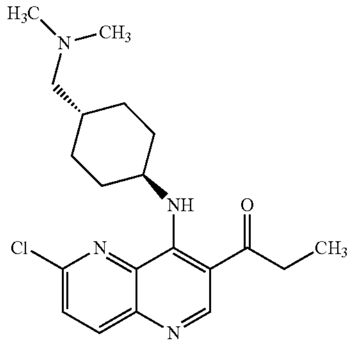

Following general procedure I, 1-(4,6-dichloro-1,5-naphthyridin-3-yl)propan-1-one (255 mg, 1.0 mmol) was reacted with trans-4-((dimethylamino)methyl)cyclohexanamine (310 mg, 2.0 mmol) to afford the product (350 mg, 93%) as a white solid: ESI MS m/z 375 $[M+H]^+$.

Example 224

1-(4,6-dichloro-1,5-naphthyridin-3-yl)propan-1-one

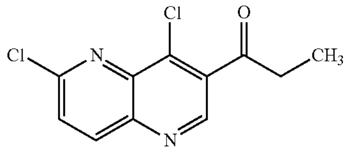 [SMILES: CCC(=O)c1cnc2ccc(Cl)nc2c1Cl]

To a suspension of 1-(4-hydroxy-6-methoxy-1,5-naphthyridin-3-yl)propan-1-one (5.2 g, 22.4 mmol) in acetonitrile (100 ml) was added trimethylsilylchloride (12 g, 112 mmol) and sodium iodide (10 g, 67 mmol) and the reaction mixture was heated at reflux for 16 h. The reaction mixture was cooled to room temperature and satd. aq. sodium thiosulfate was added. The mixture was concentrated to remove acetonitrile, diluted with brine and the solids were filtered and dried to provide the intermediate 1-(4,6-dihydroxy-1,5-naphthyridin-3-yl)propan-1-one. This intermediate was suspended in dichloroethane (10 mL) followed by the addition of phosphorus oxychloride (10 mL) and catalytic N,N-dimethylformamide and the reaction mixture was stirred with heat at 80° C. for 2 h. The reaction mixture was cooled to room temperature and quenched by pouring slowly into ice-cold satd. aq. sodium bicarbonate or 3 N sodium hydroxide. The quenched reaction mixture was concentrated to remove the dichloroethane and the resulting solids were collected by filtration and purified by chromatography (silica, hexanes/ethyl acetate) to provide the desired product (3.2 g, 56% over 2 steps) as a brown solid: ESI MS m/z 255 $[M+H]^+$.

Example 225

1-(4-hydroxy-6-methoxy-1,5-naphthyridin-3-yl)propan-1-one

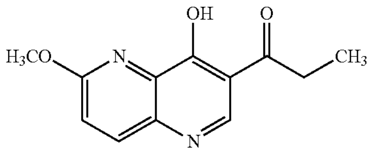 [SMILES: CCC(=O)c1cnc2ccc(OC)nc2c1O]

To a flask containing Dowtherm™ A (200 mL) at 250° C. was added ethyl 2-[(6-chloropyridin-3-ylamino)methylene]-3-oxobutanoate (10 g, 36 mmol) portion wise over 3 to 5 min and the reaction mixture was stirred for an additional 30 to 45 min. The reaction mixture was removed from the heat source, cooled to room temperature and diluted with hexanes to facilitate precipitation. The solids were filtered, washed with hexanes and dried under vacuum to afford the desired product (5.0 g, crude) as a brown solid: ESI MS m/z 241 $[M+H]^+$.

Example 226 ethyl 2-(((6-methoxypyridin-3-yl)amino)methylene)-3-oxopentanoate

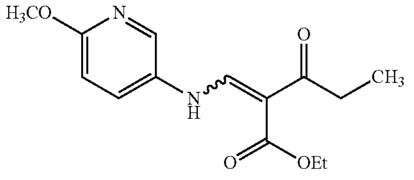 [SMILES: CCOC(=O)C(=CNc1ccc(OC)nc1)C(=O)CC]

Ethyl 2-(((6-methoxypyridin-3-yl)amino)methylene)-3-oxopentanoate was prepared with conditions described in Example 99 using 2-methoxy-5-aminopyridine and ethyl 2-(ethoxymethylene)-3-oxopentanoate.

Example 227

(S)-tert-butyl(1-(5-((6-(3,5-dichloro-4-hydroxyphenyl)-3-propionyl-1,5-naphthyridin-4-yl)amino)pyridin-2-yl)piperidin-3-yl)carbamate

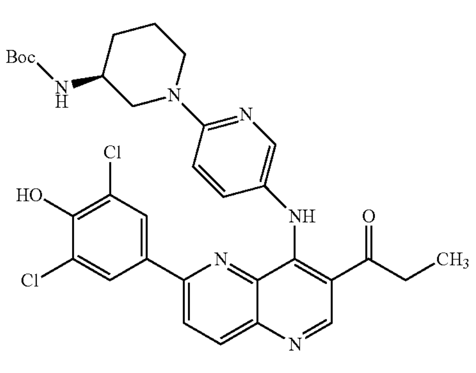 [SMILES: CCC(=O)c1cnc2ccc(-c3cc(Cl)c(O)c(Cl)c3)nc2c1Nc1ccc(N2CCC[C@H](NC(=O)OC(C)(C)C)C2)nc1]

Following general procedure II, (S)-tert-butyl(1-(5-((6-chloro-3-propionyl-1,5-naphthyridin-4-yl)amino)pyridin-2-yl)piperidin-3-yl)carbamate (100 mg, 0.20 mmol) was reacted with 2,6-dichloro-4-(4,4,5,5-tetramethyl-1,3,2-dioxaborolan-2-yl)phenol (85 mg, 0.30 mmol) to afford the product (100 mg) which was carried forward without any purification: ESI MS m/z 637 $[M+H]^+$.

Example 228

(S)-tert-butyl(1-(5-((6-chloro-3-propionyl-1,5-naphthyridin-4-yl)amino)pyridin-2-yl)piperidin-3-yl)carbamate

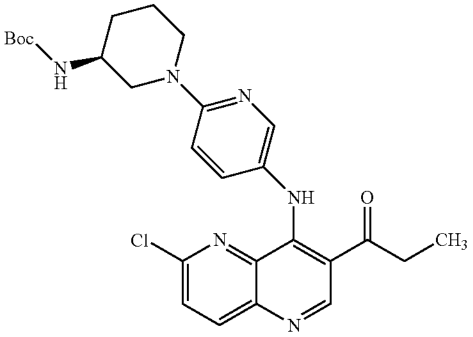 [SMILES: CCC(=O)c1cnc2ccc(Cl)nc2c1Nc1ccc(N2CCC[C@H](NC(=O)OC(C)(C)C)C2)nc1]

Following general procedure I, 1-(4,6-dichloro-1,5-naphthyridin-3-yl)propan-1-one (250 mg, 0.98 mmol) was reacted with (S)-tert-butyl 1-(5-aminopyridin-2-yl)piperidin-3-ylcarbamate (430 mg, 1.5 mmol) to afford the desired product (550 mg, crude) as an dark brown solid: $^1$H NMR (500 MHz, $CDCl_3$) δ 11.29 (s, 1H), 9.03 (s, 1H), 8.11 (d, J=9.0 Hz, 1H), 8.01 (d, J=3.0 Hz, 1H), 7.47 (d, J=9.0 Hz, 1H), 7.31-7.29 (m, 1H), 6.72 (d, J=9.0 Hz, 1H), 4.79 (br s, 1H), 3.90-3.61 (m, 4H), 3.51-3.25 (m, 2H), 3.07 (q, J=7.0 Hz, 2H), 1.96-1.84 (m, 1H), 1.82-1.70 (m, 1H), 1.72-1.55 (m, 1H), 1.45 (s, 9H), 1.26 (t, J=7.0 Hz, 3H); ESI MS m/z 511 $[M+H]^+$ Example 229

(S)-tert-butyl(1-(5-((6-(3-chloro-5-fluoro-4-hydroxyphenyl)-3-propionyl-1,5-naphthyridin-4-yl)amino)pyridin-2-yl)piperidin-3-yl)carbamate

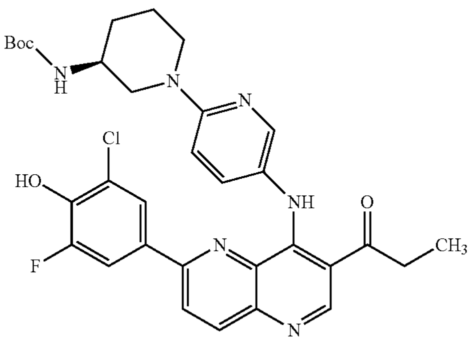 [SMILES: CCC(=O)c1cnc2ccc(-c3cc(F)c(O)c(Cl)c3)nc2c1Nc1ccc(N2CCC[C@H](NC(=O)OC(C)(C)C)C2)nc1]

Following general procedure II, (S)-tert-butyl(1-(5-((6-chloro-3-prop ionyl-1,5-naphthyridin-4-yl)amino)pyridin-2-yl)piperidin-3-yl)carbamate (100 mg, 0.20 mmol) was reacted with 2-chloro-6-fluoro-4-(4,4,5,5-tetramethyl-1,3,2-dioxaborolan-2-yl)phenol (83 mg, 0.31 mmol) to afford the product (102 mg) which was carried forward without any purification: ESI MS m/z 621 [M+H]$^+$.

Example 230

1-(6-chloro-4-((4-(((R)-3-fluoropyrrolidin-1-yl)methyl)cyclohexyl)amino)-1,5-naphthyridin-3-yl)ethanone

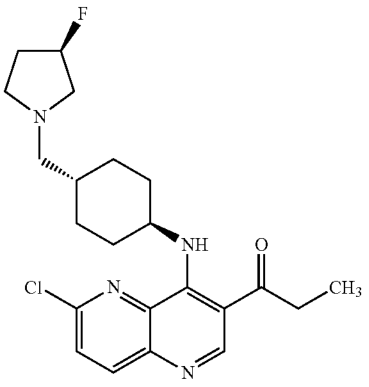 [SMILES: CCC(=O)c1cnc2ccc(Cl)nc2c1N[C@H]1CC[C@H](CN2CC[C@@H](F)C2)CC1]

Following general procedure I, 1-(4,6-dichloro-1,5-naphthyridin-3-yl)ethanone (240 mg, 1.0 mmol) was reacted with 4-(((R)-3-fluoropyrrolidin-1-yl)methyl)cyclohexanamine (100 mg, 0.5 mmol) to afford the product (61 mg, 15%) as a brown solid: ESI MS m/z 405 [M+H]$^+$.

Example 231

4-(((R)-3-fluoropyrrolidin-1-yl)methyl)cyclohexanamine

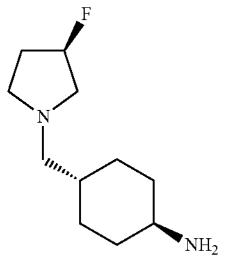 [SMILES: N[C@H]1CC[C@H](CN2CC[C@@H](F)C2)CC1]

4-(((R)-3-fluoropyrrolidin-1-yl)methyl)cyclohexanamine was prepared with conditions described in Example 117 and 118 using trans-4-[(tert-butoxycarbonyl)amino)cyclohexyl]methyl methanesulfonate and (R)-3-fluoropyrrolidine.

Example 232

(S)-tert-butyl(1-(5-((6-(3-chloro-5-fluoro-4-hydroxyphenyl)-3-(cyclobutanecarbonyl)-1,5-naphthyridin-4-yl)amino)pyridin-2-yl)piperidin-3-yl)carbamate

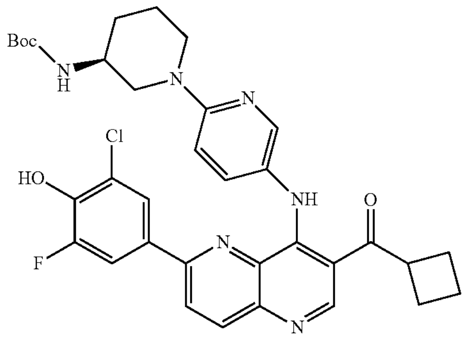 [SMILES: CC(C)(C)OC(=O)N[C@H]1CCCN(c2ccc(Nc3c(C(=O)C4CCC4)cnc4ccc(-c5cc(F)c(O)c(Cl)c5)nc34)cn2)C1]

Following general procedure II, (S)-tert-butyl(1-(5-((6-chloro-3-(cyclobutanecarbonyl)-1,5-naphthyridin-4-yl)amino)pyridin-2-yl)piperidin-3-yl)carbamate (110 mg, 0.20 mmol) was reacted with 2-chloro-6-fluoro-4-(4,4,5,5-tetramethyl-1,3,2-dioxaborolan-2-yl)phenol (82 mg, 0.30 mmol) to afford the product (134 mg) which was carried forward without any purification: ESI MS m/z 647 [M+H]$^+$.

Example 233

(S)-tert-butyl(1-(5-((6-chloro-3-(cyclobutanecarbonyl)-1,5-naphthyridin-4-yl)amino)pyridin-2-yl)piperidin-3-yl)carbamate

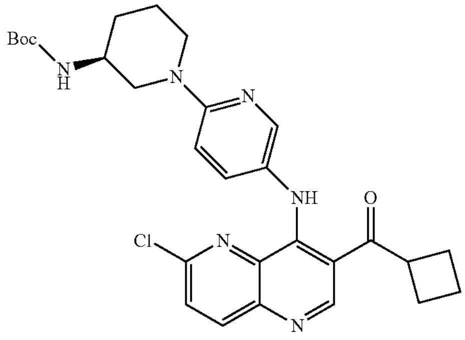 [SMILES: CC(C)(C)OC(=O)N[C@H]1CCCN(c2ccc(Nc3c(C(=O)C4CCC4)cnc4ccc(Cl)nc34)cn2)C1]

Following general procedure I, cyclobutyl(4,6-dichloro-1,5-naphthyridin-3-yl)methanone (200 mg, 0.71 mmol) was reacted with (S)-tert-butyl 1-(5-aminopyridin-2-yl)piperidin-3-ylcarbamate (311 mg, 1.1 mmol) to afford the desired product (350 mg, 78%) as an orange solid: $^1$H NMR (300 MHz, $CDCl_3$) δ 11.52 (s, 1H), 8.88 (s, 1H), 8.08 (d, J=8.7 Hz, 1H), 8.02 (d, J=2.7 Hz, 1H), 7.45 (d, J=8.7 Hz, 1H), 7.31 (dd, J=9.0, 2.7 Hz, 1H), 6.72 (d, J=9.0 Hz, 1H), 4.81 (br s, 1H), 4.15-3.97 (m, 1H), 3.91-3.60 (m, 3H), 3.58-3.31 (m, 2H), 2.54-2.21 (m, 4H), 2.20-2.00 (m, 1H), 2.00-1.85 (m, 2H), 1.82-1.63 (m, 2H), 1.51 (s, 9H); ESI MS m/z 537 [M+H]$^+$.

Example 234 cyclobutyl(4,6-dichloro-1,5-naphthyridin-3-yl)methanone

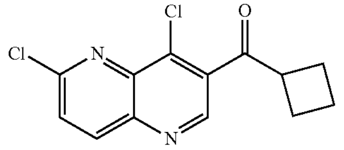 [SMILES: O=C(c1cnc2ccc(Cl)nc2c1Cl)C1CCC1]

Cyclobutyl(4,6-dichloro-1,5-naphthyridin-3-yl)methanone was prepared with conditions described in Example 101 (Scheme 2) using cyclobutyl(4-hydroxy-6-methoxy-1,5-naphthyridin-3-yl)methanone.

Example 235 cyclobutyl(4-hydroxy-6-methoxy-1,5-naphthyridin-3-yl)methanone

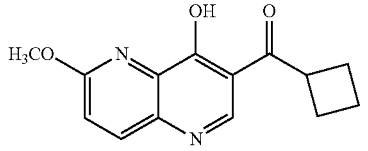 [SMILES: COc1ccc2ncc(C(=O)C3CCC3)c(O)c2n1]

Cyclobutyl(4-hydroxy-6-methoxy-1,5-naphthyridin-3-yl) methanone was prepared with conditions described in Example 100 using ethyl 2-(cyclobutanecarbonyl)-3-((6-methoxypyridin-3-yl)amino)acrylate.

Example 236 ethyl 2-(cyclobutanecarbonyl)-3-((6-methoxypyridin-3-yl)amino)acrylate

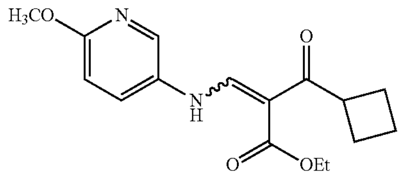 [SMILES: CCOC(=O)C(=CNc1ccc(OC)nc1)C(=O)C1CCC1]

Ethyl 2-(cyclobutanecarbonyl)-3-((6-methoxypyridin-3-yl)amino)acrylate was prepared with conditions described in Example 99 using 2-methoxy-5-aminopyridine and ethyl 2-(cyclobutanecarbonyl)-3-ethoxyacrylate.

Example 237

(6-chloro-4-((4-((dimethylamino)methyl)cyclohexyl)amino)-1,5-naphthyridin-3-yl)(cyclobutyl)methanone

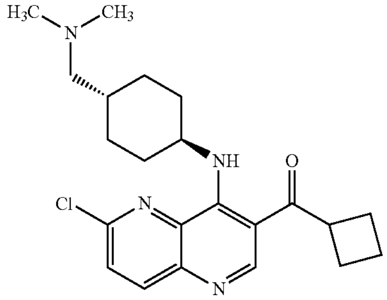 [SMILES: CN(C)C[C@H]1CC[C@H](Nc2c(C(=O)C3CCC3)cnc3ccc(Cl)nc23)CC1]

(6-Chloro-4-((4-((dimethylamino)methyl)cyclohexyl)amino)-1,5-naphthyridin-3-yl)(cyclobutyl)methanone was prepared with conditions described in Example 131 using cyclobutyl(4,6-dichloro-1,5-naphthyridin-3-yl)methanone and trans-4-((dimethylamino)methyl)cyclohexanamine.

Example 238

(R)-tert-butyl(1-(5-((6-(3-chloro-5-fluoro-4-hydroxyphenyl)-3-propionyl-1,5-naphthyridin-4-yl)amino)pyridin-2-yl)piperidin-3-yl)carbamate

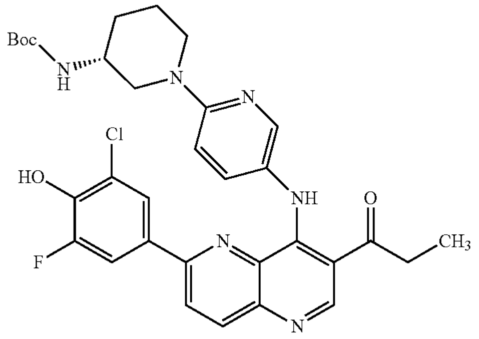 [SMILES: CCC(=O)c1cnc2ccc(-c3cc(F)c(O)c(Cl)c3)nc2c1Nc1ccc(N2CCC[C@@H](NC(=O)OC(C)(C)C)C2)nc1]

Following general procedure II, (R)-tert-butyl(1-(5-((6-chloro-3-propionyl-1,5-naphthyridin-4-yl)amino)pyridin-2-yl)piperidin-3-yl)carbamate (175 mg, 0.34 mmol) was reacted with 2-chloro-6-fluoro-4-(4,4,5,5-tetramethyl-1,3,2-dioxaborolan-2-yl)phenol (140 mg, 0.51 mmol) to afford the desired product (120 mg, 57%) as a solid: ESI MS m/z 621 $[M+H]^+$.

Example 239

(R)-tert-butyl(1-(5-((6-chloro-3-propionyl-1,5-naphthyridin-4-yl)amino)pyridin-2-yl)piperidin-3-yl)carbamate

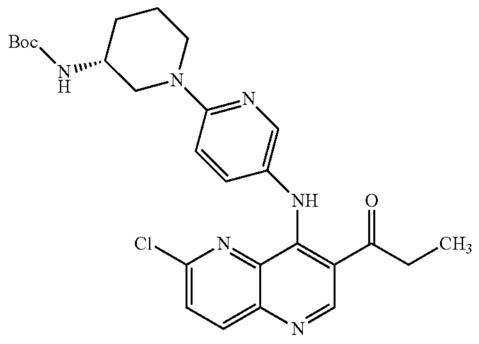 [SMILES: CCC(=O)c1cnc2ccc(Cl)nc2c1Nc1ccc(N2CCC[C@@H](NC(=O)OC(C)(C)C)C2)nc1]

Following general procedure I, 1-(4,6-dichloro-1,5-naphthyridin-3-yl)propan-1-one (500 mg, 1.96 mmol) was reacted with (R)-tert-butyl(1-(5-aminopyridin-2-yl)piperidin-3-yl)carbamate (860 mg, 2.94 mmol) to afford the desired product (850 mg, 84%) as a light brown solid: ESI MS m/z 511 $[M+H]^+$.

Example 240

(R)-tert-butyl(1-(5-((6-(3,5-dichloro-4-hydroxyphenyl)-3-propionyl-1,5-naphthyridin-4-yl)amino)pyridin-2-yl)piperidin-3-yl)carbamate

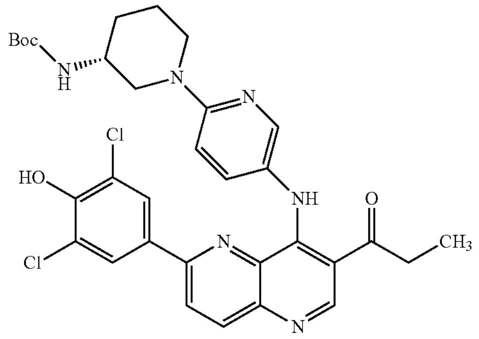 [SMILES: CCC(=O)c1cnc2ccc(-c3cc(Cl)c(O)c(Cl)c3)nc2c1Nc1ccc(N2CCC[C@@H](NC(=O)OC(C)(C)C)C2)nc1]

Following general procedure II, (R)-tert-butyl(1-(5-((6-chloro-3-propionyl-1,5-naphthyridin-4-yl)amino)pyridin-2-yl)piperidin-3-yl)carbamate (175 mg, 0.34 mmol) was reacted with 2,6-dichloro-4-(4,4,5,5-tetramethyl-1,3,2-dioxaborolan-2-yl)phenol (149 mg, 0.51 mmol) to afford the desired product (100 mg, 46%) as a solid: ESI MS m/z 637 $[M+H]^+$.

Example 241

(R)-tert-butyl(1-(5-((6-(3-chloro-5-fluoro-4-hydroxyphenyl)-3-isobutyryl-1,5-naphthyridin-4-yl)amino)pyridin-2-yl)piperidin-3-yl)carbamate

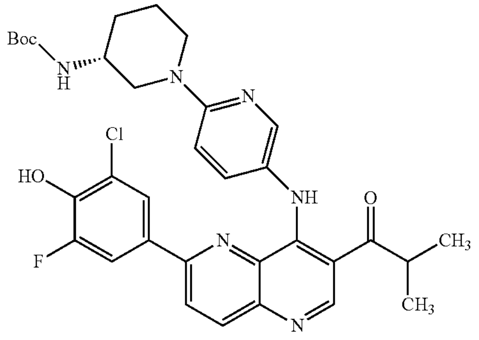 [SMILES: CC(C)C(=O)c1cnc2ccc(-c3cc(F)c(O)c(Cl)c3)nc2c1Nc1ccc(N2CCC[C@@H](NC(=O)OC(C)(C)C)C2)nc1]

Following general procedure II, (R)-tert-butyl(1-(5-((6-chloro-3-isobutyryl-1,5-naphthyridin-4-yl)amino)pyridin-2-yl)piperidin-3-yl)carbamate (225 mg, 0.63 mmol) was reacted with 2-chloro-6-fluoro-4-(4,4,5,5-tetramethyl-1,3,2-dioxaborolan-2-yl)phenol (175 mg, 0.66 mmol) to afford the desired product (168 mg, 62%) solid: ESI MS m/z 635 $[M+H]^+$.

Example 242

(R)-tert-butyl(1-(5-((6-chloro-3-isobutyryl-1,5-naphthyridin-4-yl)amino)pyridin-2-yl)piperidin-3-yl)carbamate

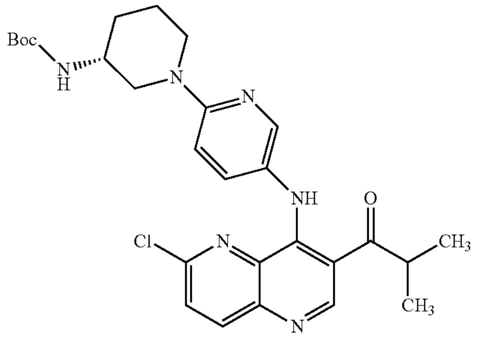 [SMILES: CC(C)C(=O)c1cnc2ccc(Cl)nc2c1Nc1ccc(N2CCC[C@@H](NC(=O)OC(C)(C)C)C2)nc1]

Following general procedure I, 1-(4,6-dichloro-1,5-naphthyridin-3-yl)-2-methylpropan-1-one (500 mg, 1.85 mmol) was reacted with (R)-tert-butyl(1-(5-aminopyridin-2-yl)piperidin-3-yl)carbamate (815 mg, 2.78 mmol) to afford the desired product (880 mg, 88%) as a red solid: ESI MS m/z 525 $[M+H]^+$.

Example 243

1-(4,6-dichloro-1,5-naphthyridin-3-yl)-2-methylpropan-1-one

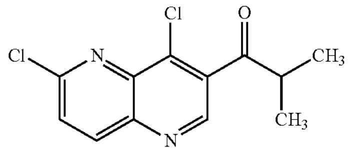 [SMILES: CC(C)C(=O)c1cnc2ccc(Cl)nc2c1Cl]

To a suspension of 1-(4,6-dihydroxy-1,5-naphthyridin-3-yl)-2-methylpropan-1-one (15.5 g, 63.0 mmol) in acetonitrile (250 ml) was added trimethylsilylchloride (20.5 g, 189 mmol) and sodium iodide (28.3 g, 189 mmol) and the reaction mixture was heated at reflux for 3 h. The reaction mixture was cooled to room temperature and satd. aq. sodium thiosulfate was added. The mixture was concentrated to remove acetonitrile, diluted with brine and the solids were filtered and dried to provide the intermediate 1-(4-hydroxy-6-methoxy-1,5-naphthyridin-3-yl)-2-methylpropan-1-one. This intermediate was suspended in phosphorus oxychloride (60 mL) and catalytic N,N-dimethylformamide and the reaction mixture was stirred with heat at 70° C. for 30 min. The reaction mixture was cooled to room temperature and quenched by pouring slowly into ice-cold satd. aq. sodium bicarbonate or 3 N sodium hydroxide. The quenched reaction mixture was concentrated to remove the dichloroethane and the resulting solids were collected by filtration and purified by chromatography (silica, hexanes/ethyl acetate) to provide the desired product (12.0 g, 75% over 2 steps) as a yellow solid: ESI MS m/z 255 $[M+H]^+$.

Example 244

1-(4-hydroxy-6-methoxy-1,5-naphthyridin-3-yl)-2-methylpropan-1-one

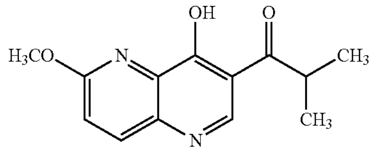 [SMILES: COc1ccc2ncc(C(=O)C(C)C)c(O)c2n1]

To a flask containing Dowtherm™ A (400 mL) at 250° C. was added ethyl 2-(((6-methoxypyridin-3-yl)amino)methylene)-4-methyl-3-oxopentanoate (11.5 g, 39.3 mmol) portion wise over 3 to 5 min and the reaction mixture was stirred for an additional 30 to 45 min. The reaction mixture was removed from the heat source, cooled to room temperature and diluted with hexanes to facilitate precipitation. The solids were filtered, washed with hexanes and dried under vacuum to afford the desired product (13.7 g, crude) as a yellow-brown solid: ESI MS m/z 247 $[M+H]^+$.

Example 245 ethyl 2-(((6-methoxypyridin-3-yl)amino)methylene)-4-methyl-3-oxopentanoate

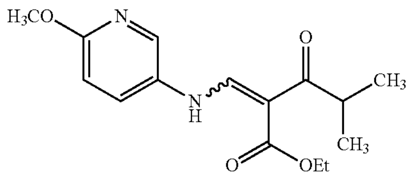 [SMILES: CCOC(=O)C(=CNc1ccc(OC)nc1)C(=O)C(C)C]

Ethyl 2-(((6-methoxypyridin-3-yl)amino)methylene)-4-methyl-3-oxopentanoate was prepared with conditions described in Example 99 using 2-methoxy-5-aminopyridine and ethyl 2-(ethoxymethylene)-4-methyl-3-oxopentanoate.

Example 246

1-(6-chloro-4-((4-((dimethylamino)methyl)cyclohexyl)amino)-1,5-naphthyridin-3-yl)-2-methylpropan-1-one

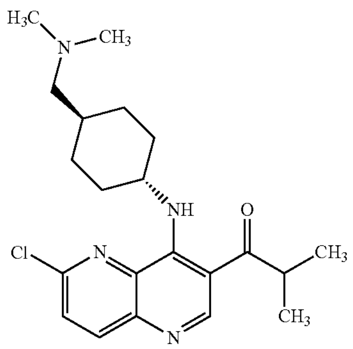 [SMILES: CC(C)C(=O)c1cnc2ccc(Cl)nc2c1N[C@H]1CC[C@H](CN(C)C)CC1]

Following general procedure I, 1-(4,6-dichloro-1,5-naphthyridin-3-yl)-2-methylpropan-1-one (500 mg, 1.85 mmol) was reacted with trans-4-((dimethylamino)methyl)cyclohexanamine (436 mg, 2.78 mmol) to afford the product (640 mg, 89%) as a white solid: ESI MS m/z 389 $[M+H]^+$.

Compounds of the invention of this application not particularly described in the Examples above were also be synthesized by similar or analogous methods by referring to the above-mentioned Examples and such.

Next, the pharmacological activities of compound (I) will be described in the following Test Examples.

TEST EXAMPLES

Kinase Assay

MELK activity was determined in the presence or absence of compounds using fluorescein isothiocyanate-labeled (FITC-labeled) histone H3 peptide as a substrate. The extent of FITC-labeled histone H3 peptide phosphorylation was measured by immobilized metal ion affinity-based fluorescence polarization (IMAP) technology (Sportsman J R, et al., Assay Drug Dev. Technol. 2: 205-14, 2004) using IMAP FP Progressive Binding System (Molecular Devices Corporation). Test compounds were dissolved in DMSO at 12.5 mM and then serially diluted as the DMSO concentration in the assays to be 1%. The serially diluted compounds, 0.8 ng/micro-L PBK (Carna Biosciences) and 100 nM FITC-labeled histone H3 peptide were reacted in a reaction buffer (20 mM HEPES, 0.01% Tween-20, 0.3 mM $MgCl_2$, 2 mM dithiothreitol, 50 micro-M ATP, pH 7.4) at room temperature for 1 hour. The reaction was stopped by the addition of three fold assay volume of progressive binding solution. Following 0.5 hour incubation at room temperature, fluorescence polarization was measured by Wallac EnVision 2103 multilabel reader (PerkinElmer). IC50 values were calculated by nonlinear four parameter fit using SigmaPlot, version 10.0 (Systat Software, Inc.).

$IC_{50}$ values of the typical compounds of the present invention are shown in the following table 2:

TABLE 2

| Example | Compound Name | $IC_{50}$ (μM) (kinase assay) |
|---|---|---|
| 1 | 1-(6-Chloro-4-{trans-4-[(dimethylamino)methyl]-cyclohexylamino}-1,5-naphthyridin-3-yl)ethanone | 0.31 |
| 2 | 1-{6-(3,5-Dichloro-4-hydroxyphenyl)-4-[trans-4-(dimethylamino)-cyclohexylamino]-1,5-naphthyridin-3-yl}ethanone dihydrochloride | 0.0003 |
| 3 | 1-{6-(3-Chloro-5-fluoro-4-hydroxyphenyl)-4-[trans-4-(dimethylamino)-cyclohexylamino]-1,5-naphthyridin-3-yl}ethanone dihydrochloride | 0.0012 |
| 4 | Cyclopropyl(6-(3,5-dichloro-4-hydroxyphenyl)-4-{trans-4-[(dimethyl-amino)methyl]cyclohexylamino}-1,5-naphthyridin-3-yl)methanone dihydrochloride | 0.0005 |
| 5 | (6-(3-Chloro-5-fluoro-4-hydroxyphenyl)-4-{trans-4-[(dimethylamino)-methyl)cyclohexylamino]-1,5-naphthyridin-3-yl}(cyclopropyl)methanone dihydrochloride | 0.0008 |
| 6 | 1-{6-(3,5-Dichloro-4-hydroxyphenyl)-4-({trans-4-[(dimethylamino)-methyl]cyclohexyl}amino)-1,5-naphthyridin-3-yl}ethanone dihydrochloride | 0.0011 |
| 7 | 1-{6-(3-Chloro-5-fluoro-4-hydroxyphenyl)-4-({trans-4-[(dimethyl-amino)methyl]cyclohexyl}amino)-1,5-naphthyridin-3-yl}ethanone dihydrochloride | 0.0013 |
| 8 | 1-(6-(3-Chloro-4-hydroxy-5-methoxyphenyl)-4-{trans-4-[(dimethyl-amino)methyl]cyclohexylamino}-1,5-naphthyridin-3-yl)ethanone dihydrochloride | 0.0015 |
| 9 | 1-[6-(3,5-Dichloro-4-hydroxyphenyl)-4-({trans-4-[2-(dimethylamino)-ethyl]cyclohexyl}amino)-1,5-naphthyridin-3-yl]ethanone dihydrochloride | 0.0007 |
| 10 | 1-(6-(3-Chloro-5-fluoro-4-hydroxyphenyl)-4-{trans-4-[2-(dimethylamino)ethyl]cyclohexylamino}-1,5-naphthyridin-3-yl)ethanone dihydrochloride | 0.0014 |
| 11 | 1-(4-{trans-4-[(Dimethylamino)methyl]cyclohexylamino}-6-[4-hydroxy-3-(trifluoromethoxy)phenyl]-1,5-naphthyridin-3-yl)ethanone dihydrochloride | 0.0027 |
| 12 | 2,6-Dichloro-4-(8-{trans-4-[(dimethylamino)methyl]cyclohexylamino}-7-(methylsulfonyl)-1,5-naphthyridin-2-yl)phenol dihydrochloride | 0.001 |
| 13 | 6-(3-Chloro-5-fluoro-4-hydroxyphenyl)-4-({trans-4-[(dimethylamino)-methyl]cyclohexyl}amino)-3-methylsulfonyl-1,5-naphthyridine dihydrochloride | 0.0014 |
| 14 | 6-(3-Chloro-4-hydroxy-5-methoxyphenyl)-4-{trans-4-[(dimethylamino)-methyl]cyclohexylamino}-3-methylsulfonyl-1,5-naphthyridine dihydrochloride | 0.0009 |
| 15 | 2,6-Dichloro-4-{8-[trans-4-(dimethylamino)cyclohexylamino]-7-(methylsulfonyl)-1,5-naphthyridin-2-yl}phenol dihydrochloride | 0.0005 |
| 16 | 2,6-Dichloro-4-(8-(4-((dimethylamino)methyl)phenylamino)-7-(methylsulfonyl)-1,5-naphthyridin-2-yl)phenol dihydrochloride | 0.0028 |
| 17 | 2-Chloro-4-(8-(4-((dimethylamino)methyl)phenylamino)-7-(methylsulfonyl)-1,5-naphthyridin-2-yl)-6-fluorophenol dihydrochloride | 0.0081 |
| 18 | 2-Chloro-4-(8-(4-((dimethylamino)methyl)phenylamino)-7-(methylsulfonyl)-1,5-naphthyridin-2-yl)-6-methoxyphenol dihydrochloride | 0.005 |
| 19 | 1-(6-(3,5-Dichloro-4-hydroxyphenyl)-4-(3-(2-(pyrrolidin-1-yl)ethyl)-phenylamino)-1,5-naphthyridin-3-yl)ethanone dihydrochloride | 0.032 |
| 20 | 1-(6-(3-Chloro-5-fluoro-4-hydroxyphenyl)-4-(3-(2-(pyrrolidin-1-yl)-ethyl)phenylamino)-1,5-naphthyridin-3-yl)ethanone dihydrochloride | 0.14 |
| 21 | 1-(6-(3,5-Dichloro-4-hydroxyphenyl)-4-(6-(2-(dimethylamino)-ethoxy)pyridin-3-ylamino)-1,5-naphthyridin-3-yl)ethanone dihydrochloride | 0.0046 |
| 22 | 1-(6-(3-Chloro-5-fluoro-4-hydroxyphenyl)-4-(6-(2-(dimethylamino)-ethoxy)pyridin-3-ylamino)-1,5-naphthyridin-3-yl)ethanone dihydrochloride | 0.015 |
| 23 | 1-(6-(3-Chloro-4-hydroxy-5-methoxyphenyl)-4-(6-(2-(dimethylamino)-ethoxy)pyridin-3-ylamino)-1,5-naphthyridin-3-yl)ethanone dihydrochloride | 0.0089 |

TABLE 2-continued

| Example | Compound Name | $IC_{50}$ (μM) (kinase assay) |
|---|---|---|
| 24 | 2,6-Dichloro-4-(8-(6-(2-(dimethylamino)ethoxy)pyridin-3-ylamino)-7-(methylsulfonyl)-1,5-naphthyridin-2-yl)phenol hydrochloride | 0.0053 |
| 25 | 2-Chloro-4-(8-(6-(2-(dimethylamino)ethoxy)pyridin-3-ylamino)-7-(methylsulfonyl)-1,5-naphthyridin-2-yl)-6-fluorophenol dihydrochloride | 0.019 |
| 26 | 2-Chloro-4-(8-(6-(2-(dimethylamino)ethoxy)pyridin-3-ylamino)-7-(methylsulfonyl)-1,5-naphthyridin-2-yl)-6-methoxyphenol dihydrochloride | 0.01 |
| 27 | 1-(6-(3,5-Dichloro-4-hydroxyphenyl)-4-((1-methylpiperidin-4-yl)methylamino)-1,5-naphthyridin-3-yl)ethanone dihydrochloride | 0.0007 |
| 28 | 1-(6-(3,5-Dichloro-4-hydroxyphenyl)-4-(trans-4-((dimethylamino-d6)-methyl)cyclohexylamino)-1,5-naphthyridin-3-yl)ethanone dihydrochloride | 0.0004 |
| 29 | 1-(6-(3,5-Dichloro-4-hydroxyphenyl)-4-(4-(2-(dimethylamino)-ethyl)phenylamino)-1,5-naphthyridin-3-yl)ethanone dihydrochloride | 0.0026 |
| 30 | 1-(6-(3-Chloro-5-fluoro-4-hydroxyphenyl)-4-(4-(2-(dimethylamino)-ethyl)phenylamino)-1,5-naphthyridin-3-yl)ethanone dihydrochloride | 0.0059 |
| 31 | 1-(6-(3-Chloro-4-hydroxy-5-methoxyphenyl)-4-(4-(2-(dimethylamino)-ethyl)phenylamino)-1,5-naphthyridin-3-yl)ethanone dihydrochloride | 0.0037 |
| 32 | 2-Chloro-4-(8-(trans-4-(dimethylamino)cyclohexylamino)-7-(methylsulfonyl)-1,5-naphthyridin-2-yl)-6-fluorophenol dihydrochloride | 0.0016 |
| 33 | 1-(6-(3,5-Dichloro-4-hydroxyphenyl)-4-(1-(1-methylpiperidin-4-yl)-1H-pyrazol-4-ylamino)-1,5-naphthyridin-3-yl)ethanone dihydrochloride | 0.0078 |
| 34 | 1-(6-(3,5-Dichloro-4-hydroxyphenyl)-4-(4-((4-methylpiperazin-1-yl)methyl)phenylamino)-1,5-naphthyridin-3-yl)ethanone trihydrochloride | 0.0061 |
| 35 | 1-(6-(3-Chloro-5-fluoro-4-hydroxyphenyl)-4-(4-((4-methylpiperazin-1-yl)methyl)phenylamino)-1,5-naphthyridin-3-yl)ethanone trihydrochloride | 0.037 |
| 36 | 1-(6-(3,5-Dichloro-4-hydroxyphenyl)-4-(4-(2-(pyrrolidin-1-yl)ethyl)piperidin-1-yl)-1,5-naphthyridin-3-yl)ethanone dihydrochloride | 0.0021 |
| 37 | 1-(6-(3-Chloro-5-fluoro-4-hydroxyphenyl)-4-(4-(2-(pyrrolidin-1-yl)-ethyl)piperidin-1-yl)-1,5-naphthyridin-3-yl)ethanone dihydrochloride | 0.01 |
| 38 | 1-(6-(3,5-Dichloro-4-hydroxyphenyl)-4-(6-(2-(dimethylamino)ethyl-amino)pyridin-3-ylamino)-1,5-naphthyridin-3-yl)ethanone trihydrochloride | 0.011 |
| 39 | 1-(6-(3-Chloro-5-fluoro-4-hydroxyphenyl)-4-(6-(2-(dimethylamino)-ethylamino)pyridin-3-ylamino)-1,5-naphthyridin-3-yl)ethanone trihydrochloride | 0.03 |
| 40 | (S)-(4-(6-(3-Aminopiperidin-1-yl)pyridin-3-ylamino)-6-(3,5-dichloro-4-hydroxyphenyl)-1,5-naphthyridin-3-yl)-(cyclopropyl)methanone trihydrochloride | 0.0012 |
| 41 | 1-(4-(2-(3-Aminopyrrolidin-1-yl)pyrimidin-5-ylamino)-6-(3,5-dichloro-4-hydroxyphenyl)-1,5-naphthyridin-3-yl)ethanone trihydrochloride | 0.0017 |
| 42 | 1-(4-{trans-4-[(Dimethylamino)methyl]cyclohexylamino}-6-(1H-pyrazol-4-yl)-1,5-naphthyridin-3-yl)ethanone trihydrochloride | 0.017 |
| 43 | 1-(6-{3,5-Dichloro-4-hydroxyphenyl)-4-[trans-4-(hydroxymethyl)-cyclohexyl]amino}-1,5-naphthyridin-3-yl)ethanone hydrochloride | 0.0031 |
| 44 | 1-[6-(3,5-Dichloro-4-hydroxyphenyl)-4-{trans-4-[(dimethylamino)-methyl]cyclohexylamino}-1,5-naphthyridin-3-yl]-2-hydroxyethanone dihydrochloride | 0.0003 |
| 45 | 1-{6-(3,5-Dichloro-4-hydroxyphenyl)-4-[(1-methylpiperidin-4-yl)amino]-1,5-naphthyridin-3-yl}ethanone | 0.0058 |
| 46 | 1-{6-(3-Chloro-5-fluoro-4-hydroxyphenyl)-4-[(1-methylpiperidin-4-yl)-amino]-1,5-naphthyridin-3-yl}ethanone | 0.0061 |
| 47 | 1-(6-(3,5-Dichloro-4-hydroxyphenyl)-4-{[4-(morpholinomethyl)-cyclohexyl]amino}-1,5-naphthyridin-3-yl)ethanone | 0.01 |
| 48 | 1-[6-(3,5-Dichloro-4-hydroxyphenyl)-4-(4-{[(2-hydroxyethyl)(methyl)-amino]methyl}cyclohexylamino)-1,5-naphthyridin-3-yl]-ethanone dihydrochloride | 0.0006 |
| 49 | 1-[6-(3-Chloro-5-fluoro-4-hydroxyphenyl)-4-(4-{[(2-hydroxyethyl)-(methyl)amino]methyl}cyclohexylamino)-1,5-naphthyridin-3-yl]-ethanone dihydrochloride | 0.001 |

TABLE 2-continued

| Example | Compound Name | $IC_{50}$ (μM) (kinase assay) |
|---|---|---|
| 50 | 1-(6-(3,5-Difluoro-4-hydroxyphenyl)-4-{4-[(dimethylamino)methyl]-cyclohexylamino}-1,5-naphthyridin-3-yl)ethanone dihydrochloride | 0.0019 |
| 51 | 1-(6-(3,5-Dichloro-4-hydroxyphenyl)-4-{6-[3-(dimethylamino)pyrrolidin-1-yl]pyridin-3-ylamino}-1,5-naphthyridin-3-yl)ethanone trihydrochloride | 0.0082 |
| 52 | 1-(6-(3-Chloro-5-fluoro-4-hydroxyphenyl)-4-{6-[3-(dimethylamino)-pyrrolidin-1-yl]pyridin-3-ylamino}-1,5-naphthyridin-3-yl)ethanone trihydrochloride | 0.027 |
| 53 | 1-(6-(3,5-Dichloro-4-hydroxyphenyl)-4-{6-[3-(methylamino)pyrrolidin-1-yl]pyridin-3-ylamino}-1,5-naphthyridin-3-yl)ethanone trihydrochloride | 0.0015 |
| 54 | 1-(6-(3-Chloro-5-fluoro-4-hydroxyphenyl)-4-{6-[3-(methylamino)-pyrrolidin-1-yl]pyridin-3-ylamino}-1,5-naphthyridin-3-yl)ethanone trihydrochloride | 0.012 |
| 55 | 1-(6-(1H-Benzo[d]imidazol-5-yl)-4-{trans-4-[(dimethylamino)methyl]-cyclohexylamino}-1,5-naphthyridin-3-yl)ethanone trihydrochloride | 0.017 |
| 56 | 1-{4-[4-(trans-4-Dimethylamino)methylcyclohexylamino]-6-(pyridin-4-yl)-1,5-naphthyridin-3-yl}ethanone trihydrochloride | 0.016 |
| 57 | 5-(7-Acetyl-8-{trans-4-[(dimethylamino)methyl]cyclohexylamino}-1,5-naphthyridin-2-yl)pyrimidine-2-carbonitrile | 0.0012 |
| 58 | 1-(6-(3,5-Dimethyl-1H-pyrazol-4-yl)-4-{trans-4-[(dimethylamino)-methyl]cyclohexylamino}-1,5-naphthyridin-3-yl)ethanone trihydrochloride | 1 |
| 59 | 1-(4-{trans-4-[(DimethylaminoDimethylamino)methyl]cyclohexylamino}-6-(4-hydroxy-3,5-dimethylphenyl)-1,5-naphthyridin-3-yl)ethanone dihydrochloride | 0.0047 |
| 60 | 1-(6-(3,5-Dichloro-4-hydroxyphenyl)-4-{6-[3-(dimethylamino)pyrrolidin-1-yl]pyridin-3-ylamino}-1,5-naphthyridin-3-yl)ethanone dihydrochloride | 0.0043 |
| 61 | 1-{6-(3,5-Dichloro-4-hydroxyphenyl)-4-[trans-4-(pyrrolidin-1-ylmethyl)-cyclohexylamino]-1,5-naphthyridin-3-yl}ethanone dihydrochloride | 0.0004 |
| 62 | 1-(6-(3-Chloro-5-fluoro-4-hydroxyphenyl)-4-{[trans-4-(pyrrolidin-1-ylmethyl)cyclohexyl]amino}-1,5-naphthyridin-3-yl)ethanone dihydrochloride | 0.0009 |
| 63 | 1-(6-(3,5-Dichloro-4-hydroxyphenyl)-4-{4-[(4-methylpiperazin-1-yl)-methyl]cyclohexylamino}-1,5-naphthyridin-3-yl)ethanone trihydrochloride | 0.0008 |
| 64 | 1-(4-{[6-(3-Aminopiperidin-1-yl)pyridin-3-yl]amino}-6-(3,5-dichloro-4-hydroxyphenyl)-1,5-naphthyridin-3-yl)ethanone trihydrochloride | 0.0012 |
| 65 | 1-(4-{[6-(3-Aminopiperidin-1-yl)pyridin-3-yl]amino}-6-(3-chloro-5-fluoro-4-hydroxyphenyl)-1,5-naphthyridin-3-yl)ethanone trihydrochloride | 0.0031 |
| 66 | 1-{4-[(4-Aminocyclohexyl)amino]-6-(3,5-dichloro-4-hydroxyphenyl)-1,5-naphthyridin-3-yl}ethanone dihydrochloride | 0.0018 |
| 67 | 1-{4-[trans-(4-Aminocyclohexyl)amino]-6-(3-chloro-5-fluoro-4-hydroxyphenyl)-1,5-naphthyridin-3-yl}ethanone dihydrochloride | 0.0012 |
| 68 | 1-(6-(3-Chloro-5-fluoro-4-hydroxyphenyl)-4-{4-[(4-methylpiperazin-1-yl)methyl]cyclohexylamino}-1,5-naphthyridin-3-yl)ethanone trihydrochloride | 0.0026 |
| 69 | N-(trans-4-{[3-Acetyl-6-(3-chloro-5-fluoro-4-hydroxyphenyl)-1,5-naphthyridin-4-yl]amino}cyclohexyl)-2-amino-3-methylbutanamide dihydrochloride | 0.0012 |
| 70 | 1-{6-(3,5-Dichloro-4-hydroxyphenyl)-4-[trans-4-(piperazin-1-ylmethyl)-cyclohexylamino]-1,5-naphthyridin-3-yl}ethanone trihydrochloride | 0.0006 |
| 71 | (S)-1-(4-{[6-(3-Aminopiperidin-1-yl)pyridin-3-yl]amino}-6-(3,5-dichloro-4-hydroxyphenyl)-1,5-naphthyridin-3-yl)ethanone trihydrochloride | 0.0005 |
| 72 | (S)-1-(4-{[6-(3-Aminopiperidin-1-yl)pyridin-3-yl]amino}-6-(3-chloro-5-fluoro-4-hydroxyphenyl)-1,5-naphthyridin-3-yl)ethanone trihydrochloride | 0.0043 |
| 73 | N-{trans-4-[3-Acetyl-6-(3,5-dichloro-4-hydroxyphenyl)-1,5-naphthyridin-4-ylamino]cyclohexyl}-2-aminopropanamide dihydrochloride | 0.0075 |
| 74 | N-{4-[3-Acetyl-6-(3-chloro-5-fluoro-4-hydroxyphenyl)-1,5-naphthyridin-trans-4-ylamino]cyclohexyl}-2-aminopropanamide dihydrochloride | 0.0026 |
| 75 | (S)-N-{4-[3-Acetyl-6-(3,5-dichloro-4-hydroxyphenyl)-1,5-naphthyridin-trans-4-ylamino]cyclohexyl}pyrrolidine-2-carboxamide dihydrochloride | 0.001 |
| 76 | (S)-N-{4-[3-Acetyl-6-(3-chloro-5-fluoro-4-hydroxyphenyl)-1,5-naphthyridin-trans-4-ylamino]cyclohexyl}pyrrolidine-2-carboxamide dihydrochloride | 0.0024 |
| 77 | 1-(6-(3-Hydroxypyrrolidin-1-yl)-4-{trans-4-[(3-hydroxypyrrolidin-1-yl)methyl]cyclohexylamino}-1,5-naphthyridin-3-yl)ethanone | 0.74 |

TABLE 2-continued

| Example | Compound Name | $IC_{50}$ (μM) (kinase assay) |
|---|---|---|
| 78 | 1-{6-(Pyrrolidin-1-yl)-4-[trans-4-(pyrrolidin-1-ylmethyl)-cyclohexylamino]-1,5-naphthyridin-3-yl}ethanone | 2 |
| 79 | N-{trans-4-[3-Acetyl-6-(3,5-dichloro-4-hydroxyphenyl)-1,5-naphthyridin-4-ylamino]cyclohexyl}-2-amino-3-methylbutanamide dihydrochloride | 0.0016 |
| 80 | Cyclopropyl{6-(3,5-dichloro-4-hydroxyphenyl)-4-[trans-4-(dimethylamino)cyclohexylamino]-1,5-naphthyridin-3-yl}methanone dihydrochloride | 0.0006 |
| 81 | 1-[6-(3-Chloro-5-fluoro-4-methoxyphenyl)-4-{trans-4-[(dimethylamino)-methyl]cyclohexylamino}-1,5-naphthyridin-3-yl]ethanone dihydrochloride | 0.0005 |
| 82 | 1-(4-{trans-4-[(Dimethylamino)methyl]cyclohexylamino}-6-(1H-pyrrolo[2,3-b]pyridin-5-yl)-1,5-naphthyridin-3-yl)ethanone trihydrochloride | 0.013 |
| 83 | (S)-{4-[6-(3-Aminopiperidin-1-yl)pyridin-3-ylamino]-6-(3-chloro-5-fluoro-4-hydroxyphenyl)-1,5-naphthyridin-3-yl}(cyclopropyl)methanone | 0.001 |
| 84 | 1-(4-{trans-4-[(Dimethylamino)methyl]cyclohexylamino}-6-(4-methoxyphenyl)-1,5-naphthyridin-3-yl)ethanone dihydrochloride | 0.031 |
| 85 | 1-[6-(3,5-Dichloro-4-methoxyphenyl)-4-{trans-4-[(dimethylamino)-methyl]cyclohexylamino}-1,5-naphthyridin-3-yl]ethanone dihydrochloride | 0.12 |
| 86 | 1-(4-{trans-4-[(Dimethylamino)methyl]cyclohexylamino}-6-(6-hydroxypyridin-3-yl)-1,5-naphthyridin-3-yl)ethanone dihydrochloride | 0.011 |
| 87 | 5-(7-Acetyl-8-{trans-4-[(dimethylamino)methyl]cyclohexylamino}-1,5-naphthyridin-2-yl)picolinonitrile dihydrochloride | 0.0045 |
| 88 | 1-(4-{trans-4-[(Dimethylamino)methyl]cyclohexylamino}-6-(4-hydroxy-phenyl)-1,5-naphthyridin-3-yl)ethanone dihydrochloride | 0.0045 |
| 89 | 1-[6-(3,5-Dichloro-4-hydroxyphenyl)-4-{[trans-4-(dimethylamino)-cyclohexyl]methylamino}-1,5-naphthyridin-3-yl]ethanone dihydrochloride | 0.0006 |
| 90 | 1-[6-(3-Chloro-5-fluoro-4-hydroxyphenyl)-4-{[trans-4-(dimethylamino)-cyclohexyl]methylamino}-1,5-naphthyridin-3-yl]ethanone dihydrochloride | 0.0024 |
| 91 | 1-[6-(3,5-Dichloro-4-hydroxyphenyl)-4-(4-hydroxycyclohexylamino)-1,5-naphthyridin-3-yl]ethanone hydrochloride | 0.015 |
| 92 | 1-[6-(3-Chloro-5-fluoro-4-hydroxyphenyl)-4-(4-hydroxycyclohexylamino)-1,5-naphthyridin-3-yl]ethanone hydrochloride | 0.012 |
| 93 | 1-{6-(3-Chloro-5-fluoro-4-hydroxyphenyl)-4-({cis-4-[(dimethylamino)-methyl]cyclohexyl}amino)-1,5-naphthyridin-3-yl}ethanone dihydrochloride | 0.0011 |
| 94 | 1-{6-(3,5-Dichloro-4-hydroxyphenyl)-4-({cis-4-[(dimethylamino)-methyl]cyclohexyl}amino)-1,5-naphthyridin-3-yl}ethanone dihydrochloride | 0.0006 |
| 95 | (R)-1-{4-[6-(3-aminopiperidin-1-yl)pyridin-3-ylamino]-6-(3,5-dichloro-4-hydroxyphenyl)-1,5-naphthyridin-3-yl}ethanone trihydrochloride | 0.002 |
| 96 | (R)-1-{4-[6-(3-Aminopiperidin-1-yl)pyridin-3-ylamino]-6-(3-chloro-5-fluoro-4-hydroxyphenyl)-1,5-naphthyridin-3-yl}ethanone | 0.0036 |
| 201 | (R)-(4-{[6-(3-aminopiperidin-1-yl)pyridin-3-yl]amino}-6-(3,5-dichloro-4-hydroxyphenyl)-1,5-naphthyridin-3-yl) (cyclopropyl)methanone | 0.00093 |
| 202 | (R)-(4-{[6-(3-aminopiperidin-1-yl) pyridin-3-yl]amino}-6-(3-chloro-5-fluoro-4-hydroxyphenyl)-1,5-naphthyridin-3-yl) (cyclopropyl) methanone | 0.00046 |
| 203 | 1-[6-(3,5-dichloro-4-hydroxyphenyl)-4-{[trans-4-(dimethylamino)cyclohexyl] amino}-1,5-naphthyridin-3-yl)-2-hydroxyethanone dihydrochloride | 0.0015 |
| 204 | 1-[6-(3-chloro-5-fluoro-4-hydroxyphenyl)-4-({trans-4-[(dimethylamino)methyl]cyclohexyl} amino)-1,5-naphthyridin-3-yl)]-2-hydroxyethanone dihydrochloride | 0.0013 |
| 205 | 1-[6-(3-chloro-5-fluoro-4-hydroxyphenyl)-4-({trans-4-[(dimethylamino)methyl] cyclohexyl} amino)-1,5-naphthyridin-3-yl)]propan-1-one dihydrochloride | 0.0028 |
| 206 | 1-[6-(3,5-dichloro-4-hydroxyphenyl)-4-({trans-4-[(dimethylamino)methyl] cyclohexyl}amino)-1,5-naphthyridin-3-yl)]propan-1-one dihydrochloride | 0.0013 |
| 207 | (S)-1-(4-{[6-(3-aminopiperidin-1-yl)pyridin-3-yl]amino}-6-(3,5-dichloro-4-hydroxyphenyl)-1,5-naphthyridin-3-yl)propan-1-one trihydrochloride | 0.0016 |
| 208 | (S)-1-(4{[6-(3-aminopiperidin-1-yl)pyridin-3-yl]amino}-6-(3-chloro-5-fluoro-4-hydroxyphenyl)-1,5-naphthyridin-3-yl)propan-1-one trihydrochloride | 0.0026 |
| 209 | 1-[6-(3,5-dichloro-4-hydroxyphenyl)-4-({4-[((R)-3-fluoropyrrolidin-1yl)methyl] cyclohexyl}amino)-1,5-naphthyridin-3-yl]ethanone dihydrochloride | 0.002 |
| 210 | (S)-(4-((6-(3-aminopiperidin-1-yl)pyridin-3-yl)amino)-6-(3-chloro-5-fluoro-4-hydroxyphenyl)-1,5-naphthyridin-3-yl)(cyclobutyl)methanone dihydrochloride | 0.0014 |

TABLE 2-continued

| Example | Compound Name | $IC_{50}$ (μM) (kinase assay) |
|---|---|---|
| 211 | (6-(3,5-dichloro-4-hydroxyphenyl)-4-((4-[(dimethylamino)methyl{cyclohexyl) amino)-1,5-naphthyridin-3-yl)(cyclobutyl)methanone dihydrochloride | 0.0027 |
| 212 | (6-(3-chloro-5-fluoro-4-hydroxyphenyl)-4-((4-((dimethylamino)methyl) cyclohexyl) amino)-1,5-naphthyridin-3-yl)(cyclobutyl)methanone dihydrochloride | 0.0016 |
| 213 | (S)-(4-{[6-(3-aminopiperidin-1-yl)pyridin-3-yl]amino}-6-(3-chloro-5-fluoro-4-hydroxyphenyl)-1,5-naphthyridin-3-yl)(cyclobutyl)methanone | 0.0011 |
| 214 | (R)-1-(4-((6-(3-aminopiperidin-1-yl)pyridin-3-yl)amino)-6-(3,5-dichloro-4-hydroxyphenyl)-1,5-naphthyridin-3-yl)propan-1-one trihydrochloride | 0.0013 |
| 215 | (R)-1-(4-{[6-(3-aminopiperidin-1-yl)pyridin-3-yl]amino}-6-(3,5-dichloro-4-hydroxyphenyl)-1,5-naphthyridin-3-yl)-2-methylpropan-1-one trihydrochloride | 0.0065 |
| 216 | 1-[6-(3,5-dichloro-5-4-hydroxyphenyl)-4-({trans-4-[(dimethylamino)methyl]cyclohexyl} amino)-1,5-naphthyridin-3-yl]-2-methylpropan-1-one dihydrochloride | 0.0019 |
| 217 | 1-[6-chloro-4-({trans-4-[(dimethylamino)methyl]cyclohexyl}amino)-1,5-naphthyridin-3-yl]-2-methylpropan-1-one dihydrochloride | 0.0018 |

Western Blot Analysis

To evaluate the expression status of MELK in several cell lines, western blot analysis was performed using crude cell lysate collected from those cells. Anti-MELK antibody (clone 31, BD Biosciences) was used to visualize the expression. Breast cancer cell lines, 22Rv1, T47D, A549 and DU4475 expressed MELK significantly although Bladder cancer cell line and HT1197 showed no expression of MELK.

Cell-Based Assay

Active candidate inhibitors against MELK were evaluated for their target-specific cytotoxicity using 22Rv1, T47D, A549, DU4475 and HT-1197 cells was used for negative control. 100 micro-L of cell suspension was seeded onto 96-well microtiter plate (ViewPlate-96FTC, PerkinElmer). The initial cell concentration of 22Rv1, T47D, A549, DU4475, and HT1197 were 3,000 cells/well, 2,000 cells/well and 2,500 cells/well, respectively. Cellular growth was determined using Cell Counting Kit-8 (DOJINDO) at 72 hours after the exposure of the candidate inhibitors. IC50 was used as an indicator of the anti-proliferative activity of the inhibitors, and calculated by serial dilution method (0, 1.5625, 3.125, 6.25, 12.5, 25, 50, and 100 micro-M). Accurate IC50 values were calculated as described previously.

$IC_{50}$ values of the typical compounds of the present invention are shown in the following table 3:

TABLE 3

| Ex. | Compound Name | IC50 (μM) (22Rvl) | IC50 (μM) (T47D) | IC50 (μM) (A549) | IC50 (μM) (DU4475) | IC50 (μM) (HTl197) |
|---|---|---|---|---|---|---|
| 1 | 1-(6-Chloro-4-{trans-4-[(dimethyl-amino)methyl]cyclohexylamino}-1,5-naphthyridin-3-yl)ethanone | 5 | 5.3 | 2.7 | 2.5 | 10 |
| 2 | 1-{6-(3,5-Dichloro-4-hydroxy-phenyl)-4-[trans-4-(dimethyl-amino)cyclohexylamino]-1,5-naphthyridin-3-yl}ethanone dihydrochloride | 0.0032 | 0.0018 | 0.004 | 0.0015 | 0.19 |
| 3 | 1-{6-(3-Chloro-5-fluoro-4-hydroxyphenyl)-4-[trans-4-(dimethylamino)cyclohexylamino]-1,5-naphthyridin-3-yl}ethanone Dihydrochloride | 0.006 | 0.0026 | 0.0091 | 0.0033 | 0.39 |
| 4 | Cyclopropyl(6-(3,5-dichloro-4-hydroxyphenyl)-4-{trans-4-[(dimethylamino)methyl]cyclo-hexylamino]-1,5-naphthyridin-3-yl)methanone dihydrochloride | 0.0064 | 0.0055 | 0.0062 | 0.0026 | 0.036 |
| 5 | (6-(3-Chloro-5-fluoro-4-hydroxy-phenyl)-4-{trans-4-[(dimethyl-amino)methyl)cyclohexylamino]-1,5-naphthyridin-3-yl}(cyclopropyl) methanone dihydrochloride | 0.0057 | 0.0029 | 0.0061 | 0.003 | 0.018 |
| 6 | 1-{6-(3,5-Dichloro-4-hydroxy-phenyl)-4-({trans-4-[(dimethyl-amino)methyl]cyclohexyl}amino)-1,5-naphthyridin-3-yl}ethanone dihydrochloride | 0.0052 | 0.0053 | 0.0089 | 0.0033 | 0.12 |
| 7 | 1-{6-(3-Chloro-5-fluoro-4-hydroxy-phenyl)-4-({trans-4-[(dimethyl- | 0.0061 | 0.0035 | 0.0097 | 0.0036 | 0.11 |

TABLE 3-continued

| Ex. | Compound Name | IC50 (μM) (22Rv1) | IC50 (μM) (T47D) | IC50 (μM) (A549) | IC50 (μM) (DU4475) | IC50 (μM) (HT1197) |
|---|---|---|---|---|---|---|
|  | amino)methyl]cyclohexyl}amino)-1,5-naphthyridin-3-yl}ethanone dihydrochloride |  |  |  |  |  |
| 8 | 1-(6-(3-Chloro-4-hydroxy-5-methoxyphenyl)-4-{trans-4-[(dimethylamino)methyl]cyclohexylamino}-1,5-naphthyridin-3-yl)ethanone dihydrochloride | 0.044 | 0.013 | 0.024 | 0.0064 | 0.24 |
| 9 | 1-[6-(3,5-Dichloro-4-hydroxyphenyl)-4-({trans-4-[2-(dimethylamino)ethyl]cyclohexyl}amino)-1,5-naphthyridin-3-yl]ethanone dihydrochloride | 0.011 | 0.0066 | 0.013 | 0.0055 | 0.27 |
| 10 | 1-(6-(3-Chloro-5-fluoro-4-hydroxyphenyl)-4-{trans-4-[2-(dimethylamino)ethyl]cyclohexylamino}-1,5-naphthyridin-3-yl)ethanone dihydrochloride | 0.01 | 0.0039 | 0.012 | 0.0049 | 0.2 |
| 11 | 1-(4-{trans-4-[(Dimethylamino)methyl]cyclohexylamino}-6-[4-hydroxy-3-(trifluoromethoxy)phenyl]-1,5-naphthyridin-3-yl)-ethanone dihydrochloride | 0.066 | 0.027 | 0.042 | 0.049 | 0.14 |
| 12 | 2,6-Dichloro-4-(8-{trans-4-[(dimethylamino)methyl]cyclohexylamino}-7-(methylsulfonyl)-1,5-naphthyridin-2-yl)phenol dihydrochloride | 0.019 | 0.019 | 0.053 | 0.0045 | 0.46 |
| 13 | 6-(3-Chloro-5-fluoro-4-hydroxyphenyl)-4-({trans-4-[(dimethylamino)methyl]cyclohexyl}amino)-3-methylsulfonyl-1,5-naphthyridine dihydrochloride | 0.019 | 0.013 | 0.073 | 0.0068 | 0.32 |
| 14 | 6-(3-Chloro-4-hydroxy-5-methoxyphenyl)-4-{trans-4-[(dimethylamino)methyl]cyclohexylamino}-3-methylsulfonyl-1,5-naphthyridine dihydrochloride | 0.05 | 0.027 | 0.033 | 0.0096 | 0.14 |
| 15 | 2,6-Dichloro-4-{8-[trans-4-(dimethylamino)cyclohexylamino]-7-(methylsulfonyl)-1,5-naphthyridin-2-yl}phenol dihydrochloride | 0.026 | 0.018 | 0.092 | 0.0027 | 2.2 |
| 16 | 2,6-Dichloro-4-(8-(4-((dimethylamino)methyl)phenylamino)-7-(methylsulfonyl)-1,5-naphthyridin-2-yl)phenol dihydrochloride | 0.17 | 0.078 | 0.47 | 0.031 | 4.4 |
| 17 | 2-Chloro-4-(8-(4-((dimethylamino)methyl)phenylamino)-7-(methylsulfonyl)-1,5-naphthyridin-2-yl)-6-fluorophenol dihydrochloride | 0.33 | 0.13 | 0.83 | 0.064 | 6.6 |
| 18 | 2-Chloro-4-(8-(4-((dimethylamino)methyl)phenylamino)-7-(methylsulfonyl)-1,5-naphthyridin-2-yl)-6-methoxyphenol dihydrochloride | 1 | 0.32 | 0.69 | 0.31 | 3.8 |
| 19 | 1-(6-(3,5-Dichloro-4-hydroxyphenyl)-4-(3-(2-(pyrrolidin-1-yl)ethyl)phenylamino)-1,5-naphthyridin-3-yl)ethanone dihydrochloride | 0.63 | 0.59 | 0.14 | 0.11 | 7 |
| 20 | 1-(6-(3-Chloro-5-fluoro-4-hydroxyphenyl)-4-(3-(2-(pyrrolidin-1-yl)ethyl)phenylamino)-1,5-naphthyridin-3-yl)ethanone dihydrochloride | 0.81 | 0.5 | 0.31 | 0.21 | 4.8 |
| 21 | 1-(6-(3,5-Dichloro-4-hydroxyphenyl)-4-(6-(2-(dimethylamino)ethoxy)pyridin-3-ylamino)-1,5-naphthyridin-3-yl)ethanone dihydrochloride | 0.27 | 0.1 | 0.21 | 0.096 | 2.3 |
| 22 | 1-(6-(3-Chloro-5-fluoro-4-hydroxyphenyl)-4-(6-(2-(dimethylamino)ethoxy)pyridin-3-ylamino)-1,5-naphthyridin-3-yl)ethanone dihydrochloride | 0.35 | 0.1 | 0.29 | 0.31 | 3.5 |

TABLE 3-continued

| Ex. | Compound Name | IC50 (μM) (22Rvl) | IC50 (μM) (T47D) | IC50 (μM) (A549) | IC50 (μM) (DU4475) | IC50 (μM) (HTl197) |
|---|---|---|---|---|---|---|
| 23 | 1-(6-(3-Chloro-4-hydroxy-5-methoxyphenyl)-4-(6-(2-(dimethylamino)ethoxy)pyridin-3-ylamino)-1,5-naphthyridin-3-yl)ethanone dihydrochloride | 1.3 | 0.38 | 0.47 | 0.41 | 8.9 |
| 24 | 2,6-Dichloro-4-(8-(6-(2-(dimethylamino)ethoxy)pyridin-3-ylamino)-7-(methylsulfonyl)-1,5-naphthyridin-2-yl)phenol hydrochloride | 1.8 | 0.58 | 5.1 | 0.38 | 15 |
| 25 | 2-Chloro-4-(8-(6-(2-(dimethylamino)ethoxy)pyridin-3-ylamino)-7-(methylsulfonyl)-1,5-naphthyridin-2-yl)-6-fluorophenol dihydrochloride | 2.8 | 0.7 | 5.9 | 0.74 | 21 |
| 26 | 2-Chloro-4-(8-(6-(2-(dimethylamino)ethoxy)pyridin-3-ylamino)-7-(methylsulfonyl)-1,5-naphthyridin-2-yl)-6-methoxyphenol dihydrochloride | 4.1 | 1 | 3.1 | 1.6 | 15 |
| 27 | 1-(6-(3,5-Dichloro-4-hydroxyphenyl)-4-((1-methylpiperidin-4-yl)methylamino)-1,5-naphthyridin-3-yl)ethanone dihydrochloride | 0.1 | 0.079 | 0.11 | 0.1 | 2 |
| 28 | 1-(6-(3,5-Dichloro-4-hydroxyphenyl)-4-(trans-4-((dimethylamino-d6)methyl)cyclohexylamino)-1,5-naphthyridin-3-yl)ethanone dihydrochloride | 0.0052 | 0.004 | 0.006 | 0.0022 | 0.14 |
| 29 | 1-(6-(3,5-Dichloro-4-hydroxyphenyl)-4-(4-(2-(dimethylamino)ethyl)phenylamino)-1,5-naphthyridin-3-yl)ethanone dihydrochloride | 0.084 | 0.085 | 0.11 | 0.028 | 0.68 |
| 30 | 1-(6-(3-Chloro-5-fluoro-4-hydroxyphenyl)-4-(4-(2-(dimethylamino)ethyl)phenylamino)-1,5-naphthyridin-3-yl)ethanone dihydrochloride | 0.17 | 0.11 | 0.14 | 0.041 | 1.2 |
| 31 | 1-(6-(3-Chloro-4-hydroxy-5-methoxyphenyl)-4-(4-(2-(dimethylamino)ethyl)phenylamino)-1,5-naphthyridin-3-yl)ethanone dihydrochloride | 0.65 | 0.41 | 0.31 | 0.19 | 4.4 |
| 32 | 2-Chloro-4-(8-(trans-4-(dimethylamino)cyclohexylamino)-7-(methylsulfonyl)-1,5-naphthyridin-2-yl)-6-fluorophenol dihydrochloride | 0.046 | 0.024 | 0.2 | 0.0063 | 3.1 |
| 33 | 1-(6-(3,5-Dichloro-4-hydroxyphenyl)-4-(1-(1-methylpiperidin-4-yl)-1H-pyrazol-4-ylamino)-1,5-naphthyridin-3-yl)ethanone dihydrochloride | 0.64 | 0.35 | 0.93 | 0.34 | 100 |
| 34 | 1-(6-(3,5-Dichloro-4-hydroxyphenyl)-4-(4-((4-methylpiperazin-1-yl)methyl)phenylamino)-1,5-naphthyridin-3-yl)ethanone trihydrochloride | 0.21 | 0.11 | 0.19 | 0.096 | 1.6 |
| 35 | 1-(6-(3-Chloro-5-fluoro-4-hydroxy phenyl)-4-(4-((4-methyl-piperazin-1-yl)methyl)phenylamino)-1,5-naphthyridin-3-yl)ethanone trihydrochloride | 0.65 | 0.22 | 0.41 | 0.31 | 3.8 |
| 36 | 1-(6-(3,5-Dichloro-4-hydroxy phenyl)-4-(4-(2-(pyrrolidin-1-yl)ethyl)piperidin-1-yl)-1,5-naphthyridin-3-yl)ethanone dihydrochloride | 0.36 | 0.21 | 0.63 | 0.22 | 4.7 |
| 37 | 1-(6-(3-Chloro-5-fluoro-4-hydroxyphenyl)-4-(4-(2-(pyrrolidin-1-yl)ethyl)piperidin-1-yl)-1,5-naphthyridin-3-yl)ethanone dihydrochloride | 0.49 | 0.25 | 1.2 | 0.42 | 7.2 |
| 38 | 1-(6-(3,5-Dichloro-4-hydroxyphenyl)-4-(6-(2-(dimethylamino)- | 0.24 | 0.11 | 0.26 | 0.069 | 9.5 |

TABLE 3-continued

| Ex. | Compound Name | IC50 (μM) (22Rvl) | IC50 (μM) (T47D) | IC50 (μM) (A549) | IC50 (μM) (DU4475) | IC50 (μM) (HTl197) |
|---|---|---|---|---|---|---|
| | ethylamino)pyridin-3-ylamino)-1,5-naphthyridin-3-yl)ethanone trihydrochloride | | | | | |
| 39 | 1-(6-(3-Chloro-5-fluoro-4-hydroxy-phenyl)-4-(6-(2-(dimethylamino)-ethylamino)pyridin-3-ylamino)-1,5-naphthyridin-3-yl)ethanone trihydrochloride | 0.38 | 0.12 | 0.44 | 0.19 | 10 |
| 40 | (S)-(4-(6-(3-Aminopiperidin-1-yl)-pyridin-3-ylamino)-6-(3,5-dichloro-4-hydroxyphenyl)-1,5-naphthyridin-3-yl) (cyclopropyl)-methanone trihydrochloride | 0.034 | 0.025 | 0.29 | 0.02 | 4.2 |
| 41 | 1-(4-(2-(3-Aminopyrrolidin-1-yl)-pyrimidin-5-ylamino)-6-(3,5-dichloro-4-hydroxyphenyl)-1,5-naphthyridin-3-yl)ethanone trihydrochloride | 0.052 | 0.027 | 0.27 | 0.026 | 100 |
| 42 | 1-(4-{4-[(Dimethylamino)methyl]-cyclohexylamino}-6-(1H-pyrazol-4-yl)-1,5-naphthyridin-3-yl)-ethanone trihydrochloride | 0.063 | 0.036 | 0.049 | 0.045 | 0.06 |
| 43 | 1-(6-{3,5-Dichloro-4-hydroxy-phenyl)-4-[4-(hydroxymethyl)-cyclohexyl]amino}-1,5-naphthyridin-3-yl)ethanone hydrochloride | 0.085 | 0.024 | 0.057 | 0.019 | 0.64 |
| 44 | 1-[6-(3,5-Dichloro-4-hydroxy phenyl)-4-{trans-4-[(dimethyl amino)methyl]cyclohexylamino}-1,5-naphthyridin-3-yl]-2-hydroxy-ethanone dihydrochloride | 0.006 | 0.0029 | 0.0067 | 0.0017 | 0.2 |
| 45 | 1-{6-(3,5-Dichloro-4-hydroxy-phenyl)-4-[(1-methylpiperidin-4-yl)amino]-1,5-naphthyridin-3-yl}-ethanone | 0.096 | 0.086 | 0.065 | 0.096 | 0.45 |
| 46 | 1-(6-(3-Chloro-5-fluoro-4-hydroxy-phenyl)-4-[(1-methylpiperidin-4-yl)amino]-1,5-naphthyridin-3-yl}-ethanone | 0.14 | 0.092 | 0.098 | 0.14 | 0.53 |
| 47 | 1-(6-(3,5-Dichloro-4-hydroxy-phenyl)-4-{[4-(morpholinomethyl)-cyclohexyl]amino}-1,5-naphthyridin-3-yl)ethanone | 0.034 | 0.015 | 0.02 | 0.009 | 0.16 |
| 48 | 1-[6-(3,5-Dichloro-4-hydroxy-phenyl)-4-(4-{[(2-hydroxyethyl)-(methyl)amino]methyl}cyclohexyl-amino)-1,5-naphthyridin-3-yl]-ethanone dihydrochloride | 0.0092 | 0.0068 | 0.02 | 0.0034 | 0.57 |
| 49 | 1-[6-(3-Chloro-5-fluoro-4-hydroxy-phenyl)-4-(4-{[(2-hydroxyethyl)-(methyl)amino]methyl}cyclohexyl-amino)-1,5-naphthyridin-3-yl]-ethanone dihydrochloride | 0.0087 | 0.0039 | 0.021 | 0.0039 | 0.49 |
| 50 | 1-(6-(3,5-Difluoro-4-hydroxy-phenyl)-4-{4-[(dimethylamino)-methyl]cyclohexylamino}-1,5-naphthyridin-3-yl)ethanone dihydrochloride | 0.017 | 0.0061 | 0.015 | 0.0053 | 0.08 |
| 51 | 1-(6-(3,5-Dichloro-4-hydroxy-phenyl)-4-{6-[3-(dimethylamino)-pyrrolidin-1-yl]pyridin-3-ylamino}-1,5-naphthyridin-3-yl)ethanone trihydrochloride | 0.36 | 0.19 | 0.32 | 0.32 | 2.8 |
| 52 | 1-(6-(3-Chloro-5-fluoro-4-hydroxyphenyl)-4-{6-[3-(dimethyl-amino)pyrrolidin-1-yl]pyridin-3-yl-amino}-1,5-naphthyridin-3-yl)-ethanone trihydrochloride | 0.44 | 0.18 | 0.39 | 0.4 | 2 |
| 53 | 1-(6-(3,5-Dichloro-4-hydroxy-phenyl)-4-{6-[3-(methylamino)-pyrrolidin-1-y]pyridin-3-ylamino}-1,5-naphthyridin-3-yl)ethanone trihydrochloride | 0.078 | 0.042 | 0.2 | 0.071 | 100 |
| 54 | 1-(6-(3-Chloro-5-fluoro-4-hydroxy-phenyl)-4-{6-[3-(methylamino)-pyrrolidin-1-yl]pyridin-3-ylamino}- | 0.086 | 0.04 | 0.17 | 0.11 | 3.9 |

TABLE 3-continued

| Ex. | Compound Name | IC50 (μM) (22Rvl) | IC50 (μM) (T47D) | IC50 (μM) (A549) | IC50 (μM) (DU4475) | IC50 (μM) (HTl197) |
|---|---|---|---|---|---|---|
| | 1,5-naphthyridin-3-yl)ethanone trihydrochloride | | | | | |
| 55 | 1-(6-(1H-Benzo[d]imidazol-5-yl)-4-{trans-4-[(dimethylamino)-methyl]cyclohexylamino}-1,5-naphthyridin-3-yl)ethanone trihydrochloride | 0.3 | 0.084 | 0.25 | 0.65 | 2 |
| 56 | 1-{4-[4-(trans-4-Dimethylamino)-methylcyclohexylamino]-6-(pyridin-4-yl)-1,5-naphthyridin-3-yl}ethanone trihydrochloride | 0.86 | 0.38 | 0.52 | 0.46 | 1.7 |
| 57 | 5-(7-Acetyl-8-{trans-4-[(dimethyl-amino)methyl]cyclohexylamino}-1,5-naphthyridin-2-yl)pyrimidine-2-carbonitrile | 0.24 | 0.089 | 0.56 | 0.22 | 0.38 |
| 58 | 1-(6-(3,5-Dimethyl-1H-pyrazol-4-yl)-4-{trans-4-[(dimethylamino)-methyl]cyclohexylamino}-1,5-naphthyridin-3-yl)ethanone trihydrochloride | 6.1 | 1.6 | 3 | 5.9 | 10 |
| 59 | 1-(4-{trans-4-[(Dimethylamino)-methyl]cyclohexylamino}-6-(4-hydroxy-3,5-dimethylphenyl)-1,5-naphthyridin-3-yl)ethanone dichloride | 2.5 | 0.39 | 0.23 | 0.21 | 7.5 |
| 60 | 1-(6-(3,5-Dichloro-4-hydroxy-phenyl)-4-{6-[3-(dimethylamino)-pyrrolidin-1-yl]pyridin-3-ylamino}-1,5-naphthyridin-3-yl)ethanone dihydrochloride | 0.1 | 0.066 | 0.11 | 0.041 | 1.1 |
| 61 | 1-{6-(3,5-Dichloro-4-hydroxy-phenyl)-4-{[trans-4-(pyrrolidin-1-ylmethyl)cyclohexylamino]-1,5-naphthyridin-3-yl}ethanone dihydrochloride | 0.011 | 0.0069 | 0.012 | 0.0044 | 0.15 |
| 62 | 1-(6-(3-Chloro-5-fluoro-4-hydroxy-phenyl)-4-{[trans-4-(pyrrolidin-1-ylmethyl)cyclohexyl]amino}-1,5-naphthyridin-3-yl)ethanone dihydrochloride | 0.0073 | 0.0034 | 0.011 | 0.0037 | 0.091 |
| 63 | 1-(6-(3,5-Dichloro-4-hydroxy-phenyl)-4-{4-[(4-methylpiperazin-1-yl)methyl]cyclohexylamino}-1,5-naphthyridin-3-yl)(ethanone trihydrochloride | 0.025 | 0.016 | 0.02 | 0.0092 | 0.13 |
| 64 | 1-(4-{[6-(3-Aminopiperidin-1-yl)-pyridin-3-yl]amino}-6-(3,5-di-chloro-4-hydroxyphenyl)-1,5-naphthyridin-3-yl)ethanone trihydrochloride | 0.016 | 0.0064 | 0.07 | 0.016 | 2.9 |
| 65 | 1-(4-{[6-(3-Aminopiperidin-1-yl)-pyridin-3-yl]amino}-6-(3-chloro-5-fluoro-4-hydroxyphenyl)-1,5-naphthyridin-3-yl)ethanone trihydrochloride | 0.013 | 0.0047 | 0.021 | 0.015 | 0.74 |
| 66 | 1-{4-[(4-Aminocyclohexyl)amino]-6-(3,5-dichloro-4-hydroxyphenyl)-1,5-naphthyridin-3-yl}ethanone dihydrochloride | 0.0045 | 0.0018 | 0.016 | 0.001 | 10 |
| 67 | 1-{4-[trans-(4-Aminocyclohexyl)-amino]-6-(3-chloro-5-fluoro-4-hydroxyphenyl)-1,5-naphthyridin-3-yl}ethanone dihydrochloride | 0.0061 | 0.0019 | 0.022 | 0.0012 | 2.8 |
| 68 | 1-(6-(3-Chloro-5-fluoro-4-hydroxy-phenyl)-4-{4-[(4-methylpiperazin-1-yl)methyl]cyclohexylamino}-1,5-naphthyridin-3-yl)ethanone trihydrochloride | 0.039 | 0.012 | 0.026 | 0.012 | 0.11 |
| 69 | N-(trans-4-{[3-Acetyl-6-(3-chloro-5-fluoro-4-hydroxyphenyl)-1,5-naphthyridin-4-yl]amino}cyclo-hexyl)-2-amino-3-methylbutan-amide dihydrochloride | 0.025 | 0.007 | 0.064 | 0.013 | 2.5 |
| 70 | 1-{6-(3,5-Dichloro-4-hydroxy-phenyl)-4-[trans-4-(piperazin-1-yl-methyl)cyclohexylamino]-1,5- | 0.031 | 0.021 | 0.084 | 0.011 | 3.9 |

TABLE 3-continued

| Ex. | Compound Name | IC50 (μM) (22Rvl) | IC50 (μM) (T47D) | IC50 (μM) (A549) | IC50 (μM) (DU4475) | IC50 (μM) (HTl197) |
|---|---|---|---|---|---|---|
| | naphthyridin-3-yl}ethanone trihydrochloride | | | | | |
| 71 | (S)-1-(4-{[6-(3-Aminopiperidin-1-yl)pyridin-3-yl]amino}-6-(3,5-di-chloro-4-hydroxyphenyl)-1,5-naphthyridin-3-yl)ethanone trihydrochloride | 0.014 | 0.0074 | 0.09 | 0.008 | 3.4 |
| 72 | (S)-1-(4-{[6-(3-Aminopiperidin-1-yl)pyridin-3-yl]amino}-6-(3-chloro-5-fluoro-4-hydroxyphenyl)-1,5-naphthyridin-3-yl)ethanone trihydrochloride | 0.014 | 0.0053 | 0.047 | 0.014 | 1.2 |
| 73 | N-{trans-4-[3-Acetyl-6-(3,5-di-chloro-4-hydroxyphenyl)-1,5-naphthyridin-4-ylamino]cyclo-hexyl}-2-aminopropanamide dihydrochloride | 0.027 | 0.0086 | 0.18 | 0.0043 | 100 |
| 74 | N-{4-[3-Acetyl-6-(3-chloro-5-fluoro-4-hydroxyphenyl)-1,5-naphthyridin-trans-4-ylamino]-cyclohexyl}-2-aminopropanamide dihydrochloride | 0.025 | 0.0043 | 0.13 | 0.0036 | 100 |
| 75 | (S)-N-{4-[3-Acetyl-6-(3,5-dichloro-4-hydroxyphenyl)-1,5-naphthyridin-trans-4-ylamino]-cyclohexyl}pyrrolidine-2-carboxamide dihydrochloride | 0.099 | 0.036 | 0.21 | 0.021 | 8.4 |
| 76 | (S)-N-{4-[3-Acetyl-6-(3-chloro-5-fluoro-4-hydroxyphenyl)-1,5-naphthyridin-trans-4-ylamino]-cyclohexyl}pyrrolidine-2-carboxamide dihydrochloride | 0.073 | 0.03 | 0.32 | 0.019 | 8.7 |
| 77 | 1-(6-(3-Hydroxypyrrolidin-1-yl)-4-trans-4-[(3-hydroxypyrrolidin-1-yl)methyl]cyclohexylamino}-1,5-naphthyridin-3-yl)ethanone | 10 | 10 | 10 | 10 | 10 |
| 78 | 1-{6-(Pyrrolidin-1-yl)-4-[trans-4-(pyrrolidin-1-ylmethyl)cyclohexyl-amino]-1,5-naphthyridin-3-yl}-ethanone | 5.6 | 5.4 | 6.8 | 7.7 | 9.8 |
| 79 | N-{trans-4-[3-Acetyl-6-(3,5-di-chloro-4-hydroxyphenyl)-1,5-naphthyridin-4-ylamino]cyclo-hexyl}-2-amino-3-methylbutanamide dihydrochloride | 0.038 | 0.018 | 0.11 | 0.016 | 3.9 |
| 80 | Cyclopropyl{6-(3,5-dichloro-4-hydroxyphenyl)-4-[trans-4-(dimethylamino)cyclohexylamino]-1,5-naphthyridin-3-yl}methanone Dihydrochloride | 0.0052 | 0.0041 | 0.0076 | 0.002 | 0.084 |
| 81 | 1-[6-(3-Chloro-5-fluoro-4-methoxy-phenyl)-4-{trans-4-[(dimethyl-amino)methyl]cyclohexylamino}-1,5-naphthyridin-3-yl]ethanone dihydrochloride | 0.0049 | 0.002 | 0.0062 | 0.0018 | 0.044 |
| 82 | 1-(4-{trans-4-[(Dimethylamino)-methyl]cyclohexylamino}-6-(1H-pyrrolo[2,3-b]pyridin-5-yl)-1,5-naphthyridin-3-yl)ethanone trihydrochloride | 0.37 | 0.32 | 0.33 | 0.65 | 2.3 |
| 83 | (S)-{4-[6-(3-Aminopiperidin-1-yl)-pyridin-3-ylamino]-6-(3-chloro-5-fluoro-4-hydroxyphenyl)-1,5-naphthyridin-3-yl}(cyclopropyl)-methanone | 0.025 | 0.012 | 0.09 | 0.015 | 2.7 |
| 84 | 1-(4-{trans-4-[(Dimethylamino)-methyl]cyclohexylamino}-6-(4-methoxyphenyl)-1,5-naphthyridin-3-yl)ethanone dihydrochloride | 0.58 | 0.25 | 2.4 | 5.2 | 6 |
| 85 | 1-[6-(3,5-Dichloro-4-methoxy-phenyl)-4-{trans-4-[(dimethyl-amino)methyl]cyclohexylamino}-1,5-naphthyridin-3-yl]ethanone dihydrochloride | 0.77 | 0.43 | 2.3 | 2.3 | 6.5 |
| 86 | 1-(4-{trans-4-[(Dimethylamino)-methyl]cyclohexylamino}-6-(6- | 5.3 | 6.2 | 8 | 6.5 | 10 |

TABLE 3-continued

| Ex. | Compound Name | IC50 (μM) (22Rvl) | IC50 (μM) (T47D) | IC50 (μM) (A549) | IC50 (μM) (DU4475) | IC50 (μM) (HTl197) |
|---|---|---|---|---|---|---|
| | hydroxypyridin-3-yl)-1,5-naphthyridin-3-yl)ethanone dihydrochloride | | | | | |
| 87 | 5-(7-Acetyl-8-{trans-4-[(dimethyl-amino)methyl]cyclohexylamino}-1,5-naphthyridin-2-yl)-picolinonitrile dihydrochloride | 0.66 | 0.66 | 1.8 | 0.74 | 2 |
| 88 | 1-(4-{trans-4-[(Dimethylamino)-methyl]cyclohexylamino}-6-(4-hydroxyphenyl)-1,5-naphthyridin-3-yl)ethanone dihydrochloride | 0.04 | 0.031 | 0.023 | 0.021 | 0.039 |
| 89 | 1-[6-(3,5-Dichloro-4-hydroxy-phenyl)-4-{[trans-4-(dimethyl-amino)cyclohexyl]methylamino}-1,5-naphthyridin-3-yl]ethanone dihydrochloride | 0.028 | 0.023 | 0.041 | 0.0063 | 0.9 |
| 90 | 1-[6-(3-Chloro-5-fluoro-4-hydroxy-phenyl)-4-{[trans-4-(dimethyl-amino)cyclohexyl]methylamino}-1,5-naphthyridin-3-yl]ethanone Dihydrochloride | 0.052 | 0.03 | 0.12 | 0.027 | 10 |
| 91 | 1-[6-(3,5-Dichloro-4-hydroxy-phenyl)-4-(4-hydroxycyclohexyl-amino)-1,5-naphthyridin-3-yl]-ethanone hydrochloride | 0.072 | 0.038 | 0.048 | 0.016 | 0.33 |
| 92 | 1-[6-(3-Chloro-5-fluoro-4-hydroxy-phenyl)-4-(4-hydroxycyclohexyl-amino)-1,5-naphthyridm-3-yl]-ethanone hydrochloride | 0.061 | 0.036 | 0.053 | 0.018 | 0.53 |
| 93 | 1-{6-(3-Chloro-5-fluoro-4-hydroxy-phenyl)-4-({cis-4-[(dimethyl-amino)methyl]cyclohexyl}amino)-1,5-naphthyridin-3-yl}ethanone Dihydrochloride | 0.032 | 0.02 | 0.039 | 0.011 | 0.19 |
| 94 | 1-{6-(3,5-Dichloro-4-hydroxy phenyl)-4-({cis-4-[(dimethyl-amino)methyl]cyclohexyl}amino)-1,5-naphthyridin-3-yl}ethanone Dihydrochloride | 0.028 | 0.02 | 0.039 | 0.0073 | 0.25 |
| 95 | (R)-1-{4-[6-(3-Aminopiperidin-1-yl)pyridin-3-ylamino]-6-(3,5-dichloro-4-hydroxyphenyl)-1,5-naphthyridin-3-yl}ethanone trihydrochloride | 0.029 | 0.022 | 0.088 | 0.03 | 1.9 |
| 96 | (R)-1-{4-[6-(3-Aminopiperidin-1-yl)pyridin-3-ylamino]-6-(3-chloro-5-fluoro-4-hydroxyphenyl)-1,5-naphthyridin-3-yl}ethanone | 0.026 | 0.018 | 0.035 | 0.024 | 0.43 |
| 201 | (R)-(4-{[6-(3-aminopiperidin-1-yl)pyridin-3-yl]amino}-6-(3,5-dichloro-4-hydroxyphenyl)-1,5-naphthyridin-3-yl) (cyclopropyl)methanone | 0.0061 | 0.0025 | 0.0061 | 0.003 | 0.032 |
| 202 | (R)-(4-{[6-(3-aminopiperidin-1-yl) pyridin-3-yl]amino}-6-(3-chloro-5-fluoro-4-hydroxyphenyl)-1,5-naphthyridin-3-yl) (cyclopropyl) methanone | 0.0044 | 0.0038 | 0.0054 | 0.001 | 0.047 |
| 203 | 1-[6-(3,5-dichloro-4-hydroxyphenyl)-4-{[trans-4-(dimethylamino)cyclohexyl] amino}-1,5-naphthyridin-3-yl)-2-hydroxyethanone dihydrochloride | 0.017 | 0.0093 | 0.034 | 0.013 | 1.2 |
| 204 | 1-[6-(3-chloro-5-fluoro-4-hydroxyphenyl)-4-({trans-4-[(dimethylamino)methyl]cyclohexyl} amino)-1,5-naphthyridin-3-yl)]-2-hydroxyethanone dihydrochloride | 0.02 | 0.014 | 0.058 | 0.013 | 10 |
| 205 | 1-[6-(3-chloro-5-fluoro-4-hydroxyphenyl)-4-({trans-4-[(dimethylamino)methyl]cyclohexyl} amino)-1,5-naphthyridin-3-yl)propan-1-one dihydrochloride | 0.022 | 0.0083 | 0.032 | 0.033 | 0.69 |
| 206 | 1-[6-(3,5-dichloro-4-hydroxyphenyl)-4-({trans-4-[(dimethylamino)methyl] cyclohexyl}amino)-1,5-naphthyridin-3-yl)]propan-1-one dihydrochloride | 0.022 | 0.01 | 0.061 | 0.023 | 10 |

TABLE 3-continued

| Ex. | Compound Name | IC50 (μM) (22Rvl) | IC50 (μM) (T47D) | IC50 (μM) (A549) | IC50 (μM) (DU4475) | IC50 (μM) (HTl197) |
|---|---|---|---|---|---|---|
| 207 | (S)-1-(4-{[6-(3-aminopiperidin-1-yl)pyridin-3-yl]amino}-6-(3,5-dichloro-4-hydroxyphenyl)-1,5-naphthyridin-3-yl)propan-1-one trihydrochloride | 0.034 | 0.018 | 0.098 | 0.024 | 3.9 |
| 208 | (S)-1-(4{[6-(3-aminopiperidin-1-yl)pyridin-3-yl]amino}-6-(3-chloro-5-fluoro-4-hydroxyphenyl)-1,5-naphthyridin-3-yl)propan-1-one trihydrochloride | 0.026 | 0.015 | 0.063 | 0.021 | 0.86 |
| 209 | 1-[6-(3,5-dichloro-4-hydroxyphenyl)-4-({4-[((R)-3-fluoropyrrolidin-1-yl)methyl]cyclohexyl}amino)-1,5-naphthyridin-3-yl]ethanone dihydrochloride | 0.032 | 0.036 | 0.037 | 0.01 | 0.12 |
| 210 | (S)-(4-((6-(3-aminopiperidin-1-yl)pyridin-3-yl)amino)-6-(3-chloro-5-fluoro-4-hydroxyphenyl)-1,5-naphthyridin-3-yl)(cyclobutyl)methanone dihydrochloride | 0.017 | 0.0093 | 0.042 | 0.022 | 1.4 |
| 211 | (6-(3,5-dichloro-4-hydroxyphenyl)-4-((4-[(dimethylamino)methyl{cyclohexyl) amino)-1,5-naphthyridin-3-yl) (cyclobutyl)methanone dihydrochloride | 0.0072 | 0.0034 | 0.0076 | 0.003 | 0.0077 |
| 212 | (6-(3-chloro-5-fluoro-4-hydroxyphenyl)-4-((4-((dimethylamino)methyl) cyclohexyl) amino)-1,5-naphthyridin-3-yl)(cyclobutyl)methanone dihydrochloride | 0.013 | 0.0074 | 0.014 | 0.003 | 0.014 |
| 213 | (S)-(4-{[6-(3-aminopiperidin-1-yl)pyridin-3-yl]amino}-6-(3-chloro-5-fluoro-4-hydroxyphenyl)-1,5-naphthyridin-3-yl)(cyclobutyl) methanone | 0.0071 | 0.0043 | 0.029 | 0.003 | 1.7 |
| 214 | (R)-1-(4-((6-(3-aminopiperidin-1-yl)pyridin-3-yl)amino)-6-(3,5-dichloro-4-hydroxyphenyl)-1,5-naphthyridin-3-yl)propan-1-one trihydrochloride | 0.0059 | 0.0028 | 0.013 | 0.004 | 0.34 |
| 215 | (R)-1-(4-{[6-(3-aminopiperidin-1-yl)pyridin-3-yl]amino}-6-(3,5-dichloro-4-hydroxyphenyl)-1,5-naphthyridin-3-yl)-2-methylpropan-1-one trihydrochloride | 0.032 | 0.016 | 0.083 | 0.014 | 1.7 |
| 216 | 1-[6-(3,5-dichloro-5-4-hydroxyphenyl)-4-({trans-4-[(dimethylamino)methyl]cyclohexyl} amino)-1,5-naphthyridin-3-yl]-2-methylpropan-1-one dihydrochloride | NT | NT | 0.012 | NT | 0.025 |
| 217 | 1-[6-chloro-4-({trans-4-[(dimethylamino)methyl]cyclohexyl} amino)-1,5-naphthyridin-3-yl]-2-methylpropan-1-one dihydrochloride | NT | NT | 0.021 | NT | 0.055 |

NT: Not tested

The growth inhibitory effect of Compound Example 6 was further examined on the growth of various cancer cell lines. In vitro anti-proliferative assay using A549 (lung), T47D (breast), DU4475 (breast), and 22Rv1 (prostate) cancer cells, in which MELK was highly expressed, revealed $IC_{50}$ values of 6.7, 4.3, 2.3, and 6.0 nM, respectively (FIG. 1*a-d*). On the other hand, HT1197 (bladder) cancer cells, in which MELK expression was hardly detectable, revealed $IC_{50}$ value of 97 nM (FIG. 1*e*), clearly implying the MELK-dependent growth inhibition effect of this compound.

Xenograft Model Antitumor Assay

MDA-MB-231 cells were injected into the mammary fat pads of NOD.CB17-Prkdc$^{scid}$/J mice (Charles River Laboratory). A549, MIAPaCa-2 and PC-14 cells ($1\times10^7$ cells) were injected subcutaneously in the left flank of female BALB/cSLC-nu/nu mice (Japan SLC, Inc.). DU145 cells were injected subcutaneously in the left flank of male BALB/cSLC-nu/nu mice (Japan SLC, Inc.). When MDA-MB-231, A549, DU145, MIAPaCa-2, and PC-14 xenografts had reached an average volume of 100, 210, 110, 250, and 250 $mm^3$, respectively, animals were randomized into groups of 6 mice (except for PC-14, for which groups of 3 mice were used). For oral administration, compounds were prepared in a vehicle of 0.5% methylcellulose and given by oral garbage at the indicated dose and schedule. For intravenous administration, compounds were formulated in 5% glucose and injected into the tail vein. An administration volume of 10 mL per kg of body weight was used for both administration routes. Concentrations were indicated in main text and Figures. Tumor volumes were determined every other day using a caliper. The results were converted to tumor volume ($mm^3$) by the formula length×width$^2$×½. The weight of the mice was determined as an indicator of tolerability on the same days. The animal experiments using A549 xenografts were conducted by contract with KAC Co., Ltd. (Shiga, Japan) in accordance with their Institutional Guidelines for the Care and Use of Laboratory Animals. The other animal experiments were conducted at OncoTherapy Science, Inc. in accordance with their Institutional Guidelines for the Care and Use of Laboratory Animals. Tumor growth inhibition (TGI) was calculated according to the formula $\{1-(T-T_0)/(C-C_0)\}\times 100$, where T and $T_0$ are the mean tumor volumes at day 14 and day 0, respectively, for the experimental group, and $C-C_0$ are those for the vehicle control group. All values were presented as means±SD. Statistical significance was computed using student's t-test, and the level of significance was set at $p<0.05$.

Figures 1, 2:
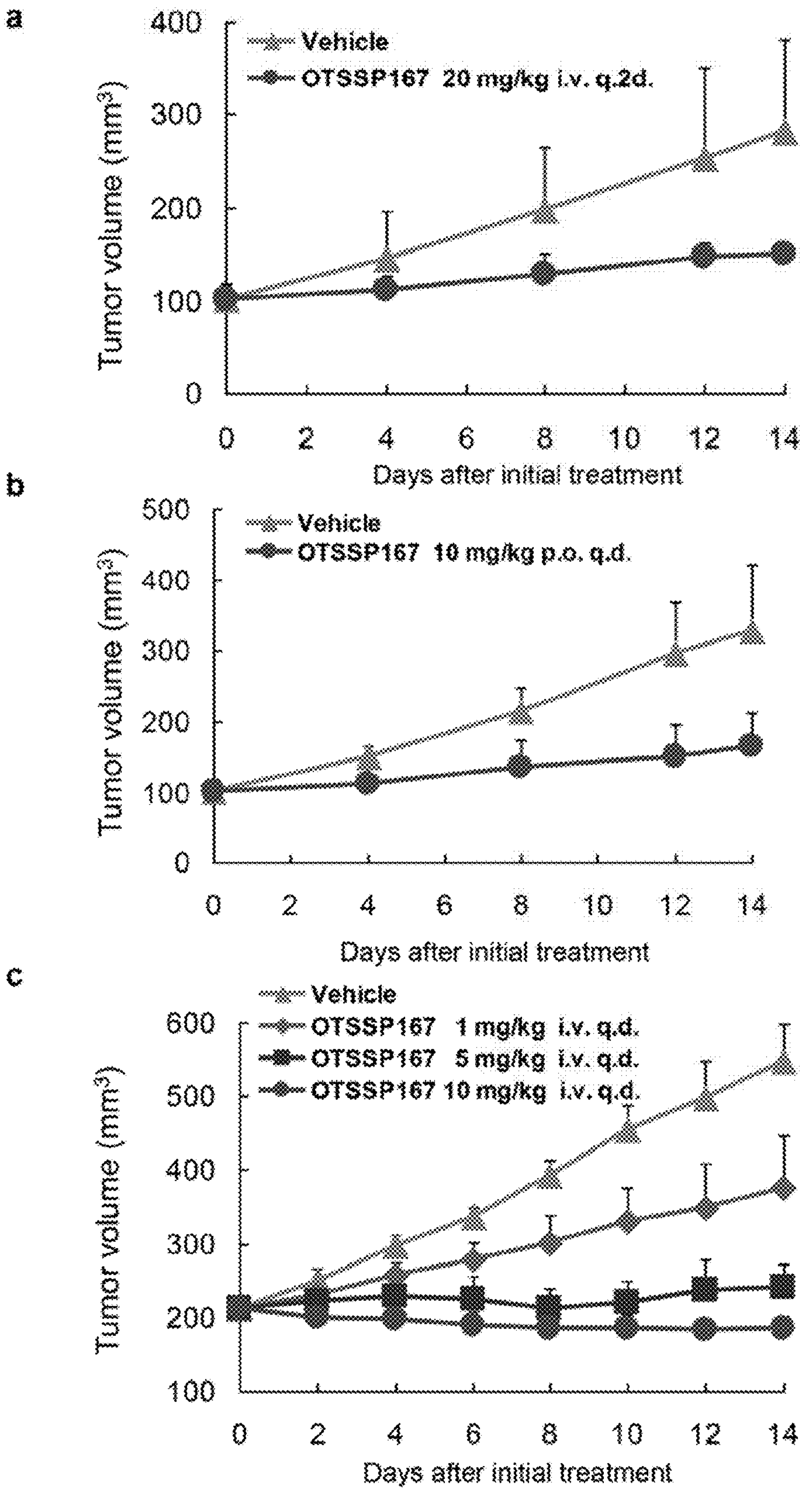
FIG. 2 is composed of a series of graphs, (a)-(h), depicting mice xenograft models showing the effectiveness of Example 6 on the growth of various human cancer xenograft. Nude mice bearing (a,b) MDA-MB-231 (triple-negative breast cancer), (c,d) A549 (lung cancer), (e) DU145 (prostate cancer), or (f) MIAPaCa-2 (pancreatic cancer) were treated with either vehicle control or Compound Example 6 of given concentrations for 14 days. The administration doses were (a) 20 mg/kg intravenously once every two days or (b) 10 mg/kg orally once a day for MDA-MB-231; (c) 1, 5, or 10 mg/kg intravenously once a day or (d) 5 or 10 mg/kg orally once a day for A549; (e) 10 mg/kg orally once a day for DU145; and (f) 10 mg/kg orally once a day for MIAPaCa-2. Mean tumor volumes ±SD (n=6 for each treatment group) are shown. (g) Lysates of tumor samples taken from A549 and PC-14 xenograft mice were immunoblotted with anti-MELK and anti-ACTB antibodies. (h) Compound Example 6 was administered to nude mice bearing PC-14 (MELK-negative bladder cancer cells) at a dose of 10 mg/kg orally once a day. Mean tumor volumes ±SD (n=3 per group) are shown. i.v. q.2d; intravenously once every two days, i.v. q.d.; intravenously once a day, p.o. q.d.; orally once a day.
Figure 2:
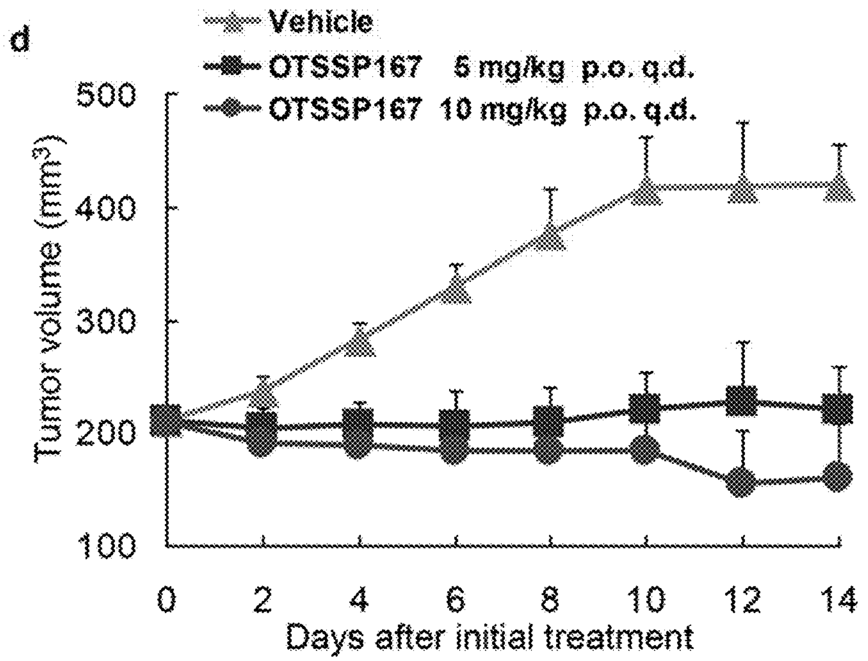
Figure 2:
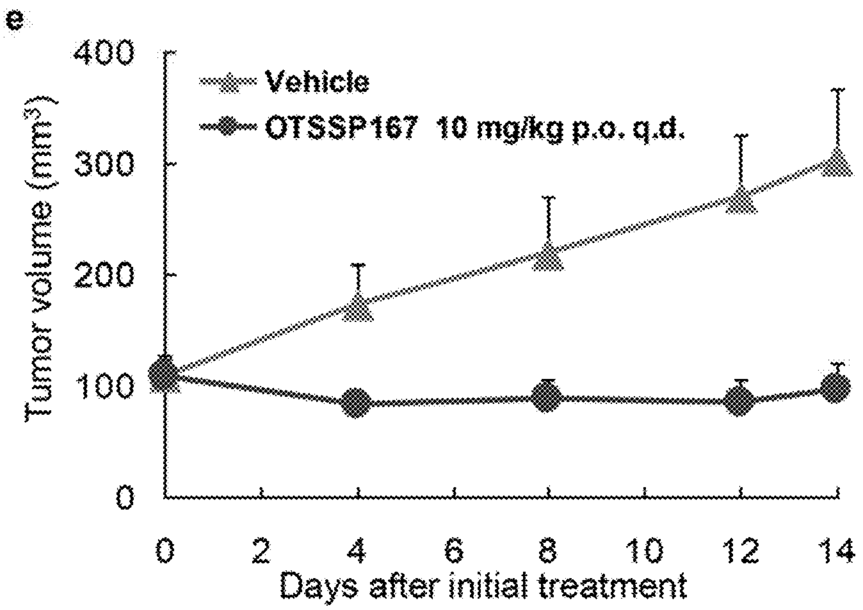
Figures 2, 3:
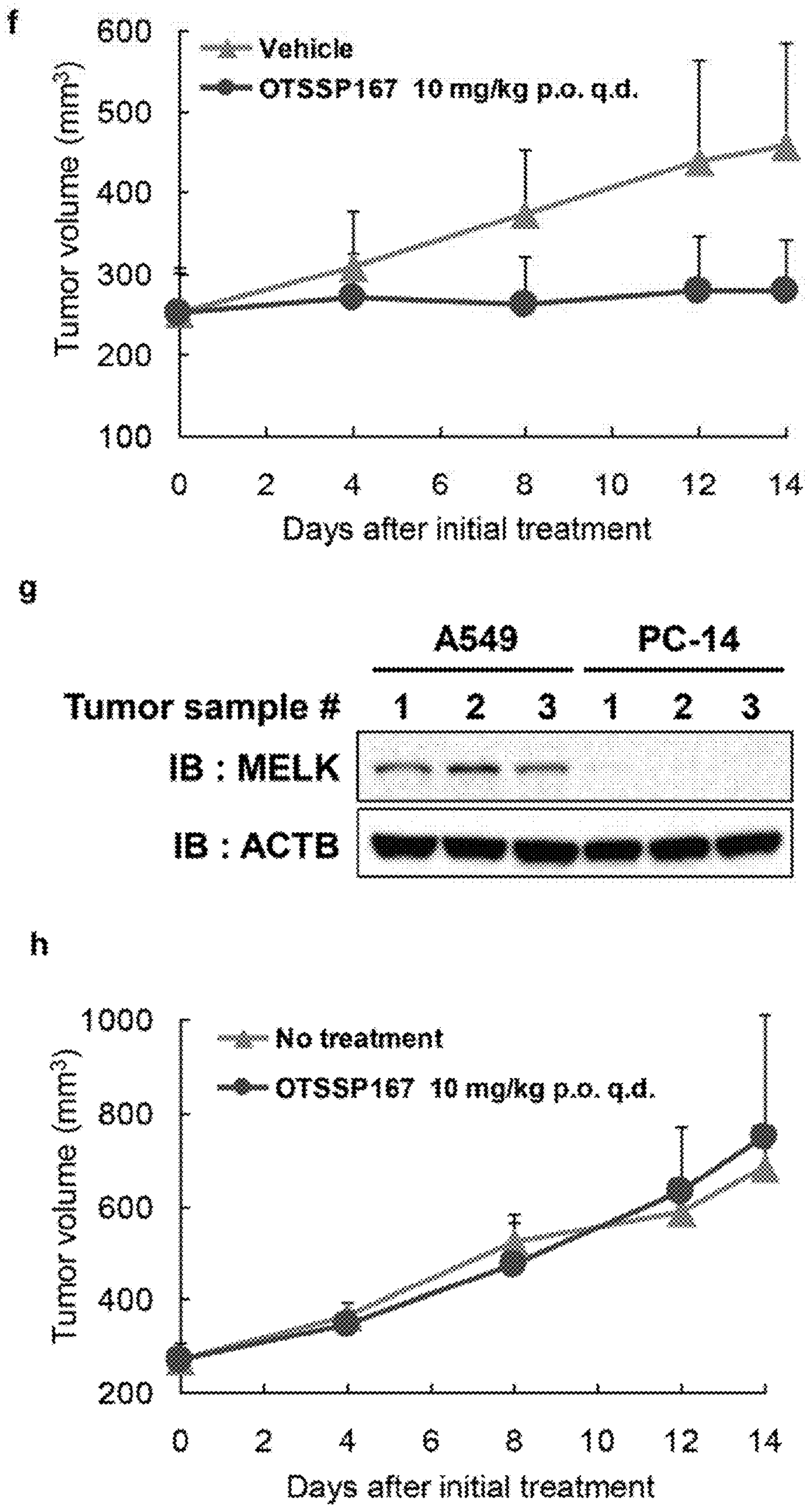
FIG. 3 is composed of a series of graphs, (a)-(f), depicting the Effect of Example 6 on body weight for mice xenograft models. Nude mice bearing (a,b) MDA-MB-231 (MELK-positive, triple negative breast cancer), (c,d) A549 (lung cancer), (e) DU145 (prostate cancer), or (f) MIAPaCa-2 (pancreatic cancer) cells were administered either vehicle control or Compound Example 6 for 14 days. Mean relative body weights ±SD (n=6 per each treatment group) in comparison with the mean body weight just before the administration (day 0) are shown. The mean relative body weights after 14 days of administration were: (a) 0.93 for 20 mg/kg intravenously once every two days. in MDA-MB-231; (b) 0.89 for 10 mg/kg orally once a day in MDA-MB-231; (c) 1.06 for 1 mg/kg intravenously once a day, 1.03 for 5 mg/kg intravenously once a day, and 1.00 for 10 mg/kg intravenously once a day in A549; (d) 0.99 for 5 mg/kg orally once a day, and 0.98 for 10 mg/kg orally once a day in A549; (e) 0.96 for 10 mg/kg orally once a day in DU145; (f) 0.97 for 10 mg/kg orally once a day in MIAPaCa-2. i.v. q.2d; intravenously once every two days, i.v. q.d.; intravenously once a day, p.o. q.d.; orally once a day.
Figures 1, 3:
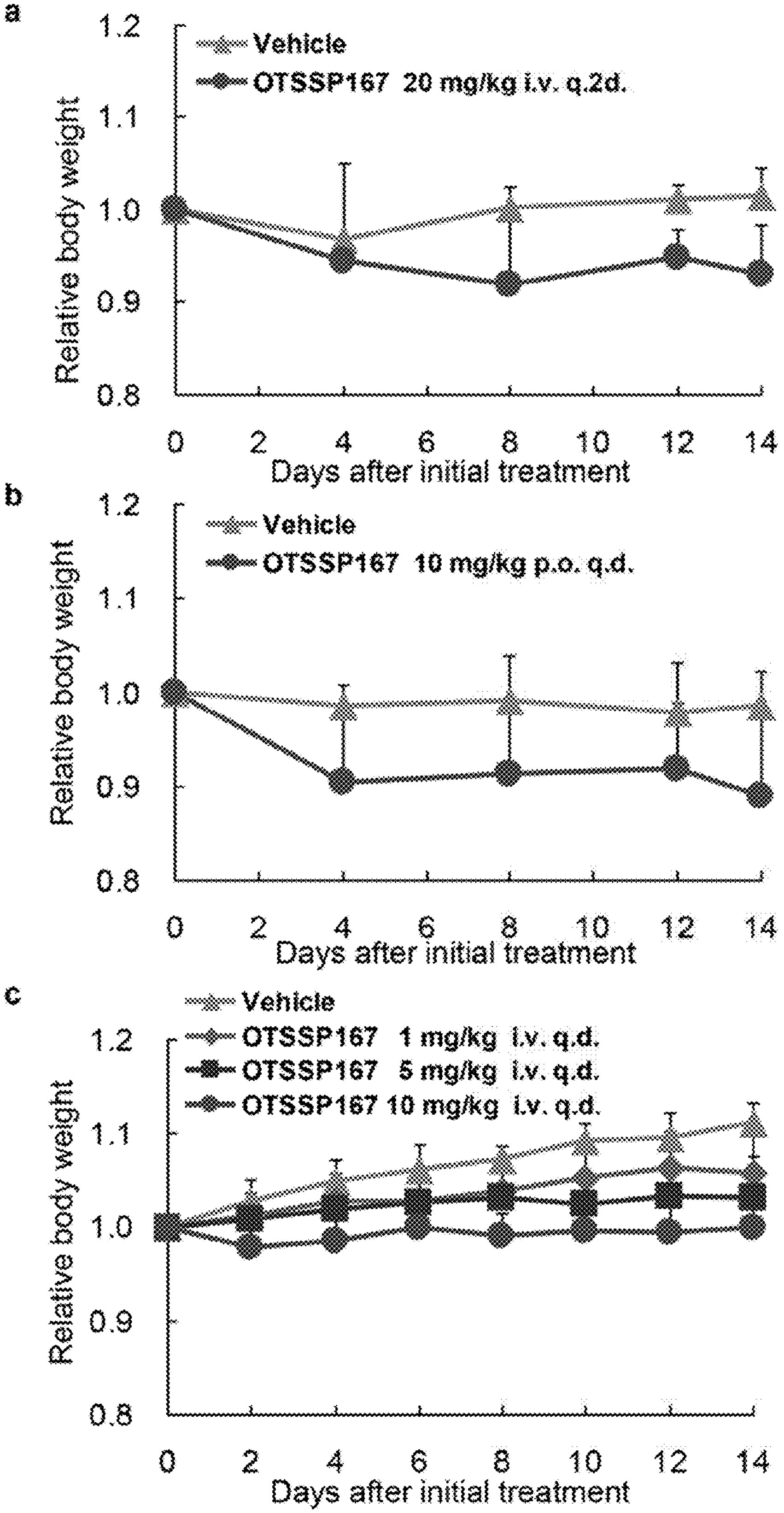
Figures 2, 3:
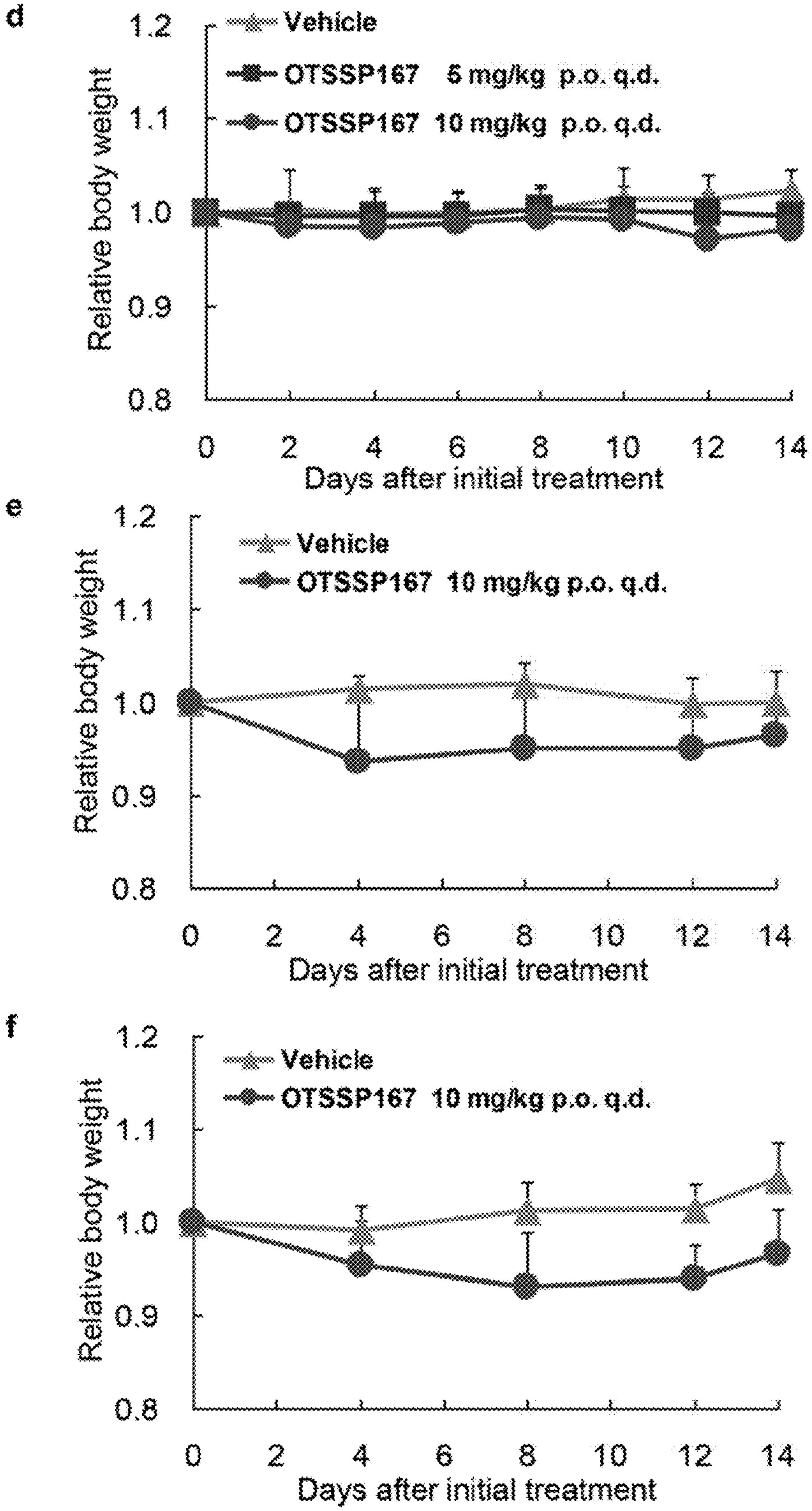

The present inventors subsequently examined in vivo antitumor effect of Compound Example 6 by a xenograft model using MDA-MB-231 cells (MELK-positive, triple-negative breast cancer cells). The compound was administered to mice bearing xenografts for 14 days after the tumor size reached about 100 $mm^3$. The tumor size was measured as a surrogate marker of drug response (tumor growth inhibition (TGI)) (see Methods). Intravenous administration of Example 6 at 20 mg/kg once every two days resulted in TGI of 73% (FIG. 2*a*). Since the bioavailability of this compound was expected to be very high (data not shown), oral administration of this compound was attempted. The oral administration at 10 mg/kg once a day revealed TGI of 72% (FIG. 2*b*). Due to the high growth-suppressive effect on various cancer cell lines, in vivo growth-suppressive effect using cancer cell lines of other types was further investigated and found significant tumor growth suppression by Example 6 for multiple cancer types in dose-dependent manners with no or a little body-weight loss (FIG. 2 and FIG. 3). For example, mice carrying A549 (lung cancer) xenografts that were treated with 1, 5, and 10 mg/kg once a day of Example 6 by intravenous administration revealed TGI of 51, 91, and 108, respectively (FIG. 2*c*) and those by oral administration of 5 and 10 mg/kg once a day revealed TGI of 95 and 124%, respectively (FIG. 2*d*). In addition, the present inventors examined DU145 (prostate cancer) and MIAPaCa-2 (pancreatic cancer) xenograft models by oral administration of 10 mg/kg once a day, and observed TGI of 106 and 87%, respectively (FIG. 2*e* and *f*). To further validate the MELK-specific in vivo tumor suppressive effect, the inventors examined PC-14 lung cancer cells in which MELK expression was hardly detectable (FIG. 2*g*). Oral administration of 10 mg/kg Example 6 once a day for 14 days showed no tumor growth suppressive effect on PC-14 xenografts (FIG. 2*h*), further supporting the MELK-dependent antitumor activity of Example 6.

INDUSTRIAL APPLICABILITY

The present invention provides a novel quinoline derivative having MELK inhibitory effect. The compounds of the present invention may be used for pharmaceutical composition for inhibiting MELK. Such pharmaceutical compositions are suitable for treating or preventing cancer.

The invention claimed is:

1. A compound represented by formula (I) or a pharmaceutically acceptable salt thereof:

(I)

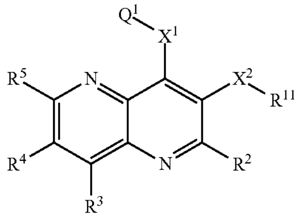

wherein, $X^1$ is selected from the group consisting of a direct bond, —$NR^{12}$—, —O—, and —S—;

$R^{12}$ is selected from the group consisting of a hydrogen atom, $C_1$-$C_6$ alkyl and $C_3$-$C_{10}$ cycloalkyl;

$Q^1$ is selected from the group consisting of $C_3$-$C_{10}$ cycloalkyl, $C_6$-$C_{10}$ aryl, 5- to 10-membered heteroaryl, 3- to 10-membered non-aromatic heterocyclyl, ($C_3$-$C_{10}$ cycloalkyl)-$C_1$-$C_6$ alkyl, ($C_6$-$C_{10}$ aryl)-$C_1$-$C_6$ alkyl, (5- to 10-membered heteroaryl)-$C_1$-$C_6$ alkyl, and (3- to 10-membered non-aromatic heterocyclyl)-$C_1$-$C_6$ alkyl; wherein $Q^1$ is optionally substituted with one or more substituents independently selected from $A^1$;

$X^2$ is selected from the group consisting of —CO—, —S—, —SO—, and —$SO_2$—;

$R^{11}$ is selected from the group consisting of $C_1$-$C_6$ alkyl, $C_3$-$C_{10}$ cycloalkyl, $C_6$-$C_{10}$ aryl, 5- to 10-membered heteroaryl, and 3- to 10-membered non-aromatic heterocyclyl; wherein $R^{11}$ is optionally substituted with one or more substituents independently selected from $A^2$;

$R^5$ is selected from the group consisting of a halogen atom, $C_3$-$C_{10}$ cycloalkyl, $C_6$-$C_{10}$ aryl, 5- to 10-membered heteroaryl, and 3- to 10-membered non-aromatic heterocyclyl; wherein the cycloalkyl, aryl, heteroaryl, and heterocyclyl are optionally substituted with one or more substituents independently selected from $A^3$;

$R^2$, $R^3$, and $R^4$ are independently selected from the group consisting of a hydrogen atom, a halogen atom, and $C_1$-$C_6$ alkyl;

$A^1$ and $A^3$ are independently selected from the group consisting of a halogen atom, cyano, —$COOR^{13}$, —$CONR^{14}R^{15}$, formyl, ($C_1$-$C_6$ alkyl)carbonyl, $C_1$-$C_6$ alkyl, $C_2$-$C_6$ alkenyl, $C_2$-$C_6$ alkynyl, nitro, —$NR^{16}R^{17}$, —$OR^{18}$, —$S(O)_nR^{19}$, $C_3$-$C_{10}$ cycloalkyl, $C_6$-$C_{10}$ aryl, 5- to 10-membered heteroaryl, and 3- to 10-membered non-aromatic heterocyclyl; wherein the alkylcarbonyl, alkyl, alkenyl, alkynyl, cycloalkyl, aryl, heteroaryl, and heterocyclyl are optionally substituted with one or more substituents independently selected from $A^4$;

$A^2$ is independently selected from the group consisting of a halogen atom, cyano, $C_3$-$C_{10}$ cycloalkyl, carboxy, formyloxy, ($C_1$-$C_6$ alkyl)carbonyloxy, hydroxy, $C_1$-$C_6$ alkoxy, amino, $C_1$-$C_6$ alkylamino, and di($C_1$-$C_6$ alkyl)amino;

$R^{13}$, $R^{14}$, and $R^{15}$ are independently selected from the group consisting of a hydrogen atom, $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 5- to 10-membered heteroaryl, and 3- to 10-membered non-aromatic heterocyclyl; wherein the alkyl, alkenyl, alkynyl, cycloalkyl, aryl, heteroaryl, and heterocyclyl are optionally substituted with one or more substituents independently selected from $A^4$; or $R^{14}$ and $R^{15}$ together with the nitrogen atom to which they are attached form 3- to 10-membered nitrogen-containing heterocyclyl, which is optionally substituted with one or more substituents independently selected from $A^4$;

$R^{16}$ and $R^{18}$ are independently selected from the group consisting of a hydrogen atom, $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 5- to 10-membered heteroaryl, 3- to 10-membered non-aromatic heterocyclyl, and —$COR^{20}$; wherein the alkyl, alkenyl, alkynyl, cycloalkyl, aryl, heteroaryl, and heterocyclyl are optionally substituted with one or more substituents independently selected from $A^4$; $R^{17}$ is selected from the group consisting of a hydrogen atom, and $C_1$-$C_6$ alkyl that is optionally substituted with one or more substituents independently selected from $A^4$; or $R^{16}$ and $R^{17}$ together with the nitrogen atom to which they are attached form 3- to 10-membered nitrogen-containing heterocyclyl, which is optionally substituted with one or more substituents independently selected from $A^4$;

$R^{19}$ is selected from the group consisting of $C_1$-$C_6$ alkyl, $C_3$-$C_{10}$ cycloalkyl, $C_6$-$C_{10}$ aryl, and 5- to 10-membered heteroaryl; wherein the alkyl, cycloalkyl, aryl, and heteroaryl are optionally substituted with one or more substituents independently selected from $A^4$;

$R^{20}$ is selected from the group consisting of a hydrogen atom, —$NR^{14}R^{15}$, $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 5- to 10-membered heteroaryl, and 3- to 10-membered non-aromatic heterocyclyl; wherein the alkyl, alkenyl, alkynyl, cycloalkyl, aryl, heteroaryl, and heterocyclyl are optionally substituted with one or more substituents independently selected from $A^4$;

n is an integer independently selected from 0 to 2;

$A^4$ is independently selected from consisting of a halogen atom, cyano, —$COOR^{21}$, —$CONR^{22}R^{23}$, formyl, ($C_1$-$C_6$ alkyl)carbonyl, $C_1$-$C_6$ alkyl, $C_2$-$C_6$ alkenyl, $C_2$-$C_6$ alkynyl, nitro, —$NR^{24}R^{25}$, —$OR^{26}$, —$S(O)_nR^{27}$, $C_3$-$C_{10}$ cycloalkyl, $C_6$-$C_{10}$ aryl, 5- to 10-membered heteroaryl, and 3- to 10-membered non-aromatic heterocyclyl; wherein the alkylcarbonyl, alkyl, alkenyl, alkynyl, cycloalkyl, aryl, heteroaryl, and heterocyclyl are optionally substituted with one or more substituents independently selected from $A^5$;

$R^{21}$, $R^{22}$, and $R^{23}$ are independently selected from the group consisting of a hydrogen atom, $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 5- to 10-membered heteroaryl, and 3- to 10-membered non-aromatic heterocyclyl; wherein the alkyl, alkenyl, alkynyl, cycloalkyl, aryl, heteroaryl, and heterocyclyl are optionally substituted with one or more substituents independently selected from $A^5$; or $R^{22}$ and $R^{23}$ together with the nitrogen atom to which they are attached form 3- to 10-membered nitrogen-containing heterocyclyl, which is optionally substituted with one or more substituents independently selected from $A^5$;

$R^{24}$ and $R^{26}$ are independently selected from the group consisting of a hydrogen atom, $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 5- to 10-membered heteroaryl, 3- to 10-membered non-aromatic heterocyclyl, and —$COR^{28}$; wherein the alkyl, alkenyl, alkynyl cycloalkyl, aryl, heteroaryl, and heterocyclyl are optionally substituted with one or more substituents independently selected from $A^5$; $R^{25}$ is selected from the group consisting of a hydrogen atom, and $C_1$-$C_6$ alkyl that is optionally substituted with one or more substituents independently selected from $A^5$; or $R^{24}$ and $R^{25}$ together with the nitrogen atom to which they are attached form 3- to 10-membered nitrogen-containing heterocyclyl, which is optionally substituted with one or more substituents independently selected from $A^5$;

$R^{27}$ is selected from the group consisting of $C_1$-$C_6$ alkyl, $C_3$-$C_{10}$ cycloalkyl, $C_6$-$C_{10}$ aryl, and 5- to 10-membered heteroaryl; wherein the alkyl, cycloalkyl, aryl, and heteroaryl are optionally substituted with one or more substituents independently selected from $A^5$;

$R^{28}$ is independently selected from the group consisting of a hydrogen atom, —$NR^{22}R^{23}$, $C_1$-$C_6$ alkyl, $C_2$-$C_6$ alkenyl, $C_2$-$C_6$ alkynyl $C_3$-$C_{10}$ cycloalkyl, $C_6$-$C_{10}$ aryl, 5- to 10-membered heteroaryl, and 3- to 10-membered non-aromatic heterocyclyl; wherein the alkyl, alkenyl, alkynyl, cycloalkyl, aryl, heteroaryl, and heterocyclyl are optionally substituted with one or more substituents independently selected from $A^5$;

$A^5$ is independently selected from consisting of a halogen atom, cyano, —$COOR^{31}$, —$CONR^{32}R^{33}$, formyl, ($C_1$-$C_6$ alkyl)carbonyl, $C_1$-$C_6$ alkyl, $C_2$-$C_6$ alkenyl, $C_2$-$C_6$ alkynyl, nitro, —$NR^{34}R^{35}$, —$OR^{36}$, —$S(O)_nR^{37}$, $C_3$-$C_{10}$ cycloalkyl, $C_6$-$C_{10}$ aryl, 5- to 10-membered heteroaryl, and 3- to 10-membered non-aromatic heterocyclyl; wherein the alkylcarbonyl, alkyl, alkenyl, alkynyl, cycloalkyl, aryl, heteroaryl, and heterocyclyl are optionally substituted with one or more substituents independently selected from $A^6$;

$R^{31}$, $R^{32}$, and $R^{33}$ are independently selected from the group consisting of a hydrogen atom, $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 5- to 10-membered heteroaryl, and 3- to 10-membered non-aromatic heterocyclyl; wherein the alkyl, alkenyl, alkynyl, cycloalkyl, aryl, heteroaryl, and heterocyclyl are optionally substituted with one or more substituents independently selected from $A^6$; or $R^{32}$ and $R^{33}$ together with the nitrogen atom to which they are attached form 3- to 10-membered nitrogen-containing heterocyclyl, which is optionally substituted with one or more substituents independently selected from $A^6$;

$R^{34}$ and $R^{36}$ are independently selected from the group consisting of a hydrogen atom, $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 5- to 10-membered heteroaryl, 3- to 10-membered non-aromatic heterocyclyl, and —$COR^{38}$; wherein the alkyl, alkenyl, alkynyl, cycloalkyl, aryl, heteroaryl, and heterocyclyl are optionally substituted with one or more substituents independently selected from $A^6$; $R^{35}$ is selected from the group consisting of a hydrogen atom, and $C_1$-$C_6$ alkyl that is optionally substituted with one or more substituents independently selected from $A^6$; or $R^{34}$ and $R^{35}$ together with the nitrogen atom to which they are attached form 3- to 10-membered nitrogen-containing heterocyclyl, which is optionally substituted with one or more substituents independently selected from $A^6$;

$R^{37}$ is selected from the group consisting of $C_1$-$C_6$ alkyl, $C_3$-$C_{10}$ cycloalkyl, $C_6$-$C_{10}$ aryl, and 5- to 10-membered heteroaryl; wherein the alkyl, cycloalkyl, aryl, and heteroaryl are optionally substituted with one or more substituents independently selected from $A^6$;

$R^{38}$ is independently selected from the group consisting of a hydrogen atom, —$NR^{32}R^{33}$, $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 5- to 10-membered heteroaryl, and 3- to 10-membered non-aromatic heterocyclyl; wherein the alkyl, alkenyl, alkynyl, cycloalkyl, aryl, heteroaryl, and heterocyclyl are optionally substituted with one or more substituents independently selected from $A^6$;

$A^6$ is independently selected from consisting of a halogen atom, cyano, carboxy, —$COOR^{41}$, —$CONR^{42}R^{43}$, formyl, ($C_1$-$C_6$ alkyl)carbonyl, $C_1$-$C_6$ alkyl, $C_2$-$C_6$ alkenyl, $C_2$-$C_6$ alkynyl, nitro, —$NR^{44}R^{45}$, —$OR^{46}$, $S(O)_nR^{47}$, $C_3$-$C_{10}$ cycloalkyl, $C_6$-$C_{10}$ aryl, 5- to 10-membered heteroaryl, and 3- to 10-membered non-aromatic heterocyclyl; wherein the alkylcarbonyl, alkyl, alkenyl, alkynyl, cycloalkyl, aryl, heteroaryl, and heterocyclyl are optionally substituted with one or more substituents independently selected from the group consisting of a halogen atom, hydroxy, $C_1$-$C_6$ alkoxy, amino, $C_1$-$C_6$ alkylamino, and di($C_1$-$C_6$ alkyl)amino;

$R^{41}$, $R^{42}$, and $R^{43}$ are independently selected from the group consisting of a hydrogen atom, $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 5- to 10-membered heteroaryl, and 3- to 10-membered non-aromatic heterocyclyl; wherein the alkyl, alkenyl, alkynyl, cycloalkyl, aryl, heteroaryl, and heterocyclyl are optionally substituted with one or more substituents independently selected from the group consisting of a halogen atom, hydroxy, $C_1$-$C_6$ alkoxy, amino, $C_1$-$C_6$ alkylamino, and di($C_1$-$C_6$ alkyl)amino;

$R^{44}$ and $R^{46}$ are independently selected from the group consisting of a hydrogen atom, $C_1$-$C_6$ alkyl, $C_3$-$C_{10}$ cycloalkyl, $C_6$-$C_{10}$ aryl, 5- to 10-membered heteroaryl, 3- to 10-membered non-aromatic heterocyclyl, and —$COR^{48}$;

$R^{45}$ is selected from the group consisting of a hydrogen atom, and $C_1$-$C_6$ alkyl;

$R^{47}$ is selected from the group consisting of $C_1$-$C_6$ alkyl, $C_3$-$C_{10}$ cycloalkyl, $C_6$-$C_{10}$ aryl, and 5- to 10-membered heteroaryl; and $R^{48}$ is independently selected from the group consisting of $C_1$-$C_6$ alkyl, $C_3$-$C_{10}$ cycloalkyl, $C_6$-$C_{10}$ aryl, 5- to 10-membered heteroaryl, and 3- to 10-membered non-aromatic heterocyclyl.

2. The compound or a pharmaceutically acceptable salt thereof according to claim 1, wherein $Q^1$ is selected from the group consisting of $C_5$-$C_7$ cycloalkyl, phenyl, pyridyl, pyrazolyl, pyrimidinyl, and piperidyl; wherein $Q^1$ is optionally substituted with one or more substituents independently selected from $A^1$.

3. The compound or a pharmaceutically acceptable salt thereof according to claim 1 wherein $X^2$ is selected from the group consisting of —CO— and —$SO_2$—; and $R^{11}$ is selected from the group consisting of $C_1$-$C_6$ alkyl and $C_3$-$C_7$ cycloalkyl, which are optionally substituted with one or more substituents independently selected from the group consisting of hydroxy and a halogen atom.

4. The compound or a pharmaceutically acceptable salt thereof according to claim 1, wherein $R^5$ is phenyl substituted with one to three substituents independently selected from the group consisting of hydroxy, a halogen atom, $C_1$-$C_6$ alkyl, and $C_1$-$C_6$ alkoxy, wherein the alkyl and alkoxy are optionally substituted with one or more halogen atoms.

5. The compound or a pharmaceutically acceptable salt thereof according to claim 1, wherein $R^2$ is a hydrogen atom.

6. The compound or a pharmaceutically acceptable salt thereof according to claim 1, wherein $R^3$ is a hydrogen atom.

7. The compound or a pharmaceutically acceptable salt thereof according to claim 1, wherein $R^4$ is a hydrogen atom.

8. The compound or a pharmaceutically acceptable salt thereof according to claim 1, wherein $X^1$ is —NH—.

9. The compound or a pharmaceutically acceptable salt thereof according to claim 1, wherein the optional substituent of $Q^1$ is selected from the group consisting of hydroxy, amino, $C_1$-$C_6$ alkoxy, $C_1$-$C_6$ alkylamino, di($C_1$-$C_6$ alkyl)amino, amino-$C_1$-$C_6$ alkyl, ($C_1$-$C_6$ alkylamino)-$C_1$-$C_6$ alkyl, di($C_1$-$C_6$ alkyl)amino-$C_1$-$C_6$ alkyl, amino-$C_1$-$C_6$ alkoxy, ($C_1$-$C_6$ alkylamino)-$C_1$-$C_6$ alkoxy, di($C_1$-$C_6$ alkyl)amino-$C_1$-$C_6$ alkoxy, hydroxy-$C_1$-$C_6$ alkyl, ($C_1$-$C_6$ alkoxy)-$C_1$-$C_6$ alkyl, carboxy-$C_1$-$C_6$ alkyl, [($C_1$-$C_6$ alkoxy)carbonyl]-$C_1$-$C_6$ alkyl, carbamoyl-$C_1$-$C_6$ alkyl, [N—($C_1$-$C_6$ alkyl) carbamoyl]-$C_1$-$C_6$ alkyl [N,N-di($C_1$-$C_6$ alkyl)carbamoyl]-$C_1$-$C_6$ alkyl, ($C_1$-$C_6$ alkyl)carbonylamino, N—($C_1$-$C_6$ alkyl)carbonyl-N—($C_1$-$C_6$ alkyl)amino, pyrrolidinyl, piperidyl, piperazinyl;

wherein the pyrrolidinyl, piperidyl, and piperazinyl defined as the optional substituent of $Q^1$ are optionally substituted with a substituent selected from the group consisting of $C_1$-$C_6$ alkyl, amino, $C_1$-$C_6$ alkylamino, di($C_1$-$C_6$ alkyl)amino, hydroxy, $C_1$-$C_6$ alkoxy, pyrrolidinyl, piperidyl, and piperazinyl; and wherein the alkyl moiety of the group defined as the optional substituent of $Q^1$ is optionally substituted with a substituent selected from the group consisting of amino, $C_1$-$C_6$ alkylamino, di($C_1$-$C_6$ alkyl)amino, hydroxy, $C_1$-$C_6$ alkoxy, pyrrolidinyl, piperidyl, and piperazinyl.

10. The compound or a pharmaceutically acceptable salt thereof according to claim 9, wherein the optional substituent of $Q^1$ is selected from the group consisting of hydroxy, amino, di($C_1$-$C_6$ alkyl)amino, $C_1$-$C_6$ alkyl, di($C_1$-$C_6$ alkyl)amino-$C_1$-$C_6$ alkyl, di($C_1$-$C_6$ alkyl)amino-$C_1$-$C_6$ alkoxy, di($C_1$-$C_6$ alkyl)amino, [(amino-$C_1$-$C_6$ alkyl)carbonyl]amino, N—($C_1$-$C_6$ alkyl)piperidyl, di($C_1$-$C_6$ alkyl)amino-pyrrolidin-1-yl, amino-pyrrolidin-1-yl, (pyrrolidin-1-yl) -$C_1$-$C_6$ alkyl, ($C_1$-$C_6$ alkyl)amino-piperidin-1-yl, amino-piperidin-1-yl, hydroxy-$C_1$-$C_6$ alkyl, [di($C_1$-$C_6$ alkyl)amino-$C_1$-$C_6$ alkyl]amino, [4-($C_1$-$C_6$ alkyl)-piperazin-1-yl]-$C_1$-$C_6$ alkyl, (piperazin-1-yl)-$C_1$-$C_6$ alkyl, pyrrolidinylcarbonyl-amino, (hydroxy-pyrrolidin-1-yl)-$C_1$-$C_6$ alkyl, morpholino-$C_1$-$C_6$ alkyl, [N-(hydroxy-$C_1$-$C_6$ alkyl)-N—($C_1$-$C_6$ alkyl)amino]-$C_1$-$C_6$ alkyl, and $(CD_3)_2N$—$C_1$-$C_6$ alkyl.

11. The compound or a pharmaceutically acceptable salt thereof according to claim 1, which is selected from the group consisting of the following compounds:

1-(6-chloro-4-(4-((dimethylamino)methyl)cyclohexylamino)-1,5-naphthyridin-3-yl)ethanone;

1-(6-(3,5-dichloro-4-hydroxyphenyl)-4-((4-(dimethylamino)cyclohexyl)amino)-1,5-naphthyridin-3-yl)ethanone;

1-(6-(3-chloro-5-fluoro-4-hydroxyphenyl)-4-((4-(dimethylamino)cyclohexyl)amino)-1,5-naphthyridin-3-yl) ethanone;

cyclopropyl(6-(3,5-dichloro-4-hydroxyphenyl)-4-(4-((dimethylamino)methyl)-cyclohexylamino)-1,5-naphthyridin-3-yl)methanone;

(6-(3-chloro-5-fluoro-4-hydroxyphenyl)-4-(4-((dimethylamino)methyl)-cyclohexylamino)-1,5-naphthyridin-3-yl)(cyclopropyl)methanone;

1-(6-(3,5-dichloro-4-hydroxyphenyl)-4-((4-((dimethylamino)methyl)cyclohexyl)-amino)-1,5-naphthyridin-3-yl)ethanone;

1-(6-(3-chloro-5-fluoro-4-hydroxyphenyl)-4-((4-((dimethylamino)methyl)cyclohexyl)-amino)-1,5-naphthyridin-3-yl)ethanone;

1-(6-(3-chloro-4-hydroxy-5-methoxyphenyl)-4-((4-((dimethylamino)methyl)-cyclohexyl)amino)-1,5-naphthyridin-3-yl)ethanone;

1-(6-(3,5-dichloro-4-hydroxyphenyl)-4-((4-(2-(dimethylamino)ethyl)cyclohexyl)-amino)-1,5-naphthyridin-3-yl)ethanone;

1-(6-(3-chloro-5-fluoro-4-hydroxyphenyl)-4-(4-(2-(dimethylamino)ethyl)-cyclohexylamino)-1,5-naphthyridin-3-yl)ethanone;

1-(4-(4-((dimethylamino)methyl)cyclohexylamino)-6-(4-hydroxy-3-(trifluoromethoxy)-phenyl)-1,5-naphthyridin-3-yl)ethanone;

2,6-dichloro-4-(8-((4-((dimethylamino)methyl)cyclohexyl)amino)-7-(methylsulfonyl)-1,5-naphthyridin-2-yl)phenol;

2-chloro-4-(8-((4-((dimethylamino)methyl)cyclohexyl)amino)-7-(methylsulfonyl)-1,5-naphthyridin-2-yl)-6-fluorophenol;

2-chloro-4-(8-((4-((dimethylamino)methyl)cyclohexyl)amino)-7-(methylsulfonyl)-1,5-naphthyridin-2-yl)-6-methoxyphenol;

2,6-dichloro-4-(8-((4-(dimethylamino)cyclohexyl)amino)-7-(methylsulfonyl)-1,5-naphthyridin-2-yl)phenol;

2,6-dichloro-4-(8-((4-((dimethylamino)methyl)phenyl)amino)-7-(methylsulfonyl)-1,5-naphthyridin-2-yl)phenol;

2-chloro-4-(8-((4-((dimethylamino)methyl)phenyl)amino)-7-(methylsulfonyl)-1,5-naphthyridin-2-yl)-6-fluorophenol;

2-chloro-4-(8-((4-((dimethylamino)methyl)phenyl)amino)-7-(methylsulfonyl)-1,5-naphthyridin-2-yl)-6-methoxyphenol;

1-(6-(3,5-dichloro-4-hydroxyphenyl)-4-((3-(2-(pyrrolidin-1-yl)ethyl)phenyl)amino)-1,5-naphthyridin-3-yl)ethanone;

1-(6-(3-chloro-5-fluoro-4-hydroxyphenyl)-4-(3-(2-(pyrrolidin-1-yl)ethyl)phenylamino)-1,5-naphthyridin-3-yl)ethanone;

1-(6-(3,5-dichloro-4-hydroxyphenyl)-4-((6-(2-(dimethylamino)ethoxy)pyridin-3-yl)-amino)-1,5-naphthyridin-3-yl)ethanone;

1-(6-(3-chloro-5-fluoro-4-hydroxyphenyl)-4-((6-(2-(dimethylamino)ethoxy)pyridin-3-yl)amino)-1,5-naphthyridin-3-yl)ethanone;

1-(6-(3-chloro-4-hydroxy-5-methoxyphenyl)-4-((6-(2-(dimethylamino)ethoxy)pyridin-3-yl)amino)-1,5-naphthyridin-3-yl)ethanone;

2,6-dichloro-4-(8-((6-(2-(dimethylamino)ethoxy)pyridin-3-yl)amino)-7-(methylsulfonyl)-1,5-naphthyridin-2-yl)phenol;

2-chloro-4-(8-((6-(2-(dimethylamino)ethoxy)pyridin-3-yl)amino)-7-(methylsulfonyl)-1,5-naphthyridin-2-yl)-6-fluorophenol;

2-chloro-4-(8-((6-(2-(dimethylamino)ethoxy)pyridin-3-yl)amino)-7-(methylsulfonyl)-1,5-naphthyridin-2-yl)-6-methoxyphenol;

1-(6-(3,5-dichloro-4-hydroxyphenyl)-4-((1-methylpiperidin-4-yl)methylamino)-1,5-naphthyridin-3-yl)ethanone;

1-(6-(3,5-dichloro-4-hydroxyphenyl)-4-((4-((dimethylamino-d6)methyl)cyclohexyl)-amino)-1,5-naphthyridin-3-yl)ethanone;

1-(6-(3,5-dichloro-4-hydroxyphenyl)-4-((4-(2-(dimethylamino)ethyl)phenyl)amino)-1,5-naphthyridin-3-yl)ethanone;

1-(6-(3-chloro-5-fluoro-4-hydroxyphenyl)-4-((4-(2-(dimethylamino)ethyl)phenyl)-amino)-1,5-naphthyridin-3-yl)ethanone;

1-(6-(3-chloro-4-hydroxy-5-methoxyphenyl)-4-((4-(2-(dimethylamino)ethyl)phenyl)-amino)-1,5-naphthyridin-3-yl)ethanone;

2-chloro-4-(8-((4-(dimethylamino)cyclohexyl)amino)-7-(methylsulfonyl)-1,5-naphthyridin-2-yl)-6-fluorophenol;

1-(6-(3,5-dichloro-4-hydroxyphenyl)-4-((1-(1-methylpiperidin-4-yl)-1H-pyrazol-4-yl)-amino)-1,5-naphthyridin-3-yl)ethanone;

1-(6-(3,5-dichloro-4-hydroxyphenyl)-4-(4-((4-methylpiperazin-1-yl)methyl)-phenylamino)-1,5-naphthyridin-3-yl)ethanone;

1-(6-(3-chloro-5-fluoro-4-hydroxyphenyl)-4-(4-((4-methylpiperazin-1-yl)methyl)-phenylamino)-1,5-naphthyridin-3-yl)ethanone;

1-(6-(3,5-dichloro-4-hydroxyphenyl)-4-(4-(2-(pyrrolidin-1-yl)ethyl)piperidin-1-yl)-1,5-naphthyridin-3-yl)ethanone;

1-(6-(3-chloro-5-fluoro-4-hydroxyphenyl)-4-(4-(2-(pyrrolidin-1-yl)ethyl)piperidin-1-yl)-1,5-naphthyridin-3-yl)ethanone;

1-(6-(3,5-dichloro-4-hydroxyphenyl)-4-(6-(2-(dimethylamino)ethylamino)pyridin-3-ylamino)-1,5-naphthyridin-3-yl)ethanone;

1-(6-(3-chloro-5-fluoro-4-hydroxyphenyl)-4-(6-(2-(dimethylamino)ethylamino)-pyridin-3-ylamino)-1,5-naphthyridin-3-yl)ethanone;

(S)-(4-(6-(3-aminopiperidin-1-yl)pyridin-3-ylamino)-6-(3,5-dichloro-4-hydroxyphenyl)-1,5-naphthyridin-3-yl)(cyclopropyl)methanone;

1-(4-((2-(3-aminopyrrolidin-1-yl)pyrimidin-5-yl)amino)-6-(3,5-dichloro-4-hydroxyphenyl)-1,5-naphthyridin-3-yl)ethanone;

1-(4-(4-((dimethylamino)methyl)cyclohexylamino)-6-(1H-pyrazol-4-yl)-1,5-naphthyridin-3-yl)ethanone;

1-(6-(3,5-dichloro-4-hydroxyphenyl)-4-(4-(hydroxymethyl)cyclohexylamino)-1,5-naphthyridin-3-yl)ethanone;

1-[6-(3,5-dichloro-4-hydroxyphenyl)-4-{4-[(dimethylamino)methyl]-cyclohexylamino}-1,5-naphthyridin-3-yl]-2-hydroxyethanone;

1-(6-(3,5-dichloro-4-hydroxyphenyl)-4-(1-methylpiperidin-4-ylamino)-1,5-naphthyridin-3-yl)ethanone;

1-(6-(3-chloro-5-fluoro-4-hydroxyphenyl)-4-(1-methylpiperidin-4-ylamino)-1,5-naphthyridin-3-yl)ethanone;

1-{6-[3,5-dichloro-4-hydroxyphenyl]-4-[4-(morpholinomethyl)cyclohexylamino]-1,5-naphthyridin-3-yl}ethanone;

1-(6-(3,5-dichloro-4-hydroxyphenyl)-4-(4-(((2-hydroxyethyl)(methyl)amino)methyl)-cyclohexylamino)-1,5-naphthyridin-3-yl)ethanone;

1-(6-(3-chloro-5-fluoro-4-hydroxyphenyl)-4-(4-(((2-hydroxyethyl)(methyl)amino)-methyl)cyclohexylamino)-1,5-naphthyridin-3-yl)ethanone;

1-(6-(3,5-difluoro-4-hydroxyphenyl)-4-(4-((dimethylamino)methyl)cyclohexylamino)-1,5-naphthyridin-3-yl)ethanone;

1-(6-(3,5-dichloro-4-hydroxyphenyl)-4-((6-(3-(dimethylamino)pyrrolidin-1-yl)pyridin-3-yl)amino)-1,5-naphthyridin-3-yl)ethanone;

1-(6-(3-chloro-5-fluoro-4-hydroxyphenyl)-4-((6-(3-(dimethylamino)pyrrolidin-1-yl)-pyridin-3-yl)amino)-1,5-naphthyridin-3-yl)ethanone;

1-(6-(3,5-dichloro-4-hydroxyphenyl)-4-(6-(3-(methylamino)pyrrolidin-1-yl)pyridin-3-ylamino)-1,5-naphthyridin-3-yl)ethanone;

1-(6-(3-chloro-5-fluoro-4-hydroxyphenyl)-4-(6-(3-(methylamino)pyrrolidin-1-yl)-pyridin-3-ylamino)-1,5-naphthyridin-3-yl)ethanone;

1-(6-(1H-benzo[d]imidazol-5-yl)-4-(4-((dimethylamino)methyl)cyclohexylamino)-1,5-naphthyridin-3-yl)ethanone;

1-(4-((4-((dimethylamino)methyl)cyclohexylamino)-6-(pyridin-4-yl)-1,5-naphthyridin-3-yl)ethanone;

5-(7-acetyl-8-(4-((dimethylamino)methyl)cyclohexylamino)-1,5-naphthyridin-2-yl)-pyrimidine-2-carbonitrile;

1-(6-(3,5-dimethyl-1H-pyrazol-4-yl)-4-(4-((dimethylamino)methyl)cyclohexylamino)-1,5-naphthyridin-3-yl)ethanone;

1-(4-(4-((dimethylamino)methyl)cyclohexylamino)-6-(4-hydroxy-3,5-dimethyl-phenyl)-1,5-naphthyridin-3-yl)ethanone;

1-(6-(3,5-dichloro-4-hydroxyphenyl)-4-(4-(pyrrolidin-1-ylmethyl)phenylamino)-1,5-naphthyridin-3-yl)ethanone;

1-(6-(3,5-dichloro-4-hydroxyphenyl)-4-(4-(pyrrolidin-1-ylmethyl)cyclohexylamino)-1,5-naphthyridin-3-yl)ethanone;

1-(6-(3-chloro-5-fluoro-4-hydroxyphenyl)-4-(4-(pyrrolidin-1-ylmethyl)cyclohexyl-amino)-1,5-naphthyridin-3-yl)ethanone;

1-(6-(3,5-dichloro-4-hydroxyphenyl)-4-(4-((4-methylpiperazin-1-yl)methyl)cyclo-hexylamino)-1,5-naphthyridin-3-yl)ethanone;

1-(4-(6-(3-aminopiperidin-1-yl)pyridin-3-ylamino)-6-(3,5-dichloro-4-hydroxyphenyl)-1,5-naphthyridin-3-yl)ethanone;

1-(4-(6-(3-aminopiperidin-1-yl)pyridin-3-ylamino)-6-(3-chloro-5-fluoro-4-hydroxy-phenyl)-1,5-naphthyridin-3-yl)ethanone;

1-(4-(4-aminocyclohexylamino)-6-(3,5-dichloro-4-hydroxyphenyl)-1,5-naphthyridin-3-yl)ethanone;

1-[4-(4-aminocyclohexylamino)-6-(3-chloro-5-fluoro-4-hydroxyphenyl)-1,5-naphthyridin-3-yl]ethanone;

1-(6-(3-chloro-5-fluoro-4-hydroxyphenyl)-4-(4-((4-methylpiperazin-1-yl)methyl)-cyclohexylamino)-1,5-naphthyridin-3-yl)ethanone;

N-(4-(3-acetyl-6-(3-chloro-5-fluoro-4-hydroxyphenyl)-1,5-naphthyridin-4-ylamino)-cyclohexyl)-2-amino-3-methylbutanamide;

1-(6-(3,5-dichloro-4-hydroxyphenyl)-4-(4-(piperazin-1-ylmethyl)cyclohexylamino)-1,5-naphthyridin-3-yl)ethanone;

(S)-1-(4-(6-(3-aminopiperidin-1-yl)pyridin-3-ylamino)-6-(3,5-dichloro-4-hydroxy-phenyl)-1,5-naphthyridin-3-yl)ethanone;

(S)-1-(4-(6-(3-aminopiperidin-1-yl)pyridin-3-ylamino)-6-(3-chloro-5-fluoro-4-hydroxy-phenyl)-1,5-naphthyridin-3-yl)ethanone;

N-(4-(3-acetyl-6-(3,5-dichloro-4-hydroxyphenyl)-1,5-naphthyridin-4-yl)amino)cyclo-hexyl)-2-aminopropanamide;

N-(4-(3-acetyl-6-(3-chloro-5-fluoro-4-hydroxyphenyl)-1,5-naphthyridin-4-ylamino)-cyclohexyl)-2-aminopropanamide;

(S)—N-((1R,4S)-4-(3-acetyl-6-(3,5-dichloro-4-hydroxyphenyl)-1,5-naphthyridin-4-yl-amino)cyclohexyl)pyrrolidine-2-carboxamide;

(S)—N-((1R,4S)-4-(3-acetyl-6-(3-chloro-5-fluoro-4-hydroxyphenyl)-1,5-naphthyridin-4-ylamino)cyclohexyl)pyrrolidine-2-carboxamide;

1-(6-(3-hydroxypyrrolidin-1-yl)-4-(4-((3-hydroxypyrrolidin-1-yl)methyl)cyclohexyl-amino)-1,5-naphthyridin-3-yl)ethanone;

1-(6-(pyrrolidin-1-yl)-4-(4-(pyrrolidin-1-ylmethyl)cyclohexylamino)-1,5-naphthyridin-3-yl)ethanone;

N-(4-(3-acetyl-6-(3,5-dichloro-4-hydroxy phenyl)-1,5-naphthyridin-4-ylamino)-cyclohexyl)-2-amino-3-methylbutanamide;

[6-(3-chloro-5-fluoro-4-hydroxyphenyl)-4-[4-(dimethylamino)cyclohexylamino]-1,5-naphthyridin-3-yl](cyclopropyl)methanone;

cyclopropyl[6-(3,5-dichloro-4-hydroxyphenyl)-4-[4-(dimethylamino)cyclohexyl-amino]-1,5-naphthyridin-3-yl]methanone;

1-(4-{4-[(dimethylamino)methyl]cyclohexylamino}-6-(1H-pyrrolo[2,3-b]pyridin-5-yl)-1,5-naphthyridin-3-yl)ethanone;

(S)-{4-[6-(3-aminopiperidin-1-yl)pyridin-3-ylamino]-6-(3-chloro-5-fluoro-4-hydroxyphenyl)-1,5-naphthyridin-3-yl}(cyclopropyl)methanone;

1-(4-{4-[(dimethylamino)methyl]cyclohexyl amino}-6-(4-methoxyphenyl)-1,5-naphthyridin-3-yl)ethanone;

1-[6-(3,5-dichloro-4-methoxyphenyl)-4-{4-[(dimethylamino)methyl]cyclohexyl-amino}-1,5-naphthyridin-3-yl]ethanone;

1-(4-{4-[(dimethylamino)methyl]cyclohexylamino}-6-(6-hydroxypyridin-3-yl)-1,5-naphthyridin-3-yl)ethanone;

5-(7-acetyl-8-{4-[(dimethylamino)methyl]cyclohexylamino}-1,5-naphthyridin-2-yl)picolinonitrile;

1-(4-{4-[(dimethylamino)methyl]cyclohexylamino}-6-(4-hydroxyphenyl)-1,5-naphthyridin-3-yl)ethanone;

1-[6-(3,5-dichloro-4-hydroxyphenyl)-4-{[4-(dimethylamino)cyclohexyl]methyl-amino}-1,5-naphthyridin-3-yl)ethanone;

1-[6-(3-chloro-5-fluoro-4-hydroxyphenyl)-4-{[4-(dimethylamino)cyclohexyl]-methylamino}-1,5-naphthyridin-3-yl]ethanone;

1-[6-(3-chloro-5-fluoro-4-hydroxyphenyl)-4-(4-hydroxy-cyclohexylamino)-1,5-naphthyridin-3-yl]ethanone;

1-[6-(3,5-dichloro-4-hydroxyphenyl)-4-(4-hydroxycyclohexylamino)-1,5-naphthyridin-3-yl]ethanone;

1-[6-(3-chloro-5-fluoro-4-hydroxyphenyl)-4-{cis-4-[(dimethylamino)methyl]cyclo-hexylamino}-1,5-naphthyridin-3-yl]ethanone;

1-[6-(3,5-dichloro-4-hydroxyphenyl)-4-{cis-4-[(dimethylamino)methyl]cyclohexyl-amino}-1,5-naphthyridin-3-yl]ethanone;

(R)-1-{4-[6-(3-aminopiperidin-1-yl)pyridin-3-ylamino]-6-(3,5-dichloro-4-hydroxy-phenyl)-1,5-naphthyridin-3-yl}ethanone;

(R)-1-{4-[6-(3-aminopiperidin-1-yl)pyridin-3-ylamino]-6-(3-chloro-5-fluoro-4-hydroxyphenyl)-1,5-naphthyridin-3-yl}ethanone;

and pharmaceutically acceptable salts thereof.

12. The compound or a pharmaceutically acceptable salt thereof according to claim 1, which is selected from the group consisting of the following compounds:

1-(6-(3,5-dichloro-4-hydroxyphenyl)-4-(trans-(4-(dimethylamino)cyclohexyl)amino)-1,5-naphthyridin-3-yl)ethanone;

cyclopropyl(6-(3,5-dichloro-4-hydroxyphenyl)-4-(trans-4-((dimethylamino)methyl)-cyclohexylamino)-1,5-naphthyridin-3-yl) methanone;

(6-(3-chloro-5-fluoro-4-hydroxyphenyl)-4-(trans-4-((dimethylamino)methyl)-cyclohexylamino)-1,5-naphthyridin-3-yl)(cyclopropyl) methanone;

1-(6-(3,5-dichloro-4-hydroxyphenyl)-4-((trans-4-((dimethylamino)methyl)cyclohexyl)-amino)-1,5-naphthyridin-3-yl) ethanone;

1-(6-(3-chloro-5-fluoro-4-hydroxyphenyl)-4-((trans-4-((dimethylamino)methyl)-cyclohexyl)amino)-1,5-naphthyridin-3-yl) ethanone;

1-(6-(3,5-dichloro-4-hydroxyphenyl)-4-((trans-4-(2-(dimethylamino)ethyl)cyclohexyl)-amino)-1,5-naphthyridin-3-yl) ethanone;

(S)-(4-(6-(3-aminopiperidin-1-yl)pyridin-3-ylamino)-6-(3,5-dichloro-4-hydroxyphenyl)-1,5-naphthyridin-3-yl)(cyclopropyl)methanone;

1-[6-(3,5-dichloro-4-hydroxyphenyl)-4-{trans-4-[(dimethylamino)methyl]cyclo-hexylamino}-1,5-naphthyridin-3-yl]-2-hydroxyethanone;

1-(4-(6-(3-aminopiperidin-1-yl)pyridin-3-ylamino)-6-(3,5-dichloro-4-hydroxyphenyl)-1,5-naphthyridin-3-yl) ethanone;

1-(4-(6-(3-aminopiperidin-1-yl)pyridin-3-ylamino)-6-(3-chloro-5-fluoro-4-hydroxy-phenyl)-1,5-naphthyridin-3-yl)ethanone;

(S)-1-(4-(6-(3-aminopiperidin-1-yl)pyridin-3-ylamino)-6-(3,5-dichloro-4-hydroxy-phenyl)-1,5-naphthyridin-3-yl)ethanone;

(S)-1-(4-(6-(3-aminopiperidin-1-yl)pyridin-3-ylamino)-6-(3-chloro-5-fluoro-4-hydroxy-phenyl)-1,5-naphthyridin-3-yl)ethanone;

(S)-{4-[6-(3-aminopiperidin-1-yl)pyridin-3-ylamino]-6-(3-chloro-5-fluoro-4-hydroxy-phenyl)-1,5-naphthyridin-3-yl}(cyclopropyl) methanone;

(R)-1-{4-[6-(3-aminopiperidin-1-yl)pyridin-3-ylamino]-6-(3,5-dichloro-4-hydroxy-phenyl)-1,5-naphthyridin-3-yl}ethanone;

(R)-1-{4-[6-(3-aminopiperidin-1-yl)pyridin-3-ylamino]-6-(3-chloro-5-fluoro-4-hydroxyphenyl)-1,5-naphthyridin-3-yl}ethanone;

(R)-(4-{[6-(3-aminopiperidin-1-yl)pyridin-3-yl]amino}-6-(3,5-dichloro-4-hydroxyphenyl)-1,5-naphthyridin-3-yl)(cyclopropyl)methanone;

(R)-(4-{[6-(3-aminopiperidin-1-yl)pyridin-3-yl]amino}-6-(3-chloro-5-fluoro-4-hydroxyphenyl)-1,5-naphthyridin-3-yl)(cyclopropyl) methanone;

1-[6-(3,5-dichloro-4-hydroxyphenyl)-4-{[trans-4-(dimethylamino)cyclohexyl]amino}-1,5-naphthyridin-3-yl)-2-hydroxyethanone dihydrochloride;

1-[6-(3-chloro-5-fluoro-4-hydroxyphenyl)-4-({trans-4-[(dimethylamino)methyl]cyclohexyl} amino)-1,5-naphthyridin-3-yl)]-2-hydroxyethanone dihydrochloride;

1-[6-(3-chloro-5-fluoro-4-hydroxyphenyl)-4-({trans-4-[(dimethylamino)methyl]cyclohexyl} amino)-1,5-naphthyridin-3-yl)]propan-1-one dihydrochloride;

1-[6-(3,5-dichloro-4-hydroxyphenyl)-4-({trans-4-[(dimethylamino)methyl]cyclohexyl}amino)-1,5-naphthyridin-3-yl)]propan-1-one dihydrochloride;

(S)-1-(4-{[6-(3-aminopiperidin-1-yl)pyridin-3-yl]amino}-6-(3,5-dichloro-4-hydroxyphenyl)-1,5-naphthyridin-3-yl)propan-1-one trihydrochloride;

(S)-1-(4 {[6-(3-aminopiperidin-1-yl)pyridin-3-yl]amino}-6-(3-chloro-5-fluoro-4-hydroxyphenyl)-1,5-naphthyridin-3-yl)propan-1-one trihydrochloride;

1-[6-(3,5-dichloro-4-hydroxyphenyl)-4-({4-[((R)-3-fluoropyrrolidin-1yl)methyl]cyclohexyl}amino)-1,5-naphthyridin-3-yl]ethanone dihydrochloride;

(S)-(4-((6-(3-aminopiperidin-1-yl)pyridin-3-yl)amino)-6-(3-chloro-5-fluoro-4-hydroxyphenyl)-1,5-naphthyridin-3-yl)(cyclobutyl)methanone dihydrochloride;

(6-(3,5-dichloro-4-hydroxyphenyl)-4-((4-[(dimethylamino)methyl{cyclohexyl)amino)-1,5-naphthyridin-3-yl)(cyclobutyl)methanone dihydrochloride;

(6-(3-chloro-5-fluoro-4-hydroxyphenyl)-4-((4-((dimethylamino)methyl)cyclohexyl)amino)-1,5-naphthyridin-3-yl)(cyclobutyl)methanone dihydrochloride;

(S)-(4-{[6-(3-aminopiperidin-1-yl)pyridin-3-yl]amino}-6-(3-chloro-5-fluoro-4-hydroxyphenyl)-1,5-naphthyridin-3-yl)(cyclobutyl)methanone;

(R)-1-(4-((6-(3-aminopiperidin-1-yl)pyridin-3-yl)amino)-6-(3,5-dichloro-4-hydroxyphenyl)-1,5-naphthyridin-3-yl)propan-1-one trihydrochloride;

(R)-1-(4-{[6-(3-aminopiperidin-1-yl)pyridin-3-yl]amino}-6-(3,5-dichloro-4-hydroxyphenyl)-1,5-naphthyridin-3-yl)-2-methylpropan-1-one trihydrochloride;

1-[6-(3,5-dichloro-5-4-hydroxyphenyl)-4-({trans-4-[(dimethylamino)methyl]cyclohexyl} amino)-1,5-naphthyridin-3-yl]-2-methylpropan-1-one dihydrochloride;

1-[6-chloro-4-({trans-4-[(dimethylamino)methyl]cyclohexyl}amino)-1,5-naphthyridin-3-yl]-2-methylpropan-1-one dihydrochloride;

and pharmaceutically acceptable salts thereof.

13. A pharmaceutical composition comprising as an active ingredient a compound or a pharmaceutically acceptable salt thereof according to claim 1.

14. A process for preparing a compound of formula (I):

(I)

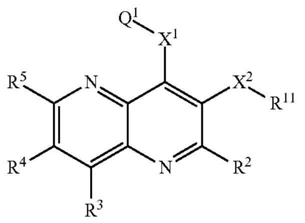

or a pharmaceutically acceptable salt thereof as defined in claim 1, wherein $R^5$ is phenyl optionally substituted with one or more substituents independently selected from $A^3$; and $Q^1$, $X^1$, $X^2$, $R^{11}$, $R^2$, $R^3$, $R^4$, and $A^3$ are the groups as defined in any one of claim 1 to 10; which comprises:

reacting a compound represented by formula (II):

(II)

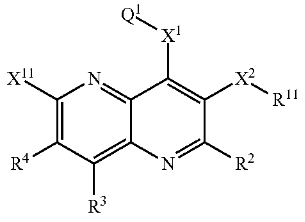

wherein $Q^1$, $X^1$, $X^2$, $R^{11}$, $R^2$, $R^3$, and $R^4$ are the groups as defined above, with the proviso that the groups may have one or more protecting groups, and $X^{11}$ is a halogen atom; with a compound represented by formula (III):

(III)

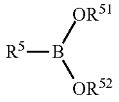

wherein $R^5$ is as defined above with the proviso that the group of $R^5$ may have one or more protecting groups; and $R^{51}$ and $R^{52}$ are independently selected from the group consisting of $C_1$-$C_6$ alkyl, or $R^{51}$ and $R^{52}$ together with the boron atom to which they are attached forms 5- to 7-membered cyclic boronic acid ester optionally substituted with one or more substituents independently selected from the group consisting of $C_1$-$C_6$ alkyl.

15. A compound represented by formula (II) or a pharmaceutically acceptable salt thereof:

(II)

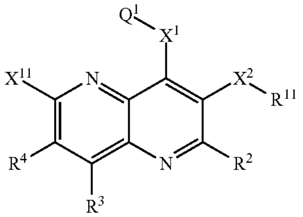

wherein $Q^1$, $X^1$, $X^2$, $R^{11}$, $R^2$, $R^3$, and $R^4$ are the groups as defined in claim 1 with the proviso that the groups may have one or more protecting groups, and $X^{11}$ is a halogen atom.

* * * * *